US011739379B2

(12) United States Patent
Heron et al.

(10) Patent No.: US 11,739,379 B2
(45) Date of Patent: Aug. 29, 2023

(54) METHOD FOR NUCLEIC ACID DETECTION BY GUIDING THROUGH A NANOPORE

(71) Applicant: Oxford Nanopore Technologies PLC, Oxford (GB)

(72) Inventors: Andrew John Heron, Oxford (GB); James Edward Graham, Oxford (GB); Richard Alexander Gutierrez, Oxford (GB); Rebecca Victoria Bowen, Oxford (GB); James White, Oxford (GB); Clive Gavin Brown, Cambridge (GB); Daniel George Fordham, Oxford (GB)

(73) Assignee: Oxford Nanopore Technologies PLC, Oxford (GB)

( * ) Notice: Subject to any disclaimer, the term of this patent is extended or adjusted under 35 U.S.C. 154(b) by 80 days.

(21) Appl. No.: 17/361,821

(22) Filed: Jun. 29, 2021

(65) Prior Publication Data
US 2022/0064723 A1 Mar. 3, 2022

Related U.S. Application Data

(63) Continuation of application No. 16/338,399, filed as application No. PCT/GB2017/052946 on Sep. 29, 2017, now Pat. No. 11,085,078.

(30) Foreign Application Priority Data

Sep. 29, 2016 (GB) ...................................... 1616590

(51) Int. Cl.
*C12Q 1/68* (2018.01)
*C12Q 1/6869* (2018.01)
(Continued)

(52) U.S. Cl.
CPC ......... *C12Q 1/6869* (2013.01); *C12Q 1/6876* (2013.01); *G01N 33/48721* (2013.01)

(58) Field of Classification Search
CPC ...................................................... C12Q 1/68
(Continued)

(56) References Cited

U.S. PATENT DOCUMENTS

| 11,085,078 B2 | 8/2021 | Heron et al. |
| 2013/0048499 A1 | 2/2013 | Mayer et al. |

(Continued)

FOREIGN PATENT DOCUMENTS

| WO | WO 2000/028312 A1 | 5/2000 |
| WO | WO 2005/124888 A1 | 12/2005 |

(Continued)

OTHER PUBLICATIONS

International Search Report and Written Opinion for Application No. PCT/GB2017/052946, dated Jan. 3, 2018.
(Continued)

*Primary Examiner* — Aaron A Priest
(74) *Attorney, Agent, or Firm* — Wolf, Greenfield & Sacks, P.C.

(57) ABSTRACT

The invention provides a method of detecting a target polynucleotide in a sample comprising: (a) contacting the sample with a guide polynucleotide that binds to a sequence in the target polynucleotide and a polynucleotide-guided effector protein, wherein the guide polynucleotide and polynucleotide-guided effector protein form a complex with any target polynucleotide present in the sample; (b) contacting the sample with a membrane comprising a transmembrane pore; (c) applying a potential to the membrane; and (d) monitoring for the presence or absence of an effect resulting from the interaction of the complex with the transmembrane (Continued)

pore to determine the presence or absence of the complex, thereby detecting the target polynucleotide in the sample.

17 Claims, 38 Drawing Sheets

Specification includes a Sequence Listing.

(51) Int. Cl.
  *C12Q 1/6876* (2018.01)
  *G01N 33/487* (2006.01)
(58) Field of Classification Search
  USPC .......................................................... 435/6.1
  See application file for complete search history.

(56) References Cited

U.S. PATENT DOCUMENTS

| | | | |
|---|---|---|---|
| 2014/0356867 A1 | 12/2014 | Peter et al. | |
| 2014/0357523 A1 | 12/2014 | Zeiner et al. | |
| 2016/0138081 A1 | 5/2016 | Fujii et al. | |

FOREIGN PATENT DOCUMENTS

| | | | |
|---|---|---|---|
| WO | WO 2006/100484 A2 | 9/2006 | |
| WO | WO 2008/102120 A1 | 8/2008 | |
| WO | WO 2008/102121 A1 | 8/2008 | |
| WO | WO 2009/035647 A1 | 3/2009 | |
| WO | WO 2009/077734 A2 | 6/2009 | |
| WO | WO 2010/086602 A1 | 8/2010 | |
| WO | WO 2010/086603 A1 | 8/2010 | |
| WO | WO 2011/067559 A1 | 6/2011 | |
| WO | WO 2012/042226 A2 | 4/2012 | |
| WO | WO 2012/107778 A2 | 8/2012 | |
| WO | WO 2013/057495 A2 | 4/2013 | |
| WO | WO 2013/098561 A1 | 7/2013 | |
| WO | WO 2013/098562 A1 | 7/2013 | |
| WO | WO 2013/153359 A1 | 10/2013 | |
| WO | WO 2013/176772 A1 | 11/2013 | |
| WO | WO 2014/013259 A1 | 1/2014 | |
| WO | WO 2014/013260 A1 | 1/2014 | |
| WO | WO 2014/013262 A1 | 1/2014 | |
| WO | WO 2014/064443 A2 | 5/2014 | |
| WO | WO 2014/064444 A1 | 5/2014 | |
| WO | WO 2014/072703 A1 | 5/2014 | |
| WO | WO 2015/022544 A1 | 2/2015 | |
| WO | WO 2015/055981 A2 | 4/2015 | |
| WO | WO 2015/075056 A1 | 5/2015 | |
| WO | WO 2015/150786 A1 | 10/2015 | |
| WO | WO 2016/014409 A1 | 1/2016 | |
| WO | WO-2016014409 A1 * | 1/2016 | ........... C12N 15/102 |
| WO | WO 2016/028843 A2 | 2/2016 | |
| WO | WO 2016/028887 A1 | 2/2016 | |
| WO | WO-2016028843 A2 * | 2/2016 | ............. C12N 15/11 |
| WO | WO 2016/034591 A2 | 3/2016 | |
| WO | WO 2016/055777 A2 | 4/2016 | |
| WO | WO 2016/059363 A1 | 4/2016 | |
| WO | WO 2016/059375 A1 | 4/2016 | |

OTHER PUBLICATIONS

International Preliminary Report on Patentability for Application No. PCT/GB2017/052946, dated Apr. 11, 2019.
Anderson, The clinical plasma proteome: a survey of clinical assays for proteins in plasma and serum. Clin Chem. Feb. 2010;56(2):177-85. doi: 10.1373/clinchem.2009.126706. Epub Nov. 2, 2009.
Braha et al., Designed protein pores as components for biosensors. Chem Biol. Jul. 1997;4(7):497-505.
Chandler et al., A new microparticle size calibration standard for use in measuring smaller microparticles using a new flow cytometer. J Thromb Haemost. Jun. 2011;9(6): 216-24. doi: 10.1111/j.1538-7836.2011.04283.x.
Colas et al., Microscopical investigations of nisin-loaded nanoliposomes prepared by Mozafari method and their bacterial targeting. Micron. 2007;38(8):841-7.
Deangelis et al., Solid-phase reversible immobilization for the isolation of PCR products. Nucleic Acids Res. Nov. 25, 1995; 23(22): 4742-4743. doi: 10.1093/nar/23.22.4742.
Edwards et al., The role of proteomics in clinical cardiovascular biomarker discovery. Mol Cell Proteomics. Oct. 2008;7( 10): 1824-37. doi: 10.1074/mcp.R800007-MCP200. Epub Jul. 30, 2008.
Eliseev et al., Molecular Recognition of Nucleotides, Nucleosides, and Sugars by Aminocyclodextrins. J. Am. Chem. Soc., 1994;116:6081-6088.
Gonzalez-Perez et al., Biomimetic triblock copolymer membrane arrays: a stable template for functional membrane proteins. Langmuir. Sep. 15, 2009;25(18):10447-50. doi: 10.1021/la902417m.
Grant et al., A facile method for attaching nitroxide spin labels at the 5' terminus of nucleic acids. Nucleic Acids Res. 2007;35(10):e77. Epub May 21, 2007.
He et al., Conjugation and Evaluation of Triazole-Linked Single Guide RNA for CRISPR-Cas9 Gene Editing. Chembiochem. Oct. 4, 2016;17(19):1809-1812. doi: 10.1002/cbic.201600320. Epub Aug. 19, 2016.
Heron et al., Direct detection of membrane channels from gels using water-in-oil droplet bilayers. J Am Chem Soc. Dec. 26, 2007;129(51):16042-7. Epub Dec. 1, 2007.
Holden et al., Functional bionetworks from nanoliter water droplets. J Am Chem Soc. Jul. 11, 2007;129(27):8650-5. Epub Jun. 16, 2007.
Hornblower et al., Single-molecule analysis of DNA-protein complexes using nanopores. Nat Methods. Apr. 2007;4(4):315-7. Epub Mar. 4, 2007.
Ivanov et al., DNA tunneling detector embedded in a nanopore. Nano Lett. Jan. 12, 2011;11(1):279-85. doi: 10.1021/nl103873a. Epub Dec. 6, 2010.
Jaquet et al., Identification of cardiac myosin-binding protein C as a candidate biomarker of myocardial infarction by proteomics analysis. Mol Cell Proteomics. Dec. 2009;8(12):2687-99. doi: 10.1074/mcp.M900176-MCP200. Epub Aug. 31, 2009.
Jiang et al., miR2Disease: a manually curated database for microRNA deregulation in human disease. Nucleic Acids Res. Jan. 2009;37(Database issue):D98-104. doi: 10.1093/nar/pkn714. Epub Oct. 15, 2008.
Kankia et al., Folding of the thrombin aptamer into a G-quadruplex with Sr(2+): stability, heat, and hydration. J Am Chem Soc. Nov. 7, 2001;123(44):10799-804.
Koonin et al., Mobile Genetic Elements and Evolution of CRISPR-Cas Systems: All the Way There and Back. Genome Biol Evol. Oct. 1, 2017;9(10):2812-2825. doi: 10.1093/gbe/evx192.
Kozarewa, 96-plex molecular barcoding for the Illumina Genome Analyzer. Methods Mol Biol. 2011;733:279-98. doi: 10.1007/978-1-61779-089-8_20.
Kumar et al., Nonradioactive labeling of synthetic oligonucleotide probes with terminal deoxynucleotidyl transferase. Anal Biochem. Mar. 1988;169(2):376-82. Erratum in: Anal Biochem Sep. 1988;173(2):469.
Langecker et al., Synthetic lipid membrane channels formed by designed DNA nanostructures. Science. Nov. 16, 2012;338(6109):932-6. doi: 10.1126/science.1225624.
Lee et al., Synthetically modified guide RNA and donor DNA are a versatile platform for CRISPR-Cas9 engineering. eLife 2017;6:e25312. DOI 10.7554/eLife.25312.
Lieberman et al., Processive replication of single DNA molecules in a nanopore catalyzed by phi29 DNA polymerase. J Am Chem Soc. Dec. 22, 2010;132(50):17961-72. doi:10.1021/ja1087612. Epub Dec. 1, 2010.
Marathias et al., Structures of the potassium-saturated, 2:1, and intermediate, 1:1, forms of a quadruplex DNA. Nucleic Acids Res. May 1, 2000;28(9):1969-77.
Marušič et al., Solution-state structure of an intramolecular G-quadruplex with propeller, diagonal and edgewise loops. Nucleic Acids Res. Aug. 2012;40(14):6946-56. doi: 10.1093/nar/gks329. Epub Apr. 24, 2012.
Montal et al., Formation of bimolecular membranes from lipid monolayers and a study of their electrical properties. Proc Natl Acad Sci U S A. Dec. 1972;69(12):3561-6.

(56) References Cited

OTHER PUBLICATIONS

Nikolov et al., Behavior of giant vesicles with anchored DNA molecules. Biophys J. Jun. 15, 2007;92(12):4356-68. Epub Mar. 23, 2007.
Nishimasu et al., Crystal structure of Cas9 in complex with guide RNA and target DNA. Cell. Feb. 27, 2014;156(5):935-49. doi: 10.1016/j.cell.2014.02.001. Epub Feb. 13, 2014.
Pfeiffer et al., Bivalent cholesterol-based coupling of oligonucletides to lipid membrane assemblies. J Am Chem Soc. Aug. 25, 2004;126(33):10224-5.
Shmakov et al., Discovery and Functional Characterization of Diverse Class 2 CRISPR-Cas Systems. Mol Cell. 2015;60(3):385-397. doi: 10.1016/j.molcel.2015.10.008.
Soni et al., Synchronous optical and electrical detection of biomolecules traversing through solid-state nanopores. Rev Sci Instrum. Jan. 2010;81(1):014301. doi: 10.1063/1.3277116.
Sternberg et al., DNA interrogation by the CRISPR RNA-guided endonuclease Cas9. Nature. Mar. 6, 2014;507(7490):62-7. doi: 10.1038/nature13011. Epub Jan. 29, 2014.
Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.
Troutt et al., Ligation-anchored PCR: a simple amplification technique with single-sided specificity. Proc Natl Acad Sci U S A. Oct. 15, 1992;89(20):9823-5. Erratum in: Proc Natl Acad Sci U S A Apr. 15, 1993;90(8):3775.
Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f.
Wiles et al., CRISPR-Cas9-mediated genome editing and guide RNA design. Mamm Genome. Oct. 2015;26(9-10):501-10. doi: 10.1007/s00335-015-9565-z. Epub May 20, 2015.
Yoshina-Ishii et al., Arrays of mobile tethered vesicles on supported lipid bilayers. J Am Chem Soc. Apr. 2, 2003;125(13):3696-7.
Yusko et al., Controlling protein translocation through nanopores with bio-inspired fluid walls. Nat Nanotechnol. Apr. 2011;6(4):253-60. doi: 10.1038/nnano.2011.12. Epub Feb. 20, 2011.

\* cited by examiner

A

C

D

| Peak | Gene | Genomic coordinates | Location of crRNA |
|---|---|---|---|
| iv | rrsA | 4035531—4037072 | 4035720 |
| v | rrsB | 4166659—4168200 | 4166848 |
| iii | rrsC | 3941808—3943349 | 3941997 |
| vii | rrsD | 3427221—3428762 | 3428573 |
| vi | rrsE | 4208147—4209688 | 4208336 |
| ii | rrsG | 2729616—2731157 | 2730968 |
| i | rrsH | 223771—225312 | 223960 |

METHOD FOR NUCLEIC ACID DETECTION BY GUIDING THROUGH A NANOPORE

RELATED APPLICATIONS

This application is a continuation of U.S. application Ser. No. 16/338,399, filed Mar. 29, 2019, which is a national stage filing under 35 U.S.C. § 371 of international application number PCT/GB2017/052946, filed Sep. 29, 2017, which claims the benefit of United Kingdom application number GB1616590.4, filed Sep. 29, 2016, each of which is herein incorporated by reference in its entirety.

FIELD OF THE INVENTION

The invention relates generally to a method of detecting and/or analysing target polynucleotides using a transmembrane pore. The invention also relates to novel probes and panels of probes for use in the method and kits for carrying out the method. The method has many uses. In particular, the method may be used for diagnosis, detection of polymorphisms and V(D)J repertoire analysis.

BACKGROUND TO THE INVENTION

There is currently a need for rapid and cheap polynucleotide (e.g. DNA or RNA) sequencing and identification technologies across a wide range of applications. Existing technologies are slow and expensive mainly because they rely on amplification techniques to produce large volumes of polynucleotide and require a high quantity of specialist fluorescent chemicals for signal detection.

Transmembrane pores (and other nanopores) have great potential as direct, electrical biosensors for polymers and a variety of small molecules. In particular, recent focus has been given to nanopores as a potential DNA sequencing technology.

When a potential is applied across a nanopore, there is a change in the current flow when an analyte, such as a nucleotide, resides transiently in the barrel for a certain period of time. Nanopore detection of the nucleotide gives a current change of known signature and duration. In the strand sequencing method, a single polynucleotide strand is passed through the pore and the identities of the nucleotides are derived. Strand sequencing can involve the use of a molecular brake to control the movement of the polynucleotide through the pore.

SUMMARY OF THE INVENTION

The present inventors have identified a novel use for the guide RNAs and DNAs and RNA-guided and DNA-guided effector proteins that form part of the CRISPR gene editing machinery. The present inventors have designed modified guide RNA sequences that can be used in conjunction with associated RNA-guided effector proteins to test for the presence, absence or amount of one or more target polynucleotides in a sample. The present inventors have developed methods of detecting target polynucleotides using guide RNAs and RNA-guided effector proteins in conjunction with a transmembrane pore. The methods can be performed in a variety of ways, but have in common that they use guide RNAs and RNA-guided effector proteins to select the target polynucleotide(s) and involve the delivery of a complex comprising the target polynucleotide, guide RNA and RNA-guided effector protein to a transmembrane pore. The methods can be extended to other polynucleotide-guided protein effector systems, including the RNA editing system using C2c2. The guide polynucleotide, such as guide RNA, may be specially adapted for use in a nanopore-based detection method.

The methods developed by the present inventors are sensitive and can be used to detect trace amounts of polynucleotide in a sample without requiring a separate separation step to extract the target polynucleotide(s) from other components in the sample. Thus, the methods are simple and do not require complex steps, such as enrichment or purification steps. Accordingly, the methods are rapid and can be used to obtain quick results and results from crude and/or "dirty" samples. The methods are therefore particularly useful in diagnostic settings where rapid diagnosis is required. The methods are also particularly useful in targeting a particular fragment or region of a gene or genome. A key benefit of the methods is that the polynucleotide guided effector protein does not actively need to be removed from the target polynucleotide prior to measurement of the target or the adaptor. In some embodiments of the invention, the target polynucleotide may be detected or characterized whilst still attached to the polynucleotide guided effector protein. In other embodiments of the invention, the polynucleotide guided effector protein may be automatically removed by the transmembrane pore during measurement of the target. In some embodiments, the method uses specifically designed guide polynucleotides to facilitate separation of the target polynucleotide(s) from other components in the sample.

The methods enable the regions of interest of polynucleotide sequence to be characterized, for example sequenced, in a sample that contains many other polynucleotide sequences as it inherently includes a separation step. For example, only genes of interest present in a large genome may be sequenced. The sequencing can be limited to regions that contain SNPs, or to other regions of interest, such as V(D)J regions in T-cells. This improves sensitivity and efficiency, with the desired information being accessed without requiring complicated or time-consuming fragmentation or pull-down sample preparation methods. It also reduces the time taken perform the nanopore experiment as only the target polynucleotide fragments of interest are measured, or an increased proportion thereof are measured relative to the total polynucleotide fragments in the sample In cases where the amount of non-target polynucleotide is in excess to that of the target polynucleotide, the time taken to detect the target polynucleotide can be significantly reduced due to the removal of or a reduction in the need to measure non-target polynucleotides. The methods also benefit from not requiring PCR or other target enrichment approaches.

Accordingly, the present invention provides a method of detecting a target polynucleotide in a sample comprising:
  (a) contacting the sample with a guide polynucleotide that binds to a sequence in the target polynucleotide and a polynucleotide-guided effector protein, wherein the guide polynucleotide and polynucleotide-guided effector protein form a complex with any target polynucleotide present in the sample;
  (b) contacting the sample with a membrane comprising a transmembrane pore;
  (c) applying a potential difference across the membrane; and
  (d) monitoring for the presence or absence of an effect resulting from the interaction of the complex with the transmembrane pore to determine the presence or absence of the complex, thereby detecting the target polynucleotide in the sample.

Also provided is a method of detecting a target polynucleotide in a sample comprising:
(a) contacting the sample with a guide polynucleotide that binds to a sequence in the target polynucleotide and a polynucleotide-guided effector protein, wherein the guide polynucleotide and polynucleotide-guided effector protein form a complex with any target polynucleotide present in the sample;
(b) contacting the sample with a nanopore;
(c) applying a potential difference across the nanopore; and
(d) monitoring for the presence or absence of an effect resulting from the interaction of the complex with the nanopore to determine the presence or absence of the complex, thereby detecting the target polynucleotide in the sample.

The invention also provides:
a guide polynucleotide comprising a nucleotide sequence that binds to a sequence in the target polynucleotide, a nucleotide sequence that binds to a polynucleotide guided effector protein and an adaptor sequence and/or an anchor capable of coupling to a surface;
a panel of two or more guide polynucleotides of the invention;
a guide polynucleotide/polynucleotide-guided effector protein complex comprising a guide polynucleotide of the invention and a polynucleotide-guided effector protein;
a kit comprising: a polynucleotide-guided effector protein and an anchor capable of coupling to a surface; and
a method of detecting a target comprising a double stranded polynucleotide in a sample comprising:
(a) contacting the sample with a first probe and a second probe, wherein the first probe and the second probe form a complex with any target polynucleotide present in the sample, the first probe binds to a first sequence in the target double stranded polynucleotide and comprises an anchor capable of coupling to a surface, and the second probe binds to a second sequence in the target double stranded polynucleotide and comprises an adaptor sequence;
(b) contacting the sample with a transmembrane pore;
(c) applying a potential to the transmembrane pore; and
(d) monitoring for the presence or absence of an effect resulting from the interaction of the complex with the transmembrane pore to determine the presence or absence of the complex, thereby detecting the target double stranded polynucleotide in the sample.

DESCRIPTION OF THE FIGURES

It is to be understood that Figures are for the purpose of illustrating particular embodiments of the invention only, and are not intended to be limiting.

FIG. 33 is a schematic of a double stranded DNA strand encountering a pore which is only big enough for a single strand of DNA to fit through. The complementary strand is stripped away by the pore as the first strand passes through.

DETAILED DESCRIPTION OF THE INVENTION

Figure 1:
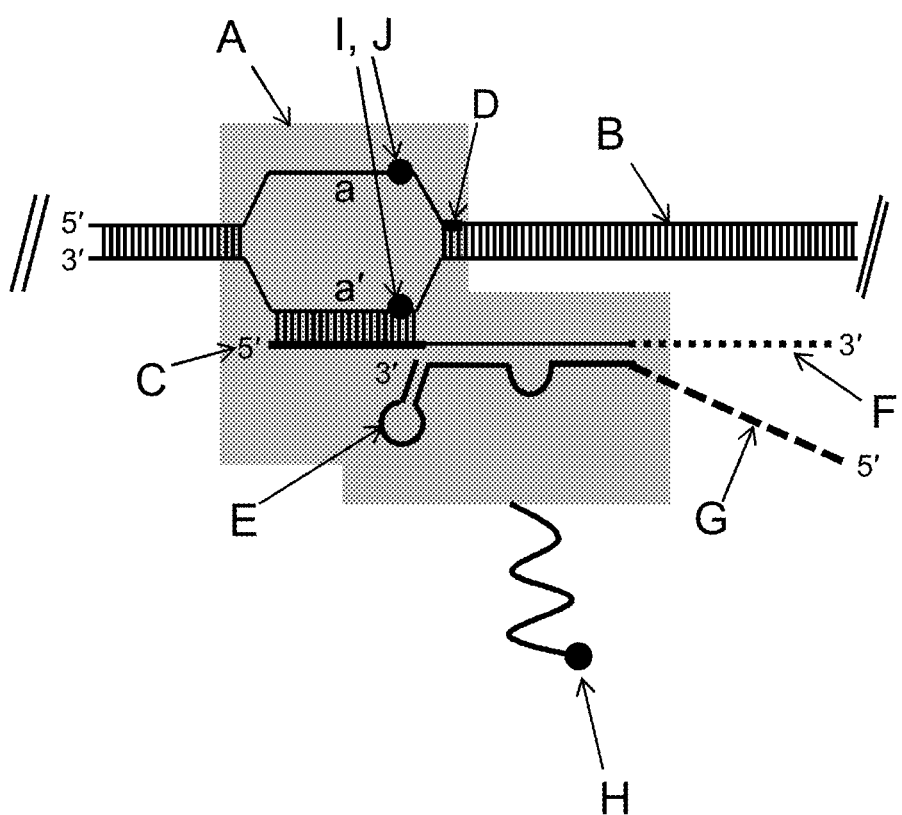
FIG. 1 shows an example of how an inactivated CRISPR-Cas9 complex bearing an extended CRISPR RNA (crDNA) may be used to contact specific genomic DNA sequence 'a'. In this figure, a Cas9 protein A contacts a specific locus a in genomic DNA B. The CRISPR RNA C bears the sequence of a, which precedes a TAM' site D. Cas9 catalyses the melting of a and hybridises to non-target strand a'. The crRNA may also carries a sequence bearing partial complementarity to tracrRNA E and an extension F which enables the hybridisation of an anchoring polynucleotide or polynucleotide binding protein loaded polynucleotide. The tracrRNA may also carry an extension G which enables the hybridisation of an anchoring polynucleotide, or polynucleotide binding protein loaded polynucleotide. Alternatively, the Cas9 may carry a peptide tag, or polynucleotide affinity tag, or reactive moiety H, which enables the binding or pulldown of the protein to a surface for anchorage or purification. Also shown are the canonical cleavage sites I, J for the wild-type Cas9 nuclease, both of which are inactivated in the 'dead' Cas9 (dCas9), and one of which is inactivated in the 'nickase' mutants of Cas9, (mutations of residues H10 and D840 in the *Streptococcus pyogenes* protein).
Figure 2:
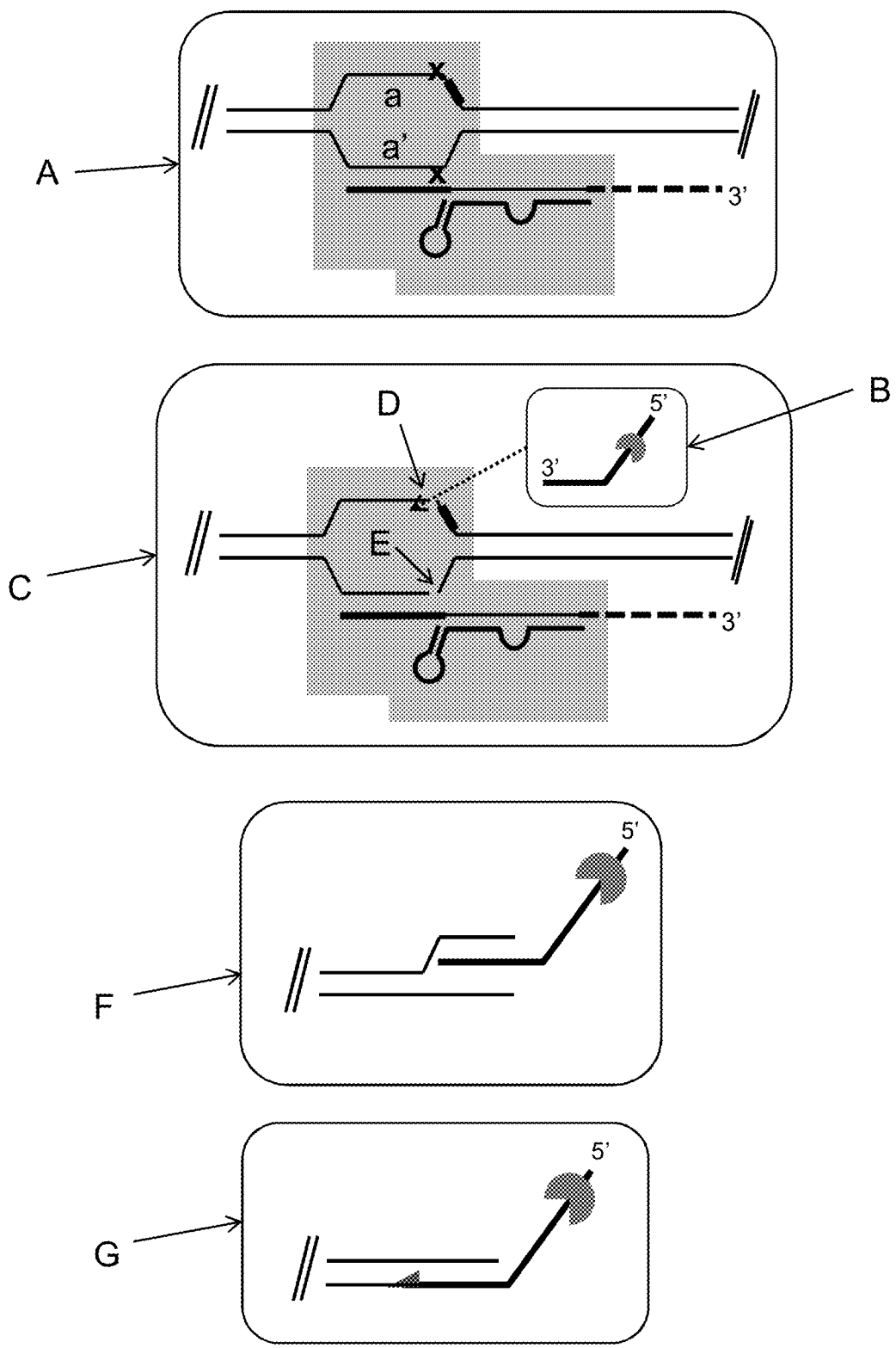
FIG. 2 shows an alternative method to FIG. 1 in which a CRISPR-Cas9 with zero or one inactivated nuclease sites is bound to a specific locus (as per FIG. 1) and an adapter carrying an enzyme B and sequence complementary to sequence a is extended and ligated directly to the target DNA. Panel C shows the double-strand break in the target induced at one or both sites D and E by the active or partially active Cas9 nuclease. Panel F shows the dissociation of the CRISPR-Cas9 complex induced by binding of species B to the displaced strand of the CRISPR-Cas9 complex. Panel G shows the effect of extending the 3' end of species B in the presence of a polymerase-exonuclease such as *E. coli* DNA polymerase I and ligase such as *E. coli* DNA ligase.
Figure 3:
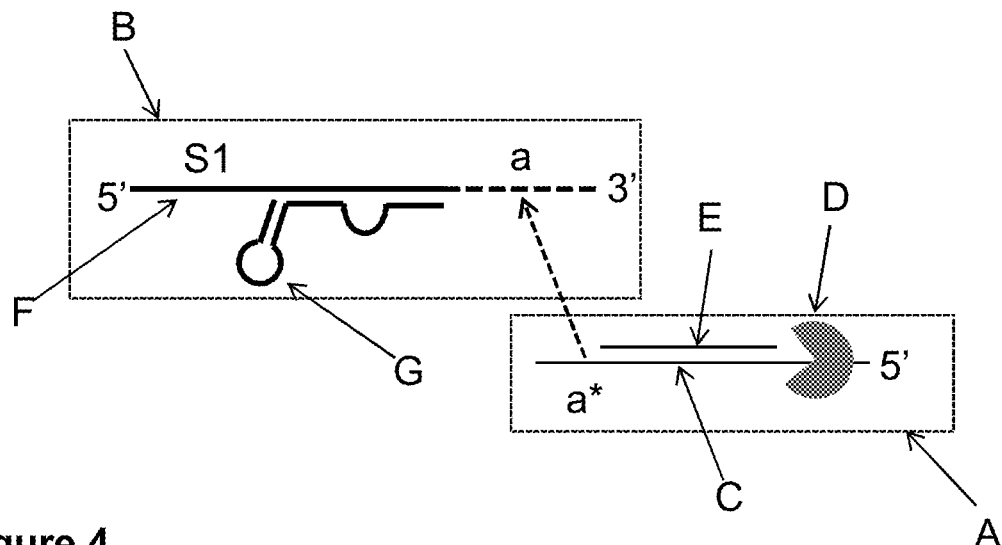
FIG. 3 shows how an enzyme-loaded adaptor ('Y-adaptor'), species A, may be hybridised to a crRNA-tracrRNA hybrid, species B, bearing an appropriate 3' extension. Species A comprises: an oligonucleotide C with partial complementarity a* to the 3' extension of species B, and a 5' extension for loading of an enzyme D; an oligonucleotide E bearing partial complementarity to species C. Oligonucleotide Species B comprises: an oligonucleotide F carrying: sequence S1, the proto spacer sequence of the crRNA, partial complementarity to tracrRNA G, and a 3' extension of sequence a, complementary to sequence a*.
Figure 4:
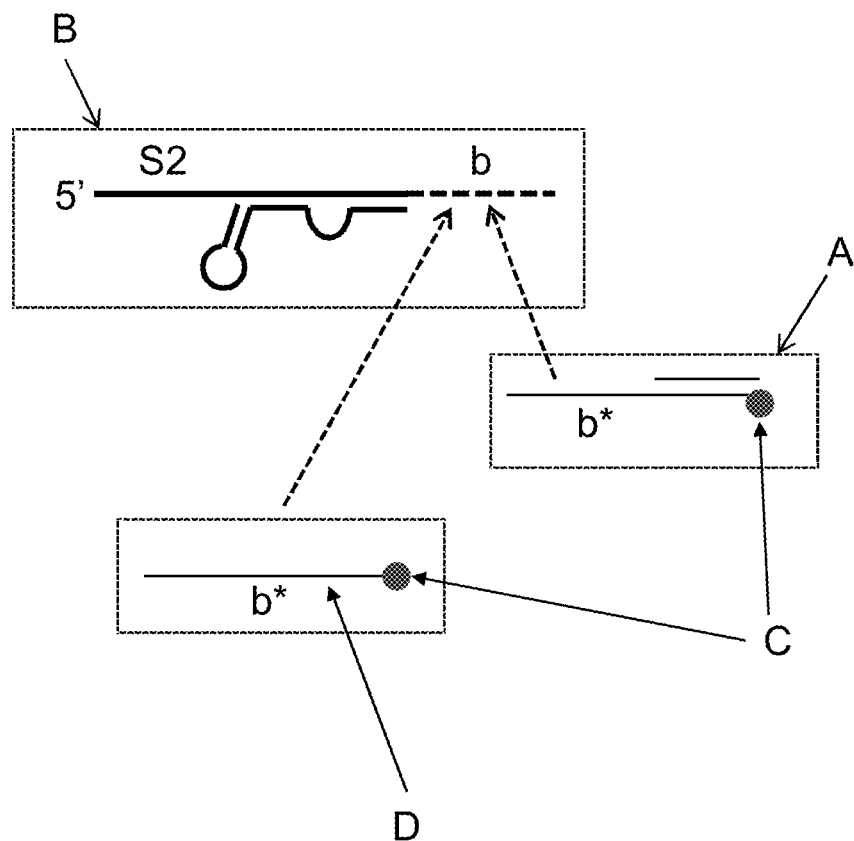
FIG. 4 shows how an anchoring species A, such as an oligonucleotide carrying a cholesterol moiety, may be hybridised to a crRNA-tracrRNA hybrid, species B, bearing an appropriate 3' extension. All parts are similar to FIG. 3 except: sequence S2 is a protospacer sequence unique to species B, and targeting a different sequence to the hybrid shown in FIG. 3; sequence b, a 3' extension to the crRNA that is complementary to sequence b*, on the anchoring species A. Species A carries an anchoring moiety C, such as a cholesterol or biotin or desthiobiotin.
Figure 5:
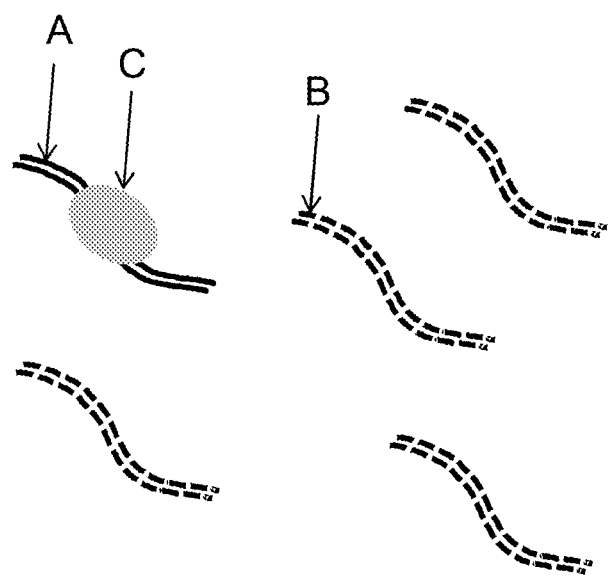
FIG. 5 shows how a double-stranded DNA target A may be differentiated from a non-specific DNA B by means of recognition by a CRISPR-Cas9 complex C.
Figure 6:
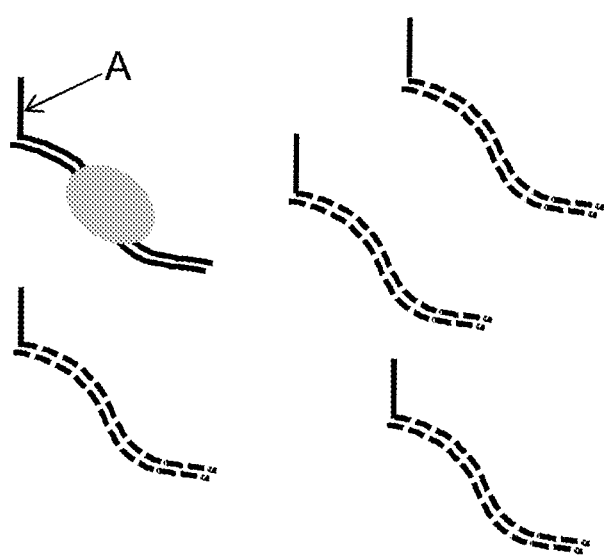
FIG. 6 is identical to FIG. 5, except that the specific and non-specific DNA in a mixture may be derivatised with an adapter moiety A may be used for capture of target and non-target DNA by a nanopore.
Figure 7:
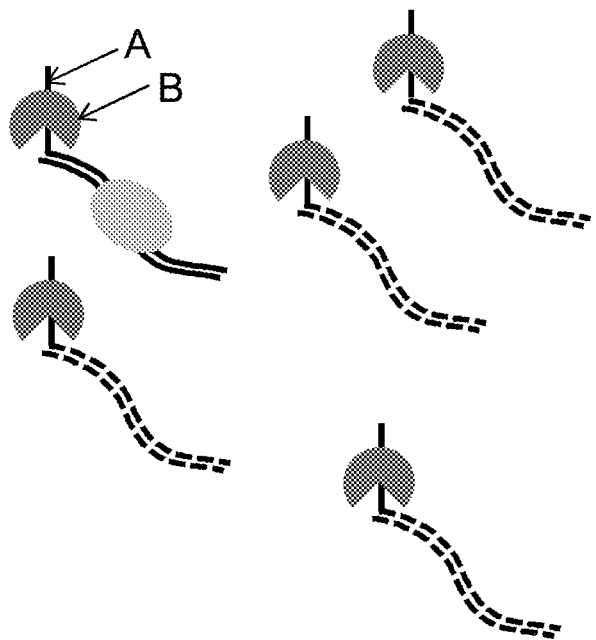
FIG. 7 is identical to FIG. 6, except that the adapter moiety A may carry an polynucleotide binding protein B used to control the movement of target and non-target DNA through a nanopore.

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a polynucleotide" includes two or more polynucleotides, reference to "an anchor" refers to two or more anchors, reference to "a helicase" includes two or more helicases, and reference to "a transmembrane pore" includes two or more pores and the like.

All publications, patents and patent applications cited herein, whether supra or infra, are hereby incorporated by reference in their entirety.

Methods

The invention provides a method of detecting a target polynucleotide in a sample comprising: (a) contacting the sample with a guide polynucleotide that binds to a sequence in the target polynucleotide and a polynucleotide-guided effector protein, wherein the guide polynucleotide and polynucleotide-guided effector protein form a complex with any target polynucleotide present in the sample; (b) contacting the sample with a membrane comprising a transmembrane pore; (c) applying a potential difference across the membrane; and (d) monitoring for the presence or absence of an effect resulting from the interaction of the complex with the transmembrane pore to determine the presence or absence of the complex, thereby detecting the target polynucleotide in the sample. Step (a) and (b) may be carried out simultaneously or sequentially in either order.

The method may comprise (a) contacting the sample with a guide polynucleotide that binds to a sequence in the target polynucleotide and a polynucleotide-guided effector protein to form a complex, wherein the sample is in contact with a membrane comprising a transmembrane pore and wherein a potential is applied to the transmembrane pore; and (b) taking one or more measurements as at least a portion of the complex moves with respect to the transmembrane pore to detect the presence or absence of the complex, thereby detecting the target polynucleotide in the sample.

In some embodiments, the method comprises: (a) contacting the sample with a guide polynucleotide that binds to a sequence in the target polynucleotide, a polynucleotide-guided effector protein and a membrane comprising a transmembrane pore; (b) applying a potential difference across the membrane; and (c) measuring the ion flow passing through the transmembrane pore, or other signal resulting from the interaction of the sample, guide polynucleotides and polynucleotide-guided effector proteins with the transmembrane pore, to determine the presence or absence of a complex comprising the guide polynucleotide, polynucleotide-guided effector protein and the target polynucleotide, thereby detecting the target polynucleotide in the sample. Measurement of ion flow may comprise measurement of the current flow through the pore.

The methods can be carried out in a number of different ways. The methods can be used to perform a variety of different applications. The methods may be used, for example, to determine the presence or absence of a single target polynucleotide, or of a number of target polynucleotides. The methods may be quantitative. For example, the amount (such as the concentration) of the target polynucleotide present in a sample may be determined using a method of the invention and/or relative amounts of different polynucleotides present in a sample may be determined. The methods can provide further information about a target polynucleotide, such as the presence or absence of a polymorphism and/or the identity of a polymorphism.

The method may comprise determining whether an adaptor attached to the guide polynucleotide interacts with the transmembrane pore. The method may be carried out such that guide polynucleotides comprising adaptors that are not bound to the target polynucleotide do not interact with the transmembrane pore. Typically such unbound guide polynucleotides are washed away before a transmembrane potential is applied to the membrane. The target polynucleotide may be tethered to a surface, for example to the membrane, to prevent bound guide polynucleotides comprising adaptors from being washed away. The target polynucleotide may have a tether, such as a membrane anchor, attached to it directly, for example, to one of its ends. Alternatively, a second guide polynucleotide/polynucleotide-guided effector protein which comprises a tether, such as a membrane anchor, may be used to tether the target polynucleotide to the surface, for example to the membrane.

The surface to which the target polynucleotide is tethered may be a bead.

The adaptor is typically unique to the target polynucleotide and produces a distinct signal on interacting with a transmembrane pore. Multiple guide polynucleotides, each selective for a different target polynucleotide and having a different adaptor may be added to the sample to detect and/or quantify different target polynucleotides on the basis of the different signals caused by the different adaptors interacting with the transmembrane pore. In this embodiment, the adaptors may be considered to comprise barcodes.

The method may use multiple guide polynucleotides that bind to different polynucleotide sequences. The different polynucleotide sequences may, for example, be different sequences in the same target polynucleotide (e.g. different portions of the target polynucleotide), sequences of different target polynucleotides or alternative sequences within a target polynucleotide, such as sequences that encompass polymorphisms, for example single nucleotide polymorphisms (SNPs).

In some embodiments, the method may comprise further characterizing the target polynucleotide. For example, the method may comprise sequencing all or part of the target polynucleotide.

In some embodiments, the method may comprise detecting the presence, absence or amount of a target polynucleotide using two or more guide polynucleotides and/or two or more polynucleotide-guided effector proteins which bind to different regions of the target polynucleotide, wherein binding of two different guide polynucleotide/polynucleotide-guided effector proteins to the target polynucleotide results in a detectable signal, for example a detectable current change, through a transmembrane pore if the target polynucleotide is present in the sample. The signal may be characteristic of an adaptor in one of the guide polynucleotides/polynucleotide-guided effector complexes, with the signal only or primarily being observed when that guide polynucleotide is "linked" to a second guide polynucleotide/polynucleotide-guided effector protein comprising a membrane anchor, and this "linkage" occurs when both guide polynucleotides/polynucleotide-guided effector proteins are bound to the target polynucleotide. In other words, the target polynucleotide serves to "link" the guide polynucleotides/polynucleotide-guided effector complex comprising an adaptor to the guide polynucleotides/polynucleotide-guided effector complex comprising a membrane anchor. In the embodiment wherein the polynucleotide-guided effector protein comprises a membrane anchor, attachment may be via the protein itself, for example by use of a strep-tag/flag-tag/his-tag.

In some embodiments, the method may comprise selectively characterizing, for example sequencing, target polynucleotides using a transmembrane pore by marking each target polynucleotide with a guide polynucleotide/polynucleotide-guided effector protein complex specific for the target polynucleotide such that the target polynucleotide can be selectively sequenced without needing to separate the target polynucleotide from other polynucleotides in the sample prior to contacting the sample with the transmembrane pore.

For example, the guide polynucleotide/polynucleotide-guided effector protein complex may be tagged with a membrane anchor so that only target polynucleotides are tethered to the membrane. Other polynucleotides in the sample may be washed away. Alternatively, a polynucleotide binding protein capable of moving along a polynucleotide may be bound to the end of the polynucleotides in the sample, for example using techniques known in the art, and the polynucleotide binding protein may be caused to move along the polynucleotides after complex formation, for example by adding a cofactor necessary for movement of the polynucleotide binding protein. In this embodiment, the bound guide polynucleotide/polynucleotide-guided effector protein complex stalls the polynucleotide binding protein on the target polynucleotide, whilst the polynucleotide binding protein is processed off the ends of non-target polynucleotides. Then, when the transmembrane potential is applied, the force of the potential and the contact with the pore displaces the bound guide polynucleotide/polynucleotide-guided effector protein complex from the target polynucleotides so that the target polynucleotide translocates through the pore. The non-target polynucleotides to which no polynucleotide binding protein is bound pass through the pore so rapidly that no signal is detected, or so that any signal obtained can easily be discriminated from signals resulting from the interaction of the target polynucleotide with the pore. The 3'-terminated strands of the polynucleotides in the sample, including both target and non-target polynucleotides, may be degraded, for example using an exonuclease. In this way the target polynucleotide can be selectively characterized, for example sequenced. The polynucleotide binding protein may be caused to move along the polynucleotides by adding a cofactor, such as ATP or another nucleoside for example and ysGTP.

Figure 27:
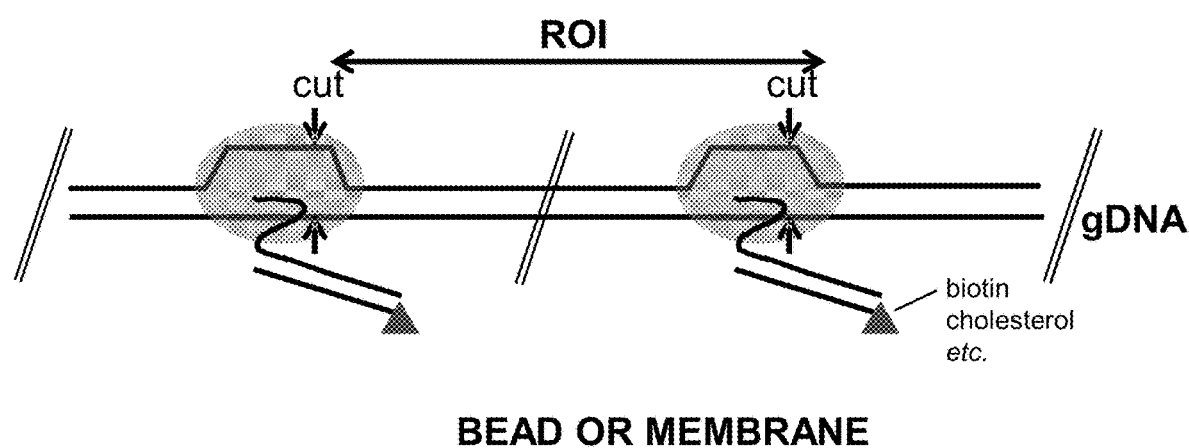
FIG. 27 shows how a pair of guide polynucleotides/polynucleotide-guided effector proteins can be used to obtain a polynucleotide fragment comprising a region of interest (ROI). The first guide polynucleotide/polynucleotide-guided effector protein could have its nuclease activity disabled such that it acts to stall a polynucleotide binding protein as shown in FIG. 11, enabling the region of interest to be characterised using a transmembrane pore.

In another embodiment, the polynucleotide-guided effector protein can be used to cut the polynucleotide at a selected point. This may be used to limit the information, such as sequence information, obtained by the method about a region of interest. For example, two polynucleotide-guided effector proteins with nuclease activity may be used to obtain a polynucleotide fragment of interest as shown in FIG. 27. As an alternative, a modified polynucleotide-guided effector protein having inactivated or disabled nuclease activity may be used to stall a polynucleotide binding protein as described above and a second polynucleotide-guided effector protein may be used to truncate the fragment being characterized. This embodiment is, for example, particularly useful in V(D)J repertoire analysis applications.

Further, in some embodiments, the guide polynucleotide/polynucleotide-guided effector protein complex tags or labels the target polynucleotide such that the effect of the guide polynucleotide/polynucleotide-guided effector protein complex on the current passing through the pore can be used to determine the presence or absence of, quantify or identify the target polynucleotide.

For example, the guide polynucleotide or polynucleotide-guided effector protein may be attached to an adaptor that may be used to identify a target polynucleotide tagged with a membrane anchor because the adaptor will only interact with the transmembrane pore when it is bound to the target polynucleotide tethered to the membrane. Unbound guide polynucleotides and polynucleotide-guided effector proteins may be washed away. Multiple guide polynucleotides, each selective for a different target polynucleotide and having a different adaptor may be added to the sample to detect and/or quantify different target polynucleotides on the basis of the different signals caused by the different adaptors interacting with the transmembrane pore.

Alternatively, the guide polynucleotide/polynucleotide-guided effector protein complex bound to the target polynucleotide may produce a detectable signal when the target polynucleotide passes through a transmembrane pore. Where the transmembrane pore is too small to allow the passage of the guide polynucleotide/polynucleotide-guided effector protein, for example a pore that allows the passage of a single stranded but not a double-stranded polynucleotide, the movement of the polynucleotide through the pore is blocked when the guide polynucleotide/polynucleotide-guided effector protein reaches the pore. This affects the current passing through the pore and allows the presence of the guide polynucleotide/polynucleotide-guided effector protein/target polynucleotide complex to be detected. For example, the guide polynucleotide/polynucleotide-guided effector protein complex may be stripped off the target polynucleotide by the force of the pore and applied potential (as the target polynucleotide is pulled through the pore by the applied potential the guide polynucleotide/polynucleotide-guided effector protein complex is brought into contact with the pore and the continued pull on the target polynucleotide forces the guide polynucleotide/polynucleotide-guided effector protein complex against the pore such that the guide polynucleotide/polynucleotide-guided effector protein complex is forced off (i.e. is caused to unbind from) the target polynucleotide), causing a detectable stutter in the current.

Two or more guide polynucleotide/polynucleotide-guided effector protein complexes binding to different parts of a target polynucleotide may be used in the method. When each of the bound polynucleotide/polynucleotide-guided effector protein complexes reaches the pore it will cause a stutter. Thus multiple guide polynucleotide/polynucleotide-guided effector protein complexes may be used to identify a target polynucleotide. For example, one or more guide polynucleotide may be designed to bind to the target polynucleotide only if a particular polymorphism is present in the target polynucleotide. The number of stutters observed as the polynucleotide passes through the pore, or the presence or absence of a particular stutter as the polynucleotide passes through the pore may indicate the presence or absence of the polymorphism.

When the transmembrane pore is sufficiently large to allow the passage of double stranded polynucleotides and bound guide polynucleotide/polynucleotide-guided effector protein complex, the passage of the double stranded polynucleotide/guide polynucleotide/polynucleotide-guided effector protein complex through the pore will produce a recognisable signal when the guide polynucleotide/polynucleotide-guided effector protein complex passes through the pore. Thus one or more guide polynucleotide/polynucleotide-guided effector protein complex may be used to identify a target polynucleotide. For example, a guide polynucleotide may be designed to bind only if a particular polymorphism is present in the target polynucleotide. The number of signals attributable to bound guide polynucleotide/polynucleotide-guided effector protein complexes observed as the target polynucleotide passes through the pore, or the presence or absence of a particular signal as the target polynucleotide passes through the pore may indicate the presence or absence of the polymorphism. Nanopores that allow the passage of double stranded polynucleotides and bound polynucleotides/polynucleotide-guided effector proteins include, for example, nanocapillaries. Hence, in this embodiment the pore may not be contained in a membrane. One or more of the guide polynucleotide, polynucleotide-guided effector protein and/or target polynucleotide are typically modified to enable the method to be carried out. Thus, the invention also provides modified guide polynucleotides, polynucleotide-guided effector proteins, guide polynucleotide/polynucleotide-guided effector protein complexes, and panels of such polynucleotide guides and effector molecules suitable for use in the invention.

The method may further comprise determining the amount of the target polypeptide or one or more characteristics of the target polynucleotide. The one or more characteristics are typically selected from (i) the length of the target polynucleotide, (ii) the identity of the target polynucleotide, (iii) the sequence of the target polynucleotide, (iv) the secondary structure of the target polynucleotide and (v) whether or not the target polynucleotide is modified.

Step (a) may further comprise contacting the sample with beads (e.g. microparticles) to which one or more components of the complex can bind. Alternatively, one or more of the components used in (a), e.g. the target polynucleotide, the guide polynucleotide or the polynucleotide-guided effector protein may be prebound to beads (e.g. microparticles).

The sample may be provided in an aqueous medium or alternatively the sample may be added to an aqueous medium containing the polynucleotide-guided effector protein and the guide polynucleotide. The aqueous medium will typically comprise ions to provide ion flow through the transmembrane pore upon application of a potential difference across the membrane. The aqueous medium will also typically comprise a buffer. The aqueous medium typically has a pH in the range of 6 to 9 and/or an ion concentration in the rage of from 100 to 200 mM salt, such as NaCl.

The bead is typically denser than the aqueous medium and sink through the medium to contact the membrane, thus effectively enhancing the concentration of the species attached to the anchor at the membrane surface.

In the method, the applied potential may be a voltage potential. Alternatively, the applied potential may be a chemical potential. An example of this is using a salt gradient across an amphiphilic layer. A salt gradient is disclosed, for example, in Holden et al., J Am Chem Soc. 2007 Jul. 11:129(27):8650-5.

In embodiments where displacement of the bound guide polynucleotide/polynucleotide-guided effector protein complex is not required, the guide polynucleotide and/or effector protein may be cross-linked to the target polynucleotide.

In the methods of the invention, the guide polynucleotide/polynucleotide-guided effector protein may be replaced by a probe that binds to a double-stranded polynucleotide. The probe may or may not be associated with an enzyme. For example, the probe may be a RecA-coated probe, a peptide nucleic acid (PNA), a bridged nucleic acid (BNA), a locked nucleic acid (LNA), gamma PNA, triplex DNA or a morpholino probe. The probe typically comprises a single stranded region complementary to a sequence in the target polynucleotide. The probe may comprise a double stranded region and/or secondary structures, such as loops, e.g. a hairpin loop, or a triplex. The probes typically has a length of from about 8 to about 50, about 10 to about 40, such as about 15 to about 30, preferably from about 18 to about 25, such as 19, 20, 21, 22, 23 or 24 nucleotides. The probe may have an anchor sequence capable of coupling to a membrane or an adaptor attached thereto. For example, the probe may be a guide polynucleotide/polynucleotide-guided effector protein complex, or a RecA coated probe. The probe may be a PNA, BNA, LNA, gamma PNA, triplex DNA or a morpholino probe. The probe may have a polynucleotide binding protein capable of moving along a polynucleotide attached thereto. The polynucleotide binding protein may be bound to a leader sequence comprised in the adaptor.

In the method, the guide polynucleotide/polynucleotide-guided effector protein may be replaced by a protein that binds to a polynucleotide having a specific nucleotide sequence. Proteins that bind to a polynucleotide having a specific nucleotide sequence include, for example, transcription activator-like effector nucleases and zinc finger nucleases. Such nucleases can be engineered to bind to particular sites within target polynucleotides.

In a particular embodiment, the method may be a method of detecting a target polynucleotide comprising a double stranded polynucleotide in a sample, the method comprising: (a) contacting the sample with a first probe and a second probe, wherein the first probe and the second probe form a complex with any target polynucleotide present in the sample, the first probe binds to a first sequence in the target double stranded polynucleotide and comprises an anchor capable of coupling to a membrane, and the second probe binds to a second sequence in the target double stranded polynucleotide and comprises an adaptor sequence; (b) contacting the sample with a transmembrane pore; (c) applying a potential to the transmembrane pore; and (d) monitoring for the presence or absence of an effect resulting from the interaction of the complex with the transmembrane pore to determine the presence or absence of the complex, thereby detecting the target double stranded polynucleotide in the sample. Any unbound probes may be washed away prior to step (c). Step (d) typically comprises monitoring for the interaction of the adaptor with the transmembrane pore. The first sequence and second sequence in the target polynucleotide are typically each a portion of the double stranded polynucleotide.

The second probe may further comprise a polynucleotide binding protein capable of moving along a polynucleotide. The adaptor in the second probe may comprise a leader sequence and the polynucleotide binding protein may be bound to the leader sequence, and/or the adaptor may comprise a barcode.

Step (a) of the method may comprise contacting the sample with two or more first probes, wherein the two or more probes bind to different sequences. Step (a) of the method may comprise contacting the sample and transmembrane pore with two or more second probes. Typically, the two or more second probes comprise different barcodes.

In methods using guide polynucleotides or probes binding to different sequences, those sequences may be present in different target polynucleotides, within the same target polynucleotide or may be alternative sequences, such as SNPs, that may be present in the target polynucleotide.

In one embodiment, the method uses multiple pairs, such as from 2 to 50, 3 to 40, 4 to 30, 5 to 25, 6 to 15 or 8 to 10 pairs, of first and second probes, wherein each pair binds to a different target polynucleotide. In an alternate embodiment, the method may use a single first probe and multiple second probes, which can be used to identify different or alternative sequences within a target polynucleotide.

The method may be used to detect one or more, such as 2, 3, 4, 5, 6, 7 8, 9, 10, 20, 30 or more, target polynucleotides in a complex background following enrichment of the target molecule. In one embodiment sequencing, e.g. nanopore sequencing, is used for the detection. Hence in this embodiment, the target DNA molecule may be identified primarily by its sequence.

The method may be carried out as a multiplex assay. The multiplex assay may utilize different barcodes. The barcodes may, for example, each have a distinct nucleotide sequence enabling the barcodes to be identified by a nanopore. In one embodiment a barcode sequence may be ligated to all polynucleotides in a sample, prior to contacting the sample with the guide polynucleotide and polynucleotide-guided binding protein. A second barcode can be added to a second sample, prior to contacting the sample with the guide polynucleotide and polynucleotide-guided binding protein. The first and second samples can be combined prior to or after addition of the guide polynucleotide and polynucleotide-guided binding protein, preferably after the guide polynucleotide and polynucleotide-guided binding protein have bound to the target polynucleotides. Where pooling of the samples occurs after the guide polynucleotide and polynucleotide-guided binding protein have bound to the target polynucleotides, purification steps (including stress, removal of non-target bound protein, and/or removal of non-target polynucleotides) may be carried out prior to or after pooling. Multiple sample, such as 2, 3, 4, 5, 6, 7 8, 9, 10, 20, 30 samples, can be labelled with barcodes and then combined in this way. In this embodiment all the samples can be sequenced simultaneously, e.g. using the same flowcell, and identified using their barcode adapter.

In another embodiment, barcodes and sequencing adapters may be added after the guide polynucleotide and polynucleotide-guided binding protein have bound to the target polynucleotides. For example, the barcodes and sequencing adaptors may be ligated on beads. The target-loaded, barcoded, adapted beads may be added to the sample after the guide polynucleotide and polynucleotide-guided binding protein have bound to the target polynucleotides and optionally after one or more purification staps (such as stress, removal of non-target bound protein, and/or removal of non-target polynucleotides) have been carried out.

The method may comprise removing any polynucleotide-guided effector protein and/or guide polynucleotide, e.g. guide polynucleotide/polynucleotide guided effector protein complex, that is not specifically bound to the target polynucleotide. The excess polynucleotide-guided effector protein and/or guide polynucleotide, e.g. guide polynucleotide/polynucleotide guided effector protein complex, present in the sample, which is not bound to target polynucleotide can produce background when monitoring the interaction of the target polynucleotide/guide polynucleotide/polynucleotide guided effector protein complex with the pore. Guide polynucleotide, polynucleotide-guided effector protein and/or polynucleotide-guided effector protein/guide polynucleotide complex that is not specifically bound to the target polynucleotide may be separated from the complex comprising the guide polynucleotide, polynucleotide-guided effector protein and target polynucleotide by binding the polynucleotides in the sample a surface, e.g. beads or a column. The target polynucleotides may also be separated from non-target polynucleotides in the sample by binding the guide polynucleotide, polynucleotide-guided effector protein and/or polynucleotide-guided effector protein/guide polynucleotide complex in the sample to a surface, e.g. beads or a column. The target polynucleotide(s) may, for example, be separated from the background by means of a 'pulldown' via a capture moiety on the guide polynucleotide/polynucleotide-guided effector protein complex.

The method may comprise selectively denaturing any polynucleotide-guided effector protein that is not specifically bound to the target polynucleotide prior to step (b). 'Off-target' effects of guide polynucleotide/polynucleotide-guided effector protein complex binding may be reduced by applying a thermal and/or chemical stress to the bound guide polynucleotide/polynucleotide-guided effector protein complex. Typically, in this embodiment, non-target bound polynucleotide-guided effector protein is selectively denatured by the heat stress or chemical stress applied. The applied heat or chemical treatment can be selected such that only free polynucleotide-guided effector protein (i.e. polynucleotide-guided effector protein that is not bound to polynucleotides in the sample, but which may be bound to guide polynucleotide) and non-target bound polynucleotide-guided effector protein (i.e. polynucleotide-guided effector protein that is bound non-specifically to polynucleotides in the sample, or "off target" polynucleotide-guided effector protein) is denatured. Target-bound polynucleotide-guided effector protein remains bound to the target polynucleotide during the heat stress or chemical stress. Any off-target polynucleotide-guided effector protein is released from its non-specific binding to the polynucleotides in the sample. In one embodiment, only polynucleotide-guided effector protein bound to a target sequence that is exactly complementary to the corresponding sequence in the guide polynucleotide remains bound to a polynucleotide during the stress.

Any suitable chemical stress can be used, such as urea (e.g. up to 6M, 5M or 4M), guanidinium hydrochloride, extreme pH (acidic or alkaline, such as below pH6, pH5 or pH4 or above pH8, pH9 or pH10) or high salt concentrations. Suitable conditions may readily be determined by the skilled person.

The chemical stress may be carried out for any time period that results in the selective disruption of non-specific binding of polynucleotide-guided effector protein to polynucleotides, without disrupting specific binding of polynucleotide-guided effector protein to target polynucleotide. The chemical stress may be carried out for from about 30 seconds to about 10 minutes, such as for about 1 minute, about 2 minutes, about 3 minutes, about 5 minutes, about 6 minutes, about 7 minutes, about 8 minutes or about 9 minutes.

The heat stress may be carried out at any suitable temperature. Typically the temperature is high enough to disrupt non-specific binding of polynucleotide-guided effector protein to polynucleotides, but is low enough that specific binding of polynucleotide-guided effector protein to target polynucleotide is not disrupted. For example, the sample may be heated to a temperature of from about 40° C. to about 65° C., about 45° C. to about 65° C., about 50° C. to about 60° C., such as about 55° C.

The heat stress may be carried out for any time period that results in the selective disruption of non-specific binding of polynucleotide-guided effector protein to polynucleotides, without disrupting specific binding of polynucleotide-guided effector protein to target polynucleotide. The heat stress may be carried out for from about 30 seconds to about 10 minutes, such as for about 1 minute, about 2 minutes, about 3 minutes, about 5 minutes, about 6 minutes, about 7 minutes, about 8 minutes or about 9 minutes.

A purification step may be used to remove excess, unbound polynucleotide-guided effector protein and/or guide polynucleotide. This may be achieved, for example, by adding polyethylene glycol (PEG) and sodium chloride to the sample and contacting the sample with paramagnetic beads coated with carboxyl groups such that the polynucleotides present in the sample bind to the beads. Suitable beads include commercially available SPRI beads and standard protocols known in the art may be used. In one embodiment, the target polynucleotide/guide polynucleotide/polynucleotide-guided effector protein complex may subsequently be separated from non-target polynucleotides using a surface, e.g. a different capture bead. Typically, here the guide polynucleotide/polynucleotide-guided effector protein may contain a binding moiety that is used to specifically bind the target polynucleotide/guide polynucleotide/polynucleotide-guided effector protein complex to the surface. Any non-bound polynucleotides may be washed away. The target polynucleotide/guide polynucleotide/polynucleotide-guided effector protein complex may be eluted from the surface by any suitable means, or the surface may be used to deliver the complex to a pore, e.g. where the surface is beads.

Figure 44:
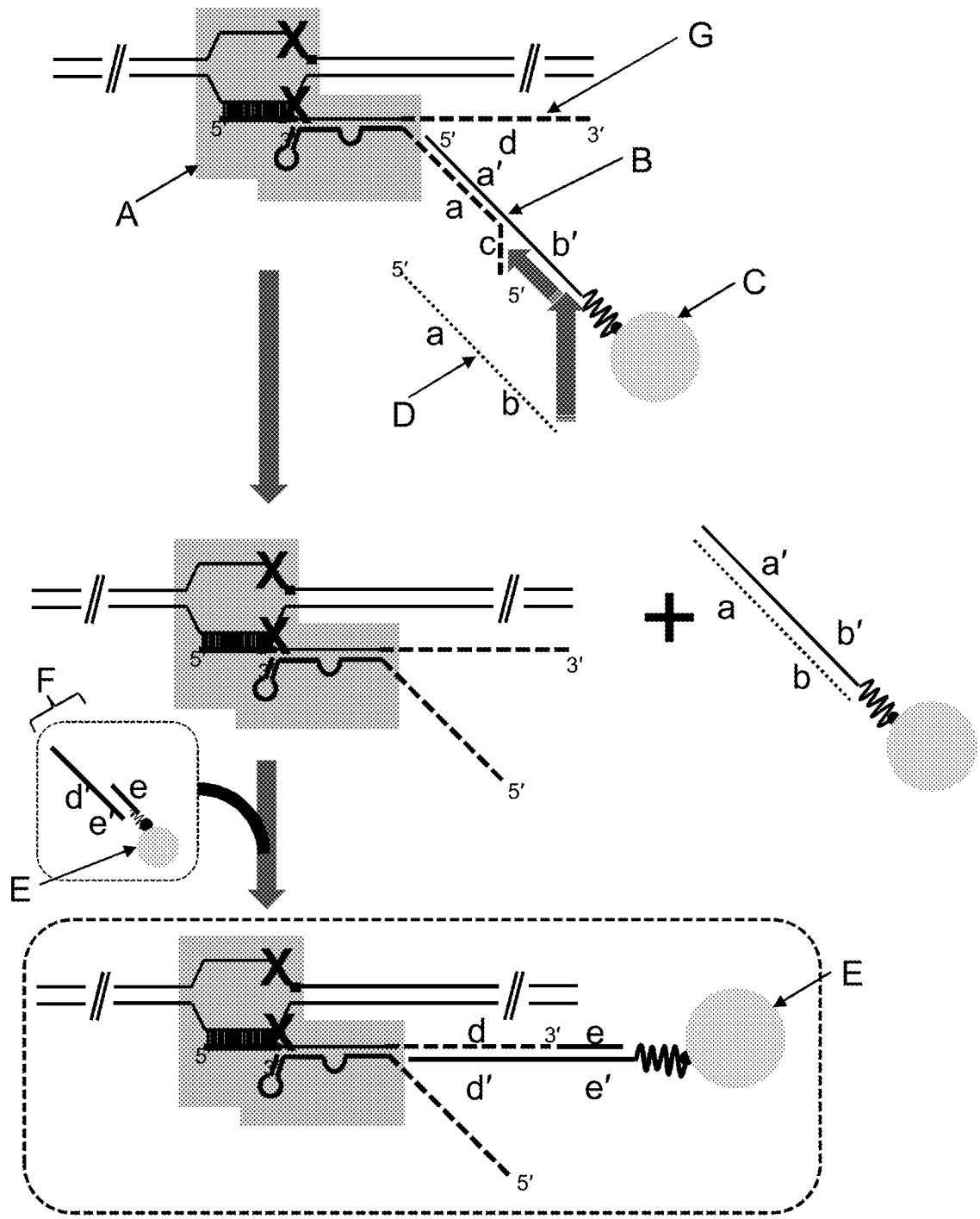
FIG. 44 shows an example of a sequential 'pull-down' and 'toehold elution' method that exploits two distinct oligonucleotide extensions, sequences [a–c] and d, from the tracrRNA and crRNA respectively of a dCas9-contacted target molecule A, and may be used to select for the presence of the tracrRNA and crRNA (or vice versa), sequentially. Oligonucleotide B, bearing sequence a'–b', partly complementary to tracrRNA extension a, is first bound to purification surface C; A is incubated with [B+C] and any non-target DNA washed away. Oligonucleotide D, bearing sequence [a+b], fully complementary to oligonucleotide B, when incubated with [A+B+C], will displace oligonucleotide B from the tracrRNA extension of A by a phenomenon known as 'toehold displacement', releasing A from [B+C]. A may either be adapted and delivered to a flowcell for nanopore sequencing or detection, as outlined in FIG. 41, or may then be bound to a second type of surface E, bearing a duplex oligonucleotide F with overhang d' that is complementary to the crRNA extension G (sequence d), to yield F. F may also be adapted and sequenced or detected as outlined in FIG. 41. Surfaces C and E may be a bead (whether in bulk or column format) or membrane.

'Off-target' effects may be minimised further by purification the target polynucleotide/guide polynucleotide/polynucleotide-guided effector protein complexes on a capture surface using a first binding moiety on the guide polynucleotide/polynucleotide-guided effector protein, e.g. on the guide polynucleotide, eluting the target polynucleotide/guide polynucleotide/polynucleotide-guided effector protein complexes and transferring the target polynucleotide/guide polynucleotide/polynucleotide-guided effector protein complexes to a second specific capture surface using a second binding moiety on the guide polynucleotide/polynucleotide-guided effector protein, e.g. on the guide polynucleotide. This can be achieved, for example, where the first binding moiety and the second binding moiety are both end extensions, or other single stranded polynucleotide sequences capable of binding to an oligonucleotide, on the guide polynucleotide. The first end extension on the guide polynucleotide has a sequence complementary to a first capture oligonucleotide on a first capture surface, e.g. a bead, and the second end extension on the guide polynucleotide has a sequence complementary to a second capture oligonucleotide on a second capture surface, e.g. a bead. One way of configuring this is depicted in FIG. 44. In FIG. 44, the crRNA comprises a 3' DNA extension used for capture of the target molecule on a bead, column or surface (sequence d of FIG. 44) and the tracrRNA comprises a 5' DNA extension (sequence a•c of FIG. 44). The release of the target from the first capture surface, e.g. a bead, may be effected by the phenomenon known as toehold displacement.

The target polynucleotide/guide polynucleotide/polynucleotide-guided effector protein complex is first separated from non-target polynucleotides by capture on beads bearing a first capture oligonucleotide complementary to the first end extension. Non-target polynucleotides are washed away. The target polynucleotide/guide polynucleotide/polynucleotide-guided effector protein complex may be eluted from the bead by toehold displacement, via the addition of a competitor oligonucleotide that competes for the binding to the bead with the first end extension on the guide polynucleotide. In this embodiment, the first capture oligonucleotide is longer than the first end extension and comprises a first sequence and a second sequence, wherein the first sequence is complementary to a sequence in the first end extension and the first and second sequences are both complementary to the sequence of the competitor oligonucleotide. Typically the first sequence has a length of from 5 to 40, such as 10 to 30 or 15 to 25 nucleotides, for example 20 nucleotides and the second sequence has a length of from 5 to 40, such as 10 to 30 or 15 to 25 nucleotides, for example 20 nucleotides. The competitor oligonucleotide may have a length of from 10 to 80, such as 20 to 60 or 30 to 50 nucleotides, for example 40 nucleotides. The first capture oligonucleotide may have a length of from 10 to 80, such as 20 to 60 or 30 to 50 nucleotides, for example 40 nucleotides. The capture oligonucleotide may have the same length as the competitor oligonucleotide, or the capture oligonucleotide may be longer or shorter than the competitor oligonucleotide, provided that capture oligonucleotide and competitor oligonucleotide have sequences that are complementary over both the first and second sequences. In this embodiment, the first end extension comprises an end portion, which is at the 5' end in a 5' end extension or at the 3' end in a 3' end extension, which has a sequence that is not complementary to a sequence in the first capture oligonucleotide, and a portion that has a sequence that is complementary to the first sequence in the first capture oligonucleotide. The end portion of the first end extension may typically have a length of from 2 to 10 nucleotides, such as 3, 4, 5 or 6 nucleotides. The portion of the first end extension that is complementary to the first capture oligonucleotide may typically have a length of from 5 to 40, such as 10 to 30 or 15 to 25 nucleotides, for example 20 nucleotides.

Following elution of the target polynucleotide/guide polynucleotide/polynucleotide-guided effector protein complex, the complex is bound to a second 'delivery' bead via second end extension on the guide polynucleotide. The second 'delivery' bead comprises a second capture oligonucleotide that is complementary to the second end extension. The second capture oligonucleotide may have a length of from 5 to 40, such as 10 to 30 or 15 to 25 nucleotides, for example 20 nucleotides or a length of from 10 to 80, such as 20 to 60 or 30 to 50 nucleotides, for example 40 nucleotides. The second end extension may have a length of from 5 to 40, such as 10 to 30 or 15 to 25 nucleotides, for example 20 nucleotides. The second capture oligonucleotide may have the same length as the second end extension, or the second capture oligonucleotide may be longer or shorter than the end extension, provided that second capture oligonucleotide and second end extension have sequences that are complementary over a length of from 5 to 40, such as 10 to 30 or 15 to 25 nucleotides, for example 20 nucleotides. The second end extension has a sequence that does hybridise to the first capture nucleotide, the first end extension or the competitor oligonucleotide. The second capture oligonucleotide also has a sequence that does hybridise to the first capture nucleotide, the first end extension or the competitor oligonucleotide.

Accordingly, where the guide polynucleotide comprises a first end extension and a second end extension, and the method may comprise prior to step (b):

(i) contacting the sample with a surface having bound thereto a first capture oligonucleotide comprising a sequence complementary to the first end extension, such that the guide polynucleotide/polynucleotide-guided effector protein/target polynucleotide complex is bound to the surface;

(ii) contacting the guide polynucleotide/polynucleotide-guided effector protein/target polynucleotide complex bound to the surface with a competitor oligonucleotide, such that the guide polynucleotide/polynucleotide-guided effector protein/target polynucleotide complex is released from the surface;

(iii) contacting the guide polynucleotide/polynucleotide-guided effector protein/target polynucleotide complex with beads having bound thereto a second capture oligonucleotide comprising a sequence complementary to the second end extension, such that the guide polynucleotide/polynucleotide-guided effector protein/target polynucleotide complex is bound to the beads; and optionally (iv) delivering the beads to the transmembrane pore.

In different embodiments of the invention, there may be: (i) no heat or chemical stress, purification to remove excess, unbound and/or non-target bound polynucleotide-guided effector protein or toehold purification; (ii) only heat or chemical stress; (iii) only purification to remove excess, unbound and/or non-target-bound polynucleotide-guided effector protein; (iv) only toehold purification; (v) heat or chemical stress and purification to remove excess, unbound and/or non-target-bound polynucleotide-guided effector protein; (vi) heat or chemical stress and toehold purification; (vii) purification to remove excess, unbound and/or non-target-bound polynucleotide-guided effector protein and toehold purification; or (viii) heat or chemical stress, purification to remove excess, unbound and/or non-target-bound polynucleotide-guided effector protein and toehold purification.

The beads to which the target polynucleotide/guide polynucleotide/polynucleotide-guided effector protein complex is bound may be used to deliver the complex to a pore. For example, the beads may be magnetic and the target polynucleotide bound to the beads may be drawn into the wells of a flowcell comprising the pore by the application of a magnetic field placed underneath the flowcell, or can be allowed to settle by gravity. Sequencing can be initiated by flowing tether, such as an oligonucleotide-cholesterol tether which hybridizes to the adaptor ends, over the beads, which tethers the beads to the membrane. Alternatively, the tether can be introduced into the membrane before the bead-target polynucleotide conjugate is added. For example, an oligonucleotide-cholesterol tether which hybridizes to the adaptor ends may be integrated into the membrane in the flowcell by flowing running buffer and the tether through the flowcell before the beads-target polynucleotide(s) are added. In this situation, when the beads-target polynucleotide(s) are added to the flowcell, they become tethered to the membrane when they encounter the oligonucleotide that is anchored in the membrane by the cholesterol.

In some embodiments, the target polynucleotides may be adapted for nanopore sequencing. For example, all of the polynucleotides in the sample may have sequencing adaptors added to one or both ends prior to step (a) of the method. The polynucleotides in the sample may be fragmented prior to addition of the sequencing adaptors. Alternatively, the target polynucleotides may have sequencing adaptors added to one or both ends after step (a).

In this embodiment, the sequencing adaptors may be added before or after separation of the target from non-target polynucleotides. The sequencing adaptor typically comprises a polynucleotide binding protein that is capable of moving along the polynucleotide. When the sequencing adaptor is added after step (a) the polynucleotide-guided effector protein/guide polynucleotide complex remains bound to the target polynucleotide. After binding of the adaptor, in some embodiments, generally where the target polynucleotide has been separated from non-target polynucleotides prior to adaptor addition, the polynucleotide-guided effector protein/guide polynucleotide complex may be displaced by the polynucleotide binding protein that is capable of moving along the polynucleotide loaded on the adaptor. Displacement of the polynucleotide-guided effector protein/guide polynucleotide complex by the polynucleotide binding protein that is capable of moving along the polynucleotide can be controlled by the addition of one or more cofactor needed for the polynucleotide binding protein to moving along a polynucleotide.

The target polynucleotide may be adapted for nanopore sequencing by ligation of adaptors to either or both of its free ends whilst bound to the surface, e.g. column or beads, via the guide polynucleotide/polynucleotide-guided effector protein. The ends may be dA-tailed to facilitate adaptor binding.

Target Polynucleotide

The polynucleotide can be a nucleic acid, such as deoxyribonucleic acid (DNA) or ribonucleic acid (RNA). The polynucleotide can comprise one strand of RNA hybridised to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains. The PNA backbone is composed of repeating N-(2-aminoethyl)-glycine units linked by peptide bonds. The GNA backbone is composed of repeating glycol units linked by phosphodiester bonds. The TNA backbone is composed of repeating threose sugars linked together by phosphodiester bonds. LNA is formed from ribonucleotides as discussed above having an extra bridge connecting the 2' oxygen and 4' carbon in the ribose moiety.

The polynucleotide is preferably DNA, RNA or a DNA or RNA hybrid, most preferably DNA. The target polynucleotide comprises a double stranded region to which the guide-polynucleotide and polynucleotide-guided effector protein bind. The target polypeptide may be double stranded. The target polypeptide may comprise single stranded regions and regions with other structures, such as hairpin loops, triplexes and/or quadruplexes. The DNA/RNA hybrid may comprise DNA and RNA on the same strand. Preferably, the DNA/RNA hybrid comprises one DNA strand hybridized to a RNA strand.

The target polynucleotide can be any length. For example, the polynucleotides can be at least 10, at least 50, at least 100, at least 150, at least 200, at least 250, at least 300, at least 400 or at least 500 nucleotides or nucleotide pairs in length. The target polynucleotide can be 1000 or more nucleotides or nucleotide pairs, 5000 or more nucleotides or nucleotide pairs in length or 100000 or more nucleotides or nucleotide pairs in length. The target polynucleotide may be an oligonucleotide. Oligonucleotides are short nucleotide polymers which typically have 50 or fewer nucleotides, such 40 or fewer, 30 or fewer, 20 or fewer, 10 or fewer or 5 or fewer nucleotides. The target oligonucleotide is preferably from about 15 to about 30 nucleotides in length, such as from about 20 to about 25 nucleotides in length. For example, the oligonucleotide can be about 15, about 16, about 17, about 18, about 19, about 20, about 21, about 22, about 23, about 24, about 25, about 26, about 27, about 28, about 29 or about 30 nucleotides in length.

The target polynucleotide may be a polynucleotide associated with a disease and/or a microorganism.

The method may detect multiple, such as from 2 to 50, 3 to 40, 4 to 30, 5 to 25, 6 to 15 or 8 to 10, target polynucleotides. The target polynucleotides may be a group of polynucleotides. For instance, the group may be associated with a particular phenotype. The group may be associated with a particular type of cell. For instance, the group may be indicative of a bacterial cell. The group may be indicative of a virus, a fungus, a bacterium—a *mycobacterium* or a parasite.

The target polynucleotides may be a group of two or more polynucleotides that are, or comprise, biomarkers associated with a particular disease or condition. The biomarkers can be used to diagnose or prognose the disease or condition. Suitable panels of biomarkers are known in the art, for example as described in Edwards, A. V. G. et al. (2008) *Mol. Cell. Proteomics* 7, p 1824-1837; Jacquet, S. et al. (2009), *Mol. Cell. Proteomics* 8, p 2687-2699; Anderson N. L. et al (2010) *Clin. Chem.* 56, 177-185. The disease or condition is preferably cancer, heart disease, including coronary heart disease and cardiovascular disease, or an infectious disease, such as tuberculosis or sepsis.

The target oligonucleotide or polynucleotide is preferably a microRNA (or miRNA) or a small interfereing RNA (siRNA). The group of two or more target polynucleotides may be a group of two or more miRNAs. Suitable miRNAs for use in the invention are well known in the art. For instance, suitable miRNAs are stored on publically available databases (Jiang Q., Wang Y., Hao Y., Juan L., Teng M., Zhang X., Li M., Wang G., Liu Y., (2009) miR2Disease: a manually curated database for microRNA deregulation in human disease. Nucleic Acids Res.).

Polynucleotide-Guided Effector Protein

The polynucleotide-guided effector protein may be any protein that binds to a guide-polynucleotide and which binds to the polynucleotide to which the guide polynucleotide binds. The polynucleotide-guided effector protein may, by way of non-limiting example, comprise a target polynucleotide recognition domain and at least one nuclease domain. The recognition domain binds a guide polynucleotide RNA) and a target polynucleotide (e.g. DNA). The polynucleotide-guided effector protein may contain one nuclease domain that cuts one or both strands of a double stranded polynucleotide, or may contain two nuclease domains wherein a first nuclease domain is positioned for cleavage of one strand of the target polynucleotide and a second nuclease domains is positioned for cleavage of the complementary strand of the target polynucleotide. The nuclease domains may be active or inactive. For example, the nuclease domain or one or both of the two nuclease domains may be inactivated by mutation.

The guide polynucleotide may be a guide RNA, a guide DNA, or a guide containing both DNA and RNA. The guide polynucleotide is preferably a guide RNA. Therefore the polynucleotide-guided effector protein is preferably a RNA-guided effector protein.

The RNA-guided effector protein may be any protein that binds to the guide-RNA. The RNA-guided effector protein typically binds to a region of guide RNA that is not the region of guide RNA which binds to the target polynucleotide. For example, where the guide RNA comprises crRNA and tracrRNA, the RNA-guided effector protein typically binds to the tracrRNA and the crRNA typically binds to the target polynucleotide. The RNA-guided effector protein preferably also binds to a target polynucleotide. The region of the guide RNA that binds to the target polynucleotide may also bind to the RNA-guided effector protein. The RNA-guided effector protein typically binds to a double stranded region of the target polynucleotide. The region of the target polynucleotide to which the RNA-guided effector protein binds is typically located close to the sequence to which the guide RNA hybridizes. The guide RNA and RNA-guided effector protein typically form a complex, which complex then binds to the target polynucleotide at a site determined by the sequence of the guide RNA.

The RNA-guided effector protein may bind upstream or downstream of the sequence to which the guide RNA binds. For example, the RNA-guided effector protein may bind to a protospacer adjacent motif (PAM) in DNA located next to the sequence to which the guide RNA binds. A PAM is a short (less than 10, typically a 2 to 6 base pair) sequence, such as 5'-NGG-3' (wherein N is any base), 5'-NGA-3', 5'-YG-3' (wherein Y is a pyrimidine), 5'TTN-3' or 5'-YTN-3'. Different RNA-guided effector proteins bind to different PAMs. RNA-guided effector proteins may bind to a target polynucleotide which does not comprise a PAM, in particular, where the target is RNA or a DNA/RNA hybrid.

The RNA-guided effector protein is typically a nuclease, such as a RNA-guided endonuclease. The RNA-guided effector protein is typically a Cas protein. The RNA-guided effector protein may be Cas, Csn2, Cpf1, Csf1, Cmr5, Csm2, Csy1, Cse1 or C2c2. The Cas protein may Cas3, Cas 4, Cas8a, Cas8b, Cas8c, Cas9, Cas10 or Cas10d. Preferably, the Cas protein is Cas9. Cas, Csn2, Cpf1, Csf1, Cmr5, Csm2, Csy1 or Cse1 is preferably used where the target polynucleotide comprises a double stranded DNA region. C2c2 is preferably used where the target polynucleotide comprises a double stranded RNA region.

A DNA-guided effector protein, such as proteins from the RecA family may be used to target DNA. Examples of proteins from the RecA family that may be used are RecA, RadA and Rad51. The nuclease activity of the RNA-guided endonuclease may be disabled. One or more of the catalytic nuclease sites of the RNA-guided endonuclease may be inactivated. For example, where the RNA-guided endonuclease comprises two catalytic nuclease sites, one or both of the catalytic sites may be inactivated. Typically one of the catalytic sites will cut one strand of the polynucleotide to which it specifically binds and the other catalytic site will cut the opposite strand of the polynucleotide. Therefore, the RNA-guided endonuclease may cut both strands, one strand or neither strand of a double stranded region of a target polynucleotide.

The polynucleotide-guided effector protein may, by way of non-limiting example, be Cas9. Cas9 has a bi-lobed, multi-domain protein structure comprising target recognition and nuclease lobes. The recognition lobe binds guide RNA and DNA. The nuclease lobe contains the HNH and RuvC nuclease domains which are positioned for cleavage of the complementary and non-complementary strands of the target DNA. The structure of Cas 9 is detailed in Nishimasu, H., et al., (2014) Crystal Structure of Cas9 in Complex with Guide RNA and Target DNA. Cell 156, 935-949, The relevant PDB reference for Cas9 is 5F9R (Crystal structure of catalytically-active *Streptococcus pyogenes* CRISPR-Cas9 in complex with single-guided RNA and double-stranded DNA primed for target DNA cleavage).

The Cas9 may be an 'enhanced specificity' Cas9 that shows reduced off-target binding compared to wild-type Cas9. An example of such an 'enhanced specificity' Cas9 is *S. pyogenes* Cas9 D10A/H840A/K848A/K1003A/R1060A. ONLP12296 is the amino acid sequence of *S. pyogenes* Cas9 D10A/H840A/K848A/K1003A/R1060A having a C-terminal Twin-Strep-tag with TEV-cleavable linker.

Catalytic sites of a RNA-guided endonuclease may be inactivated by mutation. The mutation may be a substitution, insertion or deletion mutation. For example, one or more, such as 2, 3, 4, 5, or 6 amino acids may be substituted or inserted into or deleted from the catalytic site. The mutation is preferably a substitution insertion, more preferably substitution if a single amino acid at the catalytic site. The skilled person will be readily able to identify the catalytic sites of a RNA-guided endonuclease and mutations that inactivate them. For example, where the RNA-guided endonuclease is Cas9, one catalytic site may be inactivated by a mutation at D10 and the other by a mutation at H640.

An inactivated ('dead') polynucleotide-guided effector protein that does not cut the target polynucleotide and so shows no directionality bias. An active ('live') polynucleotide-guided effector protein that cuts the target polynucleotide may remain bound to just one of the two ends of the cut site and so may show some directionality bias.

The polynucleotide-guided effector protein typically remains bound to the target polynucleotide for a prolonged period. The polynucleotide-guided effector protein preferably remains bound to the target polynucleotide for from at least about 1 to at least about 10, such as about 2 to about 8 hours or about 4 to about 6 hours in the absence of a transmembrane pore and a transmembrane potential. The polynucleotide-guided effector protein may be displaced from the target polynucleotide by the interaction with a transmembrane pore under an applied potential.

In one embodiment, the polynucleotide-guided effector protein may hold the target polypeptide in the transmembrane pore for a short period whilst it is being displaced. This results in a detectable signal, that may be seen as a stutter in a trace of the current passing through the pore, but can also be detected by other means, for example by optical measurements or tunneling.

The polynucleotide-guided effector protein may have the ability to move along and slow the polynucleotide. For example, the RNA-guided effector protein may act as a sliding molecular brake. In this embodiment, the RNA-guided effector protein may be used as a motor protein to control the movement of the target polynucleotide, or the guide RNA, through the transmembrane pore.

Guide Polynucleotide

The guide polynucleotide comprises a sequence that is capable of hybridising to a target polynucleotide and is also capable of binding to a polynucleotide-guided effector protein. The guide polynucleotide may have any structure that enables it to bind to the target polynucleotide and to a polynucleotide-guided effector protein.

The guide polynucleotide typically hybridizes to a sequence of about 20 nucleotides in the target polynucleotide. The sequence to which the guide RNA binds may be from about 10 to about 40, such as about 15 to about 30, preferably from about 18 to about 25, such as 19, 20, 21, 22, 23 or 24 nucleotides. The guide polynucleotide is typically complementary to one strand of a double stranded region of the target polynucleotide. The guide polynucleotide comprises a nucleotide sequence of from about 10 to about 40, such as about 15 to about 30, preferably from about 18 to about 25, such as 19, 20, 21, 22, 23 or 24, nucleotides that is complementary to the sequence of, or to a sequence in, the target polynucleotide. The degree of complementarity is preferably exact.

The guide RNA may be complementary to a region in the target polynucleotide that is 5' to a PAM. This is preferred where the target polynucleotide comprises DNA, particularly where the RNA effector protein is Cas9 or Cpf1. The guide RNA may be complementary to a region in the target polynucleotide that is flanked by a guanine. This is preferred where the target polynucleotide comprises RNA, particularly where the RNA effector protein is C2c2.

The guide RNA may have any structure that enables it to bind to the target polynucleotide and to a RNA-guided effector protein. The guide RNA may comprise a crRNA that binds to a sequence in the target polynucleotide and a tracrRNA. The tracrRNA typically binds to the RNA-guided effector protein. Typical structures of guide RNAs are known in the art. For example, the crRNA is typically a single stranded RNA and the tracrRNA typically has a double stranded region of which one strand is attached to the 3' end of the crRNA and a part that forms a hairpin loop at the 3' end of the strand that is not attached to the crRNA. The crRNA and tracrRNA may be transcribed in vitro as a single piece sgRNA.

The guide RNA may comprise other components, such as additional RNA bases or DNA bases or other nucleobases. The RNA and DNA bases in the guide RNA may be natural bases or modified bases. A guide DNA may be used in place of a guide RNA, and a DNA-guided effector protein used instead of a RNA-guided effector protein. The used of a guide DNA and a DNA-guided effector protein may be preferred where the target polynucleotide is RNA.

The guide polynucleotide may be specifically modified for use in a method of the invention. The invention provides a guide polynucleotide, particularly a guide RNA, that comprises (i) an adaptor sequence, optionally including a leader sequence or (ii) an anchor capable of coupling to a membrane.

The guide polynucleotide of the invention may be any of the guide polynucleotides discussed herein to which (i) an adaptor and/or (ii) an anchor capable of coupling to a membrane is attached.

The (i) the anchor or (ii) the adaptor may be present at the 5' end of the tracrRNA, the 3' end of the tracrRNA, the 3' end of the crRNA, or internally, for example, wherein the tracrRNA and crRNA are comprised in a sgRNA. See FIGS. 2-4 and 25, for examples. The (i) the anchor or (ii) the adaptor may be added to the 5' end of the crRNA, e.g. via a chemical group or spacer. The (i) the anchor or (ii) the adaptor may be added to the guide polynucleotide via a chemical group or spacer. The (i) the anchor or (ii) the adaptor may be attached to the 5' or 3' end of the guide polynucleotide, such as to the 5' or 3' end of a tracrRNA or the 5' or 3' end of a crRNA by any suitable means, e.g.

ligation, via a chemical group, e.g. thiols, click groups, biotin etc., or via a DNA, RNA, PNA, BNA, LNA, TNA spacer. Where the spacer is a polynucleotide, the spacer may have a length of from 1 to 30, such as from 2 to 20, 3 to 15, 4 to 10, such as 5, 6, 7 8 or 9, nucleotides.

The anchor may be attached to an oligonucleotide (anchor oligonucleotide) that is complementary to an end extension, or an internal loop sequence, in the guide polynucleotide. The 5' end of the tracrRNA, the 3' end of the tracrRNA, the 3' end of the crRNA or the 5' end of the crRNA may have an end extension having a length of, for example, from 5 to 40, such as 10 to 30 or 15 to 25 nucleotides, for example 20 nucleotides. The anchor oligonucleotide may have the same length as the end extension, or the anchor oligonucleotide may be longer or shorter than the end extension, provided that anchor oligonucleotide and end extension have sequences that are complementary over a length of from 5 to 40, such as 10 to 30 or 15 to 25 nucleotides, for example 20 nucleotides. The anchor oligonucleotide may have a length of, for example, from 5 to 40, such as 10 to 30 or 15 to 25 nucleotides, for example 20 nucleotides. The internal loop sequence may have any of the lengths specified above.

The guide polynucleotide may be synthetically modified. Both the 5' and 3' ends of crRNA and tracrRNA can be modified. See Lee et al., (2017) Synthetically modified guide RNA and donor DNA are a versatile platform for CRISPR-Cas9 engineering. eLIFE; 6:e25312, incorporated by reference herein. Synthetic modification may comprise incorporation of modified or artificial bases into guide RNA (or guide DNA), including DNA, RNA, PNA, LNA, BNA, DNA spacers, RNA spacers and abasic spacers e.g., Sp18. Alternatively modification may comprise modification with chemical moieties that are structurally unrelated to nucleotide bases such as planar hydrophobic molecules, chemical tags, fluorescent molecules, aptamer sequences, amines, azides, alkynes, thiols, click groups, biotins.

The guide polynucleotide of the invention may have a polynucleotide binding protein capable of moving along a polynucleotide attached thereto. The polynucleotide binding protein may be bound close to one end of a strand of the guide RNA, typically close to the 5' end. The end to which the polynucleotide binding protein is bound is typically modified by the addition of an adaptor, preferably an adaptor comprising a leader sequence. Where the guide RNA comprises a leader sequence the polynucleotide binding protein is typically bound to the leader sequence.

Where the guide RNA comprises a crRNA, the polynucleotide binding protein may be positioned such that it is capable of moving along the crRNA. Such a guide RNA is useful in a method in which the crRNA translocates through the transmembrane pore in order to detect the presence or absence of the complex.

The guide polynucleotide may be specifically adapted to enable capture of the target polynucleotide on a surface, such as a bead or column. This allows target polynucleotides to which a guide polynucleotide/polynucleotide-guided effector protein complex is bound to be captured and separated from non-target polynucleotides in a sample, which can then be washed away. The guide polynucleotide may comprise an end extension at the 3' or 5' end, which has a sequence that is complementary to the sequence of a capture oligonucleotide that is bound to a surface, such as to a bead or column. For example, the capture oligonucleotide may be bound to the surface by an affinity tag. Any suitable affinity tag may be used. One example is a biotin-streptavidin affinity tag. The capture oligonucleotide may have a length of from 5 to 40, such as 10 to 30 or 15 to 25 nucleotides, for example 20 nucleotides or a length of from 10 to 80, such as 20 to 60 or 30 to 50 nucleotides, for example 40 nucleotides. The end extension may have a length of from 5 to 40, such as 10 to 30 or 15 to 25 nucleotides, for example 20 nucleotides. The capture oligonucleotide may have the same length as the end extension, or the capture oligonucleotide may be longer or shorter than the end extension, provided that capture oligonucleotide and end extension have sequences that are complementary over a length of from 5 to 40, such as 10 to 30 or 15 to 25 nucleotides, for example 20 nucleotides.

The guide polynucleotide may comprise a first binding moiety and a second binding moiety. The first binding moiety and the second binding moiety may both be end extensions, or other single stranded polynucleotide sequences capable of binding to an oligonucleotide, on the guide polynucleotide. The first end extension on the guide polynucleotide may have a sequence complementary to a first capture oligonucleotide on a first capture surface, e.g. a bead, and the second end extension on the guide polynucleotide may have a sequence complementary to a second capture oligonucleotide on a second capture surface, e.g. a bead. One way of configuring this is depicted in FIG. 44. In FIG. 44, the crRNA comprises a 3' DNA extension used for capture of the target molecule on a bead, column or surface (sequence d of FIG. 44) and the tracrRNA comprises a 5' DNA extension (sequence a•c of FIG. 44). In one embodiment, the first end extension comprises an end portion, which is at the 5' end in a 5' end extension or at the 3' end in a 3' end extension, which has a sequence that is not complementary to a sequence in the first capture oligonucleotide, and a portion that has a sequence that is complementary to the first sequence in the first capture oligonucleotide. The end portion of the first end extension may typically have a length of from 2 to 10 nucleotides, such as 3, 4, 5 or 6 nucleotides. The portion of the first end extension that is complementary to the first capture oligonucleotide may typically have a length of from 5 to 40, such as 10 to 30 or 15 to 25 nucleotides, for example 20 nucleotides.

The second end extension has a sequence that does hybridise to the first capture nucleotide, the first end extension or the competitor oligonucleotide. The second capture oligonucleotide also has a sequence that does hybridise to the first capture nucleotide, the first end extension or the competitor oligonucleotide. The end extension may be attached to the 5' or 3' end of the guide polynucleotide, such as to the 5' or 3' end of a tracrRNA or the 5' or 3' end of a crRNA. The end extension may be attached to the guide polynucleotide by any suitable means. The end extension may, for example, be may be added via a chemical group or spacer, e.g. ligation, via a chemical group, e.g. thiols, click groups, biotin etc., or via a DNA, RNA, PNA, BNA, LNA, TNA spacer. Where the spacer is a polynucleotide, the spacer may have a length of from 1 to 30, such as from 2 to 20, 3 to 15, 4 to 10, such as 5, 6, 7 8 or 9, nucleotides. The end extension may be present at the 5' end of the tracrRNA, the 3' end of the tracrRNA, the 3' end of the crRNA, the 5' end of the crRNA or may be substituted by a sequence added internally to the guide RNA, for example, wherein the tracrRNA and crRNA are comprised in a sgRNA. See FIGS. 41 and 44 for examples. Where an internal sequence is used to perform the function described herein for the end extension, it is typically present in a loop structure within the guide polynucleotide, or is otherwise accessible for hybridization to the capture oligonucleotide.

The present invention also provides a guide polynucleotide of the invention bound to a polynucleotide-guided effector protein as defined herein.

Also provided by the invention are a panel of guide polynucleotides, preferably guide RNAs of the invention, and a panel of guide polynucleotide/polynucleotide-guided effector protein complexes, preferably guide RNA/RNA-guided effector protein complexes, of the invention. The panel of guide polynucleotides or guide polynucleotide/polynucleotide-guided effector protein complexes may be comprised in a kit.

A panel of the invention may comprise guide polynucleotides of the invention and a panel of guide polynucleotides and polynucleotide-guided effector proteins that may be used together in a method of the invention. The guide polynucleotides and polynucleotide-guided effector proteins may be present in guide polynucleotide/polynucleotide-guided effector protein complexes.

A panel may comprise a first guide polynucleotide or guide polynucleotide/polynucleotide-guided effector protein complex that comprises an anchor capable of coupling to a membrane and a second guide polynucleotide or guide polynucleotide/polynucleotide-guided effector protein complex that comprises an adaptor, wherein the first guide polynucleotide or guide polynucleotide/polynucleotide-guided effector protein complex and the second guide polynucleotide or guide polynucleotide/polynucleotide-guided effector protein complex bind to different sequences in the same target polynucleotide. The panel may comprise multiple, such as from 2 to 50, 3 to 40, 4 to 30, 5 to 25, 6 to 15 or 8 to 10, such first and second guide polynucleotide or guide polynucleotide/polynucleotide-guided effector protein complexes. Where the panel comprises multiple first and second guide polynucleotides or guide polynucleotide/polynucleotide-guided effector protein complexes, each second guide polynucleotide or guide polynucleotide/polynucleotide-guided effector protein complex typically comprises a different adaptor. This enables the panel to distinguish between different target polynucleotides present in the sample.

A panel may comprise a first guide polynucleotide or guide polynucleotide/polynucleotide-guided effector protein complex that binds to a first sequence of the target polynucleotide and a second guide polynucleotide or guide polynucleotide/polynucleotide-guided effector protein complex that binds to a second sequence of the target polynucleotide. Further guide polynucleotides or guide polynucleotide/polynucleotide-guided effector protein complexes binding to further sequences of the same target polynucleotide may be included in the panel. The first, second and further guide polynucleotides or guide polynucleotide/polynucleotide-guided effector protein complexes may comprise the same or different adaptors, or may comprise no adaptors. The first guide polynucleotides or guide polynucleotide/polynucleotide-guided effector protein complexes may comprise a membrane anchor and the second and/or further guide polynucleotides or guide polynucleotide/polynucleotide-guided effector protein complexes may comprise the same adaptors or, preferably, different adaptors.

No adaptors need to be included in the guide polynucleotides or guide polynucleotide/polynucleotide-guided effector protein complexes where the panel is for use in a method that detects the effect of the guide polynucleotide/polynucleotide-guided effector protein complex bound to the target polynucleotide interacting with the transmembrane pore by detecting a signal, e.g. change current passing through the pore, caused by the guide polynucleotide/polynucleotide-guided effector protein complex stalling passage of the target polynucleotide through the pore or by the bound guide polynucleotide/polynucleotide-guided effector protein complex passing through the pore.

The first, second and/or further guide polynucleotides or guide polynucleotide/polynucleotide-guided effector protein complexes may bind to the same part of the target polynucleotide, but may each be specific for a different polymorphism present in that part of the target polynucleotide. In this embodiment, each guide polynucleotide or guide polynucleotide/polynucleotide-guided effector protein complex that is specific for a different polymorphism may comprise a different adaptor and/or leader sequence. The method of the invention can distinguish between different adaptors and/or between different leader sequences, and hence can be used to identify a polymorphism.

A panel may comprise a first guide polynucleotide or guide polynucleotide/polynucleotide-guided effector protein complex that binds to a first target polynucleotide and a second guide polynucleotide or guide polynucleotide/polynucleotide-guided effector protein complex that binds to a second target polynucleotide. Further guide polynucleotides or guide polynucleotide/polynucleotide-guided effector protein complexes binding to further target polynucleotides may be included in the panel. For example, the first, second and/or further guide polynucleotides or guide polynucleotide/polynucleotide-guided effector proteins may each be coupled to an anchor and/or other binding moieties. Such a panel would be useful for delivering multiple polynucleotides of interest in a sample to a transmembrane pore for further characterization, for example by sequencing. For example, such a panel would select for multiple polynucleotides of interest and tether them to the membrane comprising a transmembrane pore so that other polynucleotides in the sample may be washed away prior to the application of a membrane potential.

Sample

The sample may be any suitable sample. The sample is typically one that is known to contain or is suspected of containing at least one of the target polynucleotides. The method can be used to select target polynucleotides for delivery to the transmembrane pore. Other components of the sample may be washed away, for example, they may be flushed out of a cell comprising the transmembrane pore. Such other components include one or more of the following: proteins, which may be folded or unfolded, peptides, carbohydrates, polymers, such as non-target polynucleotides, and cell debris.

The sample may be a biological sample. The invention may be carried out in vitro on a sample obtained from or extracted from any organism or microorganism. The organism or microorganism is typically archaean, prokaryotic or eukaryotic and typically belongs to one the five kingdoms: plantae, animalia, fungi, monera and protista. The invention may be carried out in vitro on a sample obtained from or extracted from any virus.

The sample is preferably a fluid sample. The sample typically comprises a body fluid. The body fluid may be obtained from a human or animal. The human or animal may have, be suspected of having or be at risk of a disease. The sample may be urine, lymph, saliva, mucus, seminal fluid or amniotic fluid, but is preferably whole blood, plasma or serum. Typically, the sample is human in origin, but alternatively it may be from another mammal such as from commercially farmed animals such as horses, cattle, sheep or pigs or may alternatively be pets such as cats or dogs.

Alternatively a sample of plant origin is typically obtained from a commercial crop, such as a cereal, legume, fruit or vegetable, for example wheat, barley, oats, canola, maize, soya, rice, bananas, apples, tomatoes, potatoes, grapes, tobacco, beans, lentils, sugar cane, cocoa, cotton, tea or coffee.

The sample may be a non-biological sample. The non-biological sample is preferably a fluid sample. Examples of non-biological samples include surgical fluids, water such as drinking water, sea water or river water, and reagents for laboratory tests.

The sample may be processed prior to being assayed, for example by centrifugation or by passage through a membrane that filters out unwanted molecules or cells, such as red blood cells. The sample may be measured immediately upon being taken. The sample may also be typically stored prior to assay, preferably below $-70°$ C.

The sample may comprise genomic DNA. The genomic DNA may be fragmented or step (a) of the method may further comprise fragmenting the genomic DNA. The DNA may be fragmented by any suitable method. For example, methods of fragmenting DNA are known in the art. Such methods may use a transposase, such as a MuA transposase.

The sample may comprise T-cell DNA.

The sample may comprise non-target polynucleotides. In one embodiment, the target polynucleotide and the non-target polynucleotides may be derived from the same gene or genome.

Monitoring Interaction of Complex with Pore

The method comprises monitoring for the presence or absence of an effect resulting from the interaction of the complex formed by the guide polynucleotide, the polynucleotide-guided effector protein and the target polynucleotide with the transmembrane pore to determine the presence or absence of the complex. The effect is indicative of the complex formed by the guide polynucleotide, the polynucleotide-guided effector protein and the target polynucleotide interacting with the transmembrane pore. The effect may be caused by the translocation through the pore of an adaptor attached to one of the components of the complex, the target polynucleotide or the guide polynucleotide. The effect is indicative of the translocation through the pore of an adaptor attached to one of the components of the complex, the target polynucleotide or the guide polynucleotide.

The effect may be monitored using an electrical measurement and/or an optical measurement. In this case, the effect is a measured change or measured changes in an electrical or optical quantity.

The electrical measurement may be a current measurement, an impedance measurement, a tunnelling measurement or a field effect transistor (FET) measurement.

The effect may be a change in ion flow through the transmembrane pore resulting in a change in current, resistance or a change in an optical property. The effect may be electron tunneling across the transmembrane pore. The effect may be a change in potential due to the interaction of the complex with the transmembrane pore wherein the effect is monitored using localized potential sensor in a FET measurement.

Adaptor

The adaptor may comprise at least one single stranded polynucleotide or non-polynucleotide region. Single stranded polynucleotides are useful because they can pass through the pore and can easily be divided into at least two different regions that affect the current flowing through the pore in different ways. For instance, different regions of a polynucleotide having different sequences typically affect the current flowing through the pore in different ways. The at least two different regions preferably correspond to at least two stretches of different nucleotides. For instance, the single stranded polynucleotide region may comprise a stretch of adenine nucleotides and a stretch of abasic nucleotides. Each stretch will affect the current flowing through the pore in a different way.

Alternatively, the at least two stretches of different nucleotides are different polynucleotide barcodes. Polynucleotide barcodes are well-known in the art (Kozarewa, I. et al., (2011), *Methods Mol. Biol.* 733, p 279-298). A barcode is a specific sequence of polynucleotide that affects the current flowing through the pore in a specific and known manner.

The adaptor may comprise a double-stranded polynucleotide that cannot pass through the pore. The presence of such a double stranded region may delay the adaptor from moving through the pore as one of the strands in the region is stripped from the probe under the influence of the potential. Such a delay produces a detectable signal, for example a change in the current flowing through the pore. The length of the double stranded region may be varied between different polynucleotide adpators such that the length of the delay can be used to identify the adaptor interacting with the pore. Typical lengths of the double stranded region are from about 4 to about 50 base pairs, such as from 5, 6, 7, 8, 9 or 10 to 20, 30 or 40 base pairs, or any integer between 4 and 50.

Including one or more double stranded polynucleotide regions in the adaptor increases the number of possible signals that can be obtained from a population of adaptors in the panel of guide polynucleotides and hence increases the number of target polynucleotides that can be assayed using the method of the invention.

A double stranded polynucleotide region may, for example, be used to hold a specific region of the adaptor, such as a barcode that is indicative of the guide polynucleotide, in the barrel or channel of the pore so that it may be read in accordance with the invention.

The adaptor may comprise a nucleotide sequence. A nucleotide typically contains a nucleobase, a sugar and at least one phosphate group. The nucleobase is typically heterocyclic. Nucleobases include, but are not limited to, purines and pyrimidines and more specifically adenine, guanine, thymine, uracil and cytosine. The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide.

Nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), 5-methylcytidine monophosphate, 5-methylcytidine diphosphate, 5-methylcytidine triphosphate, 5-hydroxymethylcytidine monophosphate, 5-hydroxymethylcytidine diphosphate, 5-hydroxymethylcytidine triphosphate, cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP), 5-methyl-2'-deoxycytidine monophosphate, 5-methyl-2'-deoxycytidine diphosphate, 5-methyl-2'-deoxycytidine triphosphate, 5-hydroxymethyl-2'-deoxycytidine monophosphate, 5-hydroxymethyl-2'-deoxycytidine diphosphate and 5-hydroxymethyl-2'-deoxycytidine triphosphate. The nucleotides in the adaptor are preferably selected from AMP, TMP, GMP, UMP, dAMP, dTMP, dGMP or dCMP. The nucleotides may be abasic (e.g. lack a nucleobase). The nucleotides may contain additional modifications. In particular, suitable modified nucleotides include, but are not limited to, 2'amino pyrimidines (such as 2'-amino cytidine and 2'-amino uridine), 2'-hyrdroxyl purines (such as, 2'-fluoro pyrimidines (such as 2'-fluorocytidine and 2'fluoro uridine), hydroxyl pyrimidines (such as 5'-α-P-borano uridine), 2'-O-methyl nucleotides (such as 2'-O-methyl adenosine, 2'-O-methyl guanosine, 2'-O-methyl cytidine and 2'-O-methyl uridine), 4'-thio pyrimidines (such as 4'-thio uridine and 4'-thio cytidine) and nucleotides have modifications of the nucleobase (such as 5-pentynyl-2'-deoxy uridine, 5-(3-aminopropyl)-uridine and 1,6-diaminohexyl-N-5-carbamoylmethyl uridine).

The adaptor may comprise one or more different nucleotide species. For instance, T k-mers (e.g. k-mers in which the central nucleotide is thymine-based, such as TTA, GTC, GTG and CTA) typically have the lowest current states. Modified versions of T nucleotides may be introduced into the modified polynucleotide to reduce the current states further and thereby increase the total current range seen when the adaptor moves through the pore.

G k-mers (e.g. k-mers in which the central nucleotide is guanine-based, such as TGA, GGC, TGT and CGA) tend to be strongly influenced by other nucleotides in the k-mer and so modifying the G nucleotides in the modified polynucleotide may help them to have more independent current positions.

Including three copies of the same nucleotide species instead of three different species may facilitate characterisation because it is then only necessary to map, for example, 3-nucleotide k-mers in the modified polynucleotide. However, such modifications do reduce the information provided by the adaptor.

Including one or more nucleotide species with abasic nucleotides in the adaptor results in characteristic current spikes. This allows the clear highlighting of the positions of the one or more nucleotide species in the adaptor.

The nucleotide species in the adaptor may comprise a chemical atom or group such as a propynyl group, a thio group, an oxo group, a methyl group, a hydroxymethyl group, a formyl group, a carboxy group, a carbonyl group, a benzyl group, a propargyl group or a propargylamine group. The chemical group or atom may be or may comprise a fluorescent molecule, biotin, digoxigenin, DNP (dinitrophenol), a photo-labile group, an alkyne, DBCO, azide, free amino group, a redox dye, a mercury atom or a selenium atom.

The adaptor may comprise a nucleotide species comprising a halogen atom. The halogen atom may be attached to any position on the different nucleotide species, such as the nucleobase and/or the sugar. The halogen atom is preferably fluorine (F), chlorine (Cl), bromine (Br) or iodine (I). The halogen atom is most preferably F or I.

The adaptor may comprise a sequence capable of forming a quadruplex. A quadruplex is a three dimensional structure formed from four sequence strands. The quadruplex is incapable of translocating or moving through the narrowest part of the pore. The quadruplex is wider than the narrowest part of the pore. For example, the narrowest part of wild-type α-HL pore is 1.3 nm is diameter. The narrowest part of α-HL-NN pore is 1.5 nm in diameter. If either of these pores is used in the invention, the quadruplex preferably has a width of greater than 1.3 nm, such as greater than 1.5 nm, such as greater than 2 nm, greater than 3 nm or greater than 5 nm. A person skilled in the art will be able to design a suitably sized quadruplex for the pore being used. The quadruplex-forming sequence is capable of translocating or moving through the narrowest part of the pore when it is not formed into a quadruplex. The quadruplex-forming sequence is preferably a polynucleotide. It may be any of the polynucleotides discussed herein.

The quadruplex may be any type of quadruplex. The quadruplex may be an intermolecular quadruplex, such as a bimolecular quadruplex or a tetramolecular quadruplex. The quadruplex-forming sequence is preferably capable of forming an intramolecular quadruplex.

The quadruplex-forming sequence is preferably capable of forming G-quadruplexes (also known as G-tetrads or G4-DNA). These are polynucleotide sequences that are rich in guanine and are capable of forming a four-stranded structure. Four guanine bases can associate through Hoogsteen hydrogen bonding to form a square planar structure called a guanine tetrad, and two or more guanine tetrads can stack on top of each other to form a G-quadruplex. The quadruplex structure is further stabilized by the presence of a cation, especially potassium, which sits in a central channel between each pair of tetrads. Forming G-quadruplexes is well known in the art (Marathias and Bolton, *Nucleic Acids Research*, 2000; 28(9): 1969-1977; Kankia and Marky, *J. Am. Chem. Soc.* 2001, 123, 10799-10804; and Marusic et al., *Nucleic Acids Research*, 2012, 1-11).

The quadruplex-forming sequence more preferably comprises the sequence Ga followed by Nb followed by Gc followed by Nd followed by Ge followed by Nf followed by Gg, wherein G is a nucleotide comprising guanine, wherein a, c, e and g are independently selected from 1, 2, 3, 4 and 5, wherein N is any nucleotide and wherein b, d and f are from 2 to 50. The values of a, c, e and g may be identical. G is preferably guanosine monophosphate (GMP), cyclic guanosine monophosphate (cGMP), deoxyguanosine monophosphate (dGMP), dideoxyguanosine monophosphate, N2-methyl-GMP, N2-methyl-cGMP, N2-methyl-dGMP, N2-methyl-dideoxyguanosine monophosphate, N2-methyl-06-methyl-GMP, N2-methyl-06-methyl-cGMP, N2-methyl-06-methyl-dGMP, N2-methyl-06-methyl-dideoxyguanosine monophosphate, 2'-O-methyl-GMP, 2'-O-methyl-cGMP, 2'-O-methyl-dGMP, 2'-O-methyl-dideoxyguanosine monophosphate, 6-thio-GMP, 6-thio-cGMP, 6-thio-dGMP, 6-thio-dideoxyguanosine monophosphate, 7-methyl-GMP, 7-methyl-cGMP, 7-methyl-dGMP, 7-methyl-dideoxyguanosine monophosphate, 7-deaza-GMP, 7-deaza-cGMP, 7-deaza-dGMP, 7-deaza-dideoxyguanosine monophosphate, 8-oxo-GMP, 8-oxo-cGMP, 8-oxo-dGMP or 8-oxo-dideoxyguanosine monophosphate.

Suitable quadruplex-forming sequences are disclosed in WO 2014/072703.

Since the quadruplex is incapable of translocating through the narrowest part of the pore, it acts like a brake and holds another, typically single stranded, region of the adaptor or guide polynucleotide in the narrowest part of the pore. The adaptor region then results in a distinctive current which identifies the guide polynucleotide and hence the target polynucleotide in the complex. After a short while, the quadruplex will typically destabilise under the influence of the applied potential and unfold. The braking action of the quadruplex is therefore typically temporary. The unfolded quadruplex-forming sequence typically translocates or moves through the pore under the influence of the applied potential.

Coupling

The complex comprising a guide polynucleotide, a polynucleotide-guided effector protein and a target polynucleotide may be coupled to the membrane using an anchor. One or more anchors may be used to couple the complex to the membrane. Typically the one or more anchors are present on the same component of the complex, such as on the target polynucleotide, the guide polynucleotide or the polynucleotide-guided effector protein. Alternatively the one or more anchors may be present on different components such as on the guide polynucleotide and the polynucleotide-guided effector protein.

If the membrane is an amphiphilic layer, such as a triblock copolymer membrane, the one or more anchors preferably comprise a polypeptide anchor and/or a hydrophobic anchor that can be inserted into the membrane. The hydrophobic anchor is preferably a lipid, fatty acid, sterol, carbon nanotube, polypeptide, protein or amino acid, for example cholesterol, palmitate or tocopherol. In preferred embodiments, the one or more anchors are not the pore.

The components of the membrane, such as the amphiphilic molecules, copolymer or lipids, may be chemically-modified or functionalised to form the one or more anchors. Examples of suitable chemical modifications and suitable ways of functionalising the components of the membrane are discussed in more detail below. Any proportion of the membrane components may be functionalised, for example at least 0.01%, at least 0.1%, at least 1%, at least 10%, at least 25%, at least 50% or 100%.

The one or more anchors preferably comprise a linker. The one or more anchors may comprise one or more, such as 2, 3, 4 or more, linkers. One linker may be used to couple both a guide polynucleotide and a polynucleotide-guided effector protein to the membrane.

Preferred linkers include, but are not limited to, polymers, such as polynucleotides, polyethylene glycols (PEGs), polysaccharides and polypeptides. These linkers may be linear, branched or circular. For instance, the linker may be a circular polynucleotide. The target polynucleotide or the guide polynucleotide may hybridise to a complementary sequence on the circular polynucleotide linker.

The one or more anchors or one or more linkers may comprise a component that can be cut or broken down, such as a restriction site or a photolabile group.

Functionalised linkers and the ways in which they can couple molecules are known in the art. For instance, linkers functionalised with maleimide groups will react with and attach to cysteine residues in proteins.

Cross-linkage of polynucleotides can be avoided using a "lock and key" arrangement. Only one end of each linker may react together to form a longer linker and the other ends of the linker each react with the polynucleotide or membrane respectively. Such linkers are described in WO 2010/086602.

The use of a linker is preferred in the sequencing methods of the invention. If a polynucleotide is permanently coupled directly to the membrane in the sense that it does not uncouple when interacting with the pore, then some sequence data will be lost as the sequencing run cannot continue to the end of the polynucleotide due to the distance between the membrane and the pore. If a linker is used, then the polynucleotide can be processed to completion.

The coupling may be permanent or stable. In other words, the coupling may be such that the complex remains coupled to the membrane when interacting with the pore.

The coupling may be transient. In other words, the coupling may be such that the complex may decouple from the membrane when interacting with the pore. For complex detection and polynucleotide sequencing, the transient nature of the coupling is preferred. If a permanent or stable linker is attached directly to either the 5' or 3' end of a polynucleotide and the linker is shorter than the distance between the membrane and the channel of the transmembrane pore, then some sequence data will be lost as the sequencing run cannot continue to the end of the polynucleotide. If the coupling is transient, then when the coupled end randomly becomes free of the membrane, then the polynucleotide can be processed to completion. Chemical groups that form permanent/stable or transient links are discussed in more detail below. The complex may be transiently coupled to an amphiphilic layer or triblock copolymer membrane using cholesterol or a fatty acyl chain. Any fatty acyl chain having a length of from 6 to 30 carbon atom, such as hexadecanoic acid, may be used.

In preferred embodiments, anchor couples the complex to an amphiphilic layer such as a triblock copolymer membrane or lipid bilayer. Coupling of nucleic acids to synthetic lipid bilayers has been carried out previously with various different tethering strategies. These are summarised in Table 1 below.

TABLE 1

| Anchor comprising | Type of coupling | Reference |
|---|---|---|
| Thiol | Stable | Yoshina-Ishii, C. and S. G. Boxer (2003). "Arrays of mobile tethered vesicles on supported lipid bilayers." *J Am Chem Soc* 125(13): 3696-7. |
| Biotin | Stable | Nikolov, V., R. Lipowsky, et al. (2007). "Behavior of giant vesicles with anchored DNA molecules." *Biophys J* 92(12): 4356-68 |
| Cholesterol | Transient | Pfeiffer, I. and F. Hook (2004). "Bivalent cholesterol-based coupling of oligo-nucletides to lipid membrane assemblies." *J Am Chem Soc* 126(33): 10224-5 |
| Surfactant (e.g. Lipid, Palmitate, etc) | Stable | van Lengerich, B., R. J. Rawle, et al. "Covalent attachment of lipid vesicles to a fluid-supported bilayer allows observation of DNA-mediated vesicle interactions." *Langmuir* 26(11): 8666-72 |

Synthetic polynucleotides and/or linkers may be functionalised using a modified phosphoramidite in the synthesis reaction, which is easily compatible for the direct addition of suitable anchoring groups, such as cholesterol, tocopherol, palmitate, thiol, lipid and biotin groups. These different attachment chemistries give a suite of options for attachment to polynucleotides. Each different modification group couples the polynucleotide in a slightly different way and coupling is not always permanent so giving different dwell times for the polynucleotide to the membrane.

Coupling of polynucleotides to a linker or to a functionalised membrane can also be achieved by a number of other means provided that a complementary reactive group or an anchoring group can be added to the polynucleotide. The addition of reactive groups to either end of a polynucleotide has been reported previously. A thiol group can be added to the 5' of ssDNA or dsDNA using T4 polynucleotide kinase and ATPγS (Grant, G. P. and P. Z. Qin (2007). "A facile method for attaching nitroxide spin labels at the 5' terminus of nucleic acids." *Nucleic Acids Res* 35(10): e77). An azide group can be added to the 5'-phosphate of ssDNA or dsDNA using T4 polynucleotide kinase and γ-[2-Azidoethyl]-ATP or γ-[6-Azidohexyl]-ATP. Using thiol or Click chemistry a tether, containing either a thiol, iodoacetamide OPSS or maleimide group (reactive to thiols) or a DIBO (dibenzocyclooxtyne) or alkyne group (reactive to azides), can be covalently attached to the polynucleotide. A more diverse selection of chemical groups, such as biotin, thiols and fluorophores, can be added using terminal transferase to incorporate modified oligonucleotides to the 3' of ssDNA (Kumar, A., P. Tchen, et al. (1988). "Nonradioactive labeling of synthetic oligonucleotide probes with terminal deoxynucleotidyl transferase." *Anal Biochem* 169(2): 376-82). Streptavidin/biotin and/or streptavidin/desthiobiotin coupling may be used for any other polynucleotide. It may also be possible that anchors may be directly added to polynucleotides using terminal transferase with suitably modified nucleotides (e.g. cholesterol or palmitate).

The one or more anchors may couple the complex to the membrane via hybridisation. The hybridisation may be between the one or more anchors and the target polynucleotide or guide polynucleotide, within the one or more anchors or between the one or more anchors and the membrane. Hybridisation in the one or more anchors allows coupling in a transient manner as discussed above. For instance, a linker may comprise two or more polynucleotides, such as 3, 4 or 5 polynucleotides, hybridised together. The one or more anchors may hybridise to the target or guide polynucleotide. The one or more anchors may hybridise directly to the target or guide polynucleotide, directly to a Y adaptor and/or leader sequence attached to the polynucleotide or directly to a hairpin loop adaptor attached to the polynucleotide. Alternatively, the one or more anchors may be hybridised to one or more, such as 2 or 3, intermediate polynucleotides (or "splints") which are hybridised to the polynucleotide, to a Y adaptor and/or leader sequence attached to the polynucleotide or to a hairpin loop adaptor attached to the polynucleotide.

The one or more anchors may comprise a single stranded or double stranded polynucleotide. One part of the anchor may be ligated to a single stranded or double stranded polynucleotide analyte. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." *Proc Natl Acad Sci USA* 89(20): 9823-5). Alternatively, either a single stranded or double stranded polynucleotide can be ligated to a double stranded polynucleotide and then the two strands separated by thermal or chemical denaturation. To a double stranded polynucleotide, it is possible to add either a piece of single stranded polynucleotide to one or both of the ends of the duplex, or a double stranded polynucleotide to one or both ends. For addition of single stranded polynucleotides to the double stranded polynucleotide, this can be achieved using T4 RNA ligase I as for ligation to other regions of single stranded polynucleotides. For addition of double stranded polynucleotides to a double stranded polynucleotide then ligation can be "blunt-ended", with complementary 3' dA/dT tails on the polynucleotide and added polynucleotide respectively (as is routinely done for many sample preparation applications to prevent concatemer or dimer formation) or using "sticky-ends" generated by restriction digestion of the polynucleotide and ligation of compatible adapters. Then, when the duplex is melted, each single strand will have either a 5' or 3' modification if a single stranded polynucleotide was used for ligation or a modification at the 5' end, the 3' end or both if a double stranded polynucleotide was used for ligation.

If the polynucleotide is a synthetic strand, the one or more anchors can be incorporated during the chemical synthesis of the polynucleotide. For instance, the polynucleotide can be synthesised using a primer having a reactive group attached to it.

Adenylated polynucleotides are intermediates in ligation reactions, where an adenosine-monophosphate is attached to the 5'-phosphate of the polynucleotide. Various kits are available for generation of this intermediate, such as the 5' DNA Adenylation Kit from NEB. By substituting ATP in the reaction for a modified nucleotide triphosphate, then addition of reactive groups (such as thiols, amines, biotin, azides, etc) to the 5' of a polynucleotide can be possible. It may also be possible that anchors could be directly added to polynucleotides using a 5' DNA adenylation kit with suitably modified nucleotides (e.g. cholesterol or palmitate).

A common technique for the amplification of sections of genomic DNA is using polymerase chain reaction (PCR). Here, using two synthetic oligonucleotide primers, a number of copies of the same section of DNA can be generated, where for each copy the 5' of each strand in the duplex will be a synthetic polynucleotide. Single or multiple nucleotides can be added to 3' end of single or double stranded DNA by employing a polymerase. Examples of polymerases which could be used include, but are not limited to, Terminal Transferase, Klenow and *E. coli* Poly(A) polymerase). By substituting ATP in the reaction for a modified nucleotide triphosphate then anchors, such as a cholesterol, thiol, amine, azide, biotin or lipid, can be incorporated into double stranded polynucleotides. Therefore, each copy of the amplified polynucleotide will contain an anchor.

Ideally, the polynucleotide is coupled to the membrane without having to functionalise the polynucleotide. This can be achieved by coupling the one or more anchors, such as a polynucleotide binding protein or a chemical group, to the membrane and allowing the one or more anchors to interact with the polynucleotide or by functionalizing the membrane. The one or more anchors may be coupled to the membrane by any of the methods described herein. In particular, the one or more anchors may comprise one or more linkers, such as maleimide functionalised linkers. In this embodiment, the polynucleotide is typically RNA, DNA, PNA, TNA or LNA and may be double or single stranded. This embodiment is particularly suited to genomic DNA polynucleotides.

The one or more anchors can comprise any group that couples to, binds to or interacts with single or double stranded polynucleotides, specific nucleotide sequences within the polynucleotide or patterns of modified nucleotides within the polynucleotide, or any other ligand that is present on the polynucleotide.

Suitable binding proteins for use in anchors include, but are not limited to, *E. coli* single stranded binding protein, P5 single stranded binding protein, T4 gp32 single stranded binding protein, the TOPO V dsDNA binding region, human histone proteins, *E. coli* HU DNA binding protein and other archaeal, prokaryotic or eukaryotic single stranded or double stranded polynucleotide (or nucleic acid) binding proteins, including those listed below.

The specific nucleotide sequences could be sequences recognised by transcription factors, ribosomes, endonucleases, topoisomerases or replication initiation factors. The patterns of modified nucleotides could be patterns of methylation or damage.

The one or more anchors can comprise any group which couples to, binds to, intercalates with or interacts with a polynucleotide. The group may intercalate or interact with the polynucleotide via electrostatic, hydrogen bonding or Van der Waals interactions. Such groups include a lysine monomer, poly-lysine (which will interact with ssDNA or dsDNA), ethidium bromide (which will intercalate with dsDNA), universal bases or universal nucleotides (which can hybridise with any polynucleotide) and osmium complexes (which can react to methylated bases). A polynucleotide may therefore be coupled to the membrane using one or more universal nucleotides attached to the membrane. Each universal nucleotide may be coupled to the membrane using one or more linkers. The universal nucleotide preferably comprises one of the following nucleobases: hypoxanthine, 4-nitroindole, 5-nitroindole, 6-nitroindole, formylindole, 3-nitropyrrole, nitroimidazole, 4-nitropyrazole, 4-nitrobenzimidazole, 5-nitroindazole, 4-aminobenzimidazole or phenyl (C6-aromatic ring). The universal nucleotide more preferably comprises one of the following nucleosides: 2'-deoxyinosine, inosine, 7-deaza-2'-deoxyinosine, 7-deaza-inosine, 2-aza-deoxyinosine, 2-aza-inosine, 2-0'-methyl-inosine, 4-nitroindole 2'-deoxyribonucleoside, 4-nitroindole ribonucleoside, 5-nitroindole 2'-deoxyribonucleoside, 5-nitroindole ribonucleoside, 6-nitroindole 2'-deoxyribonucleoside, 6-nitroindole ribonucleoside, 3-nitropyrrole 2'-deoxyribonucleoside, 3-nitropyrrole ribonucleoside, an acyclic sugar analogue of hypoxanthine, nitroimidazole 2'-deoxyribonucleoside, nitroimidazole ribonucleoside, 4-nitropyrazole 2'-deoxyribonucleoside, 4-nitropyrazole ribonucleoside, 4-nitrobenzimidazole 2'-deoxyribonucleoside, 4-nitrobenzimidazole ribonucleoside, 5-nitroindazole 2'-deoxyribonucleoside, 5-nitroindazole ribonucleoside, 4-aminobenzimidazole 2'-deoxyribonucleoside, 4-aminobenzimidazole ribonucleoside, phenyl C-ribonucleoside, phenyl C-2'-deoxyribosyl nucleoside, 2'-deoxynebularine, 2'-deoxyisoguanosine, K-T-deoxyribose, P-2'-deoxyribose and pyrrolidine. The universal nucleotide more preferably comprises 2'-deoxyinosine. The universal nucleotide is more preferably IMP or dIMP. The universal nucleotide is most preferably dPMP (2'-Deoxy-P-nucleoside monophosphate) or dKMP (N6-methoxy-2, 6-diaminopurine monophosphate).

The one or more anchors may couple to (or bind to) the polynucleotide via Hoogsteen hydrogen bonds (where two nucleobases are held together by hydrogen bonds) or reversed Hoogsteen hydrogen bonds (where one nucleobase is rotated through 180° with respect to the other nucleobase). For instance, the one or more anchors may comprise one or more nucleotides, one or more oligonucleotides or one or more polynucleotides which form Hoogsteen hydrogen bonds or reversed Hoogsteen hydrogen bonds with the polynucleotide. These types of hydrogen bonds allow a third polynucleotide strand to wind around a double stranded helix and form a triplex. The one or more anchors may couple to (or bind to) a double stranded polynucleotide by forming a triplex with the double stranded duplex.

In this embodiment at least 1%, at least 10%, at least 25%, at least 50% or 100% of the membrane components may be functionalised.

Where the one or more anchors comprise a protein, they may be able to anchor directly into the membrane without further functionalisation, for example if it already has an external hydrophobic region which is compatible with the membrane. Examples of such proteins include, but are not limited to, transmembrane proteins, intramembrane proteins and membrane proteins. Alternatively the protein may be expressed with a genetically fused hydrophobic region which is compatible with the membrane. Such hydrophobic protein regions are known in the art.

The one or more anchors are preferably mixed with the polynucleotide before delivery to the membrane, but the one or more anchors may be contacted with the membrane and subsequently contacted with the polynucleotide.

In another aspect the polynucleotide may be functionalised, using methods described above, so that it can be recognised by a specific binding group. Specifically the polynucleotide may be functionalised with a ligand such as biotin (for binding to streptavidin), amylose (for binding to maltose binding protein or a fusion protein), Ni-NTA (for binding to poly-histidine or poly-histidine tagged proteins) or peptides (such as an antigen).

According to a preferred embodiment, the one or more anchors may be used to couple a polynucleotide to the membrane when the polynucleotide is attached to a leader sequence which preferentially threads into the pore. Preferably, the polynucleotide is attached (such as ligated) to a leader sequence which preferentially threads into the pore. Such a leader sequence may comprise a homopolymeric polynucleotide or an abasic region. The leader sequence is typically designed to hybridise to the one or more anchors either directly or via one or more intermediate polynucleotides (or splints). In such instances, the one or more anchors typically comprise a polynucleotide sequence which is complementary to a sequence in the leader sequence or a sequence in the one or more intermediate polynucleotides (or splints). In such instances, the one or more splints typically comprise a polynucleotide sequence which is complementary to a sequence in the leader sequence.

Any of the methods discussed above for coupling polynucleotides to membranes, such as amphiphilic layers, can of course be applied to other polynucleotide and membrane combinations. In some embodiments, an amino acid, peptide, polypeptide or protein is coupled to an amphiphilic layer, such as a triblock copolymer layer or lipid bilayer. Various methodologies for the chemical attachment of such polynucleotides are available. An example of a molecule used in chemical attachment is EDC (1-ethyl-3-[3-dimethylaminopropyl]carbodiimide hydrochloride). Reactive groups can also be added to the 5' of polynucleotides using commercially available kits (Thermo Pierce, Part No. 22980). Suitable methods include, but are not limited to, transient affinity attachment using histidine residues and Ni-NTA, as well as more robust covalent attachment by reactive cysteines, lysines or non natural amino acids.

Leader Sequence

The leader sequence typically comprises a polymer. The polymer is preferably negatively charged. The polymer is preferably a polynucleotide, such as DNA or RNA, a modified polynucleotide (such as abasic DNA), PNA, LNA, polyethylene glycol (PEG) or a polypeptide. The leader preferably comprises a polynucleotide and more preferably comprises a single stranded polynucleotide. The single stranded leader sequence most preferably comprises a single strand of DNA, such as a poly dT section. The leader sequence preferably comprises the one or more spacers.

The leader sequence can be any length, but is typically 10 to 150 nucleotides in length, such as from 20 to 150 nucleotides in length. The length of the leader typically depends on the transmembrane pore used in the method.

The leader sequence preferentially threads into the transmembrane pore and thereby facilitates the movement of polynucleotide through the pore. The leader sequence can also be used to link the polynucleotide to the one or more anchors as discussed herein.

Sequencing Adaptors—Y Adaptors

Y-adaptors for use in nanopore sequencing are known in the art. A Y adaptor typically comprises (a) a double stranded region and (b) a single stranded region or a region that is not complementary at the other end. A Y adaptor may be described as having an overhang if it comprises a single stranded region. The presence of a non-complementary region in the Y adaptor gives the adaptor its Y shape since the two strands typically do not hybridise to each other unlike the double stranded portion. The Y adaptor may comprise one or more anchors.

The Y adaptor preferably comprises a leader sequence which preferentially threads into the pore.

The Y adaptor and/or the hairpin loop may be ligated to the polynucleotide using any method known in the art. One or both of the adaptors may be ligated using a ligase, such as T4 DNA ligase, E. coli DNA ligase, Taq DNA ligase, Tma DNA ligase and 9° N DNA ligase. Alternatively, the adaptors may be added to the polynucleotide using the methods discussed below.

In a preferred embodiment, the method comprises modifying the double stranded polynucleotides in the sample so that they comprise the Y adaptor at one end and the hairpin loop at the other end. Any manner of modification can be used. The method preferably comprises modifying the double stranded target polynucleotide.

The double stranded polynucleotide may be provided with adaptors, such as Y adaptors and hairpin loops, or anchors by contacting the polynucleotide with a MuA transposase and a population of double stranded MuA substrates. The transposase fragments the double stranded polynucleotide and ligates MuA substrates to one or both ends of the fragments. This produces a plurality of modified double stranded polynucleotides comprising an adaptor or anchor. The modified double stranded polynucleotides may then be investigated using the method of the invention.

These MuA based methods are disclosed in WO 2015/022544 and WO 2016/059363. They are also discussed in detail in WO2015/150786.

A double stranded polynucleotide may be provided with a Y adaptor at one end and a hairpin loop at the other end. For example, a proportion of the MuA substrates in the population may be Y adaptors comprising a leader sequence and a proportion of the substrates in the population may be hairpin loops.

The Y adaptor may comprise a capture sequence, affinity tag or pore tether that is revealed when a double stranded region to which the adaptor is attached is unwound. The capture sequence or tag functions to prevent the second strand of a double stranded polynucleotide from diffusing away from a nanopore when the double stranded polynucleotide is unwound as the first strand of the double stranded polynucleotide passes through a pore, wherein the pore binds to the tether or is tagged with an oligonucleotide comprising a sequence that is complementary to the capture sequence in the Y adaptor, an affinity partner of the tag on the Y-adaptor.

Hairpin Loops

Hairpin loop adaptors for use in nanopore sequencing are known in the art. A hairpin loop may be provided at one end of a double stranded polynucleotide, the method preferably further comprises providing the polynucleotide with a hairpin loop at one end of the polynucleotide. The two strands of the polynucleotide may be joined at one end with the hairpin loop.

Suitable hairpin loops can be designed using methods known in the art. The hairpin loop may be any length. The hairpin loop is typically 110 or fewer nucleotides, such as 100 or fewer nucleotides, 90 or fewer nucleotides, 80 or fewer nucleotides, 70 or fewer nucleotides, 60 or fewer nucleotides, 50 or fewer nucleotides, 40 or fewer nucleotides, 30 or fewer nucleotides, 20 or fewer nucleotides or 10 or fewer nucleotides, in length. The hairpin loop is preferably from about 1 to 110, from 2 to 100, from 5 to 80 or from 6 to 50 nucleotides in length. Longer lengths of the hairpin loop, such as from 50 to 110 nucleotides, are preferred if the loop is involved in the differential selectability of the adaptor. Similarly, shorter lengths of the hairpin loop, such as from 1 to 5 nucleotides, are preferred if the loop is not involved in the selectable binding as discussed below.

The hairpin loop may be provided at either end of the polynucleotide, e.g. the 5' or the 3' end. The hairpin loop may be ligated to the polynucleotide using any method known in the art. The hairpin loop may be ligated using a ligase, such as T4 DNA ligase, E. coli DNA ligase, Taq DNA ligase, Tma DNA ligase and 9° N DNA ligase.

In a method of characterizing a polynucleotide by sequencing, the two strands of a double stranded polynucleotide joined by a hairpin loop may be separated using any method known in the art. The two strands of the polynucleotide are then moved through the pore one strand at a time. Linking and interrogating both strands on a double stranded construct in this way increases the efficiency and accuracy of characterisation.

The hairpin loop preferably comprises a selectable binding moiety. This allows the polynucleotide to be purified or isolated. A selectable binding moiety is a moiety that can be selected on the basis of its binding properties. Hence, a selectable binding moiety is preferably a moiety that specifically binds to a surface. A selectable binding moiety specifically binds to a surface if it binds to the surface to a much greater degree than any other moiety used in the invention. In preferred embodiments, the moiety binds to a surface to which no other moiety used in the invention binds.

Suitable selective binding moieties are known in the art. Preferred selective binding moieties include, but are not limited to, biotin, a polynucleotide sequence, antibodies, antibody fragments, such as Fab and ScSv, antigens, polynucleotide binding proteins, poly histidine tails and GST tags. The most preferred selective binding moieties are biotin and a selectable polynucleotide sequence. Biotin specifically binds to a surface coated with avidins. Selectable polynucleotide sequences specifically bind (e.g. hybridise) to a surface coated with homologus sequences. Alternatively, selectable polynucleotide sequences specifically bind to a surface coated with polynucleotide binding proteins.

The hairpin loop and/or the selectable binding moiety may comprise a region that can be cut, nicked, cleaved or hydrolysed. Such a region can be designed to allow the polynucleotide to be removed from the surface to which it is bound following purification or isolation. Suitable regions are known in the art. Suitable regions include, but are not limited to, an RNA region, a region comprising desthiobiotin and streptavidin, a disulphide bond and a photocleav able region.

Beads

A bead, typically a microparticle, may be used to deliver the complex to the transmembrane pore. This is described in WO 2016/059375. Any number of microparticles can be used in the method of the invention. For instance, the method may use a single microparticle or 2, 3, 4, 5, 6, 7, 8, 9, 10, 20, 30, 50, 100, 1,000, 5,000, 10,000, 100,000, 500,000 or 1,000,000 or more microparticles. If two or more microparticles are used, the microparticles may be the same. Alternatively, a mixture of different microparticles may be used.

Each microparticle may have one complex attached. Alternatively, each microparticle may have two or more complexes, such as 3 or more, 4 or more, 5 or more, 6 or more, 7 or more, 8 or more, 9 or more, 10 or more, 20 or more, 30 or more, 50 or more, 100 or more, 500 or more, 1,000 or more, 5,000 or more, 10,000 or more, 100,000 or more, 1000,000 or more or 5000,000 or more polynucleotides, attached. A microparticle may be substantially or completed coated or covered with complexes. A microparticle may have a complex attached over substantially all of or all of its surface. A microparticle may be attached to a complex via an adaptor. The adaptor may be a Y-adaptor or a hairpin adaptor.

The complex may be attached to a microparticle via any one or more of its components. The guide polynucleotide, the polynucleotide-guided effector protein and/or the target polynucleotide may be attached to the microparticle. For example, the polynucleotide-guided effector protein, guide polynucleotide and/or the target polynucleotide may have a binding moiety attached that will bind to the surface of a microparticle.

Examples of suitable binding moieties include: protein binding tags (strep tag, flag tags, etc), conjugated attachments (polynucleotides, polymers, biotins, peptides) and amino acids (cysteines, Faz, etc).

A complex may be attached to two or more microparticles.

A microparticle is a microscopic particle whose size is typically measured in micrometres (μm). Microparticles may also known as microspheres or microbeads. The microparticle may be a nanoparticle. A nanoparticle is a microscopic particle whose size is typically measured in nanometres (nm).

A microparticle typically has a particle size of from about 0.001 μm to about 500 μm. For instance, a nanoparticle may have a particle size of from about 0.01 μm to about 200 μm or about 0.1 μm to about 100 μm. More often, a microparticle has a particle size of from about 0.5 μm to about 100 μm, or for instance from about 1 μm to about 50 μm. The microparticle may have a particle size of from about 1 nm to about 1000 nm, such as from about 10 nm to about 500 nm, about 20 nm to about 200 nm or from about 30 nm to about 100 nm.

A microparticle may be spherical or non-spherical. Spherical microparticles may be called microspheres. Non-spherical particles may for instance be plate-shaped, needle-shaped, irregular or tubular. The term "particle size" as used herein means the diameter of the particle if the particle is spherical or, if the particle is non-spherical, the volume-based particle size. The volume-based particle size is the diameter of the sphere that has the same volume as the non-spherical particle in question.

If two or more microparticles are used in the method, the average particle size of the microparticles may be any of the sizes discussed above, such as from about 0.5 μm to about 500 μm. A population of two or more microparticles preferably has a coefficient of variation (ratio of the standard deviation to the mean) of 10% or less, such as 5% or less or 2% or less.

Any method may be used to determine the size of the microparticle. Suitable methods include, but are not limited to, flow cytometry (see, for example, Chandler et al., J Thromb Haemost. 2011 June; 9(6):1216-24).

The microparticle may be formed from any material. The microparticle is preferably formed from a ceramic, glass, silica, a polymer or a metal. The polymer may be a natural polymer, such as polyhydroxyalkanoate, dextran, polylactide, agarose, cellulose, starch or chitosan, or a synthetic polymer, such as polyurethane, polystyrene, poly(vinyl chloride), silane or methacrylate. Suitable microparticles are known in the art and are commercially available. Ceramic and glass microspheres are commercially available from 3M®. Silica and polymer microparticles are commercially available from EPRUI Nanoparticles & Microspheres Co. Ltd. Microparticles are also commercially available from Polysciences Inc., Bangs Laboratories Inc. and Life Technologies.

The microparticle may be solid. The microparticle may be hollow. The microparticle may be formed from polymer fibers.

The microparticle may be derived from the kit used to extract and isolate the polynucleotide.

The surface of the microparticle may interact with and attach the analyte. The surface may naturally interact with the analyte, such as the polynucleotide, without functionalisation. The surface of the microparticle is typically functionalised to facilitate attachment of the analyte. Suitable functionalisations are known in the art. For instance, the surface of the microparticle may be functionalised with a polyhistidine-tag (hexa histidine-tag, 6×His-tag, His6 tag or His-Tag®), Ni-NTA, streptavidin, biotin, an oligonucleotide, a polynucleotide (such as DNA, RNA, PNA, GNA, TNA or LNA), carboxyl groups, quaternary amine groups, thiol groups, azide groups, alkyne groups, DIBO, lipid, FLAG-tag (FLAG octapeptide, polynucleotide binding proteins (including any of those discussed below), peptides, proteins, antibodies or antibody fragments. The microparticle may also be functionalised with any of the linkers or groups discussed herein.

The microparticle may be functionalised with a molecule or group which specifically binds to the polynucleotide. In this instance, the polynucleotide which will be attached to the microparticle and delivered to the transmembrane pore may be called the target polynucleotide. This allows the microparticle to select or capture the target polynucleotide from a sample containing other polynucleotides. A molecule or group specifically binds to the target polynucleotide if it binds to the target polynucleotide with preferential or high affinity, but does not bind or binds with only low affinity to other or different polynucleotides. A molecule or group binds with preferential or high affinity if it binds with a Kd of $1 \times 10^{-6}$ M or less, more preferably $1 \times 10^{-7}$ M or less, $5 \times 10^{-8}$ M or less, more preferably $1 \times 10^{-8}$ M or less or more preferably $5 \times 10^{-9}$ M or less. A molecule or group binds with low affinity if it binds with a Kd of $1 \times 10^{-6}$ M or more, more preferably $1\times10^{-5}$ M or more, more preferably $1\times10^{-4}$ M or more, more preferably $1\times10^{-3}$ M or more, even more preferably $1\times10^{-2}$ M or more.

Preferably, the molecule or group binds to the target polynucleotide with an affinity that is at least 10 times, such as at least 50, at least 100, at least 200, at least 300, at least 400, at least 500, at least 1000 or at least 10,000 times, greater than its affinity for other polynucleotides. Affinity can be measured using known binding assays, such as those that make use of fluorescence and radioisotopes. Competitive binding assays are also known in the art. The strength of binding between peptides or proteins and polynucleotides can be measured using nanopore force spectroscopy as described in Hornblower et al., Nature Methods. 4: 315-317. (2007).

The microparticle may be functionalised with an oligonucleotide or a polynucleotide which specifically hybridises to a target polynucleotide or guide polynucleotide or which comprises a portion or region which is complementary to a portion or region of the target polynucleotide or guide polynucleotide. This allows the microparticle to select or capture the target polynucleotide or guide polynucleotide from a sample containing other polynucleotides.

An oligonucleotide or polynucleotide specifically hybridises to a target polynucleotide when it hybridises with preferential or high affinity to the target polynucleotide but does not substantially hybridise, does not hybridise or hybridises with only low affinity to other polynucleotide. An oligonucleotide or polynucleotide specifically hybridises if it hybridises to the target polynucleotide with a melting temperature ($T_m$) that is at least 2° C., such as at least 3° C., at least 4° C., at least 5° C., at least 6° C., at least 7° C., at least 8° C., at least 9° C. or at least 10° C., greater than its $T_m$ for other sequences. More preferably, the oligonucleotide or polynucleotide hybridise to the target polynucleotide with a $T_m$ that is at least 2° C., such as at least 3° C., at least 4° C., at least 5° C., at least 6° C., at least 7° C., at least 8° C., at least 9° C., at least 10° C., at least 20° C., at least 30° C. or at least 40° C., greater than its $T_m$ for other nucleic acids. Preferably, the oligonucleotide or polynucleotide hybridises to the target polynucleotide with a $T_m$ that is at least 2° C., such as at least 3° C., at least 4° C., at least 5° C., at least 6° C., at least 7° C., at least 8° C., at least 9° C., at least 10° C., at least 20° C., at least 30° C. or at least 40° C., greater than its $T_m$ for a sequence which differs from the target polynucleotide by one or more nucleotides, such as by 1, 2, 3, 4 or 5 or more nucleotides. The oligonucleotide or polynucleotide typically hybridises to the target polynucleotide with a $T_m$ of at least 90° C., such as at least 92° C. or at least 95° C. $T_m$ can be measured experimentally using known techniques, including the use of DNA microarrays, or can be calculated using publicly available $T_m$ calculators, such as those available over the internet.

Conditions that permit the hybridisation are well-known in the art (for example, Sambrook et al., 2001, Molecular Cloning: a laboratory manual, 3rd edition, Cold Spring Harbour Laboratory Press; and Current Protocols in Molecular Biology, Chapter 2, Ausubel et al., Eds., Greene Publishing and Wiley-lnterscience, New York (1995)). Hybridisation can be carried out under low stringency conditions, for example in the presence of a buffered solution of 30 to 35% formamide, 1 M NaCl and 1% SDS (sodium dodecyl sulfate) at 37° C. followed by a 20 wash in from 1× (0.1650 M Na$^+$) to 2× (0.33 M Na$^+$) SSC (standard sodium citrate) at 50° C. Hybridisation can be carried out under moderate stringency conditions, for example in the presence of a buffer solution of 40 to 45% formamide, 1 M NaCl, and 1% SDS at 37° C., followed by a wash in from 0.5× (0.0825 M Na$^+$) to 1× (0.1650 M Na$^+$) SSC at 55° C. Hybridisation can be carried out under high stringency conditions, for example in the presence of a buffered solution of 50% formamide, 1 M NaCl, 1% SDS at 37° C., followed by a wash in 0.1× (0.0165 M Na$^+$) SSC at 60° C.

The oligonucleotide or polynucleotide may comprise a portion or region which is substantially complementary to a portion or region of the target polynucleotide or guide polynucleotide. The region or portion of the oligonucleotide or polynucleotide may therefore have 1, 2, 3, 4, 5, 6, 7, 8, 9, 10 or more mismatches across a region of 5, 10, 15, 20, 21, 22, 30, 40 or 50 nucleotides compared with the portion or region in the target polynucleotide or guide polynucleotide.

A portion of region is typically 50 nucleotides or fewer, such as 40 nucleotides or fewer, 30 nucleotides or fewer, 20 nucleotides or fewer, 10 nucleotides or fewer or 5 nucleotides or fewer.

The microparticle is preferably paramagnetic or magnetic. The microparticle preferably comprises a paramagnetic or a superparamagnetic material or a paramagnetic or a superparamagnetic metal, such as iron. Any suitable magnetic microparticle may be used. For instance, magnetic beads commercially available from, for instance, Clontech, Promega, Invitrogen ThermoFisher Scientific and NEB, may be used. In some embodiments, the microparticle comprises a magnetic particle with an organic group such as a metal-chelating group, such as nitrilotriacetic acid (NTA), attached. The organic component may, for instance, comprise a group selected from —C(=O)O—, —C—O—C—, —C(=O)—, —NH—, —C(=O)—NH, —C(=O)—CH$_2$—I, —S(=O)$_2$— and —S—. The organic component may comprise a metal chelating group, such as NTA (nitrilotriacetic acid). Usually, a metal such as gold, iron, nickel or cobalt is also attached to the metal-chelating group. Magnetic beads of this sort are commonly used for capturing His-tagged proteins, but are also suitable for use in the invention.

The microparticle is most preferably a His-Tag Dynabead® which is commercially available from Life Technologies, Mag Strep beads from IBA, Streptavidin magnetic beads from NEB, Solid Phase Reversible Immobilization (SPRI) beads or Agencourt AMPure XP beads from Beckman Coulter or Dynabeads® MyOne™ Streptavidin C1(ThermoFisher Scientific).

Membrane

Any membrane may be used in accordance with the invention. Suitable membranes are well-known in the art. The membrane is preferably an amphiphilic layer or a solid state layer.

An amphiphilic layer is a layer formed from amphiphilic molecules, such as phospholipids, which have both hydrophilic and lipophilic properties. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units that are polymerised together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (e.g. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphiphiles. The copolymer may be a triblock, tetrablock or pentablock copolymer. The membrane is preferably a triblock copolymer membrane.

Archaebacterial bipolar tetraether lipids are naturally occurring lipids that are constructed such that the lipid forms a monolayer membrane. These lipids are generally found in extremophiles that survive in harsh biological environments, thermophiles, halophiles and acidophiles. Their stability is believed to derive from the fused nature of the final bilayer. It is straightforward to construct block copolymer materials that mimic these biological entities by creating a triblock polymer that has the general motif hydrophilic-hydrophobic-hydrophilic. This material may form monomeric membranes that behave similarly to lipid bilayers and encompass a range of phase behaviours from vesicles through to laminar membranes. Membranes formed from these triblock copolymers hold several advantages over biological lipid membranes. Because the triblock copolymer is synthesised, the exact construction can be carefully controlled to provide the correct chain lengths and properties required to form membranes and to interact with pores and other proteins.

Block copolymers may also be constructed from sub-units that are not classed as lipid sub-materials; for example a hydrophobic polymer may be made from siloxane or other non-hydrocarbon based monomers. The hydrophilic sub-section of block copolymer can also possess low protein binding properties, which allows the creation of a membrane that is highly resistant when exposed to raw biological samples. This head group unit may also be derived from non-classical lipid head-groups.

Triblock copolymer membranes also have increased mechanical and environmental stability compared with biological lipid membranes, for example a much higher operational temperature or pH range. The synthetic nature of the block copolymers provides a platform to customise polymer based membranes for a wide range of applications.

The membrane is most preferably one of the membranes disclosed in WO2014/064443 or WO2014/064444.

The amphiphilic molecules may be chemically-modified or functionalised to facilitate coupling of the complex.

The amphiphilic layer may be a monolayer or a bilayer. The amphiphilic layer is typically planar. The amphiphilic layer may be curved. The amphiphilic layer may be supported. The amphiphilic layer may be concave. The amphiphilic layer may be suspended from raised pillars such that the peripheral region of the amphiphilic layer (which is attached to the pillars) is higher than the amphiphilic layer region. This may allow the microparticle to travel, move, slide or roll along the membrane as described above.

Amphiphilic membranes are typically naturally mobile, essentially acting as two dimensional fluids with lipid diffusion rates of approximately $10^{-8}$ cm s−1. This means that the pore and coupled complex can typically move within an amphiphilic membrane.

The membrane may be a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in WO 2008/102121, WO 2009/077734 and WO 2006/100484.

Methods for forming lipid bilayers are known in the art. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface. The lipid is normally added to the surface of an aqueous electrolyte solution by first dissolving it in an organic solvent and then allowing a drop of the solvent to evaporate on the surface of the aqueous solution on either side of the aperture. Once the organic solvent has evaporated, the solution/air interfaces on either side of the aperture are physically moved up and down past the aperture until a bilayer is formed. Planar lipid bilayers may be formed across an aperture in a membrane or across an opening into a recess.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

Tip-dipping bilayer formation entails touching the aperture surface (for example, a pipette tip) onto the surface of a test solution that is carrying a monolayer of lipid. Again, the lipid monolayer is first generated at the solution/air interface by allowing a drop of lipid dissolved in organic solvent to evaporate at the solution surface. The bilayer is then formed by the Langmuir-Schaefer process and requires mechanical automation to move the aperture relative to the solution surface.

For painted bilayers, a drop of lipid dissolved in organic solvent is applied directly to the aperture, which is submerged in an aqueous test solution. The lipid solution is spread thinly over the aperture using a paintbrush or an equivalent. Thinning of the solvent results in formation of a lipid bilayer. However, complete removal of the solvent from the bilayer is difficult and consequently the bilayer formed by this method is less stable and more prone to noise during electrochemical measurement.

Patch-clamping is commonly used in the study of biological cell membranes. The cell membrane is clamped to the end of a pipette by suction and a patch of the membrane becomes attached over the aperture. The method has been adapted for producing lipid bilayers by clamping liposomes which then burst to leave a lipid bilayer sealing over the aperture of the pipette. The method requires stable, giant and unilamellar liposomes and the fabrication of small apertures in materials having a glass surface.

Liposomes can be formed by sonication, extrusion or the Mozafari method (Colas et al. (2007) Micron 38:841-847).

In a preferred embodiment, the lipid bilayer is formed as described in WO 2009/077734. Advantageously in this method, the lipid bilayer is formed from dried lipids. In a most preferred embodiment, the lipid bilayer is formed across an opening as described in WO2009/077734.

A lipid bilayer is formed from two opposing layers of lipids. The two layers of lipids are arranged such that their hydrophobic tail groups face towards each other to form a hydrophobic interior. The hydrophilic head groups of the lipids face outwards towards the aqueous environment on each side of the bilayer. The bilayer may be present in a number of lipid phases including, but not limited to, the liquid disordered phase (fluid lamellar), liquid ordered phase, solid ordered phase (lamellar gel phase, interdigitated gel phase) and planar bilayer crystals (lamellar sub-gel phase, lamellar crystalline phase).

Any lipid composition that forms a lipid bilayer may be used. The lipid composition is chosen such that a lipid bilayer having the required properties, such as surface charge, ability to support membrane proteins, packing density or mechanical properties, is formed. The lipid composition can comprise one or more different lipids. For instance, the lipid composition can contain up to 100 lipids. The lipid composition preferably contains 1 to 10 lipids. The lipid composition may comprise naturally-occurring lipids and/or artificial lipids.

The lipids typically comprise a head group, an interfacial moiety and two hydrophobic tail groups which may be the same or different. Suitable head groups include, but are not limited to, neutral head groups, such as diacylglycerides (DG) and ceramides (CM); zwitterionic head groups, such as phosphatidylcholine (PC), phosphatidylethanolamine (PE) and sphingomyelin (SM); negatively charged head groups, such as phosphatidylglycerol (PG); phosphatidylserine (PS), phosphatidylinositol (PI), phosphatic acid (PA) and cardiolipin (CA); and positively charged headgroups, such as trimethylammonium-Propane (TAP). Suitable interfacial moieties include, but are not limited to, naturally-occurring interfacial moieties, such as glycerol-based or ceramide-based moieties. Suitable hydrophobic tail groups include, but are not limited to, saturated hydrocarbon chains, such as lauric acid (n-Dodecanolic acid), myristic acid (n-Tetradeconic acid), palmitic acid (n-Hexadecanoic acid), stearic acid (n-Octadecanoic) and arachidic (n-Eicosanoic); unsaturated hydrocarbon chains, such as oleic acid (cis-9-Octadecanoic); and branched hydrocarbon chains, such as phytanoyl. The length of the chain and the position and number of the double bonds in the unsaturated hydrocarbon chains can vary. The length of the chains and the position and number of the branches, such as methyl groups, in the branched hydrocarbon chains can vary. The hydrophobic tail groups can be linked to the interfacial moiety as an ether or an ester. The lipids may be mycolic acid.

The lipids can also be chemically-modified. The head group or the tail group of the lipids may be chemically-modified. Suitable lipids whose head groups have been chemically-modified include, but are not limited to, PEG-modified lipids, such as 1,2-Diacyl-sn-Glycero-3-Phosphoethanolamine-N-[Methoxy(Polyethylene glycol)-2000]; functionalised PEG Lipids, such as 1,2-Distearoyl-sn-Glycero-3 Phosphoethanolamine-N-[Biotinyl(Polyethylene Glycol)2000]; and lipids modified for conjugation, such as 1,2-Dioleoyl-sn-Glycero-3-Phosphoethanolamine-N-(succinyl) and 1,2-Dipalmitoyl-sn-Glycero-3-Phosphoethanolamine-N-(Biotinyl). Suitable lipids whose tail groups have been chemically-modified include, but are not limited to, polymerisable lipids, such as 1,2-bis(10,12-tricosadiynoyl)-sn-Glycero-3-Phosphocholine; fluorinated lipids, such as 1-Palmitoyl-2-(16-Fluoropalmitoyl)-sn-Glycero-3-Phosphocholine; deuterated lipids, such as 1,2-Dipalmitoyl-D62-sn-Glycero-3-Phosphocholine; and ether linked lipids, such as 1,2-Di-O-phytanyl-sn-Glycero-3-Phosphocholine. The lipids may be chemically-modified or functionalised to facilitate coupling of the complex.

The amphiphilic layer, for example the lipid composition, typically comprises one or more additives that will affect the properties of the layer. Suitable additives include, but are not limited to, fatty acids, such as palmitic acid, myristic acid and oleic acid; fatty alcohols, such as palmitic alcohol, myristic alcohol and oleic alcohol; sterols, such as cholesterol, ergosterol, lanosterol, sitosterol and stigmasterol; lysophospholipids, such as 1-Acyl-2-Hydroxy-sn-Glycero-3-Phosphocholine; and ceramides.

Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from graphene. Suitable graphene layers are disclosed in WO 2009/035647. Yusko et al., Nature Nanotechnology, 2011; 6: 253-260 and US Patent Application No. 2013/0048499 describe the delivery of proteins to transmembrane pores in solid state layers without the use of microparticles. The method of the invention may be used to improve the delivery in the methods disclosed in these documents.

The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial triblock copolymer layer. The layer may comprise other transmembrane and/or intramembrane proteins as well as other molecules in addition to the pore. Suitable apparatus and conditions are discussed below. The method of the invention is typically carried out in vitro.

The membrane to which the complex is delivered is typically contained in a liquid. The liquid keeps the membrane "wet" and stops it drying out. The liquid is typically an aqueous solution. The aqueous solution typically has the same density as water. The density of the aqueous solution is typically about 1 $g/cm^3$. The density of the solution may vary depending on temperature and the exact composition of the solution. The aqueous solution typically has a density between about 0.97 and about 1.03 $g/cm^3$.

The membrane typically separates two volumes of aqueous solution. The membrane resists the flow of electrical current between the volumes. The transmembrane pore inserted into the membrane selectively allows the passage of ions across the membrane, which can be recorded as an electrical signal detected by electrodes in the two volumes of aqueous solution. The presence of a complex comprising the target polynucleotide modulates the flow of ions and is detected by observing the resultant variations in the electrical signal.

Array

The membrane is typically part of an array of membranes, wherein each membrane preferably comprises a transmembrane pore. Therefore, the invention provides a method of detecting a target polynucleotide using an array of membranes.

The membrane may be comprised in an apparatus having an array of electrically isolated membranes, each individually addressed using its own electrode, such that the array is equivalent to many individual sensors measuring in parallel from a test sample. The membranes may be relatively densely packed, allowing a large number of membranes to be used for a given volume of test sample. Suitable arrays of membranes and apparatuses are described in the art, for example in WO 2009/077734 and WO2012/042226. WO 2009/077734, for example, discloses a plurality of individually addressable lipid bilayers formed across an array of microwell apertures, each microwell containing an electrode and an aqueous medium in contact with the lipid bilayer.

The apparatus is typically provided to the end user in a 'ready to use' state wherein the membranes and transmembrane pores are pre-inserted. A typical apparatus provided in a 'ready to use' state comprises an array of amphiphilic membranes, each membrane comprising a transmembrane pore and being provided across a well containing a liquid. Such an apparatus and method of making it are disclosed by WO2014/064443. Test liquid to be analysed is applied to the upper surface of the amphiphilic membranes.

Providing an apparatus in a 'ready to use' state however has additional considerations in that care needs to be taken that the sensor does not dry out, namely that liquid is not lost from the well by passage through the amphiphilic membrane, which may result in a loss of performance or damage the sensor. One solution to address the problem of drying out of the sensor is to provide the device with a buffer liquid over the surface of the amphiphilic membrane such that any evaporation through the surface of the membrane is minimised and the liquids provided on either side of the membrane may have the same ionic strength so as to reduce any osmotic effects. In use the buffer liquid may be removed from the surface of the amphiphilic membrane and a test liquid to be analysed is introduced to contact the surface.

Some applications may use measurement of electrical properties across the membranes, for example ion current flow. To provide for such measurements, the apparatus may further comprise respective electrodes in each compartment making electrical contact with the volumes comprising polar medium. Other types of measurements may be carried out for example optical measurements such as fluorescence measurements and FET measurements. Optical measurements and electrical measurements may be carried out simultaneously (Heron A J et al., J Am Chem Soc. 2009; 131(5):1652-3).

The apparatus may further comprise a common electrode. The apparatus may further comprise an electrical circuit connected between the common electrode and the respective electrodes in each compartment, the electrical circuit being arranged to take electrical measurements. Such electrical measurements may be dependent on a process occurring at or through the membranes.

The apparatus may comprise FET array for making measurements of the nanopore array.

Pore

A nanopore is an aperture with at least one dimension on the nanometre scale. A nanopore may be created by a pore-forming protein or as a hole in synthetic materials such as silicon or graphene. Alternatively a nanopore may be a hybrid of these e.g., a protein channel set in a synthetic membrane. A nanopore may also be a DNA origami pore or a glass capillary. A nanopore is typically less than about 20 nm diameter but can be up to about 100 nm in diameter.

A transmembrane pore is a structure that crosses a membrane to some degree. It permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well, gap, channel, trench or slit in the membrane along which or into which hydrated ions may flow.

Any transmembrane pore may be used in the invention. The pore may be biological or artificial. Suitable pores include, but are not limited to, protein pores, polynucleotide pores and solid state pores. The pore may be a DNA origami pore (Langecker et al., Science, 2012; 338: 932-936). The transmembrane pore is preferably a transmembrane protein pore. A transmembrane protein pore is a polypeptide or a collection of polypeptides that permits hydrated ions, such as polynucleotide, to flow from one side of a membrane to the other side of the membrane. In the present invention, the transmembrane protein pore is capable of forming a pore that permits hydrated ions driven by an applied potential to flow from one side of the membrane to the other. The transmembrane protein pore preferably permits polynucleotides to flow from one side of the membrane, such as a triblock copolymer membrane, to the other. The transmembrane protein pore allows a polynucleotide, such as DNA or RNA, to be moved through the pore.

The transmembrane protein pore may be a monomer or an oligomer. The pore is preferably made up of several repeating subunits, such as at least 6, at least 7, at least 8, at least 9, at least 10, at least 11, at least 12, at least 13, at least 14, at least 15, or at least 16 subunits. The pore is preferably a hexameric, heptameric, octameric or nonameric pore. The pore may be a homo-oligomer or a hetero-oligomer.

The transmembrane protein pore typically comprises a barrel or channel through which the ions may flow. The subunits of the pore typically surround a central axis and contribute strands to a transmembrane β barrel or channel or a transmembrane α-helix bundle or channel.

The barrel or channel of the transmembrane protein pore typically comprises amino acids that facilitate interaction with s, such as nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA, MspB, MspC or MspD, CsgG, outer membrane porin F (OmpF), outer membrane porin G (OmpG), outer membrane phospholipase A and *Neisseria* autotransporter lipoprotein (NalP) and other pores, such as lysenin. α-helix bundle pores comprise a barrel or channel that is formed from α-helices. Suitable α-helix bundle pores include, but are not limited to, inner membrane proteins and α outer membrane proteins, such as WZA and ClyA toxin.

The transmembrane pore may be derived from or based on Msp, α-hemolysin (α-HL), lysenin, CsgG, ClyA, Sp1 and haemolytic protein fragaceatoxin C (FraC). The transmembrane protein pore is preferably derived from CsgG, more preferably from CsgG from *E. coli* Str. K-12 substr. MC4100. Suitable pores derived from CsgG are disclosed in WO 2016/034591. The transmembrane pore may be derived from lysenin. Suitable pores derived from lysenin are disclosed in WO 2013/153359.

The wild type α-hemolysin pore is formed of 7 identical monomers or sub-units (i.e., it is heptameric). The sequence of one monomer or sub-unit of α-hemolysin-NN is disclosed in, for example, WO2016/059375.

The transmembrane protein pore is preferably derived from Msp, more preferably from MspA. Suitable pores derived from MspA are disclosed in WO 2012/107778.

Any of the proteins described herein, such as the transmembrane protein pores, may be modified to assist their identification or purification, for example by the addition of histidine residues (a his tag), aspartic acid residues (an asp tag), a streptavidin tag, a flag tag, a SUMO tag, a GST tag or a MBP tag, or by the addition of a signal sequence to promote their secretion from a cell where the polypeptide does not naturally contain such a sequence. An alternative to introducing a genetic tag is to chemically react a tag onto a native or engineered position on the pore or construct. An example of this would be to react a gel-shift reagent to a cysteine engineered on the outside of the pore. This has been demonstrated as a method for separating hemolysin heterooligomers (Chem Biol. 1997 July; 4(7):497-505).

The pore may be labelled with a revealing label. The revealing label may be any suitable label which allows the pore to be detected. Suitable labels include, but are not limited to, fluorescent molecules, radioisotopes, e.g. $^{125}I$, $^{35}S$, enzymes, antibodies, antigens, polynucleotides and ligands such as biotin.

Any of the proteins described herein, such as the transmembrane protein pores, may be made synthetically or by recombinant means. For example, the pore may be synthesised by in vitro translation and transcription (IVTT). The amino acid sequence of the pore may be modified to include non-naturally occurring amino acids or to increase the stability of the protein. When a protein is produced by synthetic means, such amino acids may be introduced during production. The pore may also be altered following either synthetic or recombinant production.

Any of the proteins described herein, such as the transmembrane protein pores, can be produced using standard methods known in the art. Polynucleotide sequences encoding a pore or construct may be derived and replicated using standard methods in the art. Polynucleotide sequences encoding a pore or construct may be expressed in a bacterial host cell using standard techniques in the art. The pore may be produced in a cell by in situ expression of the polypeptide from a recombinant expression vector. The expression vector optionally carries an inducible promoter to control the expression of the polypeptide. These methods are described in Sambrook, J. and Russell, D. (2001). Molecular Cloning: A Laboratory Manual, 3rd Edition. Cold Spring Harbor Laboratory Press, Cold Spring Harbor, N.Y.

The pore may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

Diagnosis

The methods of the invention can be used to diagnose or prognose a disease or condition. The disease or condition is preferably cancer, coronary heart disease, cardiovascular disease, tuberculosis or sepsis.

Examples of the disease or condition include abdominal aortic aneurysm, acute lymphoblastic leukemia (ALL), acute myeloid leukemia (AML), acute myocardial infarction, acute promyelocytic leukemia (APL), adenoma, adrenocortical carcinoma, alcoholic liver disease, Alzheimer's disease, anaplastic thyroid carcinoma (ATC), anxiety disorder, asthma, astrocytoma, atopic dermatitis, autism spectrum disorder (ASD), B-cell chronic lymphocytic leukemia, B-cell lymphoma, Becker muscular dystrophy (BMD), bladder cancer, brain neoplasm, breast cancer, Burkitt lymphoma, cardiac hypertrophy, cardiomyopathy, cardiovascular disease, cerebellar neurodegeneration, cervical cancer, cholangiocarcinoma, cholesteatoma, choriocarcinoma, chronic lymphocytic leukemia, chronic myeloid leukemia, chronic pancreatitis, colon carcinoma, colorectal cancer, congenital heart disease, coronary artery disease, cowden syndrome, dermatomyositis (DM), diabetic nephropathy, diarrhea predominant irritable bowel syndrome, diffuse large B-cell lymphoma, dilated cardiomyopathy, down syndrome (DS), duchenne muscular dystrophy (DMD), endometrial cancer, endometrial endometrioid adenocarcinoma, endometriosis, epithelial ovarian cancer, esophageal cancer, esophagus squamous cell carcinoma, essential thrombocythemia (ET), facioscapulohumeral muscular dystrophy (FSHD), follicular lymphoma (FL), follicular thyroid carcinoma (FTC), frontotemporal dementia, gastric cancer (stomach cancer), glioblastoma, glioblastoma multiforme (GBM), glioma, glomerular disease, glomerulosclerosis, hamartoma, HBV-related cirrhosis, HCV infection, head and neck cancer, head and neck squamous cell carcinoma (HNSCC), hearing loss, heart disease, heart failure, hepatitis B, hepatitis C, hepatocellular carcinoma (HCC), hilar cholangiocarcinoma, Hodgkin's lymphoma, homozygous sickle cell disease (HbSS), Huntington's disease (HD), hypertension, hypopharyngeal cancer, inclusion body myositis (IBM), insulinoma, intrahepatic cholangiocarcinoma (ICC), kidney cancer, kidney disease, laryngeal carcinoma, late insomnia (sleep disease), leiomyoma of lung, leukemia, limb-girdle muscular dystrophies types 2A (LGMD2A), lipoma, lung adenocarcinoma, lung cancer, lymphoproliferative disease, malignant lymphoma, malignant melanoma, malignant mesothelioma (MM), mantle cell lymphoma (MCL), medulloblastoma, melanoma, meningioma, metabolic disease, miyoshi myopathy (MM), multiple myeloma (MM), multiple sclerosis, MYC-rearranged lymphoma, myelodysplastic syndrome, myeloproliferative disorder, myocardial infarction, myocardial injury, myoma, nasopharyngeal carcinoma (NPC), nemaline myopathy (NM), nephritis, neuroblastoma (NB), neutrophilia, Niemann-Pick type C (NPC) disease, non-alcoholic fatty liver disease (NAFLD), non-small cell lung cancer (NSCLC), obesity, oral carcinomaosteosarcoma ovarian cancer (OC), pancreatic cancer, pancreatic ductal adenocarcinoma (PDAC), pancreatic neoplasia, panic disease, papillary thyroid carcinoma (PTC), Parkinson's disease, PFV-1 infection, pharyngeal disease, pituitary adenoma, polycystic kidney disease, polycystic liver disease, polycythemia vera (PV), polymyositis (PM), primary biliary cirrhosis (PBC), primary myelofibrosis, prion disease, prostate cancer, psoriasic arthritis, psoriasis, pulmonary hypertension, recurrent ovarian cancer, renal cell carcinoma, renal clear cell carcinoma, retinitis pigmentosa (RP), retinoblastoma, rhabdomyosarcoma, rheumatic heart disease and atrial fibrillation, rheumatoid arthritis, sarcoma, schizophrenia, sepsis, serous ovarian cancer, Sezary syndrome, skin disease, small cell lung cancer, spinocerebellar ataxia, squamous carcinoma, T-cell leukemia, teratocarcinoma, testicular germ cell tumor, thalassemia, thyroid cancer, tongue squamous cell carcinoma, tourette's syndrome, type 2 diabetes, ulcerative colitis (UC), uterine leiomyoma (ULM), uveal melanoma, vascular disease, vesicular stomatitis or Waldenstrom macroglobulinemia (WM).

Since in an embodiment using a multiplex method the presence of absence of two or more target polynucleotides (e.g. at least 5 ore more, 10 or more, 20 or more or 30 or more) may be determined, it is possible to prognose or diagnose two or more (e.g. 3, 4, 5, 6 or more) of any of the diseases listed above. Accordingly, a multiplex method for detecting and/or analyzing a plurality (e.g. at least 2 or more, at least 3 or more, at least 10 or more, at least 20 or more or at least 30 or more) of target polynucleotides is provided.

The method may also be used to detect polynucleotides derived from a microorganism or group of microorganisms. This is useful in disease diagnosis and monitoring, but also has other applications. For example, the method may be used to analyse gut or vaginal flora, microorganisms present on the skin or elsewhere. The microorganism may, for example, be a bacterium, virus, fungus or *mycobacterium*. The method may be used to determine which infectious agent is causing a disease and hence to determine the best course of treatment. For example, urinary tract infections and other infections are increasingly developing antibacterial resistance. The method may be used to determine the bacterium responsible for an infection and hence to identify an antibiotic or other treatment that will successfully treat the infection.

The method may be used to characterize genomic DNA. In one particular exemplary embodiment, the method may be used to identity polymorphisms, such as SNPs. In another embodiment the method so the invention may be used for repertoire analysis, for example of V(D)J regions. Such methods may use samples derived from blood cells, or T-cells for analysis.

The methods may also be used to characterize unknown sequences.

Polynucleotide Binding Protein

The polynucleotide binding protein may be any protein that is capable of binding to the polynucleotide and controlling its movement through the pore. It is straightforward in the art to determine whether or not a protein binds to a polynucleotide. The protein typically interacts with and modifies at least one property of the polynucleotide. The protein may modify the polynucleotide by cleaving it to form individual nucleotides or shorter chains of nucleotides, such as di- or trinucleotides. The moiety may modify the polynucleotide by orienting it or moving it to a specific position, e.g. controlling its movement.

The polynucleotide binding protein is preferably derived from a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the polynucleotide and controlling its movement through the pore. For instance, the enzyme may be modified to remove its enzymatic activity or may be used under conditions which prevent it from acting as an enzyme. Such conditions are discussed in more detail below.

The polynucleotide handling enzyme is preferably derived from a nucleolytic enzyme. The polynucleotide handling enzyme used in the construct of the enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in WO 2010/086603.

Preferred enzymes are polymerases, exonucleases, helicases, translocases and topoisomerases, such as gyrases. Suitable enzymes include, but are not limited to, exonuclease I from *E. coli*, exonuclease III enzyme from *E. coli*, RecJ from *T. thermophilus* and bacteriophage lambda exonuclease, TatD exonuclease and variants thereof. The polymerase may be PyroPhage® 3173 DNA Polymerase (which is commercially available from Lucigen® Corporation), SD Polymerase (commercially available from Bioron®) or variants thereof. The enzyme is preferably Phi29 DNA polymerase or a variant thereof. The topoisomerase is preferably a member of any of the Moiety Classification (EC) groups 5.99.1.2 and 5.99.1.3.

The enzyme is most preferably derived from a helicase. The helicase may be or be derived from a Hel308 helicase, a RecD helicase, such as TraI helicase or a TrwC helicase, a XPD helicase or a Dda helicase. The helicase may be or be derived from Hel308 Mbu, Hel308 Csy Hel308 Tga, Hel308 Mhu, TraI Eco, XPD Mbu or a variant thereof.

The helicase may be any of the helicases, modified helicases or helicase constructs disclosed in WO 2013/057495, WO 2013/098562, WO2013098561, WO 2014/013260, WO 2014/013259, WO 2014/013262 and WO/2015/055981.

The Dda helicase preferably comprises any of the modifications disclosed in WO/2015/055981 and WO 2016/055777.

Any number of helicases may be used in accordance with the invention. For instance, 1, 2, 3, 4, 5, 6, 7, 8, 9, 10 or more helicases may be used. In some embodiments, different numbers of helicases may be used. Any combination of two or more of the helicases mentioned above may be used. The two or more helicases may be two or more Dda helicases. The two or more helicases may be one or more Dda helicases and one or more TrwC helicases. The two or more helicases may be different variants of the same helicase.

The two or more helicases are preferably attached to one another. The two or more helicases are more preferably covalently attached to one another. The helicases may be attached in any order and using any method. Preferred helicase constructs for use in the invention are described in WO 2014/013260, WO 2014/013259, WO 2014/013262 and WO2015/055981.

Polynucleotide binding ability can be measured using any method known in the art. For instance, the protein can be contacted with a polynucleotide and its ability to bind to and move along the polynucleotide can be measured. The protein may include modifications that facilitate binding of the polynucleotide and/or facilitate its activity at high salt concentrations and/or room temperature. Proteins may be modified such that they bind polynucleotides (e.g. retain polynucleotide binding ability) but do not function as a helicase (e.g. do not move along polynucleotides when provided with all the necessary components to facilitate movement, e.g. ATP and $Mg^{2+}$). Such modifications are known in the art. For instance, modification of the $Mg^{2+}$ binding domain in helicases typically results in variants which do not function as helicases. These types of variants may act as molecular brakes.

The enzyme may be covalently attached to the pore. Any method may be used to covalently attach the enzyme to the pore.

In strand sequencing, the polynucleotide is translocated through the pore either with or against an applied potential. Exonucleases that act progressively or processively on double stranded polynucleotides can be used on the cis side of the pore to feed the remaining single strand through under an applied potential or the trans side under a reverse potential. Likewise, a helicase that unwinds the double stranded DNA can also be used in a similar manner. A polymerase may also be used. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential.

Any helicase may be used in the invention. Helicases may work in two modes with respect to the pore. First, the method is preferably carried out using a helicase such that it moves the polynucleotide through the pore with the field resulting from the applied voltage. In this mode the 5' end of the polynucleotide is first captured in the pore, and the helicase moves the polynucleotide into the pore such that it is passed through the pore with the field until it finally translocates through to the trans side of the membrane. Alternatively, the method is preferably carried out such that a helicase moves the polynucleotide through the pore against the field resulting from the applied voltage. In this mode the 3' end of the polynucleotide is first captured in the pore, and the helicase moves the polynucleotide through the pore such that it is pulled out of the pore against the applied field until finally ejected back to the cis side of the membrane.

The method may also be carried out in the opposite direction. The 3' end of the polynucleotide may be first captured in the pore and the helicase may move the polynucleotide into the pore such that it is passed through the pore with the field until it finally translocates through to the trans side of the membrane.

When the helicase is not provided with the necessary components to facilitate movement or is modified to hinder or prevent its movement, it can bind to the polynucleotide and act as a brake slowing the movement of the polynucleotide when it is pulled into the pore by the applied field. In the inactive mode, it does not matter whether the polynucleotide is captured either 3' or 5' down, it is the applied field which pulls the polynucleotide into the pore towards the trans side with the enzyme acting as a brake. When in the inactive mode, the movement control of the polynucleotide by the helicase can be described in a number of ways including ratcheting, sliding and braking. Helicase variants which lack helicase activity can also be used in this way.

The polynucleotide may be contacted with the polynucleotide binding protein and the pore in any order. It is preferred that, when the polynucleotide is contacted with the polynucleotide binding protein, such as a helicase, and the pore, the polynucleotide firstly forms a complex with the protein. When the voltage is applied across the pore, the polynucleotide/protein complex then forms a complex with the pore and controls the movement of the polynucleotide through the pore.

Any steps in the method using a polynucleotide binding protein are typically carried out in the presence of free nucleotides or free nucleotide analogues and an enzyme cofactor that facilitates the action of the polynucleotide binding protein. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guano sine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the construct to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$.

The molecular brakes may be any compound or molecule which binds to the polynucleotide and slows the movement of the polynucleotide through the pore. The molecular brake may be any of those discussed above. The molecular brake preferably comprises a compound which binds to the polynucleotide. The compound is preferably a macrocycle. Suitable macrocycles include, but are not limited to, cyclodextrins, calixarenes, cyclic peptides, crown ethers, cucurbiturils, pillararenes, derivatives thereof or a combination thereof. The cyclodextrin or derivative thereof may be any of those disclosed in Eliseev, A. V., and Schneider, H-J. (1994) J. Am. Chem. Soc. 116, 6081-6088. The cyclodextrin is more preferably heptakis-6-amino-β-cyclodextrin (ami-βCD), 6-monodeoxy-6-monoamino-β-cyclodextrin ($am_1$-βCD) or heptakis-(6-deoxy-6-guanidino)-cyclodextrin (guy-βCD).

Polynucleotide Characterisation

The method may involve characterising the target polynucleotide. As the target polynucleotide is contacted with the pore, one or more measurements which are indicative of one or more characteristics of the target polynucleotide are taken as the polynucleotide moves with respect to the pore.

The method may involve measuring two, three, four or five or more characteristics of each polynucleotide. The one or more characteristics are preferably selected from (i) the length of the polynucleotide, (ii) the identity of the polynucleotide, (iii) the sequence of the polynucleotide, (iv) the secondary structure of the polynucleotide and (v) whether or not the polynucleotide is modified. Any combination of (i) to (v) may be measured in accordance with the invention, such as {i}, {ii}, {iii}, {iv}, {v}, {i, iii}, {i, iv}, {i, v}, {ii, iv}, {ii, v}, {iii, iv}, {iii, v}, {iv, v}, {i, ii, iv}, {i, ii, v}, {i, iii, iv}, {i, iii, v}, {i, iv, v}, {ii, iii, iv}, {ii, iii, v}, {ii, iv, v}, {iii, iv, v}, {i, ii, iii, v}, {i, ii, iii, v}, {i, ii, iv, v}, {i, iii, iv, v}, {ii, iii, iv, v} or {i, ii, iii, iv, v}.

For (i), the length of the polynucleotide may be measured for example by determining the number of interactions between the polynucleotide and the pore or the duration of interaction between the polynucleotide and the pore.

For (ii), the identity of the polynucleotide may be measured in a number of ways. The identity of the polynucleotide may be measured in conjunction with measurement of the sequence of the polynucleotide or without measurement of the sequence of the polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the polynucleotide as coming from a particular source.

For (iii), the sequence of the polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem Soc. 2010; 132(50):17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the polynucleotide is modified by methylation, by oxidation, by damage, with one or more proteins or with one or more labels, tags or spacers. Specific modifications will result in specific interactions with the pore which can be measured using the methods described below. For instance, methylcyotsine may be distinguished from cytosine on the basis of the current flowing through the pore during its interaction with each nucleotide.

The methods may be carried out using any apparatus that is suitable for investigating a membrane/pore system in which a pore is present in a membrane. The method may be carried out using any apparatus that is suitable for transmembrane pore sensing. For example, the apparatus comprises a chamber comprising an aqueous solution and a barrier that separates the chamber into two sections. The barrier typically has an aperture in which the membrane containing the pore is formed. Alternatively the barrier forms the membrane in which the pore is present.

The methods may be carried out using the apparatus described in WO 2008/102120).

A variety of different types of measurements may be made. This includes without limitation: electrical measurements and optical measurements. A suitable optical method involving the measurement of fluorescence is disclosed by J. Am. Chem. Soc. 2009, 131 1652-1653. Possible electrical measurements include: current measurements, impedance measurements, tunnelling measurements (Ivanov A P et al., Nano Lett. 2011 Jan. 12; 11(1):279-85), and FET measurements (International Application WO 2005/124888). Optical measurements may be combined with electrical measurements (Soni G V et al., Rev Sci Instrum. 2010 January; 81(1):014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO 2000/28312. Alternatively, electrical measurements may be made using a multi-channel system, for example as described in International Application WO 2009/077734 and International Application WO 2011/067559.

The method is preferably carried out with a potential applied across the membrane. The applied potential may be a voltage potential. Alternatively, the applied potential may be a chemical potential. An example of this is using a salt gradient across a membrane, such as an amphiphilic layer. A salt gradient is disclosed in Holden et al., J Am Chem Soc. 2007 Jul. 11; 129(27):8650-5. In some instances, the current passing through the pore as a polynucleotide moves with respect to the pore is used to estimate or determine the sequence of the polynucleotide. This is strand sequencing.

The methods may involve measuring the current passing through the pore as the polynucleotide moves with respect to the pore. Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods may involve the measuring of a current passing through the pore as the polynucleotide moves with respect to the pore. Suitable conditions for measuring ionic currents through transmembrane protein pores are known in the art and disclosed in the Example. The method is typically carried out with a voltage applied across the membrane and pore. The voltage used is typically from +5 V to −5 V, such as from +4 V to −4 V, +3 V to −3 V or +2 V to −2 V. The voltage used is typically from −600 mV to +600 mV or −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The charge carriers may be asymmetric across the membrane. For instance, the type and/or concentration of the charge carriers may be different on each side of the membrane.

The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is phosphate buffer. Other suitable buffers are HEPES and Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

Free Nucleotides and Co-Factors

The method may be carried out in the presence of free nucleotides or free nucleotide analogues and/or an enzyme cofactor that facilitates the action of the polynucleotide binding protein. The method may also be carried out in the absence of free nucleotides or free nucleotide analogues and in the absence of an enzyme cofactor. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the polynucleotide binding protein to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$.

Measurement Types

A variety of different types of measurements may be made. This includes without limitation: electrical measurements and optical measurements. A suitable optical method involving the measurement of fluorescence is disclosed by J. Am. Chem. Soc. 2009, 131 1652-1653. Possible electrical measurements include: current measurements, impedance measurements, tunnelling measurements (Ivanov A P et al., Nano Lett. 2011 Jan. 12; 11(1):279-85), and FET measurements (International Application WO 2005/124888). Optical measurements may be combined with electrical measurements (Soni G V et al., Rev Sci Instrum. 2010 January; 81(1):014301). The measurement may be a transmembrane current measurement such as measurement of ionic current flowing through the pore. Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO 2000/28312. Alternatively, electrical measurements may be made using a multi-channel system, for example as described in International Application WO 2009/077734 and International Application WO 2011/067559.

The method is preferably carried out with a potential applied across the membrane. The applied potential may be a voltage potential. Alternatively, the applied potential may be a chemical potential. An example of this is using a salt gradient across a membrane, such as an amphiphilic layer. A salt gradient is disclosed in Holden et al., J Am Chem Soc. 2007 Jul. 11; 129(27):8650-5. In some instances, the current passing through the pore as a polynucleotide moves with respect to the pore is used to estimate or determine the sequence of the polynucleotide. This is strand sequencing.

Kits

The invention also provides a kit for use in a method of the invention. The kit typically comprises: a polynucleotide-guided effector protein and an anchor capable of coupling to a membrane. The kit may further comprise one or more of a guide polynucleotide, an adaptor sequence, a polynucleotide binding protein capable of moving along a polynucleotide and/or a leader sequence. The kit may further comprise a microparticle.

The guide polynucleotide, polynucleotide-guided effector protein, anchor, adaptor, polynucleotide binding protein, leader sequence and/or microparticle may be any of those defined herein. The kit may comprise a panel of guide polynucleotides or of guide polynucleotide/polynucleotide-guided effector protein complexes. The panel is typically designed for a particular purpose, such as to detect a particular microorganism, markers associated with a disease, particular polymorphisms etc.

The kit may comprise components of any of the membranes disclosed above, such as an amphiphilic layer or a triblock copolymer membrane. The kit may further comprise a transmembrane pore. Any of the embodiments discussed above with reference to the method equally apply to the kits.

The kit may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides, a membrane as defined above or voltage or patch clamp apparatus. Reagents may be present in the kit in a dry state such that a fluid sample is used to resuspend the reagents. The kit may also, optionally, comprise instructions to enable the kit to be used in the methods described herein or details regarding for which organism the method may be used. The kit may comprise a magnet or an electromagnet. The kit may, optionally, comprise nucleotides.

The kit may comprise a guide polynucleotide having an end extension, or first and second end extensions as described herein and a capture oligonucleotide or first and second capture oligonucleotides as described herein. The kit may further comprise a competitor oligonucleotide as described herein. The kit may further comprise beads comprising one half of an affinity molecule pair (e.g. streptavidin) and first and second capture oligonucleotides comprising the other half of an affinity molecule pair (e.g. biotin). The first and second capture oligonucleotides may each be bound to a separate surface, e.g. to a separate population of beads. The first capture oligonucleotide may be bound, for example, to "purification" beads or to a "purification" column. The second capture oligonucleotide may be bound, for example, to "delivery" beads. The "purification" beads and/or the "delivery" beads may be magnetic.

Also provided is a system for detecting a target polynucleotide in a sample comprising: a nanopore; a polynucleotide-guided effector protein comprising a guide polynucleotide binding domain; and a guide polynucleotide comprising a first portion that is complementary to a sequence in a portion of the target polynucleotide and a structure that is adapted to bind to the guide polynucleotide binding domain of the polynucleotide-guided effector protein. In one embodiment, the system further comprises a membrane, wherein the nanopore is present in the membrane. In one embodiment, the system further comprises a target polynucleotide. In one embodiment of the system, the target polynucleotide, guide polynucleotde and polynucleotide-guided effector protein form a complex. In one embodiment of the system, the target polynucleotide is coupled to a membrane.

The following non-limiting Examples illustrate the invention.

Example 1

This Example describes a method for detection of a specific target polynucleotide in a mixture by a nanopore. In this Example, the target DNA is identified using two types of CRISPR-Cas probes that bind to a target polynucleotide. The first contains an extension that anchors the target polynucleotide to the membrane via a cholesterol-tagged CRISPR-Cas probe. The second ("the analyte") bears an extension carrying a bound polynucleotide binding protein (helicase), and positively identifies the target polynucleotide indirectly via polynucleotide binding protein controlled movement of a barcode sequence on the analyte through a nanopore.

Materials and Methods

Oligonucleotides AR131 and AR132 were annealed, each at 40 µM, in 10 mM Tris-Cl (pH 8.0), 1 mM EDTA, 100 mM NaCl, from 95° C. to 25° C. at 0.6° C. per minute. The hybridised DNA was known as "cholesterol hyb" (ONLA17351).

Oligonucleotides AR130 and ONLA11326 were annealed, each at 40 µM, in 10 mM Tris-Cl (pH 8.0), 1 mM EDTA, 100 mM NaCl, from 95° C. to 25° C. at 0.6° C. per minute. The hybridised DNA was known as ONLA17350. The polynucleotide binding protein was loaded and closed on the stall-containing strand of ONLA17350 as follows: the helicase was buffer-exchanged into 50 mM HEPES (pH 8.0), 100 mM potassium acetate, 1 mM EDTA using a Zeba desalting column (Thermo); the helicase was loaded on ONLA17350 by incubation (200 µl) of 500 nM (molecules) ONLA17350 with a 3.5 µM buffer-exchanged helicase in 50 mM HEPES (pH 8.0), 100 mM potassium acetate at room temperature for 5 min. The helicase was then closed around DNA by incubation of the mixture with 100 µM TMAD for 1 h at room temperature (final volume, 220 µl). Non-specifically bound and unclosed helicase was run off the adaptor using 0.25-volume equivalent of a salt-ATP stress buffer (55 µl) comprising 5 mM ATP, 10 mM MgCl$_2$, 2.5 M NaCl, 100 mM Tris (pH 8.0) (final volume, 275 µl), for 25 min at room temperature. The complex was subjected to SPRI purification by addition of 3.7-volume equivalents of SPRI beads in 25 mM Tris-Cl (pH 7.5 at 21° C.), 28% (w/v) PEG-8000, 2.5 M NaCl for 5 min at room temperature. The beads were pelleted on a magnetic rack and the supernatant removed. While still on the magnetic rack the beads were washed with 500 ul of 50 mM Tris (pH 7.5 at 21° C.), 2.5 M NaCl, 20% PEG (w/v) 8,000, turning through 360° to bathe the pellet on the rack. The wash buffer was removed and the pellet pulsed briefly in a centrifuge before returning to the magnetic rack to remove the last remnants of solution. The pellet was then resuspended in 30 ul of 25 mM Tris-Cl (pH 7.5 at 21° C.), 20 mM NaCl for 5 mins at room temperature before being placed on a magnetic rack to recover the purified adapter which was known as "helicase-Y-adaptor hyb".

A 3.6-kilobase test analyte was amplified by PCR using specific primers directed against lambda phage genomic DNA, resulting in a double-stranded DNA analyte bearing blunt ends. This analyte was known as "blunt lambda 3.6 kb".

CRISPR RNAs ("crRNAs") bearing 3' extensions that allow hybridisation to either "cholesterol hyb" or "helicase-Y-adaptor hyb" were hybridised with tracrRNA by annealing 40 µM "Alt-R™" tracrRNA (purchased from IDT) with each crRNA separately in 10 mM Tris-Cl (pH 8.0), 1 mM EDTA, 100 mM NaCl from 65° C. to 25° C. at 1.0° C. per minute, resulting in complex known as a "guide RNA". CRISPR-dCas9 complexes were formed by incubating 100 nM "guide RNA" with 100 nM dCas9 (ONLP11836) in Cas9 binding buffer (20 mM HEPES-NaOH, 100 mM NaCl, 5 mM MgCl$_2$, 0.1 mM EDTA, pH 6.5 at 25° C.), for 10 minutes at 21° C., yielding 100 nM of CRISPR-dCas9 complex. These complexes, with bound dCas9, were known as "anchor probes" or "helicase probes", according to whether "cholesterol hyb" or "helicase-Y-adaptor hyb" can anneal to the crRNA 3' extension, respectively.

In this example, the "anchor probes" comprised oligonucleotide AR145 or AR138 or AR141 or AR142, hybridised separately to tracrRNA, with bound dCas9, at a molecular concentration of 100 nM of each named species.

In this Example, the "helicase probes" comprised 100 nM oligonucleotides AR133 or AR134 or AR135, hybridised separately to tracrRNA, with bound dCas9, at a molecular concentration of 100 nM of each named species.

The "anchor probes" and "helicase probes" were pooled together in the following combinations, to a total of 204 according to the table below:

| "Probe combination" | "Anchor probes" | "Helicase probes" |
| --- | --- | --- |
| A | AR145 | AR133 |
| B | None (control) | AR133 |
| C | AR145 | None (control) |
| D | AR138, AR141, AR142 | AR134, AR135 |
| E | None (control) | None (control) |

These mixtures were known as "probe combinations".

To 20 µl of "probe combinations" (100 nM molecules) was added 1.1 µl of target DNA ("blunt 3.6 kb, ONLA17510") to a final concentration of 10 nM molecules of ONLA17510, resulting in a complex known as "probe-target complex". 21.1 µL of "probe-target complex" was diluted to a final volume of 100 µL in a mixture of "helicase-Y-adaptor hyb", "cholesterol hyb", HEPES-KOH, KCl, MgCl$_2$ and rATP, resulting in final concentrations of 25 mM HEPES-KOH, 500 mM KCl, 10 mM MgCl$_2$, 10 mM rATP, 30 nM "helicase-Y-adaptor hyb", 100 nM "cholesterol hyb", 10 nM "CRISPR-dCas9 complex", pH 8.0, known as "MinION reaction mix". The "MinION reaction mix" was incubated for 10 min at ambient temperature before subjecting the mixture to nanopore analysis, as follows: Electrical measurements were acquired from single CsgG nanopores inserted in block co-polymer in buffer at 37° C. (25 mM HEPES-KOH, 150 mM potassium ferrocyanide (II), 150 mM potassium ferricyanide (III), pH 8.0). After achieving a single pore inserted in the block co-polymer, buffer (2 mL, 25 mM HEPES-KOH, 150 mM potassium ferrocyanide (II), 150 mM potassium ferricyanide (III), pH 8.0) was flowed through the system to remove any excess CsgG nanopores. All subsequent steps were performed at 34° C. The cis compartment was equilibrated with 500 µl of 25 mM HEPES-KOH (pH 8.0), 500 mM KCl, 10 mM MgCl$_2$ and 10 mM rATP (known as "wash buffer"), with 10 mins between each wash. 75 µl of "MinION reaction mix", pre-incubated for 10 min at 21° C., was applied to the flow-cell and incubated for 10 min to allow any probe-dCas9 complexes contacting target DNA to attach to the block co-polymer. After a further 10 min, a further 2 mL of "wash buffer" was perfused through the flow-cell to remove any non-specific target DNA, including any dCas9-bound CRISPR probes and "helicase-Y-adaptor hybs" not contacting the target. The experiment was run at 180 mV and helicase-controlled DNA movement monitored. The electrical signals resulting from the translocation of DNA strands were analysed by counting the frequency of nanopore of the helicase-Y-adaptor hyb, identified by its distinctive electrical current signal.

Results

Figure 8:
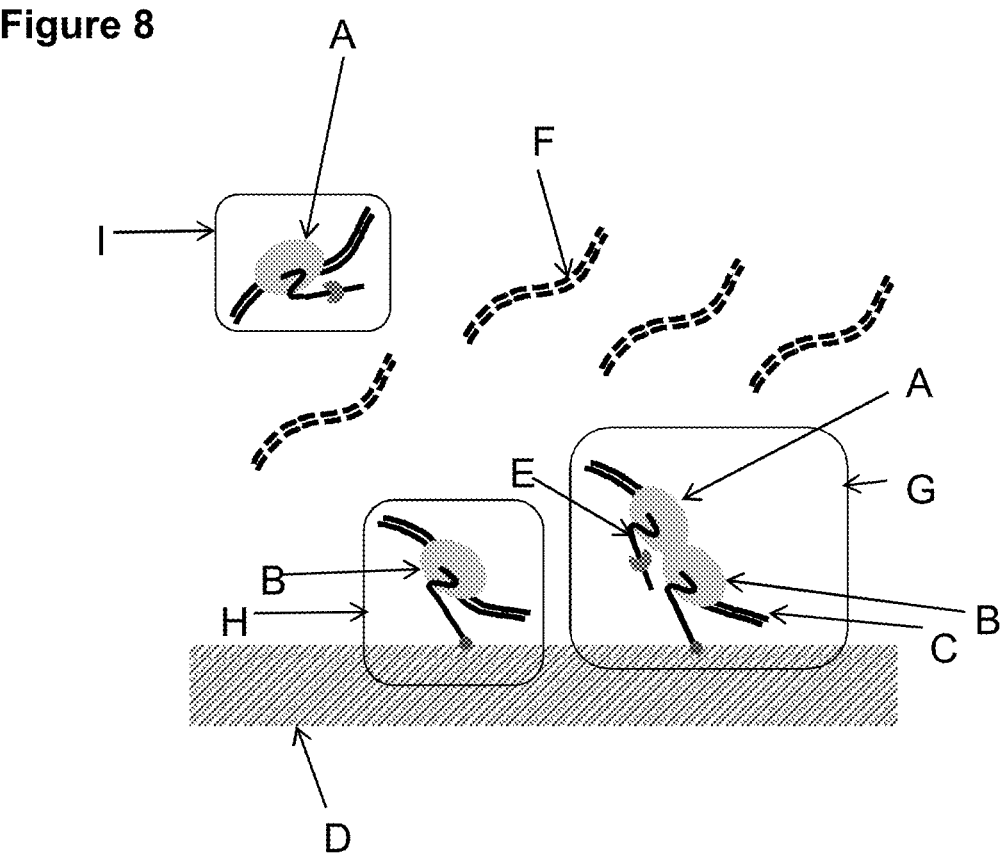
FIG. 8 shows an example in which CRISPR-Cas9 complexes (A, B) directed against two adjacent loci on a target DNA C may be used to positively identify a sample. Complex A contains a crRNA bearing an enzyme-loaded extension, as per FIG. 3. Complex B contains a crRNA complex bearing an anchoring extension, as per FIG. 4. DNA bearing a locus that binds Complex B binds to surface D such as a tri-block polymer membrane. The enzyme bound to Complex A may control the movement of a barcoded DNA analyte E through a nanopore. Following the removal of non-specific analytes (including species with no target loci, F) from solution, via flushing the system, only entity G bearing the two loci will be detected, and not entities F, H or I.
Figure 23:
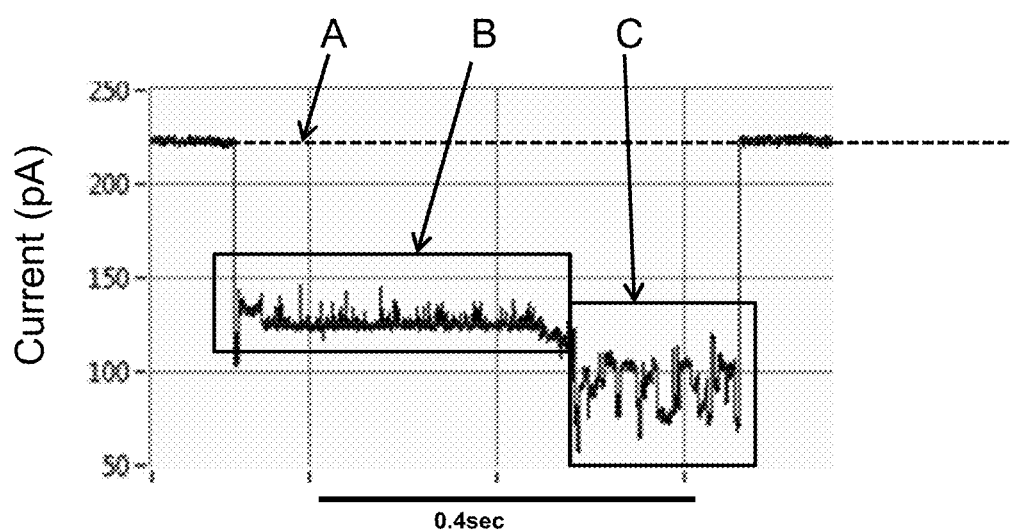
FIG. 23 shows an example trace of the nanopore current signature detected by enzyme-controlled movement of a barcoded oligonucleotide on an enzyme-extended dCas9, as per FIG. 16. The current trace comprises: open pore level A, leader signature B, and barcode signature C.
Figure 24:
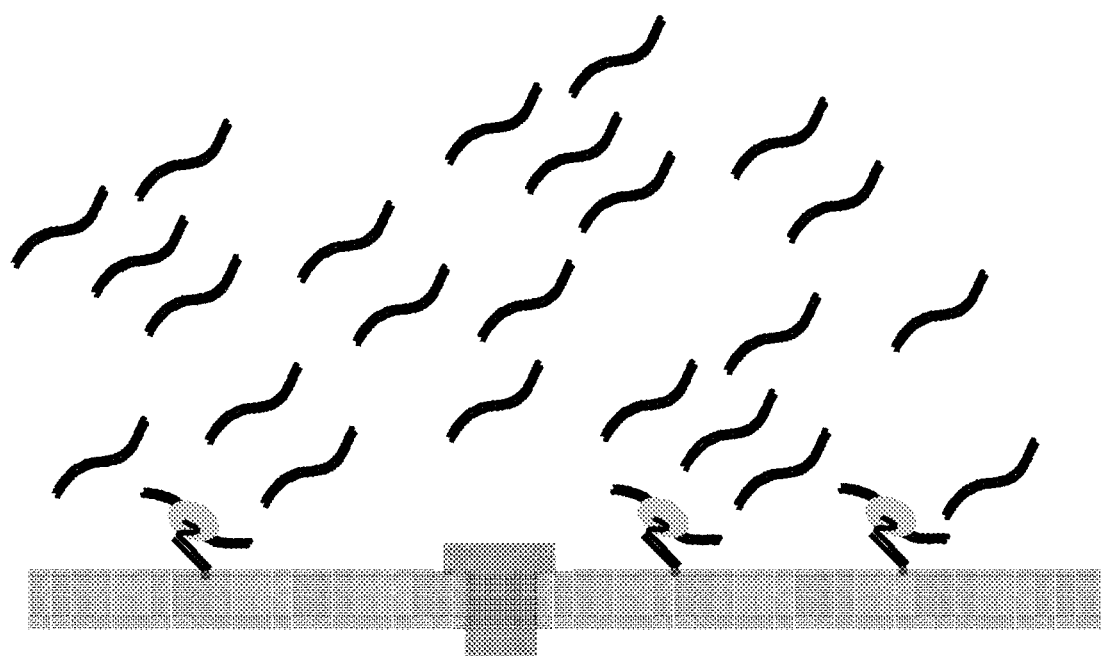
FIG. 24 illustrates how guide polynucleotide/polynucleotide-guided effector proteins may be used to bring polynucleotide targets to a membrane comprising a transmembrane pore. The unbound polynucleotides may be flushed away prior to application of a transmembrane potential and detection of the polynucleotide/polynucleotide-guided effector protein/target polynucleotide complex using the transmembrane pore.
Figure 25:
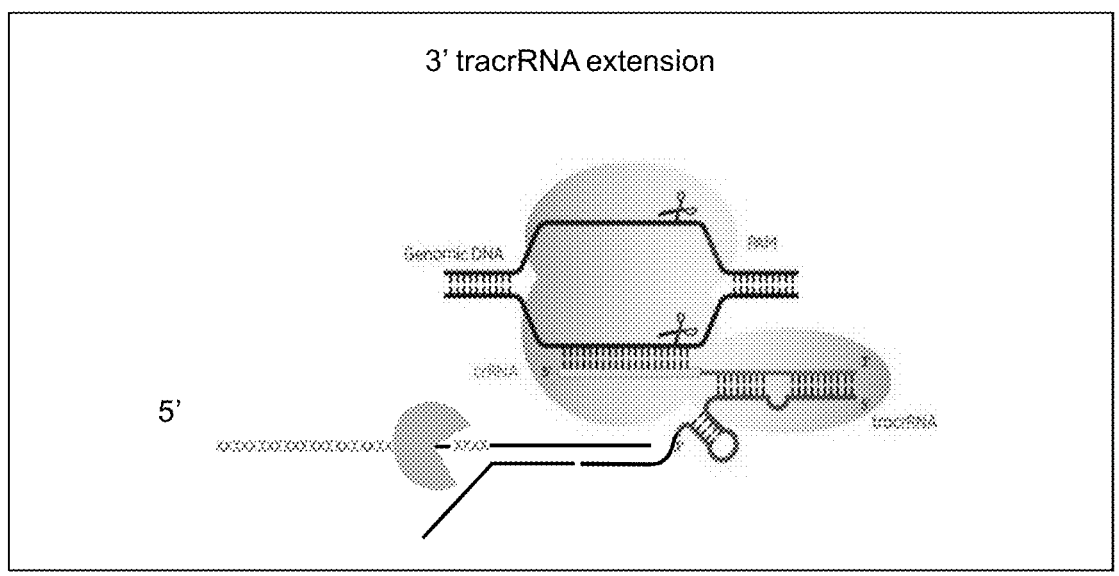
FIG. 25 shows examples of how an adaptors and leader sequence may be attached to guide RNA.
Figure 25:
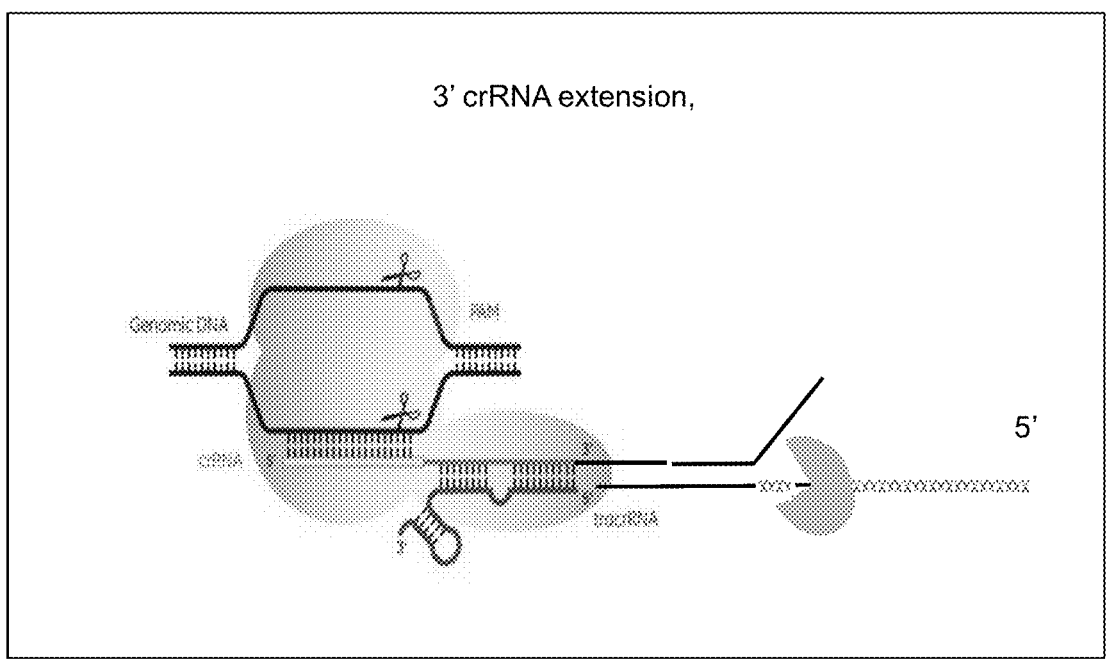
Figure 26:
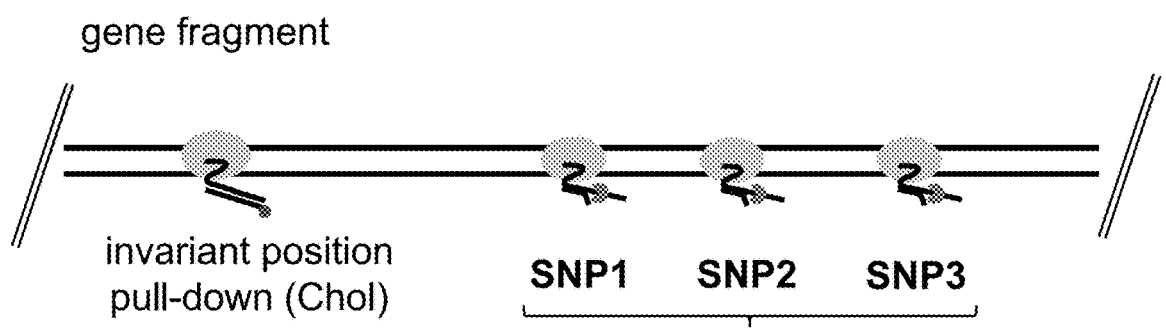
FIG. 26 shows how the method of the invention may be used to detect the presence or absence of SNPs using a guide polynucleotide/polynucleotide-guided effector protein comprising a membrane anchor to tether a polynucleotide to a membrane and guide polynucleotide/polynucleotide-guided effector proteins specific for different SNPs and comprising barcoded adaptors to distinguish between the SNPs.

The helicase was used to control the movement of Cas-contacted pre-sequencing mix, tethered to tri-block copolymer via "cholesterol hyb", through an CsgG nanopore. FIG. 8 shows a target DNA molecule bearing two CRISPR-dCas9 probes bound to their cognate sites in the target DNA. FIG. 23 shows the electrical signal resulting from helicase-controlled translocation of the analyte through the nanopore. The example signals show that both the "anchor probes" and the "helicase probes" contacted the target DNA. The data demonstrate that immobilisation of the target polynucleotide via a tethered CRISPR-dCas9 complex successfully identified the target DNA polynucleotide.

Example 2

This Example describes a method for direct enrichment and sequencing of a fragment containing a specific 20 nt target DNA polynucleotide sequence ("target") from a mixture by nanopore sequencing, wherein the target DNA contacts a cholesterol-tagged CRISPR-Cas probe and movement of DNA through the nanopore is controlled by a DNA motor protein. In this example, the "target" is positively identified directly by its sequence. The bound CRISPR-Cas probe may temporarily stall the translocation of the helicase and may thus also be used to additionally positively identify the sample.

Materials and Methods

Oligonucleotides AR131 and AR132 were annealed, each at 40 µM, in 10 mM Tris-Cl (pH 8.0), 1 mM EDTA, 100 mM NaCl, from 95° C. to 25° C. at 0.6° C. per minute. The hybridised DNA was known as "cholesterol hyb" (ONLA17351).

CRISPR RNAs ("crRNAs") bearing 3' extensions that allow hybridisation to a "cholesterol hyb" were hybridised with tracrRNA by annealing 40 µM "Alt-R™" tracrRNA (purchased from IDT) with oligonucleotide AR139 in 10 mM Tris-Cl (pH 8.0), 1 mM EDTA, 100 mM NaCl from 65° C. to 25° C. at 1.0° C. per minute, resulting in a complex known as a "guide RNA". CRISPR-dCas9 complexes were formed by incubating 100 nM "guide RNA" with 100 nM dCas9 (ONLP11836) in Cas9 binding buffer (20 mM HEPES-NaOH, 100 mM NaCl, 5 mM MgCl$_2$, 0.1 mM EDTA, pH 6.5 at 25° C.), for 10 minutes at 21° C., yielding 100 nM of CRISPR-dCas9 complex. These complexes, with bound dCas9, were known as "anchor probes" because "cholesterol hyb" could anneal to the crRNA 3' extension. Enterobacteria lambda phage genomic DNA was fragmented to an average size of approximately 1 kb using a gTube (Covaris, Inc.). The fragmented DNA was end-repaired and dA-tailed using an NEBNext End-Repair/dA-tailing Module (NEB). Standard SK007 adapter was ligated to end-repaired, fragmented lambda phage DNA purified using SPRI beads. To the resultant library (25 µl; 1 µg total DNA) was added 275 nM (molecules) of ONLA16941 at room temperature for >5 minutes to block the leader against non-specific hybridisation of "cholesterol hyb". The resultant DNA library, bearing end-ligated, loaded helicase on both DNA ends, was known as "pre-sequencing mix".

To 12 µl pre-sequencing mix was added 33 µl "anchor probe", yielding a mixture containing 73 nM "anchor probe" and approx. 0.32 nM target sites. The binding was allowed to proceed for 10 min at 21° C., after which the mixture was subjected to purification step using SPRI magnetic beads, as follows: 0.4 volume equivalents of AMPure XP SPRI magnetic beads (Beckman Coulter) were added to the mixture and the resultant mixture agitated for 5 min at 21° C. The magnetic beads were pelleted using a magnetic separator, the supernatant aspirated, and 100 µl of 50 mM Tris-Cl, 2.5 M NaCl, 20% PEG 8,000 (pH 7.5 at 25° C.) added to the beads while still on the rack, turning the pellet through 360° to wash the pellet on the rack. The beads were immediately pelleted once more and the supernatant aspirated, after which the tube was removed from the rack and 45 µl of a buffer containing of 25 mM Tris-Cl, 20 mM NaCl (pH 7.5 at 25° C.) added to the beads to elute the DNA by incubation for 5 min at 21° C. The beads were pelleted using the magnetic separator, and the eluate retained (known as "probe-target complex").

45 µL of "probe-target complex" was diluted to a final volume of 330 µL in a mixture of ONLA17351, HEPES-KOH, KCl, MgCl$_2$ and rATP, resulting in final concentrations of 25 mM HEPES-KOH, 500 mM KCl, 10 mM MgCl$_2$, 10 mM rATP, 10 nM ONLA17351, 10 nM "CRISPR-dCas9 complex" and approx. 44 pM target sites, pH 8.0, known as "MinION reaction mix".

Electrical measurements were acquired from single CsgG nanopores inserted in block co-polymer in buffer at 37° C. (25 mM HEPES-KOH, 150 mM potassium ferrocyanide (II), 150 mM potassium ferricyanide (III), pH 8.0). After achieving a single pore inserted in the block co-polymer, buffer (2 mL, 25 mM HEPES-KOH, 150 mM potassium ferrocyanide (II), 150 mM potassium ferricyanide (III), pH 8.0) was flowed through the system to remove any excess CsgG nanopores. All subsequent steps were performed at 34° C. The cis compartment was equilibrated with 500 µl of 25 mM HEPES-KOH (pH 8.0), 500 mM KCl, 10 mM MgCl$_2$ and 10 mM rATP (known as "wash buffer"), with 10 mins between each wash. 150 µl of "MinION reaction mix", pre-incubated for 10 min at 21° C., was applied to the flow-cell and incubated for 10 min to allow any cholesterol: CRISPR probed:Cas9 complexes contacting target DNA to attach to the block co-polymer. After a further 10 min, a further 2 mL of "wash buffer" was perfused through the flow-cell to remove any non-specific target DNA. The experiment was run at 180 mV and helicase-controlled DNA movement monitored. The electrical signals resulting from the translocation of DNA strands were analysed and their nucleotide sequences determined.

Results

Figure 9:
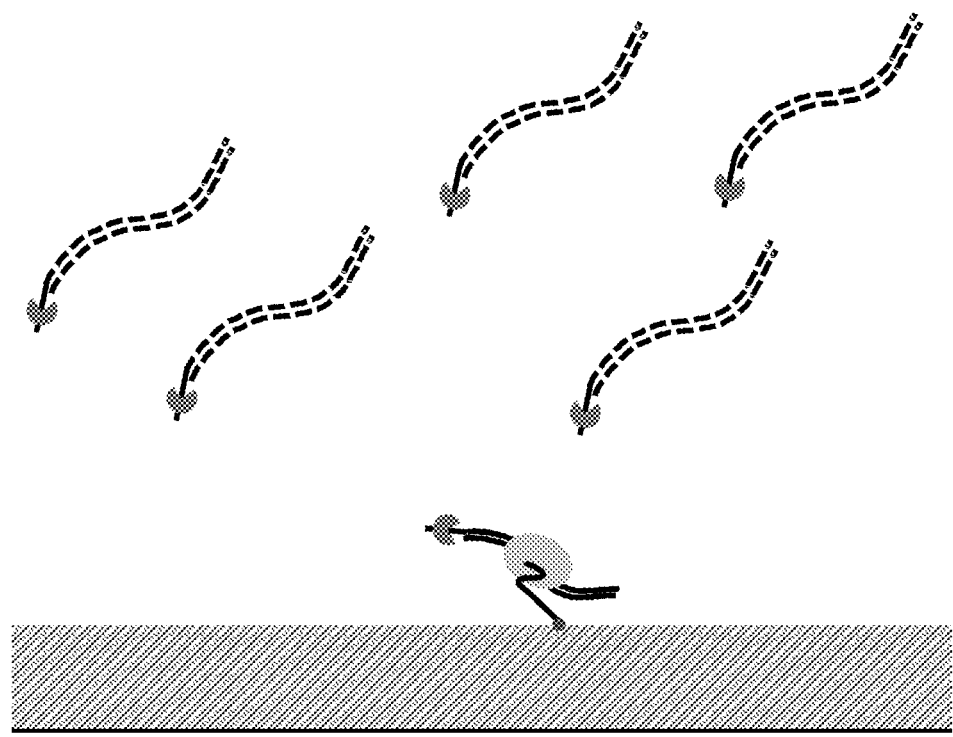
FIG. 9 shows an example in which an inactive Cas9 ('dCas9') bearing an extension containing an anchoring moiety may be used to enrich and determine the sequence of a target analyte via polynucleotide binding protein controlled translocation through a nanopore. In this example, an enzyme-bound adapter moiety is ligated to one or both ends of all DNA in solution. Only DNA containing the target locus binds the anchoring dCas9 complex.
Figure 10:
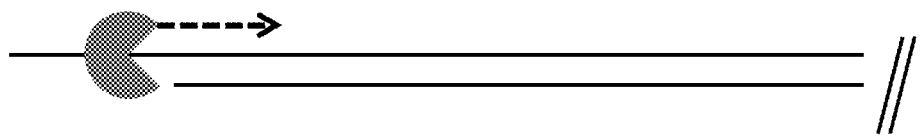
FIG. 10 shows a DNA analyte with a ligated, enzyme-bound adapter that may be used to control the movement of a DNA analyte through a nanopore.
Figure 11:
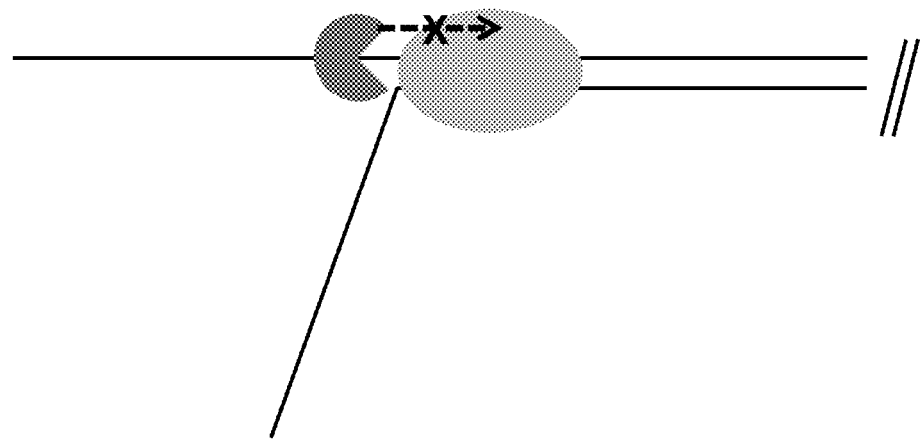
FIG. 11 shows a DNA analyte with bound enzyme, similar to FIG. 10, in which the translocation of the enzyme may be temporarily stalled by a CRISPR-dCas9 complex bound to a specific locus.
Figure 15:
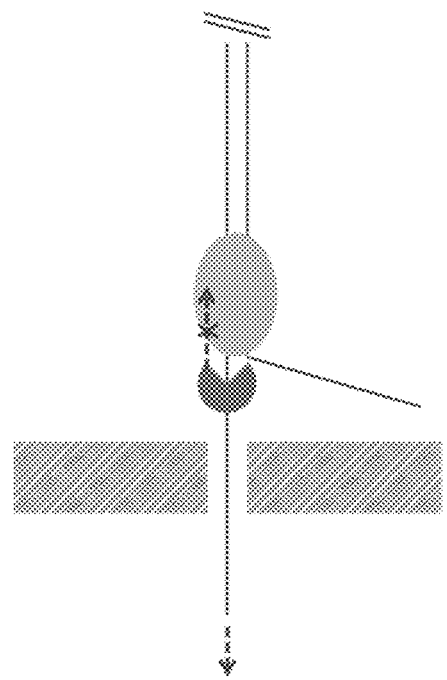
FIG. 15 shows a method for the sequencing of a target analyte with bound dCas9 in which the target analyte is derivatised with a polynucleotide binding protein bound adaptor, as per FIG. 7, and in which translocation of one of the two strands of the polynucleotide analyte is controlled through the nanopore by the polynucleotide binding protein. In this example, the dCas9 bound to the target analyte may produce a characteristic stall in the translocation of the polynucleotide binding protein, and thus in the ionic current measured through the nanopore.
Figure 16:
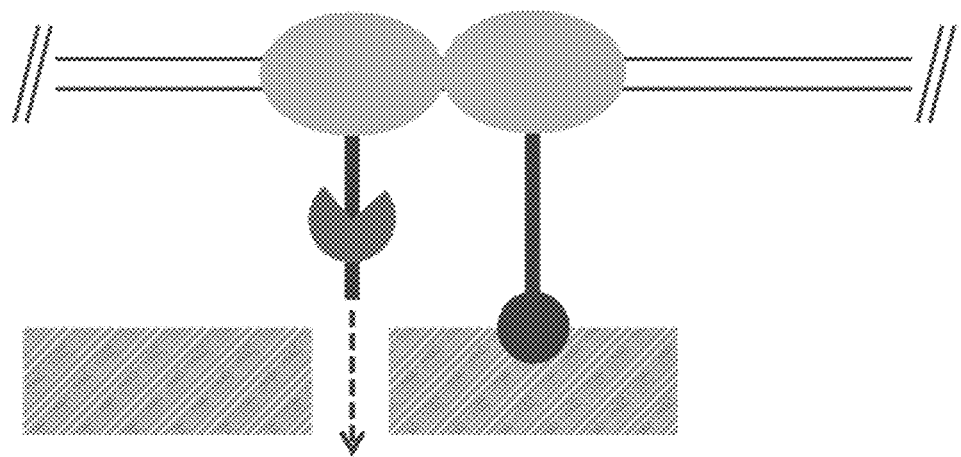
FIG. 16 shows a method for the identification of a target DNA anchored to a membrane, as per FIG. 8, via an extended CRISPR-dCas9 bearing a cholesterol moiety, as per FIG. 4, and identified by controlled movement of a barcoded, polynucleotide binding protein loaded oligonucleotide analyte hybridised to an extended CRISPR-dCas9 complex, as per FIG. 3, and which binds to a locus adjacent to the cholesterol-extended CRISPR-dCas9.
Figure 17:
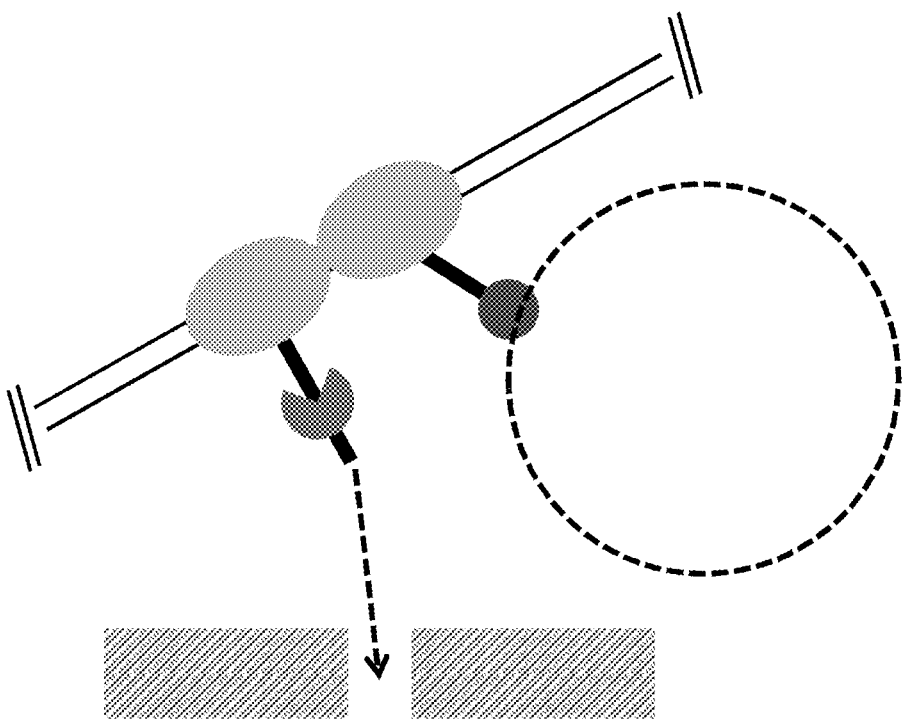
FIG. 17 shows a derivative of FIG. 16 in which the anchoring moiety may be, for example, biotin or desthiotin, and the anchoring moiety may bind to a streptavidin-derivatised bead or nanoparticle.
Figure 18:
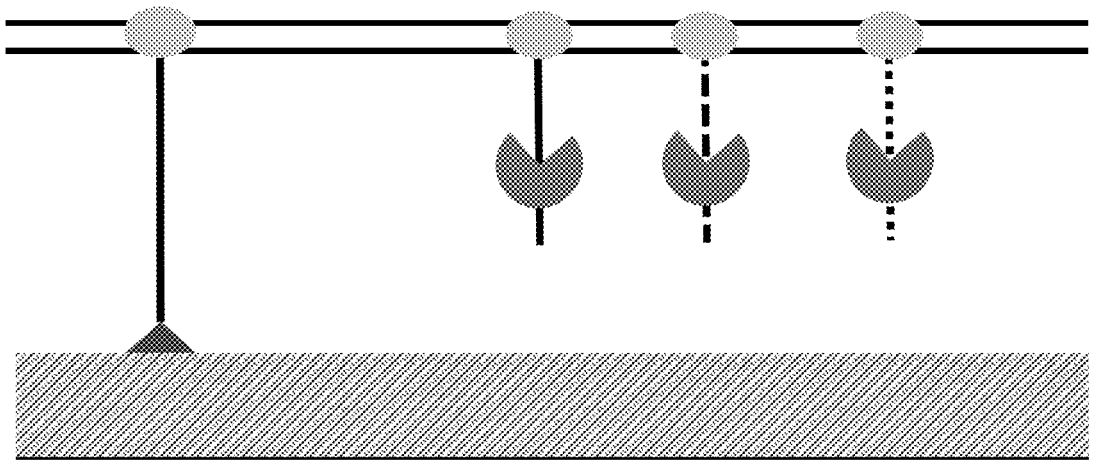
FIG. 18 shows an example of a target DNA that is anchored to a membrane via a cholesterol-extended CRISPR-dCas9 complex that binds to a known or common locus, and in which the same target DNA contains a number of unknown sequences whose presence or absence is determined by enzyme-extended CRISPR-dCas9 complexes. In this example, each enzyme-extended CRISPR-dCas9 complex carries a unique barcode that may be used to positively identify the presence or absence of the loci in combination, as per FIG. 16. The target DNA could also be directly coupled to the membrane rather than via the cholesterol-extended CRISPR-dCas9 complex.
Figure 19:
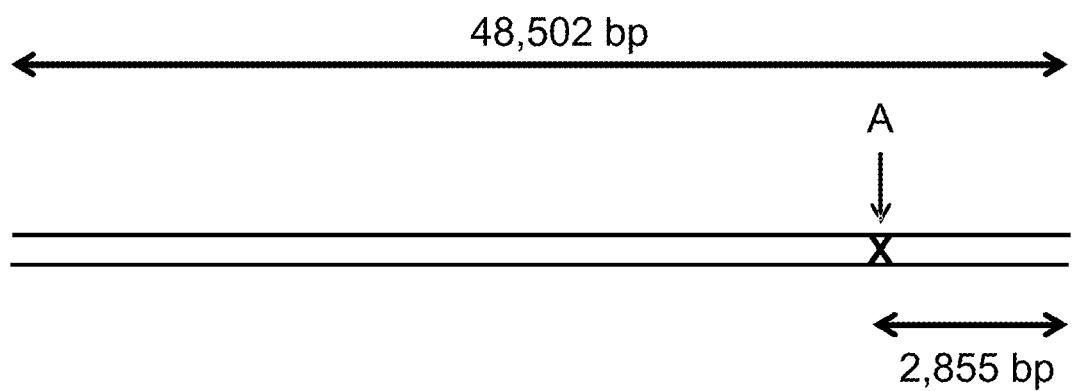
FIG. 19 shows an example polynucleotide, lambda phage DNA, and the position of a specific target locus A that is 2,855 bp from the end of the genome.
Figure 20:
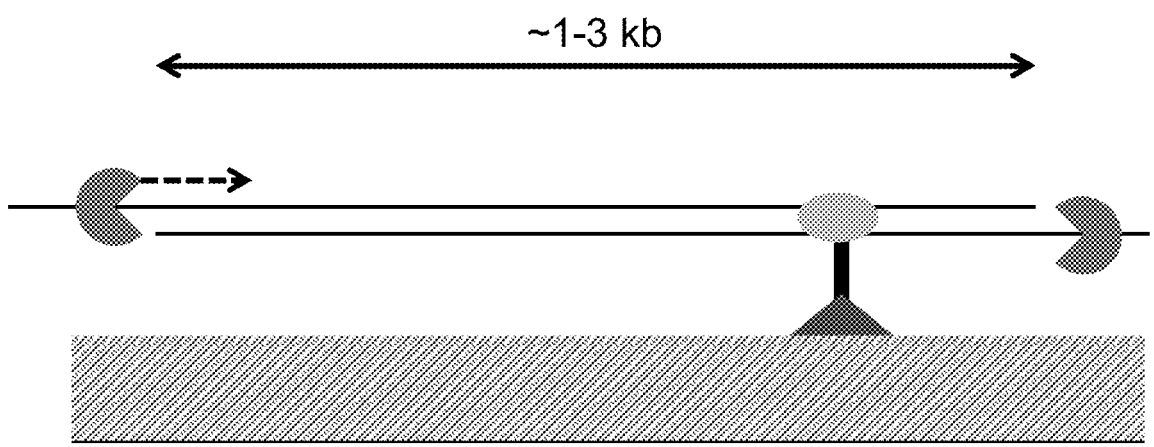
FIG. 20 shows the target locus of FIG. 19, with bound CRISPR-dCas9 bearing a cholesterol extension, fragmented randomly into 1-3 kb segments, with each segment bearing an polynucleotide binding protein loaded Y-adaptor at either or both ends for determining the sequence of the target polynucleotide. The assembly is anchored to a membrane surface via the cholesterol moiety.
Figure 21:
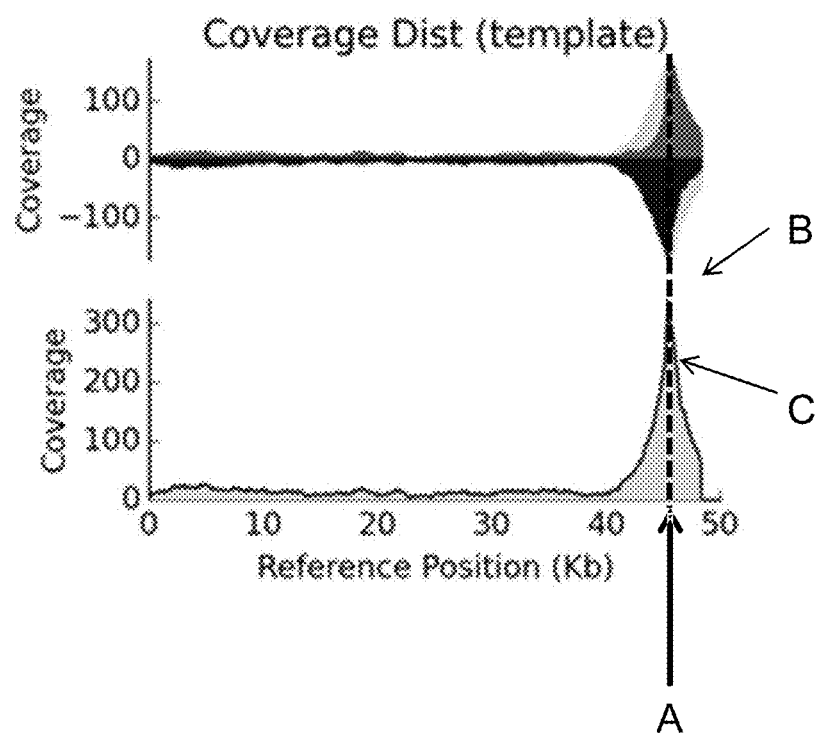
FIG. 21 shows a coverage plot of sequence data aligned against a phage lambda reference from an experiment in which phage lambda DNA was randomly fragmented into 1-3 kb segments; enzyme-Y-adaptor was ligated to the fragmented DNA; and a cholesterol-extended CRISPR-dCas9 was bound to the target shown in FIG. 19. The coverage plot shows enrichment of the specific locus A in the expected location (2,855 bp from the end of the lambda phage genome). The top panel shows the alignments accumulated from the forwards (B) and reverse (C) read directions, and the bottom panel shows the aggregate of the forwards and reverse orientations.
Figure 22:
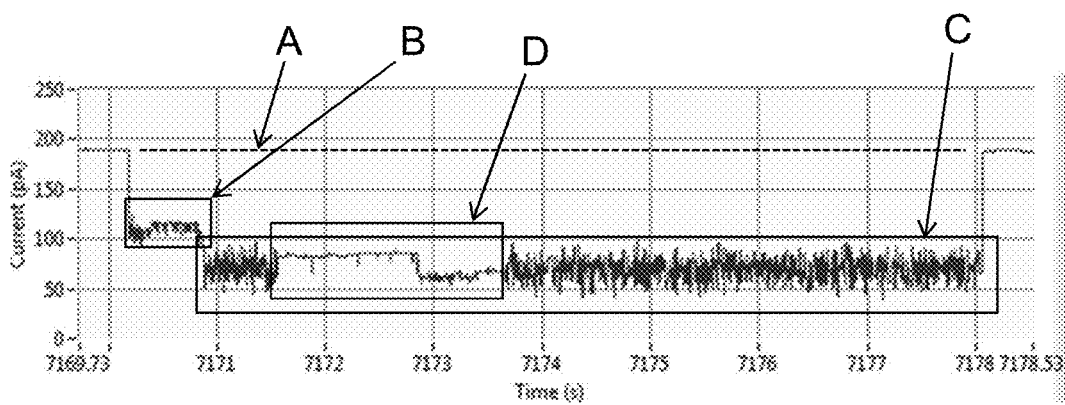
FIG. 22 shows an example trace of the nanopore current signature detected by polynucleotide binding protein controlled translocation of a target DNA bearing a bound, cholesterol-extended dCas9 at the locus shown in FIGS. 19 and 20. In this example, the dCas9 transiently stalls the translocation of the enzyme. The current traces comprises: open pore level A, leader signature B, target analyte signature C, and stall D.

The helicase was used to control the movement of Cas-contacted pre-sequencing mix, tethered to tri-block copolymer via "cholesterol hyb", through an CsgG nanopore. FIG. 9 shows a target DNA molecule bearing an end-loaded helicase, CRISPR-dCas9 bound to its cognate site and the cholesterol tether. FIG. 15 shows the path of the helicase and how its translocation might be transiently stalled upon encounter of the bound CRISPR-dCas9 complex. FIG. 22 shows the electrical signal resulting from helicase-controlled translocation of target DNA (in this case, a 3.6-kilobase fragment of lambda DNA) through the nanopore and one such transient stalling event, mid-way through the translocation event. The example signal shows that dCas9 contacted the target DNA, and that the helicase contacted the dCas9. The data demonstrate that immobilisation of the target polynucleotide via a tethered CRISPR-dCas9 complex successfully enriched (see FIG. 21) and sequenced the target DNA polynucleotide in preference to the other non-specific fragments.

Example 3

This Example describes a method for direct enrichment and sequencing of a fragment containing a specific 20 nt target DNA polynucleotide sequence ("target") from a mixture of DNA polynucleotides ("DNA") by nanopore sequencing, wherein the target DNA contacts a cholesterol-tagged CRISPR-Cas probe. In this Example, the mixture of oligonucleotides bear an polynucleotide binding protein loaded on a Y-adaptor at each end of the mixture of DNA. In this example, Y-adaptor does not contain a stall site, but is anchored to a membrane surface via a tether oligonucleotide containing a cholesterol moiety hybridised to the Y-adaptor. The motor protein fully unwinds any DNA in the mixture that does not contain a bound CRISPR-Cas complex, thereby releasing non-target DNA from the membrane. Additionally, an exonuclease, such as E. coli Exonuclease I, may be used to degrade the non-translocated strand of the target concomitantly with DNA motor translocation, as well as any non-target DNA in the sample that is fully unwound. The polynucleotide binding protein partially unwinds any DNA that contains a bound CRISPR-Cas complex, but stalls upon encounter of the CRISPR-Cas complex independent of the nanopore. Upon capture of the target by the nanopore, the CRISPR-Cas complex is dislodged from the target by the applied potential, thereby resuming the translocation of the polynucleotide binding protein on the target. The sequence of the analyte and the position of the stall may be used to positively identify the sample.

Methods

Oligonucleotides AR131 and AR132 were annealed, each at 40 µM, in 10 mM Tris-Cl (pH 8.0), 1 mM EDTA, 100 mM NaCl, from 95° C. to 25° C. at 0.6° C. per minute. The hybridised DNA was known as "cholesterol hyb" (ONLA17351).

CRISPR RNAs ("crRNAs") bearing 3' extensions that allow hybridisation to a "cholesterol hyb" were hybridised with tracrRNA by annealing 40 µM "Alt-R™" tracrRNA (purchased from IDT) with oligonucleotide AR145 in 10 mM Tris-Cl (pH 8.0), 1 mM EDTA, 100 mM NaCl from 65° C. to 25° C. at 1.0° C. per minute, resulting in a complex known as a "guide RNA". CRISPR-dCas9 complexes were formed by incubating 100 nM "guide RNA" with 100 nM dCas9 (ONLP11836) in Cas9 binding buffer (20 mM HEPES-NaOH, 100 mM NaCl, 5 mM $MgCl_2$, 0.1 mM EDTA, pH 6.5 at 25° C.), for 10 minutes at 21° C., yielding 100 nM of CRISPR-dCas9 complex. These complexes, with bound dCas9, were known as "anchor probes" because "cholesterol hyb" could anneal to the crRNA 3' extension.

Approx. 20 nM of Y-adapter ONLA17917, bearing the helicase, was ligated to 1 µg, of end-repaired, dA-tailed 3.6 kb DNA CS (ONLA17510) using 20,000 units of NEB Quick T4 DNA ligase in 66 mM Tris-Cl (pH. 8.0), 10 mM $MgCl_2$, 2 mM ATPγS, 4.5% (w/v) PEG-8000 in a volume of 100 µl at ambient temperature for 10 min. The ligated DNA was purified by SPRI purification as detailed in Example 2, except the DNA was eluted in 24 µl of 20 mM: CAPS, 40 mM KCl (pH 10). To this DNA was added 1.0 nM (molecules) of "anchor probes", and the sample incubated for 10 min at ambient temperature to allow the anchor probes to contact the target. To this DNA was added 10 nM (molecules) of SK43, an oligonucleotide bearing a cholesterol moiety that can hybridise to the Y-adaptor. This yielded a 3.6-kilobase target double-stranded DNA bearing an polynucleotide binding protein loaded Y-adaptor on each end, known as "MinION sequencing mix".

Pre-sequencing mix was diluted to a volume of 150 µl for analysis resulting in a mixture containing: 25 mM HEPES-KOH (pH 8.0), 500 mM KCl, 10 nM cholesterol hyb (ONLA17351), and approx. 250 ng of MinION sequencing mix.

Electrical measurements were acquired from single CsgG nanopores inserted in block co-polymer in buffer at 37° C. (25 mM HEPES-KOH, 150 mM potassium ferrocyanide (II), 150 mM potassium ferricyanide (III), pH 8.0). After achieving a single pore inserted in the block co-polymer, buffer (2 mL, 25 mM HEPES-KOH, 150 mM potassium ferrocyanide (II), 150 mM potassium ferricyanide (III), pH 8.0) was flowed through the system to remove any excess CsgG nanopores. All subsequent steps were performed at 34° C. The cis compartment was equilibrated twice with 500 µl of 25 mM HEPES-KOH (pH 8.0), 500 mM KCl (known as "fuel-less wash buffer"), with 10 mins between each wash. 150 µl of "MinION reaction mix", pre-incubated for 10 min at 21° C., was applied to the flow-cell and incubated for 10 min to allow any cholesterol: CRISPR probe:dCas9 complexes contacting target DNA to attach to the block co-polymer. After a further 10 min, a further 2 mL of "fuel-less wash buffer" was perfused through the flow-cell to remove any unbound target DNA. The experiment was run at 180 mV and nanopore currents monitored for approx. 800 s, after which the flow-cell was perfused with 2 mL of 25 mM HEPES-KOH (pH 8.0), 500 mM KCl, 10 mM ATP, 0.1 mM $MgCl_2$. The electrical signals resulting from the translocation of DNA strands were analysed and their nucleotide sequences determined.

Results

Figure 28A:
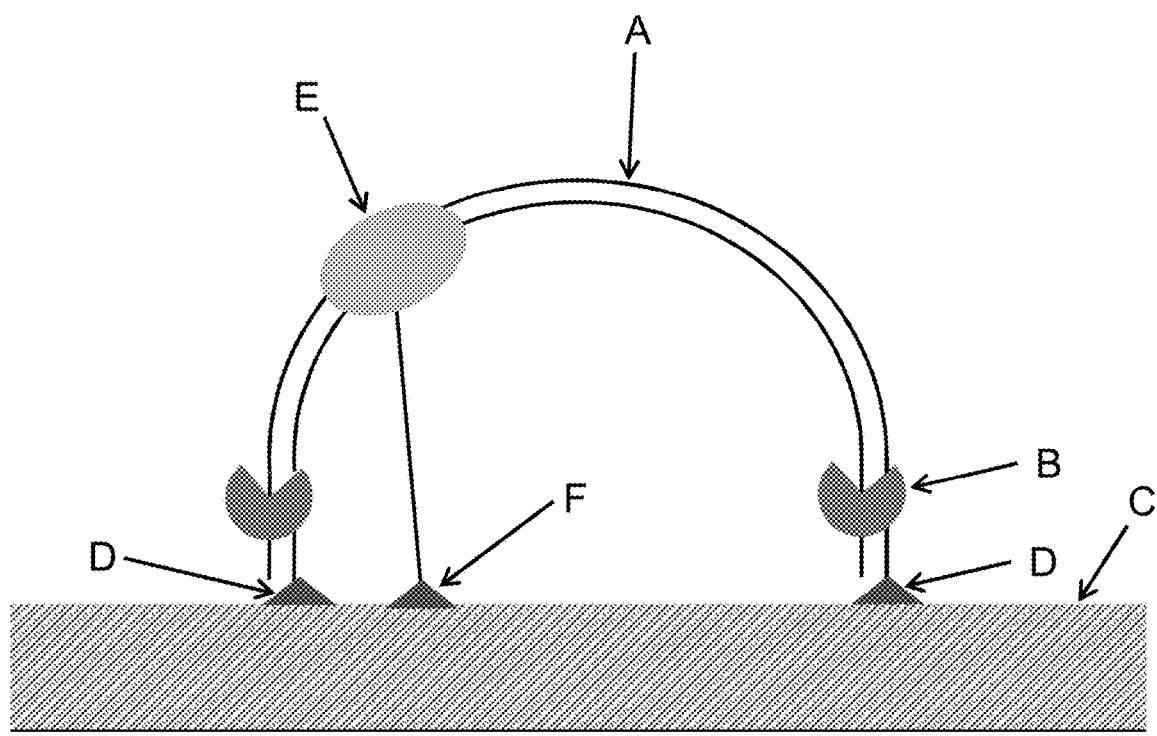
FIG. 28A shows the immobilisation of a target DNA analyte (A) comprising an enzyme-bound Y-adaptor (B) ligated to both ends, and tethered at both ends on a membrane (C) surface via oligonucleotides each bearing a cholesterol moiety (D). A bound CRISPR-dCas9 (E) bearing a cholesterol anchor (F), tethers the analyte to the membrane in a third position. This figure shows the system before the addition of MgATP to initiate enzyme translocation on DNA.
Figure 28B:
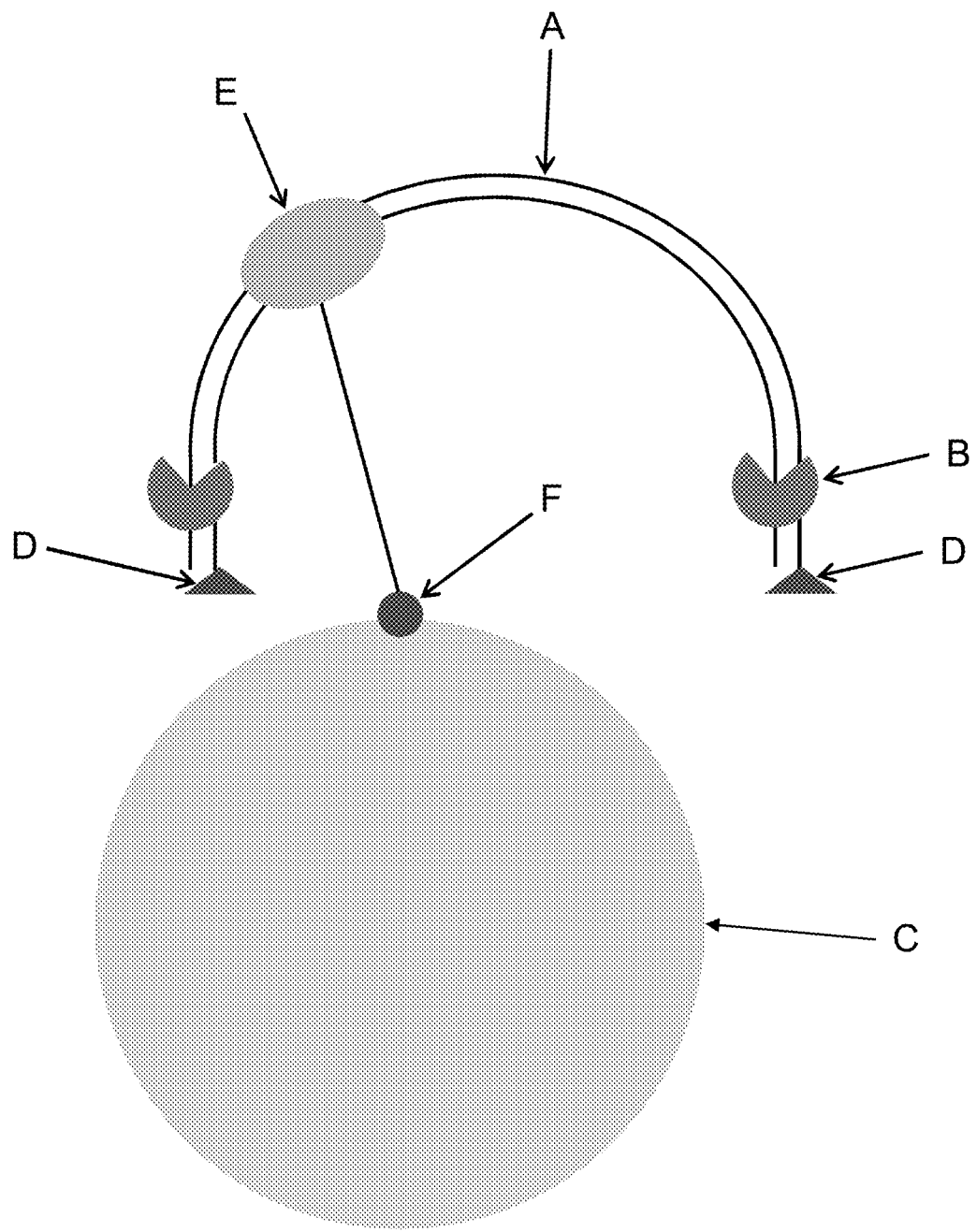
FIG. 28B shows the immobilisation of a target DNA analyte (A) comprising an enzyme-bound Y-adaptor (B) ligated to both ends, each bearing a cholesterol moiety (D). A bound CRISPR-dCas9 (E) bearing an affinity tag such as a biotin moiety (F), tethers the analyte to a bead (C) such as streptavadin. This Figure shows the system before the addition of MgATP to initiate enzyme translocation on DNA.
Figure 28C:
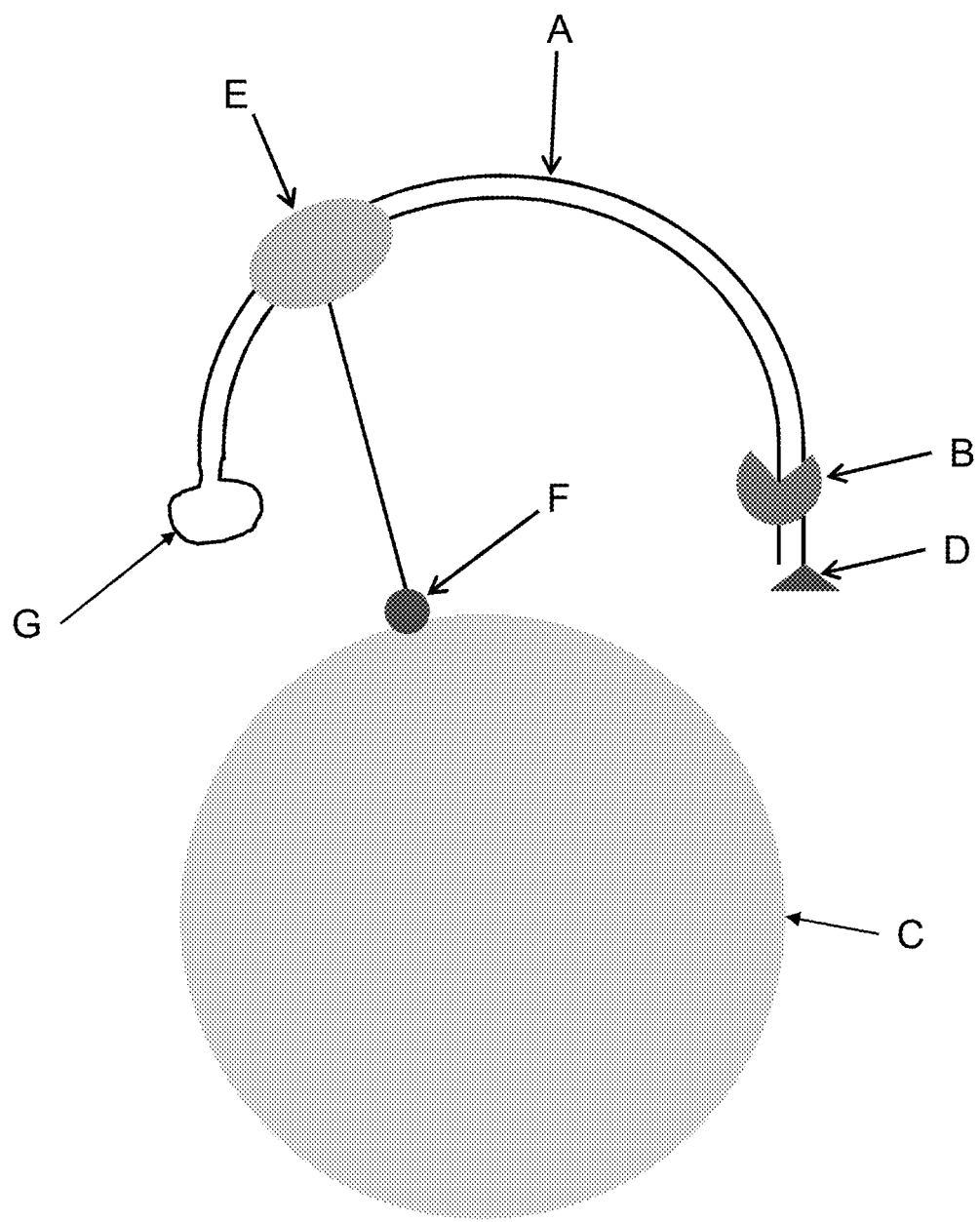
FIG. 28C shows the immobilisation of a target DNA analyte (A) comprising an enzyme-bound Y-adaptor (B) ligated to one end bearing a cholesterol moiety (D). The other end has a hairpin (G). A bound CRISPR-dCas9 (E) bearing an affinity tag such as a biotin moiety (F), tethers the analyte to a bead (C) such as streptavadin. This Figure shows the system before the addition of MgATP to initiate enzyme translocation on DNA.
Figure 29:
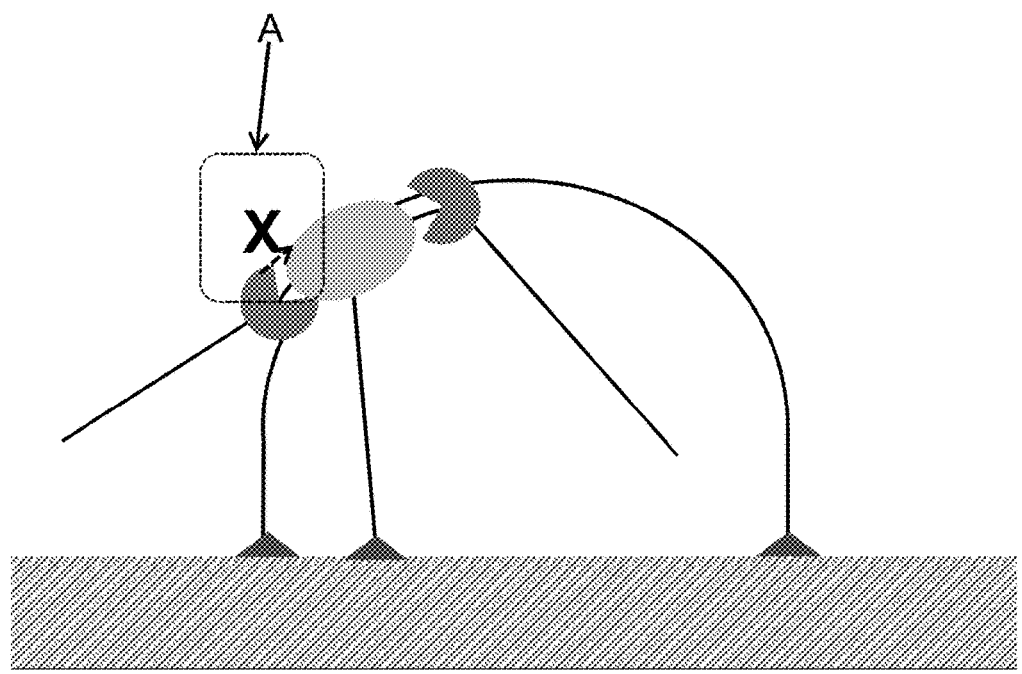
FIG. 29 shows the system introduced by FIG. 28 upon the addition of MgATP. The translocation of enzyme towards the CRISPR-dCas9 complex is halted upon encounter of the CRISPR-dCas9 complex (A).
Figure 30:
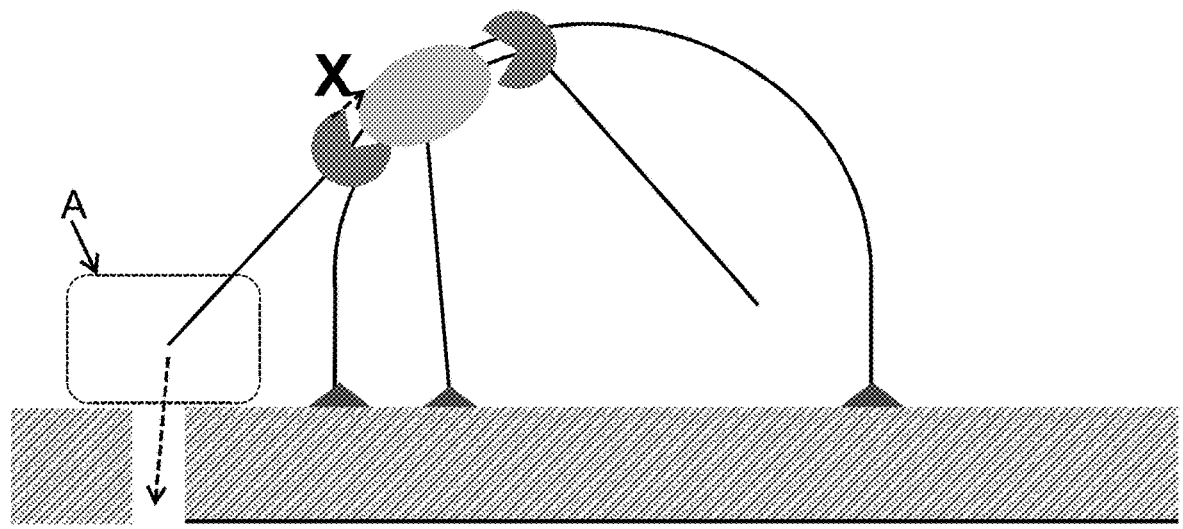
FIG. 30 shows the system introduced by FIG. 29 upon the application of a potential across the membrane, and capture of the end of the target analyte by a nanopore (A).
Figure 31:
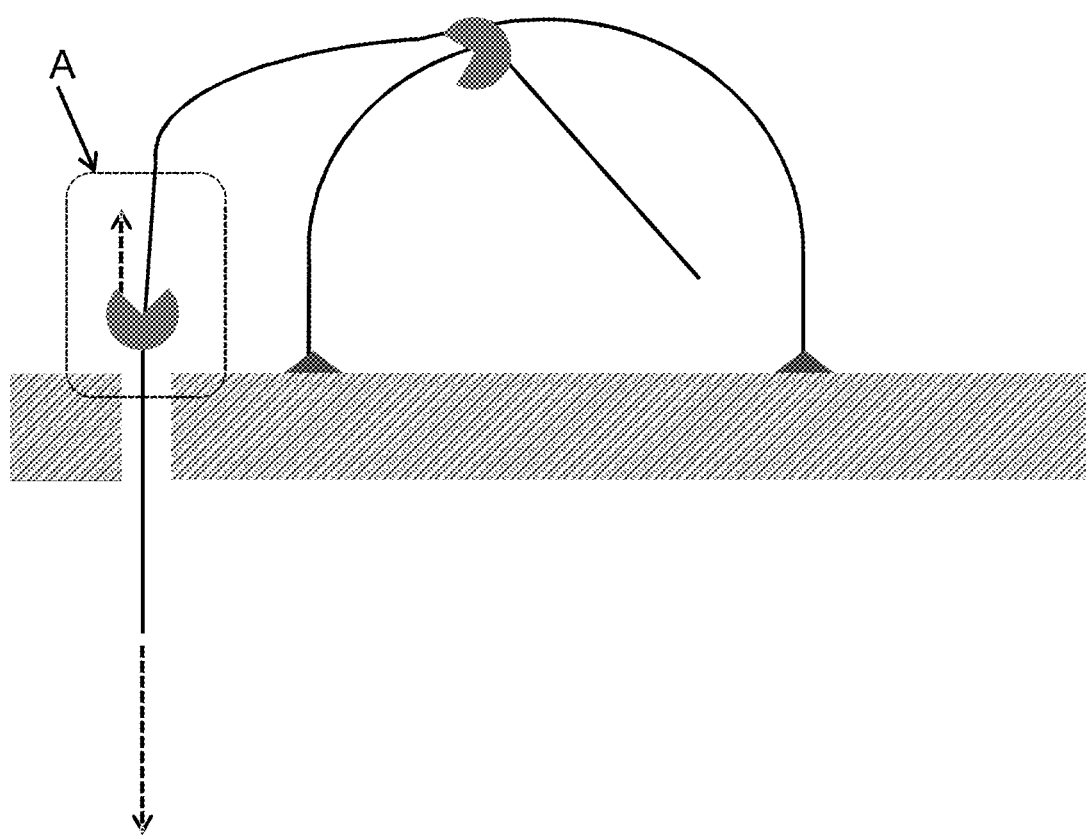
FIG. 31 shows the system introduced by FIG. 30 whereupon the potential applied to the analyte has released the enzyme bound to the CRISPR-dCas9 complex and the enzyme has resumed translocation (A).
Figure 32:
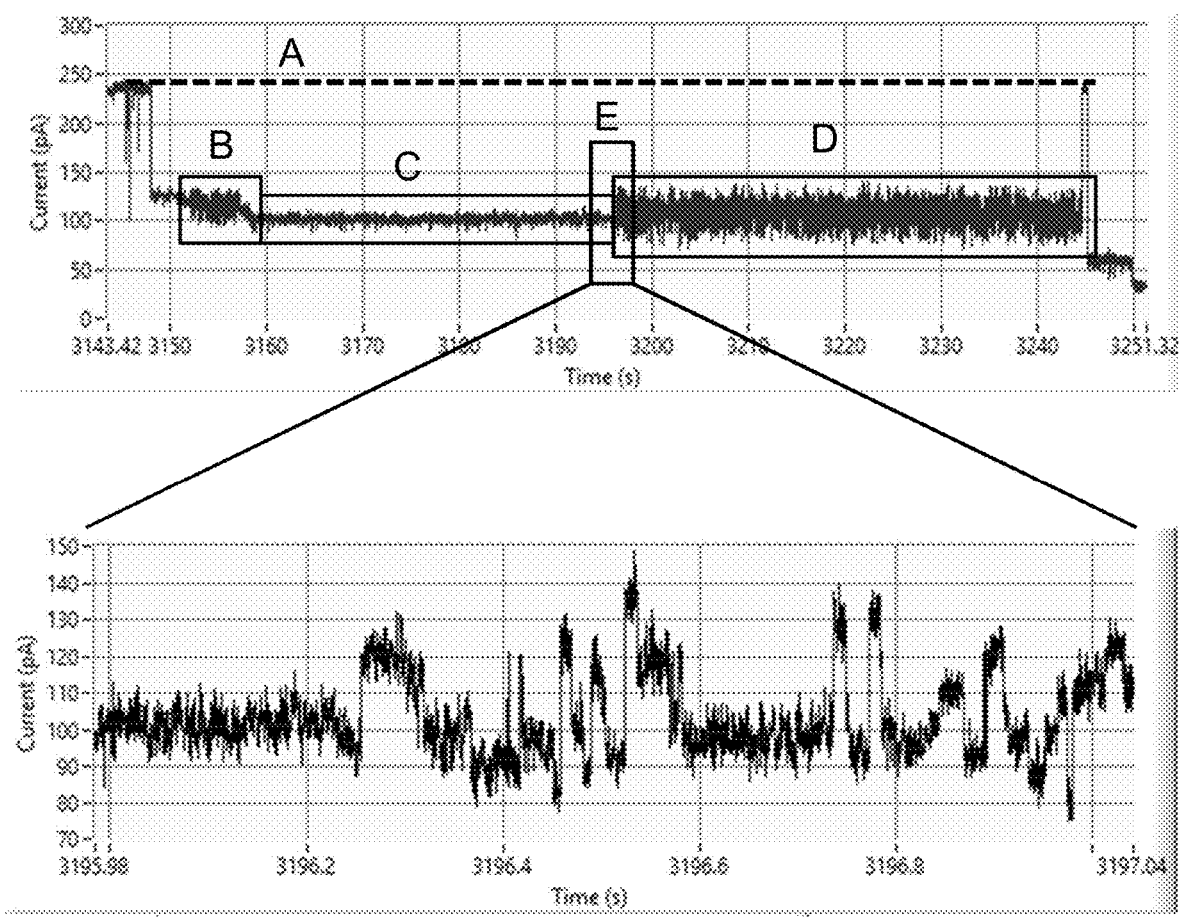
FIG. 32 shows an example trace, ~2350 secs after the addition of MgATP, comprising an initial, pre-dCas9 translocation event (B), stalling (C), and resumption of translocation (D). The resumption from the stall is highlighted and expanded (E).

The helicase was ligated on both ends of the target in the presence of non-hydrolysable ATP analogue ATPγS, and used to unwind any target DNA that did not contain a bound CRISPR-dCas9, or which preceded the CRISPR-dCas9 stall, independent of a nanopore. CRISPR-dCas9 and ligated Y-adaptor were tethered to tri-block copolymer via "cholesterol hyb" and via an oligonucleotide hybridized to both ends of the target. FIG. 28 shows the immobilization of the target to a membrane surface. The target bears a bound CRISPR-dCas9 probe, and, in the absence of MgATP, the helicase is located at the ends of the target DNA. FIG. 29 shows the translocation and stalling of both helicases towards the bound CRISPR-dCas9 complex upon the addition of MgATP. The stalling may be accomplished by one or both helicases. FIG. 30 shows the capture of the target analyte by a nanopore upon application of potential. FIG. 31 shows dislodgement of the bound CRISPR-dCas9 complex by the helicase upon capture of the target by a nanopore. FIG. 32 shows an example trace, ~2350 secs after the addition of MgATP, comprising an initial, pre-dCas9 translocation event (B), stalling (C), and resumption of translocation (M. The resumption from the stall is highlighted and expanded (E).

Sequences
Oligonucleotides
tracrRNA
The tracrRNA used throughout was a 67mer purchased from IDT ("Alt-R™" tracrRNA; catalogue #1072534)
Custom Oligonucleotides Used in this Filing:

| INTERNAL REFERENCE | SEQUENCE (5'-3') |
|---|---|
| AR130 | /5Phos/CAGACGCCGCAATATCAGCACCAACAGAAA/iBNA-meC//iBNA-A//iBNA-A//iBNA-meC//iBNA-meC/TTT |
| ONLA11326 | 3333333333333333333333333333333TTTTTTTTTTTT/iSp18//iSp18//iSp18//iSp18/*GGTTGTTTCTGTTGGTGCTGATATTGC*GGCGTCTGCTTGGGTGTTTAACCT |
| AR131 | /5Phos/TGTTCTGATCGGAACGATCG/iSp18//iSp18//iSp18//3CholTEG/ |
| AR132 | /5PhoS/CGATCGTTCCGATCAGAACA<u>CAAAGATGTATTGCT</u> |
| AR133 | /5Phos/<u>rCrUrUrCrGrCrGrGrCrArGrArUrArUrArArUrGrGrGrUrUrUrArGrArGrCrUrArUrGrCrU</u>AGGTTAAACACCCAAG |
| AR134 | /5Phos/<u>rCrCrGrArCrCrArCrGrCrCrArGrCrArUrArUrCrGrGrUrUrUrArGrArGrCrUrArUrGrCrU</u>AGGTTAAACACCCAAG |
| AR135 | /5Phos/<u>rUrGrCrArArCrGrGrUrCrGrArUrUrGrCrCrUrGrArGrUrUrUrArGrArGrCrUrArUrGrCrU</u>AGGTTAAACACCCAAG |
| AR136 | /5Phos/<u>rGrGrUrGrArArUrArArUrCrCrCrGrUrUrCrArGrUrUrUrArGrArGrCrUrArUrGrCrU</u>AGGTTAAACACCCAAG |
| AR137 | /5Phos/<u>rCrCrGrGrArCrGrUrUrArUrGrArUrUrArUrGrCrGrUrUrUrArGrArGrCrUrArUrGrCrU</u>AGGTTAAACACCCAAG |
| AR138 | /5Phos/<u>rCrUrUrCrGrCrGrGrCrArGrArUrArUrArUrGrGrGrUrUrUrArGrArGrCrUrArUrGrCrU</u>AGCAATACATCTTTG |
| AR139 | /5Phos/<u>rCrCrGrArCrCrArCrGrCrCrArGrCrArUrArUrCrGrGrUrUrUrArGrArGrCrUrArUrGrCrU</u>AGCAATACATCTTTG |
| AR140 | /5Phos/<u>rUrGrCrArArCrGrGrUrCrGrArUrUrGrCrCrUrGrArGrUrUrUrArGrArGrCrUrArUrGrCrU</u>AGCAATACATCTTTG |
| AR141 | /5Phos/<u>rGrGrUrGrArArArUrArArUrCrCrCrGrUrUrCrArGrUrUrUrArGrArGrCrUrArUrGrCrU</u>AGCAATACATCTTTG |
| AR142 | /5Phos/<u>rCrCrGrGrArCrGrUrUrArUrGrArUrUrArUrGrCrGrUrUrUrArGrArGrCrUrArUrGrCrU</u>AGCAATACATCTTTG |
| AR143 | /5Phos/<u>rGrGrUrArCrGrCrCrArUrUrGrCrArArArCrGrCrArGrUrUrUrArGrArGrCrUrArUrGrCrU</u>AGCAATACATCTTTG |
| AR144 | /5Phos/<u>rArCrGrArArUrGrArArCrUrArGrGrCrGrArUrArArGrUrUrUrArGrArGrCrUrArUrGrCrU</u>AGCAATACATCTTTG |
| AR145 | /5Phos/<u>rArArArArArArGrCrCrGrGrArGrUrArGrGrArArGrArGrUrUrUrArGrArGrCrUrArUrGrCrU</u>AGCAATACATCTTTG |
| AR146 | /5Phos/<u>rGrArCrGrUrCrArUrArArCrCrArUrGrArUrUrCrGrUrUrUrArGrArGrCrUrArUrGrCrU</u>AGCAATACATCTTTG |
| ONLA16941 | TTGACCGCTCGCCTC |

/5Phos/ = 5' phosphate moiety; /iBNA-meC/ = branched nucleic acid methyl cytosine base; /iBNA-A/ = branched nucleic acid adenosine base; /3CholTEG/ = 3' cholesterol moiety, linked via triethylene glycol; r = ribonucleotide base (RNA); 3 = C3 spacer; iSp18 = internal Sp18 spacer DNA SAMPLE LIBRARIES: SEQUENCES AND PREPARATION
•3.6 kb derivative of enterobacteria phage lambda ("lambda 3.6 kb")
>lambda_3.6kb
GCCATCAGATTGTGTTTGTTAGTCGCTGCCATCAGATTGTGTTTGTTAGTCGCTTTTTTTTTTGGAATTTTTTTTTGGAATTTTTTTTTGCGCT
AACAACCTCCTGCCGTTTTGCCCGTGCATATCGGTCACGAACAAATCTGATTACTAAACACAGTAGCCTGGATTTGTTCTATCAGTAATCGACCTTA
TTCCTAATTAAATAGAGCAAATCCCCTTATTGGGGGTAAGACATGAAGATGCCAGAAAAACATGACCTGTTGGCCGCCATTCTCGCGGCAAAGGAAC -continued
```
AAGGCATCGGGGCAATCCTTGCGTTTGCAATGGCGTACCTTCGCGGCAGATATAATGGCGGTGCGTTTACAAAAACAGTAATCGACGCAACGATGTG
CGCCATTATCGCCTAGTTCATTCGTGACCTTCTCGACTTCGCCGGACTAAGTAGCAATCTCGCTTATATAACGAGCGTGTTTATCGGCTACATCGGT
ACTGACTCGATTGGTTCGCTTATCAAACGCTTCGCTGCTAAAAAAGCCGGAGTAGAAGATGGTAGAAATCAATAATCAACGTAAGGCGTTCCTCGAT
ATGCTGGCGTGGTCGGAGGGAACTGATAACGGACGTCAGAAAACCAGAAATCATGGTTATGACGTCATTGTAGGCGGAGAGCTATTTACTGATTACT
CCGATCACCCTCGCAAACTTGTCACGCTAAACCCAAAACTCAAATCAACAGGCGCCGACGCTACCAGCTTCTTTCCCGTTGGTGGGATGCCTACCG
CAAGCAGCTTGGCCTGAAAGACTTCTCTCCGAAAAGTCAGGACGCTGTGGCATTGCAGCAGATTAAGGAGCGTGGCGCTTTACCTATGATTGATCGT
GGTGATATCCGTCAGGCAATCGACCGTTGCAGCAATATCTGGGCTTCACTGCCGGGCGCTGGTTATGGTCAGTTCGAGCATAAGGCTGACAGCCTGA
TTGCAAAATTCAAAGAAGCGGGCGGAACGGTCAGAGAGATTGATGTATGAGCAGAGTCACCGCGATTATCTCCGCTCTGGTTATCTGCATCATCGTC
TGCCTGTCATGGGCTGTTAATCATTACCGTGATAACGCCATTACCTACAAAGCCCAGCGCGACAAAAATGCCAGAGAACTGAAGCTGGCGAACGCGG
CAATTACTGACATGCAGATGCGTCAGCGTGATGTTGCTGCGCTCGATGCAAAATACACGAAGGAGTTAGCTGATGCTAAAGCTGAAAATGATGCTCT
GCGTGATGATGTTGCCGCTGGTCGTCGTCGGTTGCACATCAAAGCAGTCTGTCAGTCAGTGCGTGAAGCCACCACCGCCTCCGGCGTGGATAATGCA
GCCTCCCCCGACTGGCAGACACCGCTGAACGGGATTATTTCACCCTCAGAGAGAGGCTGATCACTATGCAAAAACAACTGGAAGGAACCCAGAAGT
ATATTAATGAGCAGTGCAGATAGAGTTGCCCATATCGATGGGCAACTCATGCAATTATTGTGAGCAATACACACGCGCTTCCAGCGGAGTATAAATG
CCTAAAGTAATAAAACCGAGCAATCCATTTACGAATGTTTGCTGGGTTTCTGTTTTAACAACATTTTCTGCGCCGCCACAAATTTTGGCTGCATCGA
CAGTTTTCTTCTGCCCAATTCCAGAAACGAAGAAATGATGGGTGATGGTTTCCTTTGGTGCTACTGCTGCCGGTTTGTTTTGAACAGTAAACGTCTG
TTGAGCACATCCTGTAATAAGCAGGGCCAGCGCAGTAGCGAGTAGCATTTTTTTCATGGTGTTATTCCCGATGCTTTTTGAAGTTCGCAGAATCGTA
TGTGTAGAAAATTAAACAAACCCTAAACAATGAGTTGAAATTTCATATTGTTAATATTTATTAATGTATGTCAGGTGCGATGAATCGTCATTGTATT
CCCGGATTAACTATGTCCACAGCCCTGACGGGGAACTTCTCTGCGGGAGTGTCCGGGAATAATTAAAACGATGCACACAGGGTTTAGCGCGTACACG
TATTGCATTATGCCAACGCCCCGGTGCTGACACGGAAGAAACCGGACGTTATGATTTAGCGTGGAAAGATTTGTGTAGTGTTCTGAATGCTCTCAGT
AAATAGTAATGAATTATCAAAGGTATAGTAATATCTTTTATGTTCATGGATATTTGTAACCCATCGGAAAACTCCTGCTTTAGCAAGATTTTCCCTG
TATTGCTGAAATGTGATTTCTCTTGATTTCAACCTATCATAGGACGTTTCTATAAGATGCGTGTTTCTTGAGAATTTAACATTTACAACCTTTTTAA
GTCCTTTTATTAACACGGTGTTATCGTTTTCTAACACGATGTGAATATTATCTGTGGCTAGATAGTAAATAATGTGAGACGTTGTGACGTTTTAG
TTCAGAATAAAACAATTCACAGTCTAAATCTTTTCGCACTTGATCGAATATTTCTTTAAAAATGGCAACCTGAGCCATTGGTAAAACCTTCCATGTG
ATACGAGGGCGCGTAGTTTGCATTATCGTTTTTATCGTTTCAATCTGGTCTGACCTCCTTGTGTTTTGTTGATGATTTATGTCAAATATTAGGAATG
TTTTCACTTAATAGTATTGGTTGCGTAACAAAGTGCGGTCCTGCTGGCATTCTGGAGGGAAATACAACCGACAGATGTATGTAAGGCCAACGTGCTC
AAATCTTCATACAGAAAGATTTGAAGTAATATTTTAACCGCTAGATGAAGAGCAAACGCATGGAGCGACAAAATGAATAAAGAACAATCTGCTGATG
ATCCCTCCGTGGATCTGATTCGTGTAAAAAATATGCTTAATAGCACCATTTCTATGAGTTACCCTGATGTTGTAATTGCATGTATAGAACATAAGGT
GTCTCTGGAAGCATTCAGAGCAATTGAGGCAGCGTTGGTGAAGCACGATAATAATATGAAGGATTATTCCCTGGTGGTTGACTGATCACCATAACTG
CTAATCATTCAAACTATTTAGTCTGTGACAGAGCCAACACGCAGTCTGTCACTGTCAGGAAAGTGGTAAAACTGCAACTCAATTACTGCAATGCCCT
CGTAATTAAGTGAATTTACAATATCGTCCTGTTCGGAGGGAAGAACGCGGGATGTTCATTCTTCATCACTTTTAATTGATGTATATGCTCTCTTTTC
TGACGTTAGTCTCCGACGGCAGGCTTCAATGACCCAGGCTGAGAAATTCCCGGACCCTTTTTGCTCAAGAGCGATGTTAATTTGTTCAATCATTTGG
TTAGGAAAGCGGATGTTGCGGGTTGTTGTTCTGCGGGTTCTGTTCTTCGTTGACATGAGGTTGCCCCGTATTCAGTGTCGCTGATTTGTATTGTCTG
AAGTTGTTTTTACGTTAAGTTGATGCAGATCAATTAATACGATACCTGCGTCATAATTGATTATTTGACGTGGTTTGATGGCCTCCACGCACGTTGT
GATATGTAGATGATAATCATTATCACTTTACGGGTCCTTTCCGGTGAAAAAAAGGTACCAAAAAAAACATCGTCGTGAGTAGTGAACCGTAAGC
```

•Enterobacteria phage lambda genome: GenBank accession ID J02459.1

•Seven-fragment derivative of bacteriophage lambda, ONLA15339

Bacteriophage lambda DNA (GenBank accession ID J02459.1; obtained from NEB) was digested with SnaBI and BamHI-HF (NEB), and end-repaired and dA-tailed using an NEBNext Ultra End Repair/dA-Tailing Module (NEB). Helicase loaded adapters were ligated to dA-tailed DNA using NEB Blunt/TA Ligase Master Mix.

Fragment 1 (positions 1-5505 of phage lambda)
```
GGGCGGCGAC CTCGCGGGTT TTCGCTATTT

ATGAAAATTT TCCGGTTTAA

GGCGTTTCCG TTCTTCTTCG TCATAACTTA

ATGTTTTTAT TTAAAATACC

CTCTGAAAAG AAAGGAAACG ACAGGTGCTG

AAAGCGAGGC TTTTTGGCCT

CTGTCGTTTC CTTTCTCTGT TTTTGTCCGT

GGAATGAACA ATGGAAGTCA

ACAAAAAGCA GCTGGCTGAC ATTTTCGGTG

CGAGTATCCG TACCATTCAG

AACTGGCAGG AACAGGGAAT GCCCGTTCTG

CGAGGCGGTG GCAAGGGTAA

TGAGGTGCTT TATGACTCTG CCGCCGTCAT

AAAATGGTAT GCCGAAAGGG

ATGCTGAAAT TGAGAACGAA AAGCTGCGCC

GGGAGGTTGA AGAACTGCGG

CAGGCCAGCG AGGCAGATCT CCAGCCAGGA

ACTATTGAGT ACGAACGCCA

TCGACTTACG CGTGCGCAGG CCGACGCACA

GGAACTGAAG AATGCCAGAG

ACTCCGCTGA AGTGGTGGAA ACCGCATTCT

GTACTTTCGT GCTGTCGCGG

ATCGCAGGTG AAATTGCCAG TATTCTCGAC

GGGCTCCCCC TGTCGGTGCA

GCGGCGTTTT CCGGAACTGG AAAACCGACA

TGTTGATTTC CTGAAACGGG

ATATCATCAA AGCCATGAAC AAAGCAGCCG

CGCTGGATGA ACTGATACCG

GGGTTGCTGA GTGAATATAT CGAACAGTCA

GGTTAACAGG CTGCGGCATT

TTGTCCGCGC CGGGCTTCGC TCACTGTTCA

GGCCGGAGCC ACAGACCGCC

GTTGAATGGG CGGATGCTAA TTACTATCTC

CCGAAAGAAT CCGCATACCA

GGAAGGGCGC TGGGAAACAC TGCCCTTTCA
```

-continued

```
GCGGGCCATC ATGAATGCGA

TGGGCAGCGA CTACATCCGT GAGGTGAATG

TGGTGAAGTC TGCCCGTGTC

GGTTATTCCA AAATGCTGCT GGGTGTTTAT

GCCTACTTTA TAGAGCATAA

GCAGCGCAAC ACCCTTATCT GGTTGCCGAC

GGATGGTGAT GCCGAGAACT

TTATGAAAAC CCACGTTGAG CCGACTATTC

GTGATATTCC GTCGCTGCTG

GCGCTGGCCC CGTGGTATGG CAAAAAGCAC

CGGGATAACA CGCTCACCAT

GAAGCGTTTC ACTAATGGGC GTGGCTTCTG

GTGCCTGGGC GGTAAAGCGG

CAAAAAACTA CCGTGAAAAG TCGGTGGATG

TGGCGGGTTA TGATGAACTT

GCTGCTTTTG ATGATGATAT TGAACAGGAA

GGCTCTCCGA CGTTCCTGGG

TGACAAGCGT ATTGAAGGCT CGGTCTGGCC

AAAGTCCATC CGTGGCTCCA

CGCCAAAAGT GAGAGGCACC TGTCAGATTG

AGCGTGCAGC CAGTGAATCC

CCGCATTTTA TGCGTTTTCA TGTTGCCTGC

CCGCATTGCG GGGAGGAGCA

GTATCTTAAA TTTGGCGACA AAGAGACGCC

GTTTGGCCTC AAATGGACGC

CGGATGACCC CTCCAGCGTG TTTTATCTCT

GCGAGCATAA TGCCTGCGTC

ATCCGCCAGC AGGAGCTGGA CTTTACTGAT

GCCCGTTATA TCTGCGAAAA

GACCGGGATC TGGACCCGTG ATGGCATTCT

CTGGTTTTCG TCATCCGGTG

AAGAGATTGA GCCACCTGAC AGTGTGACCT

TTCACATCTG GACAGCGTAC

AGCCCGTTCA CCACCTGGGT GCAGATTGTC

AAAGACTGGA TGAAAACGAA

AGGGGATACG GGAAAACGTA AAACCTTCGT

AAACACCACG CTCGGTGAGA

CGTGGGAGGC GAAAATTGGC GAACGTCCGG

ATGCTGAAGT GATGGCAGAG

CGGAAAGAGC ATTATTCAGC GCCCGTTCCT

GACCGTGTGG CTTACCTGAC

CGCCGGTATC GACTCCCAGC TGGACCGCTA

CGAAATGCGC GTATGGGGAT

GGGGGCCGGG TGAGGAAAGC TGGCTGATTG

ACCGGCAGAT TATTATGGGC

CGCCACGACG ATGAACAGAC GCTGCTGCGT

GTGGATGAGG CCATCAATAA

AACCTATACC CGCCGGAATG GTGCAGAAAT

GTCGATATCC CGTATCTGCT

GGGATACTGG CGGGATTGAC CCGACCATTG

TGTATGAACG CTCGAAAAAA

CATGGGCTGT TCCGGGTGAT CCCCATTAAA

GGGGCATCCG TCTACGGAAA

GCCGGTGGCC AGCATGCCAC GTAAGCGAAA

CAAAAACGGG GTTTACCTTA

CCGAAATCGG TACGGATACC GCGAAAGAGC

AGATTTATAA CCGCTTCACA

CTGACGCCGG AAGGGGATGA ACCGCTTCCC

GGTGCCGTTC ACTTCCCGAA

TAACCCGGAT ATTTTTGATC TGACCGAAGC

GCAGCAGCTG ACTGCTGAAG

AGCAGGTCGA AAAATGGGTG GATGGCAGGA

AAAAAATACT GTGGGACAGC

AAAAAGCGAC GCAATGAGGC ACTCGACTGC

TTCGTTTATG CGCTGGCGGC

GCTGCGCATC AGTATTTCCC GCTGGCAGCT

GGATCTCAGT GCGCTGCTGG

CGAGCCTGCA GGAAGAGGAT GGTGCAGCAA

CCAACAAGAA AACACTGGCA

GATTACGCCC GTGCCTTATC CGGAGAGGAT

GAATGACGCG ACAGGAAGAA

CTTGCCGCTG CCCGTGCGGC ACTGCATGAC

CTGATGACAG GTAAACGGGT

GGCAACAGTA CAGAAAGACG GACGAAGGGT

GGAGTTTACG GCCACTTCCG

TGTCTGACCT GAAAAAATAT ATTGCAGAGC

TGGAAGTGCA GACCGGCATG

ACACAGCGAC GCAGGGGACC TGCAGGATTT

TATGTATGAA AACGCCCACC

ATTCCCACCC TTCTGGGGCC GGACGGCATG

ACATCGCTGC GCGAATATGC

CGGTTATCAC GGCGGTGGCA GCGGATTTGG
```

AGGGCAGTTG CGGTCGTGGA

ACCCACCGAG TGAAAGTGTG GATGCAGCCC

TGTTGCCCAA CTTTACCCGT

GGCAATGCCC GCGCAGACGA TCTGGTACGC

AATAACGGCT ATGCCGCCAA

CGCCATCCAG CTGCATCAGG ATCATATCGT

CGGGTCTTTT TTCCGGCTCA

GTCATCGCCC AAGCTGGCGC TATCTGGGCA

TCGGGGAGGA AGAAGCCCGT

GCCTTTTCCC GCGAGGTTGA AGCGGCATGG

AAAGAGTTTG CCGAGGATGA

CTGCTGCTGC ATTGACGTTG AGCGAAAACG

CACGTTTACC ATGATGATTC

GGGAAGGTGT GGCCATGCAC GCCTTTAACG

GTGAACTGTT CGTTCAGGCC

ACCTGGGATA CCAGTTCGTC GCGGCTTTTC

CGGACACAGT TCCGGATGGT

CAGCCCGAAG CGCATCAGCA ACCCGAACAA

TACCGGCGAC AGCCGGAACT

GCCGTGCCGG TGTGCAGATT AATGACAGCG

GTGCGGCGCT GGGATATTAC

GTCAGCGAGG ACGGGTATCC TGGCTGGATG

CCGCAGAAAT GGACATGGAT

ACCCCGTGAG TTACCCGGCG GGCGCGCCTC

GTTCATTCAC GTTTTTGAAC

CCGTGGAGGA CGGGCAGACT CGCGGTGCAA

ATGTGTTTTA CAGCGTGATG

GAGCAGATGA AGATGCTCGA CACGCTGCAG

AACACGCAGC TGCAGAGCGC

CATTGTGAAG GCGATGTATG CCGCCACCAT

TGAGAGTGAG CTGGATACGC

AGTCAGCGAT GGATTTTATT CTGGGCGCGA

ACAGTCAGGA GCAGCGGGAA

AGGCTGACCG GCTGGATTGG TGAAATTGCC

GCGTATTACG CCGCAGCGCC

GGTCCGGCTG GGAGGCGCAA AAGTACCGCA

CCTGATGCCG GGTGACTCAC

TGAACCTGCA GACGGCTCAG GATACGGATA

ACGGCTACTC CGTGTTTGAG

CAGTCACTGC TGCGGTATAT CGCTGCCGGG

CTGGGTGTCT CGTATGAGCA

GCTTTCCCGG AATTACGCCC AGATGAGCTA

CTCCACGGCA CGGGCCAGTG

CGAACGAGTC GTGGGCGTAC TTTATGGGGC

GGCGAAAATT CGTCGCATCC

CGTCAGGCGA GCCAGATGTT TCTGTGCTGG

CTGGAAGAGG CCATCGTTCG

CCGCGTGGTG ACGTTACCTT CAAAAGCGCG

CTTCAGTTTT CAGGAAGCCC

GCAGTGCCTG GGGGAACTGC GACTGGATAG

GCTCCGGTCG TATGGCCATC

GATGGTCTGA AAGAAGTTCA GGAAGCGGTG

ATGCTGATAG AAGCCGGACT

GAGTACCTAC GAGAAAGAGT GCGCAAAACG

CGGTGACGAC TATCAGGAAA

TTTTTGCCCA GCAGGTCCGT GAAACGATGG

AGCGCCGTGC AGCCGGTCTT

AAACCGCCCG CCTGGGCGGC TGCAGCATTT

GAATCCGGGC TGCGACAATC

AACAGAGGAG GAGAAGAGTG ACAGCAGAGC

TGCGTAATCT CCCGCATATT

GCCAGCATGG CCTTTAATGA GCCGCTGATG

CTTGAACCCG CCTATGCGCG

GGTTTTCTTT TGTGCGCTTG CAGGCCAGCT

TGGGATCAGC AGCCTGACGG

ATGCGGTGTC CGGCGACAGC CTGACTGCCC

AGGAGGCACT CGCGACGCTG

GCATTATCCG GTGATGATGA CGGACCACGA

CAGGCCCGCA GTTATCAGGT

CATGAACGGC ATCGCCGTGC TGCCGGTGTC

CGGCACGCTG GTCAGCCGGA

CGCGGGCGCT GCAGCCGTAC TCGGGGATGA

CCGGTTACAA CGGCATTATC

GCCCGTCTGC AACAGGCTGC CAGCGATCCG

ATGGTGGACG GCATTCTGCT

CGATATGGAC ACGCCCGGCG GGATGGTGGC

GGGGGCATTT GACTGCGCTG

ACATCATCGC CCGTGTGCGT GACATAAAAC

CGGTATGGGC GCTTGCCAAC

GACATGAACT GCAGTGCAGG TCAGTTGCTT

GCCAGTGCCG CCTCCCGGCG

TCTGGTCACG CAGACCGCCC GGACAGGCTC

```
-continued
CATCGGCGTC ATGATGGCTC

ACAGTAATTA CGGTGCTGCG CTGGAGAAAC

AGGGTGTGGA AATCACGCTG

ATTTACAGCG GCAGCCATAA GGTGGATGGC

AACCCCTACA GCCATCTTCC

GGATGACGTC CGGGAGACAC TGCAGTCCCG

GATGGACGCA ACCCGCCAGA

TGTTTGCGCA GAAGGTGTCG GCATATACCG

GCCTGTCCGT GCAGGTTGTG

CTGGATACCG AGGCTGCAGT GTACAGCGGT

CAGGAGGCCA TTGATGCCGG

ACTGGCTGAT GAACTTGTTA ACAGCACCGA

TGCGATCACC GTCATGCGTG

ATGCACTGGA TGCACGTAAA TCCCGTCTCT

CAGGAGGGCG AATGACCAAA

GAGACTCAAT CAACAACTGT TTCAGCCACT

GCTTCGCAGG CTGACGTTAC

TGACGTGGTG CCAGCGACGG AGGGCGAGAA

CGCCAGCGCG GCGCAGCCGG

ACGTGAACGC GCAGATCACC GCAGCGGTTG

CGGCAGAAAA CAGCCGCATT

ATGGG

Fragment 2 (positions 5509-12910 of phage lambda)
GATCCTCAAC TGTGAGGAGG CTCACGGACG
CGAAGAACAG GCACGCGTGC
TGGCAGAAAC CCCCGGTATG ACCGTGAAAA
CGGCCCGCCG CATTCTGGCC
GCAGCACCAC AGAGTGCACA GGCGCGCAGT
GACACTGCGC TGGATCGTCT
GATGCAGGGG GCACCGGCAC CGCTGGCTGC
AGGTAACCCG GCATCTGATG
CCGTTAACGA TTTGCTGAAC ACACCAGTGT
AAGGGATGTT TATGACGAGC
AAAGAAACCT TTACCCATTA CCAGCCGCAG
GGCAACAGTG ACCCGGCTCA
TACCGCAACC GCGCCCGGCG GATTGAGTGC
GAAAGCGCCT GCAATGACCC
CGCTGATGCT GGACACCTCC AGCCGTAAGC
TGGTTGCGTG GGATGCCACC
ACCGACGGTG CTGCCGTTGG CATTCTTGCG
GTTGCTGCTG ACCAGACCAG
CACCACGCTG ACGTTCTACA AGTCCGGCAC
GTTCCGTTAT GAGGATGTGC
TCTGGCCGGA GGCTGCCAGC GACGAGACGA
AAAAACGGAC CGCGTTTGCC
GGAACGGCAA TCAGCATCGT TTAACTTTAC
CCTTCATCAC TAAAGGCCGC
CTGTGCGGCT TTTTTTACGG GATTTTTTTA
TGTCGATGTA CACAACCGCC
CAACTGCTGG CGGCAAATGA GCAGAAATTT
AAGTTTGATC CGCTGTTTCT
GCGTCTCTTT TTCCGTGAGA GCTATCCCTT
CACCACGGAG AAAGTCTATC
TCTCACAAAT TCCGGGACTG GTAAACATGG
CGCTGTACGT TTCGCCGATT
GTTTCCGGTG AGGTTATCCG TTCCCGTGGC
```

```
-continued
GGCTCCACCT CTGAATTTAC
GCCGGGATAT GTCAAGCCGA AGCATGAAGT
GAATCCGCAG ATGACCCTGC
GTCGCCTGCC GGATGAAGAT CCGCAGAATC
TGGCGGACCC GGCTTACCGC
CGCCGTCGCA TCATCATGCA GAACATGCGT
GACGAAGAGC TGGCCATTGC
TCAGGTCGAA GAGATGCAGG CAGTTTCTGC
CGTGCTTAAG GGCAAATACA
CCATGACCGG TGAAGCCTTC GATCCGGTTG
AGGTGGATAT GGGCCGCAGT
GAGGAGAATA ACATCACGCA GTCCGGCGGC
ACGGAGTGGA GCAAGCGTGA
CAAGTCCACG TATGACCCGA CCGACGATAT
CGAAGCCTAC GCGCTGAACG
CCAGCGGTGT GGTGAATATC ATCGTGTTCG
ATCCGAAAGG CTGGGCGCTG
TTCCGTTCCT TCAAAGCCGT CAAGGAGAAG
CTGGATACCC GTCGTGGCTC
TAATTCCGAG CTGGAGACAG CGGTGAAAGA
CCTGGGCAAA GCGGTGTCCT
ATAAGGGGAT GTATGCGGAT GTGGCCATCG
TCGTGTATTC CGGACAGTAC
GTGGAAAACG GCGTCAAAAA GAACTTCCTG
CCGGACAACA CGATGGTGCT
GGGGAACACT CAGGCACGCG GTCTGCGCAC
CTATGCTGCG ATTCAGGATG
CGGACGCACA GCGCGAAGGC ATTAACGCCT
CTGCCCGTTA CCCGAAAAAC
TGGGTGACCA CCGGCGATCC GGCGCGTGAG
TTCACCATGA TTCAGTCAGC
ACCGCTGATG CTGCTGGCTG ACCCTGATGA
GTTCGTGTCC GTACAACTGG
CGTAATCATG GCCCTTCGGG GCCATTGTTT
CTCTGTGGAG GAGTCCATGA
CGAAAGATGA ACTGATTGCC CGTCTCCGCT
CGCTGGGTGA ACAACTGAAC
CGTGATGTCA GCCTGACGGG GACGAAAGAA
GAACTGGCGC TCCGTGTGGC
AGAGCTGAAA GAGGAGCTTG ATGACACGGA
TGAAACTGCC GGTCAGGACA
CCCCTCTCAG CCGGGAAAAT GTGCTGACCG
GACATGAAAA TGAGGTGGGA
TCAGCGCAGC CGGATACCGT GATTCTGGAT
ACGTCTGAAC TGGTCACGGT
CGTGGCACTG GTGAAGCTGC ATACTGATGC
ACTTCACGCC ACGCGGGATG
AACCTGTGGC ATTTGTGCTG CCGGGAACGG
CGTTTCGTGT CTCTGCCGGT
GTGGCAGCCG AAATGACAGA GCGCGGCCTG
GCCAGAATGC AATAACGGGA
GGCGCTGTGG CTGATTTCGA TAACCTGTTC
GATGCTGCCA TTGCCCGCGC
CGATGAAACG ATACGCGGGT ACATGGGAAC
GTCAGCCACC ATTACATCCG
GTGAGCAGTC AGGTGCGGTG ATACGTGGTG
TTTTTGATGA CCCTGAAAAT
ATCAGCTATG CCGGACAGGG CGTGCGCGTT
GAAGGCTCCA GCCCGTCCCT
GTTTGTCCGG ACTGATGAGG TGCGGCAGCT
GCGGCGTGGA GACACGCTGA
CCATCGGTGA GGAAAATTTC TGGGTAGATC
GGGTTTCGCC GGATGATGGC
GGAAGTTGTC ATCTCTGGCT TGGACGGGGC
GTACCGCCTG CCGTTAACCG
TCGCCGCTGA AAGGGGGATG TATGGCCATA
AAAGGTCTTG AGCAGGCCGT
TGAAAACCTC AGCCGTATCA GCAAAACGGC
GGTGCCTGGT GCCGCCGCAA
TGGCCATTAA CCGCGTTGCT TCATCCGCGA
TATCGCAGTC GGCGTCACAG
GTTGCCCGTG AGACAAGGAT ACGCCGGAAA
CTGGTAAAGG AAAGGGCCAG
GCTGAAAAGG GCCACGGTCA AAAATCCGCA
GGCCAGAATC AAAGTTAACC
GGGGGATTT GCCCGTAATC AAGCTGGGTA
ATGCGCGGGT TGTCCTTTCG
CGCCGCAGGC GTCGTAAAAA GGGGCAGCGT
TCATCCCTGA AAGGTGGCGG
CAGCGTGCTT GTGGTGGGTA ACCGTCGTAT
TCCCGGCGCG TTTATTCAGC
```

-continued

```
AACTGAAAAA TGGCCGGTGG CATGTCATGC
AGCGTGTGGC TGGGAAAAAC
CGTTACCCCA TTGATGTGGT GAAAATCCCG
ATGGCGGTGC CGCTGACCAC
GGCGTTTAAA CAAAATATTG AGCGGATACG
GCGTGAACGT CTTCCGAAAG
AGCTGGGCTA TGCGCTGCAG CATCAACTGA
GGATGGTAAT AAAGCGATGA
AACATACTGA ACTCCGTGCA GCCGTACTGG
ATGCACTGGA GAAGCATGAC
ACCGGGGCGA CGTTTTTTGA TGGTCGCCCC
GCTGTTTTTG ATGAGGCGGA
TTTTCCGGCA GTTGCCGTTT ATCTCACCGG
CGCTGAATAC ACGGGCGAAG
AGCTGGACAG CGATACCTGG CAGGCGGAGC
TGCATATCGA AGTTTTCCTG
CCTGCTCAGG TGCCGGATTC AGAGCTGGAT
GCGTGGATGG AGTCCCGGAT
TTATCCGGTG ATGAGCGATA TCCCGGCACT
GTCAGATTTG ATCACCAGTA
TGGTGGCCAG CGGCTATGAC TACCGGCGCG
ACGATGATGC GGGCTTGTGG
AGTTCAGCCG ATCTGACTTA TGTCATTACC
TATGAAATGT GAGGACGCTA
TGCCTGTACC AAATCCTACA ATGCCGGTGA
AAGGTGCCGG GACCACCCTG
TGGGTTTATA AGGGGAGCGG TGACCCTTAC
GCGAATCCGC TTTCAGACGT
TGACTGGTCG CGTCTGGCAA AAGTTAAAGA
CCTGACGCCC GGCGAACTGA
CCGCTGAGTC CTATGACGAC AGCTATCTCG
ATGATGAAGA TGCAGACTGG
ACTGCGACCG GGCAGGGGCA GAAATCTGCC
GGAGATACCA GCTTCACGCT
GGCGTGGATG CCCGGAGAGC AGGGGCAGCA
GGCGCTGCTG GCGTGGTTTA
ATGAAGGCGA TACCCGTGCC TATAAAATCC
GCTTCCCGAA CGGCACGGTC
GATGTGTTCC GTGGCTGGGT CAGCAGTATC
GGTAAGGCGG TGACGGCGAA
GGAAGTGATC ACCCGCACGG TGAAAGTCAC
CAATGTGGGA CGTCCGTCGA
TGGCAGAAGA TCGCAGCACA GTAACAGCGG
CAACCGGCAT GACCGTGACG
CCTGCCAGCA CCTCGGTGGT GAAAGGGCAG
AGCACCACGC TGACCGTGGC
CTTCCAGCCG GAGGGCGTAA CCGACAAGAG
CTTTCGTGCG GTGTCTGCGG
ATAAAACAAA AGCCACCGTG TCGGTCAGTG
GTATGACCAT CACCGTGAAC
GGCGTTGCTG CAGGCAAGGT CAACATTCCG
GTTGTATCCG GTAATGGTGA
GTTTGCTGCG GTTGCAGAAA TTACCGTCAC
CGCCAGTTAA TCCGGAGAGT
CAGCGATGTT CCTGAAAACC GAATCATTTG
AACATAACGG TGTGACCGTC
ACGCTTTCTG AACTGTCAGC CCTGCAGCGC
ATTGAGCATC TCGCCCTGAT
GAAACGCAAG GCAGAACAGG CGGAGTCAGA
CAGCAACCGG AAGTTTACTG
TGGAAGACGC CATCAGAACC GGCGCGTTTC
TGGTGGCGAT GTCCCTGTGG
CATAACCATC CGCAGAAGAC GCAGATGCCG
TCCATGAATG AAGCCGTTAA
ACAGATTGAG CAGGAAGTGC TTACCACCTG
GCCCACGGAG GCAATTTCTC
ATGCTGAAAA CGTGGTGTAC CGGCTGTCTG
GTATGTATGA GTTTGTGGTG
AATAATGCCC CTGAACAGAC AGAGGACGCC
GGGCCCGCAG AGCCTGTTTC
TGCGGGAAAG TGTTCGACGG TGAGCTGAGT
TTTGCCCTGA AACTGGCGCG
TGAGATGGGG CGACCCGACT GGCGTGCCAT
GCTTGCCGGG ATGTCATCCA
CGGAGTATGC CGACTGGCAC CGCTTTTACA
GTACCCATTA TTTTCATGAT
GTTCTGCTGG ATATGCACTT TTCCGGGCTG
ACGTACACCG TGCTCAGCCT
GTTTTTCAGC GATCCGGATA TGCATCCGCT
GGATTTCAGT CTGCTGAACC
GGCGCGAGGC TGACGAAGAG CCTGAAGATG
```

```
ATGTGCTGAT GCAGAAAGCG
GCAGGGCTTG CCGGAGGTGT CCGCTTTGGC
CCGGACGGGA ATGAAGTTAT
CCCCGCTTCC CCGGATGTGG CGGACATGAC
GGAGGATGAC GTAATGCTGA
TGACAGTATC AGAAGGGATC GCAGGAGGAG
TCCGGTATGG CTGAACCGGT
AGGCGATCTG GTCGTTGATT TGAGTCTGGA
TGCGGCCAGA TTTGACGAGC
AGATGGCCAG AGTCAGGCGT CATTTTTCTG
GTACGGAAAG TGATGCGAAA
AAAACAGCGG CAGTCGTTGA ACAGTCGCTG
AGCCGACAGG CGCTGGCTGC
ACAGAAAGCG GGGATTTCCG TCGGGCAGTA
TAAAGCCGCC ATGCGTATGC
TGCCTGCACA GTTCACCGAC GTGGCCACGC
AGCTTGCAGG CGGGCAAAGT
CCGTGGCTGA TCCTGCTGCA ACAGGGGGGG
CAGGTGAAGG ACTCCTTCGG
CGGGATGATC CCCATGTTCA GGGGGCTTGC
CGGTGCGATC ACCCTGCCGA
TGGTGGGGGC CACCTCGCTG GCGGTGGCGA
CCGGTGCGCT GGCGTATGCC
TGGTATCAGG GCAACTCAAC CCTGTCCGAT
TTCAACAAAA CGCTGGTCCT
TTCCGGCAAT CAGGCGGGAC TGACGGCAGA
TCGTATGCTG GTCCTGTCCA
GAGCCGGGCA GGCGGCAGGG CTGACGTTTA
ACCAGACCAG CGAGTCACTC
AGCGCACTGG TTAAGGCGGG GGTAAGCGGT
GAGGCTCAGA TTGCGTCCAT
CAGCCAGAGT GTGGCGCGTT TCTCCTCTGC
ATCCGGCGTG GAGGTGGACA
AGGTCGCTGA AGCCTTCGGG AAGCTGACCA
CAGACCCGAC GTCGGGGCTG
ACGGCGATGG CTCGCCAGTT CCATAACGTG
TCGGCGGAGC AGATTGCGTA
TGTTGCTCAG TTGCAGCGTT CCGGCGATGA
AGCCGGGGCA TTGCAGGCGG
CGAACGAGGC CGCAACGAAA GGGTTTGATG
ACCAGACCCG CCGCCTGAAA
GAGAACATGG GCACGCTGGA GACCTGGGCA
GACAGGACTG CGCGGGCATT
CAAATCCATG TGGGATGCGG TGCTGGATAT
TGGTCGTCCT GATACCGCGC
AGGAGATGCT GATTAAGGCA GAGGCTGCGT
ATAAGAAAGC AGACGACATC
TGGAATCTGC GCAAGGATGA TTATTTTGTT
AACGATGAAG CGCGGGCGCG
TTACTGGGAT GATCGTGAAA AGGCCCGTCT
TGCGCTTGAA GCCGCCCGAA
AGAAGGCTGA GCAGCAGACT CAACAGGACA
AAAATGCGCA GCAGCAGAGC
GATACCGAAG CGTCACGGCT GAAATATACC
GAAGAGGCGC AGAAGGCTTA
CGAACGGCTG CAGACGCCGC TGGAGAAATA
TACCGCCCGT CAGGAAGAAC
TGAACAAGGC ACTGAAAGAC GGGAAAATCC
TGCAGGCGGA TTACAACACG
CTGATGGCGG CGGCGAAAAA GGATTATGAA
GCGACGCTGA AAAAGCCGAA
ACAGTCCAGC GTGAAGGTGT CTGCGGGCGA
TCGTCAGGAA GACAGTGCTC
ATGCTGCCCT GCTGACGCTT CAGGCAGAAC
TCCGGACGCT GGAGAAGCAT
GCCGGAGCAA ATGAGAAAAT CAGCCAGCAG
CGCCGGGATT TGTGGAAGGC
GGAGAGTCAG TTCGCGGTAC TGGAGGAGGC
GGCGCAACGT CGCCAGCTGT
CTGCACAGGA GAAATCCCTG CTGGCGCATA
AAGATGAGAC GCTGGAGTAC
AAACGCCAGC TGGCTGCACT TGGCGACAAG GTTAC
```

Fragment 3 (positions 12910-22346 of phage lambda)
```
GTATCAGGAG CGCCTGAACG CGCTGGCGCA

GCAGGCGGAT AAATTCGCAC
```

```
AGCAGCAACG GGCAAAACGG GCCGCCATTG

ATGCGAAAAG CCGGGGGCTG

ACTGACCGGC AGGCAGAACG GGAAGCCACG

GAACAGCGCC TGAAGGAACA

GTATGGCGAT AATCCGCTGG CGCTGAATAA

CGTCATGTCA GAGCAGAAAA

AGACCTGGGC GGCTGAAGAC CAGCTTCGCG

GGAACTGGAT GGCAGGCCTG

AAGTCCGGCT GGAGTGAGTG GGAAGAGAGC

GCCACGGACA GTATGTCGCA

GGTAAAAAGT GCAGCCACGC AGACCTTTGA

TGGTATTGCA CAGAATATGG

CGGCGATGCT GACCGGCAGT GAGCAGAACT

GGCGCAGCTT CACCCGTTCC

GTGCTGTCCA TGATGACAGA AATTCTGCTT

AAGCAGGCAA TGGTGGGGAT

TGTCGGGAGT ATCGGCAGCG CCATTGGCGG

GGCTGTTGGT GGCGGCGCAT

CCGCGTCAGG CGGTACAGCC ATTCAGGCCG

CTGCGGCGAA ATTCCATTTT

GCAACCGGAG GATTTACGGG AACCGGCGGC

AAATATGAGC CAGCGGGGAT

TGTTCACCGT GGTGAGTTTG TCTTCACGAA

GGAGGCAACC AGCCGGATTG

GCGTGGGGAA TCTTTACCGG CTGATGCGCG

GCTATGCCAC CGGCGGTTAT

GTCGGTACAC CGGGCAGCAT GGCAGACAGC

CGGTCGCAGG CGTCCGGGAC

GTTTGAGCAG AATAACCATG TGGTGATTAA

CAACGACGGC ACGAACGGGC

AGATAGGTCC GGCTGCTCTG AAGGCGGTGT

ATGACATGGC CCGCAAGGGT

GCCCGTGATG AAATTCAGAC ACAGATGCGT

GATGGTGGCC TGTTCTCCGG

AGGTGGACGA TGAAGACCTT CCGCTGGAAA

GTGAAACCCG GTATGGATGT

GGCTTCGGTC CCTTCTGTAA GAAAGGTGCG

CTTTGGTGAT GGCTATTCTC

AGCGAGCGCC TGCCGGGCTG AATGCCAACC

TGAAAACGTA CAGCGTGACG

CTTTCTGTCC CCCGTGAGGA GGCCACGGTA
```

```
CTGGAGTCGT TTCTGGAAGA

GCACGGGGC TGGAAATCCT TTCTGTGGAC

GCCGCCTTAT GAGTGGCGGC

AGATAAAGGT GACCTGCGCA AAATGGTCGT

CGCGGGTCAG TATGCTGCGT

GTTGAGTTCA GCGCAGAGTT TGAACAGGTG

GTGAACTGAT GCAGGATATC

CGGCAGGAAA CACTGAATGA ATGCACCCGT

GCGGAGCAGT CGGCCAGCGT

GGTGCTCTGG AAATCGACC TGACAGAGGT

CGGTGGAGAA CGTTATTTTT

TCTGTAATGA GCAGAACGAA AAAGGTGAGC

CGGTCACCTG GCAGGGGCGA

CAGTATCAGC CGTATCCCAT TCAGGGGAGC

GGTTTTGAAC TGAATGGCAA

AGGCACCAGT ACGCGCCCCA CGCTGACGGT

TTCTAACCTG TACGGTATGG

TCACCGGGAT GGCGGAAGAT ATGCAGAGTC

TGGTCGGCGG AACGGTGGTC

CGGCGTAAGG TTTACGCCCG TTTTCTGGAT

GCGGTGAACT TCGTCAACGG

AAACAGTTAC GCCGATCCGG AGCAGGAGGT

GATCAGCCGC TGGCGCATTG

AGCAGTGCAG CGAACTGAGC GCGGTGAGTG

CCTCCTTTGT ACTGTCCACG

CCGACGGAAA CGGATGGCGC TGTTTTTCCG

GGACGTATCA TGCTGGCCAA

CACCTGCACC TGGACCTATC GCGGTGACGA

GTGCGGTTAT AGCGGTCCGG

CTGTCGCGGA TGAATATGAC CAGCCAACGT

CCGATATCAC GAAGGATAAA

TGCAGCAAAT GCCTGAGCGG TTGTAAGTTC

CGCAATAACG TCGGCAACTT

TGGCGGCTTC CTTTCCATTA ACAAACTTTC

GCAGTAAATC CCATGACACA

GACAGAATCA GCGATTCTGG CGCACGCCCG

GCGATGTGCG CCAGCGGAGT

CGTGCGGCTT CGTGGTAAGC ACGCCGGAGG

GGGAAAGATA TTTCCCCTGC

GTGAATATCT CCGGTGAGCC GGAGGCTATT

TCCGTATGTC GCCGGAAGAC
```

```
TGGCTGCAGG CAGAAATGCA GGGTGAGATT

GTGGCGCTGG TCCACAGCCA

CCCCGGTGGT CTGCCCTGGC TGAGTGAGGC

CGACCGGCGG CTGCAGGTGC

AGAGTGATTT GCCGTGGTGG CTGGTCTGCC

GGGGGACGAT TCATAAGTTC

CGCTGTGTGC CGCATCTCAC CGGGCGGCGC

TTTGAGCACG GTGTGACGGA

CTGTTACACA CTGTTCCGGG ATGCTTATCA

TCTGGCGGGG ATTGAGATGC

CGGACTTTCA TCGTGAGGAT GACTGGTGGC

GTAACGGCCA GAATCTCTAT

CTGGATAATC TGGAGGCGAC GGGGCTGTAT

CAGGTGCCGT TGTCAGCGGC

ACAGCCGGGC GATGTGCTGC TGTGCTGTTT

TGGTTCATCA GTGCCGAATC

ACGCCGCAAT TTACTGCGGC GACGGCGAGC

TGCTGCACCA TATTCCTGAA

CAACTGAGCA AACGAGAGAG GTACACCGAC

AAATGGCAGC GACGCACACA

CTCCCTCTGG CGTCACCGGG CATGGCGCGC

ATCTGCCTTT ACGGGGATTT

ACAACGATTT GGTCGCCGCA TCGACCTTCG

TGTGAAAACG GGGGCTGAAG

CCATCCGGGC ACTGGCCACA CAGCTCCCGG

CGTTTCGTCA GAAACTGAGC

GACGGCTGGT ATCAGGTACG GATTGCCGGG

CGGGACGTCA GCACGTCCGG

GTTAACGGCG CAGTTACATG AGACTCTGCC

TGATGGCGCT GTAATTCATA

TTGTTCCCAG AGTCGCCGGG GCCAAGTCAG

GTGGCGTATT CCAGATTGTC

CTGGGGCTG CCGCCATTGC CGGATCATTC

TTTACCGCCG GAGCCACCCT

TGCAGCATGG GGGGCAGCCA TTGGGGCCGG

TGGTATGACC GGCATCCTGT

TTTCTCTCGG TGCCAGTATG GTGCTCGGTG

GTGTGGCGCA GATGCTGGCA

CCGAAAGCCA GAACTCCCCG TATACAGACA

ACGGATAACG GTAAGCAGAA

CACCTATTTC TCCTCACTGG ATAACATGGT
```
```
TGCCCAGGGC AATGTTCTGC

CTGTTCTGTA CGGGGAAATG CGCGTGGGGT

CACGCGTGGT TTCTCAGGAG

ATCAGCACGG CAGACGAAGG GGACGGTGGT

CAGGTTGTGG TGATTGGTCG

CTGATGCAAA ATGTTTTATG TGAAACCGCC

TGCGGGCGGT TTTGTCATTT

ATGGAGCGTG AGGAATGGGT AAAGGAAGCA

GTAAGGGGCA TACCCCGCGC

GAAGCGAAGG ACAACCTGAA GTCCACGCAG

TTGCTGAGTG TGATCGATGC

CATCAGCGAA GGGCCGATTG AAGGTCCGGT

GGATGGCTTA AAAAGCGTGC

TGCTGAACAG TACGCCGGTG CTGGACACTG

AGGGGAATAC CAACATATCC

GGTGTCACGG TGGTGTTCCG GGCTGGTGAG

CAGGAGCAGA CTCCGCCGGA

GGGATTTGAA TCCTCCGGCT CCGAGACGGT

GCTGGGTACG GAAGTGAAAT

ATGACACGCC GATCACCCGC ACCATTACGT

CTGCAAACAT CGACCGTCTG

CGCTTTACCT TCGGTGTACA GGCACTGGTG

GAAACCACCT CAAAGGGTGA

CAGGAATCCG TCGGAAGTCC GCCTGCTGGT

TCAGATACAA CGTAACGGTG

GCTGGGTGAC GGAAAAAGAC ATCACCATTA

AGGGCAAAAC CACCTCGCAG

TATCTGGCCT CGGTGGTGAT GGGTAACCTG

CCGCCGCGCC CGTTTAATAT

CCGGATGCGC AGGATGACGC CGGACAGCAC

CACAGACCAG CTGCAGAACA

AAACGCTCTG GTCGTCATAC ACTGAAATCA

TCGATGTGAA ACAGTGCTAC

CCGAACACGG CACTGGTCGG CGTGCAGGTG

GACTCGGAGC AGTTCGGCAG

CCAGCAGGTG AGCCGTAATT ATCATCTGCG

CGGGCGTATT CTGCAGGTGC

CGTCGAACTA TAACCCGCAG ACGCGGCAAT

ACAGCGGTAT CTGGGACGGA

ACGTTTAAAC CGGCATACAG CAACAACATG

GCCTGGTGTC TGTGGGATAT
```

```
GCTGACCCAT CCGCGCTACG GCATGGGGAA

ACGTCTTGGT GCGGCGGATG

TGGATAAATG GGCGCTGTAT GTCATCGGCC

AGTACTGCGA CCAGTCAGTG

CCGGACGGCT TTGGCGGCAC GGAGCCGCGC

ATCACCTGTA ATGCGTACCT

GACCACACAG CGTAAGGCGT GGGATGTGCT

CAGCGATTTC TGCTCGGCGA

TGCGCTGTAT GCCGGTATGG AACGGGCAGA

CGCTGACGTT CGTGCAGGAC

CGACCGTCGG ATAAGACGTG GACCTATAAC

CGCAGTAATG TGGTGATGCC

GGATGATGGC GCGCCGTTCC GCTACAGCTT

CAGCGCCCTG AAGGACCGCC

ATAATGCCGT TGAGGTGAAC TGGATTGACC

CGAACAACGG CTGGGAGACG

GCGACAGAGC TTGTTGAAGA TACGCAGGCC

ATTGCCCGTT ACGGTCGTAA

TGTTACGAAG ATGGATGCCT TTGGCTGTAC

CAGCCGGGGG CAGGCACACC

GCGCCGGGCT GTGGCTGATT AAAACAGAAC

TGCTGGAAAC GCAGACCGTG

GATTTCAGCG TCGGCGCAGA AGGGCTTCGC

CATGTACCGG GCGATGTTAT

TGAAATCTGC GATGATGACT ATGCCGGTAT

CAGCACCGGT GGTCGTGTGC

TGGCGGTGAA CAGCCAGACC CGGACGCTGA

CGCTCGACCG TGAAATCACG

CTGCCATCCT CCGGTACCGC GCTGATAAGC

CTGGTTGACG GAAGTGGCAA

TCCGGTCAGC GTGGAGGTTC AGTCCGTCAC

CGACGGCGTG AAGGTAAAAG

TGAGCCGTGT TCCTGACGGT GTTGCTGAAT

ACAGCGTATG GGAGCTGAAG

CTGCCGACGC TGCGCCAGCG ACTGTTCCGC

TGCGTGAGTA TCCGTGAGAA

CGACGACGGC ACGTATGCCA TCACCGCCGT

GCAGCATGTG CCGGAAAAAG

AGGCCATCGT GGATAACGGG GCGCACTTTG

ACGGCGAACA GAGTGGCACG

GTGAATGGTG TCACGCCGCC AGCGGTGCAG

CACCTGACCG CAGAAGTCAC

TGCAGACAGC GGGGAATATC AGGTGCTGGC

GCGATGGGAC ACACCGAAGG

TGGTGAAGGG CGTGAGTTTC CTGCTCCGTC

TGACCGTAAC AGCGGACGAC

GGCAGTGAGC GGCTGGTCAG CACGGCCCGG

ACGACGGAAA CCACATACCG

CTTCACGCAA CTGGCGCTGG GGAACTACAG

GCTGACAGTC CGGGCGGTAA

ATGCGTGGGG GCAGCAGGGC GATCCGGCGT

CGGTATCGTT CCGGATTGCC

GCACCGGCAG CACCGTCGAG GATTGAGCTG

ACGCCGGGCT ATTTTCAGAT

AACCGCCACG CCGCATCTTG CCGTTTATGA

CCCGACGGTA CAGTTTGAGT

TCTGGTTCTC GGAAAAGCAG ATTGCGGATA

TCAGACAGGT TGAAACCAGC

ACGCGTTATC TTGGTACGGC GCTGTACTGG

ATAGCCGCCA GTATCAATAT

CAAACCGGGC CATGATTATT ACTTTTATAT

CCGCAGTGTG AACACCGTTG

GCAAATCGGC ATTCGTGGAG GCCGTCGGTC

GGGCGAGCGA TGATGCGAA

GGTTACCTGG ATTTTTTCAA AGGCAAGATA

ACCGAATCCC ATCTCGGCAA

GGAGCTGCTG GAAAAAGTCG AGCTGACGGA

GGATAACGCC AGCAGACTGG

AGGAGTTTTC GAAAGAGTGG AAGGATGCCA

GTGATAAGTG GAATGCCATG

TGGGCTGTCA AAATTGAGCA GACCAAAGAC

GGCAAACATT ATGTCGCGGG

TATTGGCCTC AGCATGGAGG ACACGGAGGA

AGGCAAACTG AGCCAGTTTC

TGGTTGCCGC CAATCGTATC GCATTTATTG

ACCCGGCAAA CGGGAATGAA

ACGCCGATGT TGTGGCGCA GGGCAACCAG

ATATTCATGA ACGACGTGTT

CCTGAAGCGC CTGACGGCCC CCACCATTAC

CAGCGGCGGC AATCCTCCGG

CCTTTTCCCT GACACCGGAC GGAAAGCTGA

CCGCTAAAAA TGCGGATATC
```

```
-continued
AGTGGCAGTG TGAATGCGAA CTCCGGGACG

CTCAGTAATG TGACGATAGC

TGAAAACTGT ACGATAAACG GTACGCTGAG

GGCGGAAAAA ATCGTCGGGG

ACATTGTAAA GGCGGCGAGC GCGGCTTTTC

CGCGCCAGCG TGAAAGCAGT

GTGGACTGGC CGTCAGGTAC CCGTACTGTC

ACCGTGACCG ATGACCATCC

TTTTGATCGC CAGATAGTGG TGCTTCCGCT

GACGTTTCGC GGAAGTAAGC

GTACTGTCAG CGGCAGGACA ACGTATTCGA

TGTGTTATCT GAAAGTACTG

ATGAACGGTG CGGTGATTTA TGATGGCGCG

GCGAACGAGG CGGTACAGGT

GTTCTCCCGT ATTGTTGACA TGCCAGCGGG

TCGGGGAAAC GTGATCCTGA

CGTTCACGCT TACGTCCACA CGGCATTCGG

CAGATATTCC GCCGTATACG

TTTGCCAGCG ATGTGCAGGT TATGGTGATT

AAGAAACAGG CGCTGGGCAT

CAGCGTGGTC TGAGTGTGTT ACAGAGGTTC

GTCCGGGAAC GGGCGTTTTA

TTATAAAACA GTGAGAGGTG AACGATGCGT

AATGTGTGTA TTGCCGTTGC

TGTCTTTGCC GCACTTGCGG TGACAGTCAC

TCCGGCCCGT GCGGAAGGTG

GACATGGTAC GTTACGGTG GGCTATTTTC

AAGTGAAACC GGGTACATTG

CCGTCGTTGT CGGGCGGGGA TACCGGTGTG

AGTCATCTGA AAGGGATTAA

CGTGAAGTAC CGTTATGAGC TGACGGACAG

TGTGGGGGTG ATGGCTTCCC

TGGGGTTCGC CGCGTCGAAA AAGAGCAGCA

CAGTGATGAC CGGGGAGGAT

ACGTTTCACT ATGAGAGCCT GCGTGGACGT

TATGTGAGCG TGATGGCCGG

ACCGGTTTTA CAAATCAGTA AGCAGGTCAG

TGCGTACGCC ATGGCCGGAG

TGGCTCACAG TCGGTGGTCC GGCAGTACAA

TGGATTACCG TAAGACGGAA

ATCACTCCCG GGTATATGAA AGAGACGACC
```

```
-continued
ACTGCCAGGG ACGAAAGTGC

AATGCGGCAT ACCTCAGTGG CGTGGAGTGC

AGGTATACAG ATTAATCCGG

CAGCGTCCGT CGTTGTTGAT ATTGCTTATG

AAGGCTCCGG CAGTGGCGAC

TGGCGTACTG ACGGATTCAT CGTTGGGGTC

GGTTATAAAT TCTGATTAGC

CAGGTAACAC AGTGTTATGA CAGCCCGCCG

GAACCGGTGG GCTTTTTTGT

GGGGTGAATA TGGCAGTAAA GATTTCAGGA

GTCCTGAAAG ACGGCACAGG

AAAACCGGTA CAGAACTGCA CCATTCAGCT

GAAAGCCAGA CGTAACAGCA

CCACGGTGGT GGTGAACACG GTGGGCTCAG

AGAATCCGGA TGAAGCCGGG

CGTTACAGCA TGGATGTGGA GTACGGTCAG

TACAGTGTCA TCCTGCAGGT

TGACGGTTTT CCACCATCGC ACGCCGGGAC

CATCACCGTG TATGAAGATT

CACAACCGGG GACGCTGAAT GATTTTCTCT

GTGCCATGAC GGAGGATGAT

GCCCGGCCGG AGGTGCTGCG TCGTCTTGAA

CTGATGGTGG AAGAGGTGGC

GCGTAACGCG TCCGTGGTGG CACAGAGTAC

GGCAGACGCG AAGAAATCAG

CCGGCGATGC CAGTGCATCA GCTGCTCAGG

TCGCGGCCCT TGTGACTGAT

GCAACTGACT CAGCACGCGC CGCCAGCACG

TCCGCCGGAC AGGCTGCATC

GTCAGCTCAG GAAGCGTCCT CCGGCGCAGA

AGCGGCATCA GCAAAGGCCA

CTGAAGCGGA AAAAGTGCC GCAGCCGCAG

AGTCCTCAAA AACGCGGCG

GCCACCAGTG CCGGTGCGGC GAAAACGTCA

GAAACGAATG CTGCAGCGTC

ACAACAATCA GCCGCCACGT CTGCCTCCAC

CGCGGCCACG AAAGCGTCAG

AGGCCGCCAC TTCAGCACGA GATGCGGTGG

CCTCAAAAGA GGCAGCAAAA

TCATCAGAAA CGAACGCATC ATCAAGTGCC

GGTCGTGCAG CTTCCTCGGC
```

```
AACGGCGGCA GAAAATTCTG CCAGGGCGGC

AAAAACGTCC GAGACGAATG

CCAGGTCATC TGAAACAGCA GCGGAACGGA

GCGCCTCTGC CGCGGCAGAC

GCAAAAACAG CGGCGGCGGG GAGTGCGTCA

ACGGCATCCA CGAAGGCGAC

AGAGGCTGCG GGAAGTGCGG TATCAGCATC

GCAGAGCAAA AGTGCGGCAG

AAGCGGCGGC AATACGTGCA AAAAATTCGG

CAAAACGTGC AGAAGATATA

GCTTCAGCTG TCGCGCTTGA GGATGCGGAC

ACAACGAGAA AGGGGATAGT

GCAGCTCAGC AGTGCAACCA ACAGCACGTC

TGAAACGCTT GCTGCAACGC

CAAAGGCGGT TAAGGTGGTA ATGGATGAAA

CGAACAGAAA AGCCCACTGG

ACAGTCCGGC ACTGACCGGA ACGCCAACAG

CACCAACCGC GCTCAGGGGA

ACAAACAATA CCCAGATTGC GAACACCGCT

TTTGTACTGG CCGCGATTGC

AGATGTTATC GACGCGTCAC CTGACGCACT

GAATACGCTG AATGAACTGG

CCGCAGCGCT CGGGAATGAT CCAGATTTTG

CTACCACCAT GACTAACGCG

CTTGCGGGTA ACAACCGAA GAATGCGACA

CTGACGGCGC TGGCAGGGCT

TTCCACGGCG AAAAATAAAT TACCGTATTT

TGCGGAAAAT GATGCCGCCA

GCCTGACTGA ACTGACTCAG GTTGGCAGGG

ATATTCTGGC AAAAAATTCC

GTTGCAGATG TTCTTGAATA CCTTGGGGCC

GGTGAGAATT CGGCCTTTCC

GGCAGGTGCG CCGATCCCGT GGCCATCAGA

TATCGTTCCG TCTGGCTACG

TCCTGATGCA GGGGCAGGCG TTTGACAAAT

CAGCCTACCC AAAACTTGCT

GTCGCGTATC CATCGGGTGT GCTTCCTGAT

ATGCGAGGCT GGACAATCAA

GGGGAAACCC GCCAGCGGTC GTGCTGTATT

GTCTCAGGAA CAGGATGGAA

TTAAGTCGCA CACCCACAGT GCCAGTGCAT
```

```
CCGGTACGGA TTTGGGGACG

AAAACCACAT CGTCGTTTGA TTACGGGACG

AAAACAACAG GCAGTTTCGA

TTACGGCACC AAATCGACGA ATAACACGGG

GGCTCATGCT CACAGTCTGA

GCGGTTCAAC AGGGGCCGCG GGTGCTCATG

CCCACACAAG TGGTTTAAGG

ATGAACAGTT CTGGCTGGAG TCAGTATGGA

ACAGCAACCA TTACAGGAAG

TTTATCCACA GTTAAAGGAA CCAGCACACA

GGGTATTGCT TATTTATCGA

AAACGGACAG TCAGGGCAGC CACAGTCACT

CATTGTCCGG TACAGCCGTG

AGTGCCGGTG CACATGCGCA TACAGTTGGT

ATTGGTGCGC ACCAGCATCC

GGTTGTTATC GGTGCTCATG CCCATTCTTT

CAGTATTGGT TCACACGGAC

ACACCATCAC CGTTAACGCT GCGGGTAACG

CGGAAAACAC CGTCAAAAAC

ATTGCATTTA ACTATATTGT GAGGCTTGCA

TAATGGCATT CAGAATGAGT

GAACAACCAC GGACCATAAA AATTTATAAT

CTGCTGGCCG GAACTAATGA

ATTTATTGGT GAAGGTGACG CATATATTCC

GCCTCATACC GGTCTGCCTG

CAAACAGTAC CGATATTGCA CCGCCAGATA

TTCCGGCTGG CTTTGTGGCT

GTTTTCAACA GTGATGAGGC ATCGTGGCAT

CTCGTTGAAG ACCATCGGGG

TAAAACCGTC TATGACGTGG CTTCCGGCGA

CGCGTTATTT ATTTCTGAAC

TCGGTCCGTT ACCGGAAAAT TTTACCTGGT

TATCGCCGGG AGGGGAATAT

CAGAAGTGGA ACGGCACAGC CTGGGTGAAG

GATACGGAAG CAGAAAAACT

GTTCCG

Fragment 4 (positions 22350-27972 of phage lambda)
GATCCGGGAG GCGGAAGAAA CAAAAAAAAG

CCTGATGCAG GTAGCCAGTG

AGCATATTGC GCCGCTTCAG GATGCTGCAG
```

-continued

ATCTGGAAAT TGCAACGAAG

GAAGAAACCT CGTTGCTGGA AGCCTGGAAG

AAGTATCGGG TGTTGCTGAA

CCGTGTTGAT ACATCAACTG CACCTGATAT

TGAGTGGCCT GCTGTCCCTG

TTATGGAGTA ATCGTTTTGT GATATGCCGC

AGAAACGTTG TATGAAATAA

CGTTCTGCGG TTAGTTAGTA TATTGTAAAG

CTGAGTATTG GTTTATTTGG

CGATTATTAT CTTCAGGAGA ATAATGGAAG

TTCTATGACT CAATTGTTCA

TAGTGTTTAC ATCACCGCCA ATTGCTTTTA

AGACTGAACG CATGAAATAT

GGTTTTTCGT CATGTTTTGA GTCTGCTGTT

GATATTTCTA AAGTCGGTTT

TTTTTCTTCG TTTTCTCTAA CTATTTTCCA

TGAAATACAT TTTTGATTAT

TATTTGAATC AATTCCAATT ACCTGAAGTC

TTTCATCTAT AATTGGCATT

GTATGTATTG GTTTATTGGA GTAGATGCTT

GCTTTTCTGA GCCATAGCTC

TGATATCCAA ATGAAGCCAT AGGCATTTGT

TATTTTGGCT CTGTCAGCTG

CATAACGCCA AAAAATATAT TTATCTGCTT

GATCTTCAAA TGTTGTATTG

ATTAAATCAA TTGGATGGAA TTGTTTATCA

TAAAAAATTA ATGTTTGAAT

GTGATAACCG TCCTTTAAAA AAGTCGTTTC

TGCAAGCTTG GCTGTATAGT

CAACTAACTC TTCTGTCGAA GTGATATTTT

TAGGCTTATC TACCAGTTTT

AGACGCTCTT TAATATCTTC AGGAATTATT

TTATTGTCAT ATTGTATCAT

GCTAAATGAC AATTTGCTTA TGGAGTAATC

TTTTAATTTT AAATAAGTTA

TTCTCCTGGC TTCATCAAAT AAAGAGTCGA

ATGATGTTGG CGAAATCACA

TCGTCACCCA TTGGATTGTT TATTTGTATG

CCAAGAGAGT TACAGCAGTT

ATACATTCTG CCATAGATTA TAGCTAAGGC

ATGTAATAAT TCGTAATCTT

-continued

TTAGCGTATT AGCGACCCAT CGTCTTTCTG

ATTTAATAAT AGATGATTCA

GTTAAATATG AAGGTAATTT CTTTTGTGCA

AGTCTGACTA ACTTTTTTAT

ACCAATGTTT AACATACTTT CATTTGTAAT

AAACTCAATG TCATTTTCTT

CAATGTAAGA TGAAATAAGA GTAGCCTTTG

CCTCGCTATA CATTTCTAAA

TCGCCTTGTT TTTCTATCGT ATTGCGAGAA

TTTTTAGCCC AAGCCATTAA

TGGATCATTT TTCCATTTTT CAATAACATT

ATTGTTATAC CAAATGTCAT

ATCCTATAAT CTGGTTTTTG TTTTTTTGAA

TAATAAATGT TACTGTTCTT

GCGGTTTGGA GGAATTGATT CAAATTCAAG

CGAAATAATT CAGGGTCAAA

ATATGTATCA ATGCAGCATT TGAGCAAGTG

CGATAAATCT TTAAGTCTTC

TTTCCCATGG TTTTTTAGTC ATAAAACTCT

CCATTTTGAT AGGTTGCATG

CTAGATGCTG ATATATTTTA GAGGTGATAA

AATTAACTGC TTAACTGTCA

ATGTAATACA AGTTGTTGA TCTTTGCAAT

GATTCTTATC AGAAACCATA

TAGTAAATTA GTTACACAGG AAATTTTTAA

TATTATTATT ATCATTCATT

ATGTATTAAA ATTAGAGTTG TGGCTTGGCT

CTGCTAACAC GTTGCTCATA

GGAGATATGG TAGAGCCGCA GACACGTCGT

ATGCAGGAAC GTGCTGCGGC

TGGCTGGTGA ACTTCCGATA GTGCGGGTGT

TGAATGATTT CCAGTTGCTA

CCGATTTTAC ATATTTTTTG CATGAGAGAA

TTTGTACCAC CTCCCACCGA

CCATCTATGA CTGTACGCCA CTGTCCCTAG

GACTGCTATG TGCCGGAGCG

GACATTACAA ACGTCCTTCT CGGTGCATGC

CACTGTTGCC AATGACCTGC

CTAGGAATTG GTTAGCAAGT TACTACCGGA

TTTTGTAAAA ACAGCCCTCC

TCATATAAAA AGTATTCGTT CACTTCCGAT

```
AAGCGTCGTA ATTTTCTATC

TTTCATCATA TTCTAGATCC CTCTGAAAAA

ATCTTCCGAG TTTGCTAGGC

ACTGATACAT AACTCTTTTC CAATAATTGG

GGAAGTCATT CAAATCTATA

ATAGGTTTCA GATTTGCTTC AATAAATTCT

GACTGTAGCT GCTGAAACGT

TGCGGTTGAA CTATATTTCC TTATAACTTT

TACGAAAGAG TTTCTTTGAG

TAATCACTTC ACTCAAGTGC TTCCCTGCCT

CCAAACGATA CCTGTTAGCA

ATATTTAATA GCTTGAAATG ATGAAGAGCT

CTGTGTTTGT CTTCCTGCCT

CCAGTTCGCC GGGCATTCAA CATAAAAACT

GATAGCACCC GGAGTTCCGG

AAACGAAATT TGCATATACC CATTGCTCAC

GAAAAAAAT GTCCTTGTCG

ATATAGGGAT GAATCGCTTG GTGTACCTCA

TCTACTGCGA AAACTTGACC

TTTCTCTCCC ATATTGCAGT CGCGGCACGA

TGGAACTAAA TTAATAGGCA

TCACCGAAAA TTCAGGATAA TGTGCAATAG

GAAGAAAATG ATCTATATTT

TTTGTCTGTC CTATATCACC ACAAAATGGA

CATTTTTCAC CTGATGAAAC

AAGCATGTCA TCGTAATATG TTCTAGCGGG

TTTGTTTTTA TCTCGGAGAT

TATTTTCATA AAGCTTTTCT AATTTAACCT

TTGTCAGGTT ACCAACTACT

AAGGTTGTAG GCTCAAGAGG GTGTGTCCTG

TCGTAGGTAA ATAACTGACC

TGTCGAGCTT AATATTCTAT ATTGTTGTTC

TTTCTGCAAA AAAGTGGGGA

AGTGAGTAAT GAAATTATTT CTAACATTTA

TCTGCATCAT ACCTTCCGAG

CATTTATTAA GCATTTCGCT ATAAGTTCTC

GCTGGAAGAG GTAGTTTTTT

CATTGTACTT TACCTTCATC TCTGTTCATT

ATCATCGCTT TTAAAACGGT

TCGACCTTCT AATCCTATCT GACCATTATA

ATTTTTTAGA ATGGTTTCAT

AAGAAAGCTC TGAATCAACG GACTGCGATA

ATAAGTGGTG GTATCCAGAA

TTTGTCACTT CAAGTAAAAA CACCTCACGA

GTTAAAACAC CTAAGTTCTC

ACCGAATGTC TCAATATCCG GACGGATAAT

ATTTATTGCT TCTCTTGACC

GTAGGACTTT CCACATGCAG GATTTTGGAA

CCTCTTGCAG TACTACTGGG

GAATGAGTTG CAATTATTGC TACACCATTG

CGTGCATCGA GTAAGTCGCT

TAATGTTCGT AAAAAAGCAG AGAGCAAAGG

TGGATGCAGA TGAACCTCTG

GTTCATCGAA TAAAACTAAT GACTTTTCGC

CAACGACATC TACTAATCTT

GTGATAGTAA ATAAAACAAT TGCATGTCCA

GAGCTCATTC GAAGCAGATA

TTTCTGGATA TTGTCATAAA ACAATTTAGT

GAATTTATCA TCGTCCACTT

GAATCTGTGG TTCATTACGT CTTAACTCTT

CATATTTAGA AATGAGGCTG

ATGAGTTCCA TATTTGAAAA GTTTTCATCA

CTACTTAGTT TTTTGATAGC

TTCAAGCCAG AGTTGTCTTT TTCTATCTAC

TCTCATACAA CCAATAAATG

CTGAAATGAA TTCTAAGCGG AGATCGCCTA

GTGATTTTAA ACTATTGCTG

GCAGCATTCT TGAGTCCAAT ATAAAAGTAT

TGTGTACCTT TTGCTGGGTC

AGGTTGTTCT TTAGGAGGAG TAAAAGGATC

AAATGCACTA AACGAAACTG

AAACAAGCGA TCGAAAATAT CCCTTTGGGA

TTCTTGACTC GATAAGTCTA

TTATTTTCAG AGAAAAAATA TTCATTGTTT

TCTGGGTTGG TGATTGCACC

AATCATTCCA TTCAAAATTG TTGTTTTACC

ACACCCATTC CGCCCGATAA

AAGCATGAAT GTTCGTGCTG GGCATAGAAT

TAACCGTCAC CTCAAAAGGT

ATAGTTAAAT CACTGAATCC GGGAGCACTT

TTTCTATTAA ATGAAAGTG

GAAATCTGAC AATTCTGGCA AACCATTTAA
```

```
CACACGTGCG AACTGTCCAT
GAATTTCTGA AAGAGTTACC CCTCTAAGTA
ATGAGGTGTT AAGGACGCTT
TCATTTTCAA TGTCGGCTAA TCGATTTGGC
CATACTACTA AATCCTGAAT
AGCTTTAAGA AGGTTATGTT TAAAACCATC
GCTTAATTTG CTGAGATTAA
CATAGTAGTC AATGCTTTCA CCTAAGGAAA
AAAACATTTC AGGGAGTTGA
CTGAATTTTT TATCTATTAA TGAATAAGTG
CTTACTTCTT CTTTTTGACC
TACAAAACCA ATTTTAACAT TTCCGATATC
GCATTTTTCA CCATGCTCAT
CAAAGACAGT AAGATAAAAC ATTGTAACAA
AGGAATAGTC ATTCCAACCA
TCTGCTCGTA GGAATGCCTT ATTTTTTTCT
ACTGCAGGAA TATACCCGCC
TCTTTCAATA ACACTAAACT CCAACATATA
GTAACCCTTA ATTTTATTAA
AATAACCGCA ATTTATTTGG CGGCAACACA
GGATCTCTCT TTTAAGTTAC
TCTCTATTAC ATACGTTTTC CATCTAAAAA
TTAGTAGTAT TGAACTTAAC
GGGGCATCGT ATTGTAGTTT TCCATATTTA
GCTTTCTGCT TCCTTTTGGA
TAACCCACTG TTATTCATGT TGCATGGTGC
ACTGTTTATA CCAACGATAT
AGTCTATTAA TGCATATATA GTATCGCCGA
ACGATTAGCT CTTCAGGCTT
CTGAAGAAGC GTTTCAAGTA CTAATAAGCC
GATAGATAGC CACGGACTTC
GTAGCCATTT TTCATAAGTG TTAACTTCCG
CTCCTCGCTC ATAACAGACA
TTCACTACAG TTATGGCGGA AAGGTATGCA
TGCTGGGTGT GGGGAAGTCG
TGAAAGAAAA GAAGTCAGCT GCGTCGTTTG
ACATCACTGC TATCTTCTTA
CTGGTTATGC AGGTCGTAGT GGGTGGCACA
CAAAGCTTTG CACTGGATTG
CGAGGCTTTG TGCTTCTCTG GAGTGCGACA
GGTTTGATGA CAAAAAATTA

GCGCAAGAAG ACAAAAATCA CCTTGCGCTA
ATGCTCTGTT ACAGGTCACT
AATACCATCT AAGTAGTTGA TTCATAGTGA
CTGCATATGT TGTGTTTTAC
AGTATTATGT AGTCTGTTTT TTATGCAAAA
TCTAATTTAA TATATTGATA
TTTATATCAT TTTACGTTTC TCGTTCAGCT
TTTTTATACT AAGTTGGCAT
TATAAAAAAG CATTGCTTAT CAATTTGTTG
CAACGAACAG GTCACTATCA
GTCAAAATAA AATCATTATT TGATTTCAAT
TTTGTCCCAC TCCCTGCCTC
TGTCATCACG ATACTGTGAT GCCATGGTGT
CCGACTTATG CCCGAGAAGA
TGTTGAGCAA ACTTATCGCT TATCTGCTTC
TCATAGAGTC TTGCAGACAA
ACTGCGCAAC TCGTGAAAGG TAGGCG

Fragment 5 (positions 27976-34499 of phage lambda)
GATCCCCTTC GAAGGAAAGA CCTGATGCTT
TTCGTGCGCG CATAAAATAC
CTTGATACTG TGCCGGATGA AAGCGGTTCG
CGACGAGTAG ATGCAATTAT
GGTTTCTCCG CCAAGAATCT CTTTGCATTT
ATCAAGTGTT TCCTTCATTG
ATATTCCGAG AGCATCAATA TGCAATGCTG
TTGGGATGGC AATTTTTACG
CCTGTTTTGC TTTGCTCGAC ATAAAGATAT
CCATCTACGA TATCAGACCA
CTTCATTTCG CATAAATCAC CAACTCGTTG
CCCGGTAACA ACAGCCAGTT
CCATTGCAAG TCTGAGCCAA CATGGTGATG
ATTCTGCTGC TTGATAAATT
TTCAGGTATT CGTCAGCCGT AAGTCTTGAT
CTCCTTACCT CTGATTTTGC
TGCGCGAGTG GCAGCGACAT GGTTTGTTGT
TATATGGCCT TCAGCTATTG
CCTCTCGGAA TGCATCGCTC AGTGTTGATC
TGATTAACTT GGCTGACGCC
GCCTTGCCCT CGTCTATGTA TCCATTGAGC
ATTGCCGCAA TTTCTTTTGT
```

```
GGTGATGTCT TCAAGTGGAG CATCAGGCAG
ACCCCTCCTT ATTGCTTTAA
TTTTGCTCAT GTAATTTATG AGTGTCTTCT
GCTTGATTCC TCTGCTGGCC
AGGATTTTTT CGTAGCGATC AAGCCATGAA
TGTAACGTAA CGGAATTATC
ACTGTTGATT CTCGCTGTCA GAGGCTTGTG
TTTGTGTCCT GAAAATAACT
CAATGTTGGC CTGTATAGCT TCAGTGATTG
CGATTCGCCT GTCTCTGCCT
AATCCAAACT CTTTACCCGT CCTTGGGTCC
CTGTAGCAGT AATATCCATT
GTTTCTTATA TAAAGGTTAG GGGGTAAATC
CCGGCGCTCA TGACTTCGCC
TTCTTCCCAT TTCTGATCCT CTTCAAAGG
CCACCTGTTA CTGGTCGATT
TAAGTCAACC TTTACCGCTG ATTCGTGGAA
CAGATACTCT CTTCCATCCT
TAACCGGAGG TGGGAATATC CTGCATTCCC
GAACCCATCG ACGAACTGTT
TCAAGGCTTC TTGGACGTCG CTGGCGTGCG
TTCCACTCCT GAAGTGTCAA
GTACATCGCA AAGTCTCCGC AATTACACGC
AAGAAAAAAC CGCCATCAGG
CGGCTTGGTG TTCTTTCAGT TCTTCAATTC
GAATATTGGT TACGTCTGCA
TGTGCTATCT GCGCCCATAT CATCCAGTGG
TCGTAGCAGT CGTTGATGTT
CTCCGCTTCG ATAACTCTGT TGAATGGCTC
TCCATTCCAT TCTCCTGTGA
CTCGGAAGTG CATTTATCAT CTCCATAAAA
CAAAACCCGC CGTAGCGAGT
TCAGATAAAA TAAATCCCCG CGAGTGCGAG
GATTGTTATG TAATATTGGG
TTTAATCATC TATATGTTTT GTACAGAGAG
GGCAAGTATC GTTTCCACCG
TACTCGTGAT AATAATTTTG CACGGTATCA
GTCATTTCTC GCACATTGCA
GAATGGGGAT TGTCTTCAT TAGACTTATA
AACCTTCATG GAATATTTGT
ATGCCGACTC TATATCTATA CCTTCATCTA
```

```
CATAAACACC TTCGTGATGT
CTGCATGGAG ACAAGACACC GGATCTGCAC
AACATTGATA ACGCCCAATC
TTTTTGCTCA GACTCTAACT CATTGATACT
CATTTATAAA CTCCTTGCAA
TGTATGTCGT TTCAGCTAAA CGGTATCAGC
AATGTTTATG TAAAGAAACA
GTAAGATAAT ACTCAACCCG ATGTTTGAGT
ACGGTCATCA TCTGACACTA
CAGACTCTGG CATCGCTGTG AAGACGACGC
GAAATTCAGC ATTTTCACAA
GCGTTATCTT TTACAAAACC GATCTCACTC
TCCTTTGATG CGAATGCCAG
CGTCAGACAT CATATGCAGA TACTCACCTG
CATCCTGAAC CCATTGACCT
CCAACCCCGT AATAGCGATG CGTAATGATG
TCGATAGTTA CTAACGGGTC
TTGTTCGATT AACTGCCGCA GAAACTCTTC
CAGGTCACCA GTGCAGTGCT
TGATAACAGG AGTCTTCCCA GGATGGCGAA
CAACAAGAAA CTGGTTTCCG
TCTTCACGGA CTTCGTTGCT TTCCAGTTTA
GCAATACGCT TACTCCCATC
CGAGATAACA CCTTCGTAAT ACTCACGCTG
CTCGTTGAGT TTTGATTTTG
CTGTTTCAAG CTCAACACGC AGTTTCCCTA
CTGTTAGCGC AATATCCTCG
TTCTCCTGGT CGCGGCGTTT GATGTATTGC
TGGTTTCTTT CCCGTTCATC
CAGCAGTTCC AGCACAATCG ATGGTGTTAC
CAATTCATGG AAAAGGTCTG
CGTCAAATCC CCAGTCGTCA TGCATTGCCT
GCTCTGCCGC TTCACGCAGT
GCCTGAGAGT TAATTTCGCT CACTTCGAAC
CTCTCTGTTT ACTGATAAGT
TCCAGATCCT CCTGGCAACT TGCACAAGTC
CGACAACCCT GAACGACCAG
GCGTCTTCGT TCATCTATCG GATCGCCACA
CTCACAACAA TGAGTGGCAG
ATATAGCCTG GTGGTTCAGG CGGCGCATTT
TTATTGCTGT GTTGCGCTGT
```

-continued

```
AATTCTTCTA TTTCTGATGC TGAATCAATG

ATGTCTGCCA TCTTTCATTA

ATCCCTGAAC TGTTGGTTAA TACGCTTGAG

GGTGAATGCG AATAATAAAA

AAGGAGCCTG TAGCTCCCTG ATGATTTTGC

TTTTCATGTT CATCGTTCCT

TAAAGACGCC GTTTAACATG CCGATTGCCA

GGCTTAAATG AGTCGGTGTG

AATCCCATCA GCGTTACCGT TTCGCGGTGC

TTCTTCAGTA CGCTACGGCA

AATGTCATCG ACGTTTTTAT CCGGAAACTG

CTGTCTGGCT TTTTTTGATT

TCAGAATTAG CCTGACGGGC AATGCTGCGA

AGGGCGTTTT CCTGCTGAGG

TGTCATTGAA CAAGTCCCAT GTCGGCAAGC

ATAAGCACAC AGAATATGAA

GCCCGCTGCC AGAAAATGC ATTCCGTGGT

TGTCATACCT GGTTTCTCTC

ATCTGCTTCT GCTTTCGCCA CCATCATTTC

CAGCTTTTGT GAAAGGGATG

CGGCTAACGT ATGAAATTCT TCGTCTGTTT

CTACTGGTAT TGGCACAAAC

CTGATTCCAA TTTGAGCAAG CTATGTGCC

ATCTCGATAC TCGTTCTTAA

CTCAACAGAA GATGCTTTGT GCATACAGCC

CCTCGTTTAT TATTTATCTC

CTCAGCCAGC CGCTGTGCTT TCAGTGGATT

TCGGATAACA GAAAGGCCGG

GAAATACCCA GCCTCGCTTT GTAACGGAGT

AGACGAAAGT GATTGCGCCT

ACCCGGATAT TATCGTGAGG ATGCGTCATC

GCCATTGCTC CCCAAATACA

AAACCAATTT CAGCCAGTGC CTCGTCCATT

TTTTCGATGA ACTCCGGCAC

GATCTCGTCA AAACTCGCCA TGTACTTTTC

ATCCCGCTCA ATCACGACAT

AATGCAGGCC TTCACGCTTC ATACGCGGGT

CATAGTTGGC AAAGTACCAG

GCATTTTTC GCGTCACCCA CATGCTGTAC

TGCACCTGGG CCATGTAAGC

TGACTTTATG GCCTCGAAAC CACCGAGCCG

GAACTTCATG AAATCCCGGG

AGGTAAACGG GCATTTCAGT TCAAGGCCGT

TGCCGTCACT GCATAAACCA

TCGGGAGAGC AGGCGGTACG CATACTTTCG

TCGCGATAGA TGATCGGGGA

TTCAGTAACA TTCACGCCGG AAGTGAATTC

AAACAGGGTT CTGGCGTCGT

TCTCGTACTG TTTTCCCCAG GCCAGTGCTT

TAGCGTTAAC TTCCGGAGCC

ACACCGGTGC AAACCTCAGC AAGCAGGGTG

TGGAAGTAGG ACATTTTCAT

GTCAGGCCAC TTCTTTCCGG AGCGGGGTTT

TGCTATCACG TTGTGAACTT

CTGAAGCGGT GATGACGCCG AGCCGTAATT

TGTGCCACGC ATCATCCCCC

TGTTCGACAG CTCTCACATC GATCCCGGTA

CGCTGCAGGA TAATGTCCGG

TGTCATGCTG CCACCTTCTG CTCTGCGGCT

TTCTGTTTCA GGAATCCAAG

AGCTTTTACT GCTTCGGCCT GTGTCAGTTC

TGACGATGCA CGAATGTCGC

GGCGAAATAT CTGGGAACAG AGCGGCAATA

AGTCGTCATC CCATGTTTTA

TCCAGGGCGA TCAGCAGAGT GTTAATCTCC

TGCATGGTTT CATCGTTAAC

CGGAGTGATG TCGCGTTCCG GCTGACGTTC

TGCAGTGTAT GCAGTATTTT

CGACAATGCG CTCGGCTTCA TCCTTGTCAT

AGATACCAGC AAATCCGAAG

GCCAGACGGG CACACTGAAT CATGGCTTTA

TGACGTAACA TCCGTTTGGG

ATGCGACTGC CACGGCCCCG TGATTTCTCT

GCCTTCGCGA GTTTTGAATG

GTTCGCGGCG GCATTCATCC ATCCATTCGG

TAACGCAGAT CGGATGATTA

CGGTCCTTGC GGTAAATCCG GCATGTACAG

GATTCATTGT CCTGCTCAAA

GTCCATGCCA TCAAACTGCT GGTTTTCATT

GATGATGCGG GACCAGCCAT

CAACGCCCAC CACCGGAACG ATGCCATTCT

GCTTATCAGG AAAGGCGTAA
```

-continued

ATTTCTTTCG TCCACGGATT AAGGCCGTAC

TGGTTGGCAA CGATCAGTAA

TGCGATGAAC TGCGCATCGC TGGCATCACC

TTTAAATGCC GTCTGGCGAA

GAGTGGTGAT CAGTTCCTGT GGGTCGACAG

AATCCATGCC GACACGTTCA

GCCAGCTTCC CAGCCAGCGT TGCGAGTGCA

GTACTCATTC GTTTTATACC

TCTGAATCAA TATCAACCTG GTGGTGAGCA

ATGGTTTCAA CCATGTACCG

GATGTGTTCT GCCATGCGCT CCTGAAACTC

AACATCGTCA TCAAACGCAC

GGGTAATGGA TTTTTTGCTG GCCCCGTGGC

GTTGCAAATG ATCGATGCAT

AGCGATTCAA ACAGGTGCTG GGGCAGGCCT

TTTTCCATGT CGTCTGCCAG

TTCTGCCTCT TTCTCTTCAC GGGCGAGCTG

CTGGTAGTGA CGCGCCCAGC

TCTGAGCCTC AAGACGATCC TGAATGTAAT

AAGCGTTCAT GGCTGAACTC

CTGAAATAGC TGTGAAAATA TCGCCCGCGA

AATGCCGGGC TGATTAGGAA

AACAGGAAAG GGGGTTAGTG AATGCTTTTG

CTTGATCTCA GTTTCAGTAT

TAATATCCAT TTTTTATAAG CGTCGACGGC

TTCACGAAAC ATCTTTTCAT

CGCCAATAAA AGTGGCGATA GTGAATTTAG

TCTGGATAGC CATAAGTGTT

TGATCCATTC TTTGGGACTC CTGGCTGATT

AAGTATGTCG ATAAGGCGTT

TCCATCCGTC ACGTAATTTA CGGGTGATTC

GTTCAAGTAA AGATTCGGAA

GGGCAGCCAG CAACAGGCCA CCCTGCAATG

GCATATTGCA TGGTGTGCTC

CTTATTTATA CATAACGAAA AACGCCTCGA

GTGAAGCGTT ATTGGTATGC

GGTAAAACCG CACTCAGGCG GCCTTGATAG

TCATATCATC TGAATCAAAT

ATTCCTGATG TATCGATATC GGTAATTCTT

ATTCCTTCGC TACCATCCAT

TGGAGGCCAT CCTTCCTGAC CATTTCCATC

-continued

ATTCCAGTCG AACTCACACA

CAACACCATA TGCATTTAAG TCGCTTGAAA

TTGCTATAAG CAGAGCATGT

TGCGCCAGCA TGATTAATAC AGCATTTAAT

ACAGAGCCGT GTTTATTGAG

TCGGTATTCA GAGTCTGACC AGAAATTATT

AATCTGGTGA AGTTTTTCCT

CTGTCATTAC GTCATGGTCG ATTTCAATTT

CTATTGATGC TTTCCAGTCG

TAATCAATGA TGTATTTTTT GATGTTTGAC

ATCTGTTCAT ATCCTCACAG

ATAAAAAATC GCCCTCACAC TGGAGGGCAA

AGAAGATTTC CAATAATCAG

AACAAGTCGG CTCCTGTTTA GTTACGAGCG

ACATTGCTCC GTGTATTCAC

TCGTTGGAAT GAATACACAG TGCAGTGTTT

ATTCTGTTAT TTATGCCAAA

AATAAAGGCC ACTATCAGGC AGCTTTGTTG

TTCTGTTTAC CAAGTTCTCT

GGCAATCATT GCCGTCGTTC GTATTGCCCA

TTTATCGACA TATTTCCCAT

CTTCCATTAC AGGAAACATT TCTTCAGGCT

TAACCATGCA TTCCGATTGC

AGCTTGCATC CATTGCATCG CTTGAATTGT

CCACACCATT GATTTTTATC

AATAGTCGTA GTCATACGGA TAGTCCTGGT

ATTGTTCCAT CACATCCTGA

GGATGCTCTT CGAACTCTTC AAATTCTTCT

TCCATATATC ACCTTAAATA

GTGGATTGCG GTAGTAAAGA TTGTGCCTGT

CTTTTAACCA CATCAGGCTC

GGTGGTTCTC GTGTACCCCT ACAGCGAGAA

ATCGGATAAA CTATTACAAC

CCCTACAGTT TGATGAGTAT AGAAATG

Fragment 6 (positions 34503-41732 of phage lambda)
GATCCACTCG TTATTCTCGG ACGAGTGTTC

AGTAATGAAC CTCTGGAGAG

AACCATGTAT ATGATCGTTA TCTGGGTTGG

ACTTCTGCTT TTAAGCCCAG

ATAACTGGCC TGAATATGTT AATGAGAGAA

```
TCGGTATTCC TCATGTGTGG

CATGTTTTCG TCTTTGCTCT TGCATTTTCG

CTAGCAATTA ATGTGCATCG

ATTATCAGCT ATTGCCAGCG CCAGATATAA

GCGATTTAAG CTAAGAAAAC

GCATTAAGAT GCAAAACGAT AAAGTGCGAT

CAGTAATTCA AAACCTTACA

GAAGAGCAAT CTATGGTTTT GTGCGCAGCC

CTTAATGAAG GCAGGAAGTA

TGTGGTTACA TCAAAACAAT TCCCATACAT

TAGTGAGTTG ATTGAGCTTG

GTGTGTTGAA CAAACTTTT TCCCGATGGA

ATGGAAAGCA TATATTATTC

CCTATTGAGG ATATTTACTG GACTGAATTA

GTTGCCAGCT ATGATCCATA

TAATATTGAG ATAAAGCCAA GGCCAATATC

TAAGTAACTA GATAAGAGGA

ATCGATTTTC CCTTAATTTT CTGGCGTCCA

CTGCATGTTA TGCCGCGTTC

GCCAGGCTTG CTGTACCATG TGCGCTGATT

CTTGCGCTCA ATACGTTGCA

GGTTGCTTTC AATCTGTTTG TGGTATTCAG

CCAGCACTGT AAGGTCTATC

GGATTTAGTG CGCTTTCTAC TCGTGATTTC

GGTTTGCGAT TCAGCGAGAG

AATAGGGCGG TTAACTGGTT TTGCGCTTAC

CCCAACCAAC AGGGGATTTG

CTGCTTTCCA TTGAGCCTGT TTCTCTGCGC

GACGTTCGCG GCGGCGTGTT

TGTGCATCCA TCTGGATTCT CCTGTCAGTT

AGCTTTGGTG GTGTGTGGCA

GTTGTAGTCC TGAACGAAAA CCCCCCGCGA

TTGGCACATT GGCAGCTAAT

CCGGAATCGC ACTTACGGCC AATGCTTCGT

TTCGTATCAC ACACCCCAAA

GCCTTCTGCT TTGAATGCTG CCCTTCTTCA

GGGCTTAATT TTTAAGAGCG

TCACCTTCAT GGTGGTCAGT GCGTCCTGCT

GATGTGCTCA GTATCACCGC

CAGTGGTATT TATGTCAACA CCGCCAGAGA

TAATTTATCA CCGCAGATGG

TTATCTGTAT GTTTTTTATA TGAATTTATT

TTTTGCAGGG GGGCATTGTT

TGGTAGGTGA GAGATCTGAA TTGCTATGTT

TAGTGAGTTG TATCTATTTA

TTTTTCAATA AATACAATTG GTTATGTGTT

TTGGGGGCGA TCGTGAGGCA

AAGAAACCC GGCGCTGAGG CCGGGTTATT

CTTGTTCTCT GGTCAAATTA

TATAGTTGGA AAACAAGGAT GCATATATGA

ATGAACGATG CAGAGGCAAT

GCCGATGGCG ATAGTGGGTA TCATGTAGCC

GCTTATGCTG GAAAGAAGCA

ATAACCCGCA GAAAACAAA GCTCCAAGCT

CAACAAAACT AAGGGCATAG

ACAATAACTA CCGATGTCAT ATACCCATAC

TCTCTAATCT TGGCCAGTCG

GCGCGTTCTG CTTCCGATTA GAAACGTCAA

GGCAGCAATC AGGATTGCAA

TCATGGTTCC TGCATATGAT GACAATGTCG

CCCCAAGACC ATCTCTATGA

GCTGAAAAAG AAACACCAGG AATGTAGTGG

CGGAAAAGGA GATAGCAAAT

GCTTACGATA ACGTAAGGAA TTATTACTAT

GTAAACACCA GGCATGATTC

TGTTCCGCAT AATTACTCCT GATAATTAAT

CCTTAACTTT GCCCACCTGC

CTTTTAAAAC ATTCCAGTAT ATCACTTTTC

ATTCTTGCGT AGCAATATGC

CATCTCTTCA GCTATCTCAG CATTGGTGAC

CTTGTTCAGA GGCGCTGAGA

GATGGCCTTT TTCTGATAGA TAATGTTCTG

TTAAAATATC TCCGGCCTCA

TCTTTTGCCC GCAGGCTAAT GTCTGAAAAT

TGAGGTGACG GGTTAAAAAT

AATATCCTTG GCAACCTTTT TTATATCCCT

TTTAAATTTT GGCTTAATGA

CTATATCCAA TGAGTCAAAA AGCTCCCCTT

CAATATCTGT TGCCCCTAAG

ACCTTTAATA TATCGCCAAA TACAGGTAGC

TTGGCTTCTA CCTTCACCGT

TGTTCGGCCG ATGAAATGCA TATGCATAAC
```

-continued

```
ATCGTCTTTG GTGGTTCCCC

TCATCAGTGG CTCTATCTGA ACGCGCTCTC

CACTGCTTAA TGACATTCCT

TTCCCGATTA AAAAATCTGT CAGATCGGAT

GTGGTCGGCC CGAAAACAGT

TCTGGCAAAA CCAATGGTGT CGCCTTCAAC

AAACAAAAAA GATGGGAATC

CCAATGATTC GTCATCTGCG AGGCTGTTCT

TAATATCTTC AACTGAAGCT

TTAGAGCGAT TTATCTTCTG AACCAGACTC

TTGTCATTTG TTTTGGTAAA

GAGAAAGTT TTTCCATCGA TTTTATGAAT

ATACAAATAA TTGGAGCCAA

CCTGCAGGTG ATGATTATCA GCCAGCAGAG

AATTAAGGAA AACAGACAGG

TTTATTGAGC GCTTATCTTT CCCTTTATTT

TTGCTGCGGT AAGTCGCATA

AAAACCATTC TTCATAATTC AATCCATTTA

CTATGTTATG TTCTGAGGGG

AGTGAAAATT CCCCTAATTC GATGAAGATT

CTTGCTCAAT TGTTATCAGC

TATGCGCCGA CCAGAACACC TTGCCGATCA

GCCAAACGTC TCTTCAGGCC

ACTGACTAGC GATAACTTTC CCCACAACGG

AACAACTCTC ATTGCATGGG

ATCATTGGGT ACTGTGGGTT TAGTGGTTGT

AAAAACACCT GACCGCTATC

CCTGATCAGT TTCTTGAAGG TAAACTCATC

ACCCCCAAGT CTGGCTATGC

AGAAATCACC TGGCTCAACA GCCTGCTCAG

GGTCAACGAG AATTAACATT

CCGTCAGGAA AGCTTGGCTT GGAGCCTGTT

GGTGCGGTCA TGGAATTACC

TTCAACCTCA AGCCAGAATG CAGAATCACT

GGCTTTTTTG GTTGTGCTTA

CCCATCTCTC CGCATCACCT TTGGTAAAGG

TTCTAAGCTT AGGTGAGAAC

ATCCCTGCCT GAACATGAGA AAAACAGGG

TACTCATACT CACTTCTAAG

TGACGGCTGC ATACTAACCG CTTCATACAT

CTCGTAGATT TCTCTGGCGA
```

-continued

```
TTGAAGGGCT AAATTCTTCA ACGCTAACTT

TGAGAATTTT TGTAAGCAAT

GCGGCGTTAT AAGCATTTAA TGCATTGATG

CCATTAAATA AAGCACCAAC

GCCTGACTGC CCCATCCCCA TCTTGTCTGC

GACAGATTCC TGGGATAAGC

CAAGTTCATT TTTCTTTTTT TCATAAATTG

CTTTAAGGCG ACGTGCGTCC

TCAAGCTGCT CTTGTGTTAA TGGTTTCTTT

TTTGTGCTCA TACGTTAAAT

CTATCACCGC AAGGGATAAA TATCTAACAC

CGTGCGTGTT GACTATTTTA

CCTCTGGCGG TGATAATGGT TGCATGTACT

AAGGAGGTTG TATGGAACAA

CGCATAACCC TGAAAGATTA TGCAATGCGC

TTTGGGCAAA CCAAGACAGC

TAAAGATCTC GGCGTATATC AAAGCGCGAT

CAACAAGGCC ATTCATGCAG

GCCGAAAGAT TTTTTTAACT ATAAACGCTG

ATGGAAGCGT TTATGCGGAA

GAGGTAAAGC CCTTCCCGAG TAACAAAAAA

ACAACAGCAT AAATAACCCC

GCTCTTACAC ATTCCAGCCC TGAAAAGGG

CATCAAATTA AACCACACCT

ATGGTGTATG CATTTATTTG CATACATTCA

ATCAATTGTT ATCTAAGGAA

ATACTTACAT ATGGTTCGTG CAAACAAACG

CAACGAGGCT CTACGAATCG

AGAGTGCGTT GCTTAACAAA TCGCAATGC

TTGGAACTGA GAAGACAGCG

GAAGCTGTGG GCGTTGATAA GTCGCAGATC

AGCAGGTGGA AGAGGGACTG

GATTCCAAAG TTCTCAATGC TGCTTGCTGT

TCTTGAATGG GGGGTCGTTG

ACGACGACAT GGCTCGATTG GCGCGACAAG

TTGCTGCGAT TCTCACCAAT

AAAAACGCC CGGCGGCAAC CGAGCGTTCT

GAACAAATCC AGATGGAGTT

CTGAGGTCAT TACTGGATCT ATCAACAGGA

GTCATTATGA CAAATACAGC

AAAAATACTC AACTTCGGCA GAGGTAACTT
```

```
TGCCGGACAG GAGCGTAATG
TGGCAGATCT CGATGATGGT TACGCCAGAC
TATCAAATAT GCTGCTTGAG
GCTTATTCGG GCGCAGATCT GACCAAGCGA
CAGTTTAAAG TGCTGCTTGC
CATTCTGCGT AAAACCTATG GGTGGAATAA
ACCAATGGAC AGAATCACCG
ATTCTCAACT TAGCGAGATT ACAAAGTTAC
CTGTCAAACG GTGCAATGAA
GCCAAGTTAG AACTCGTCAG AATGAATATT
ATCAAGCAGC AAGGCGGCAT
GTTTGGACCA AATAAAAACA TCTCAGAATG
GTGCATCCCT CAAAACGAGG
GAAAATCCCC TAAAACGAGG GATAAAACAT
CCCTCAAATT GGGGGATTGC
TATCCCTCAA ACAGGGGGA CACAAAAGAC
ACTATTACAA AAGAAAAAAG
AAAAGATTAT TCGTCAGAGA ATTCTGGCGA
ATCCTCTGAC CAGCCAGAAA
ACGACCTTTC TGTGGTGAAA CCGGATGCTG
CAATTCAGAG CGGCAGCAAG
TGGGGGACAG CAGAAGACCT GACCGCCGCA
GAGTGGATGT TTGACATGGT
GAAGACTATC GCACCATCAG CCAGAAAACC
GAATTTTGCT GGGTGGGCTA
ACGATATCCG CCTGATGCGT GAACGTGACG
GACGTAACCA CCGCGACATG
TGTGTGCTGT TCCGCTGGGC ATGCCAGGAC
AACTTCTGGT CCGGTAACGT
GCTGAGCCCG GCCAAACTCC GCGATAAGTG
GACCCAACTC GAAATCAACC
GTAACAAGCA ACAGGCAGGC GTGACAGCCA
GCAAACCAAA ACTCGACCTG
ACAAACACAG ACTGGATTTA CGGGGTGGAT
CTATGAAAAA CATCGCCGCA
CAGATGGTTA ACTTTGACCG TGAGCAGATG
CGTCGGATCG CCAACAACAT
GCCGGAACAG TACGACGAAA AGCCGCAGGT
ACAGCAGGTA GCGCAGATCA
TCAACGGTGT GTTCAGCCAG TTACTGGCAA
CTTTCCCGGC GAGCCTGGCT
```

```
AACCGTGACC AGAACGAAGT GAACGAAATC
CGTCGCCAGT GGGTTCTGGC
TTTTCGGGAA AACGGGATCA CCACGATGGA
ACAGGTTAAC GCAGGAATGC
GCGTAGCCCG TCGGCAGAAT CGACCATTTC
TGCCATCACC CGGGCAGTTT
GTTGCATGGT GCCGGGAAGA AGCATCCGTT
ACCGCCGGAC TGCCAAACGT
CAGCGAGCTG GTTGATATGG TTTACGAGTA
TTGCCGGAAG CGAGGCCTGT
ATCCGGATGC GGAGTCTTAT CCGTGGAAAT
CAAACGCGCA CTACTGGCTG
GTTACCAACC TGTATCAGAA CATGCGGGCC
AATGCGCTTA CTGATGCGGA
ATTACGCCGT AAGGCCGCAG ATGAGCTTGT
CCATATGACT GCGAGAATTA
ACCGTGGTGA GGCGATCCCT GAACCAGTAA
AACAACTTCC TGTCATGGGC
GGTAGACCTC TAAATCGTGC ACAGGCTCTG
GCGAAGATCG CAGAAATCAA
AGCTAAGTTC GGACTGAAAG GAGCAAGTGT
ATGACGGGCA AAGAGGCAAT
TATTCATTAC CTGGGGACGC ATAATAGCTT
CTGTGCGCCG GACGTTGCCG
CGCTAACAGG CGCAACAGTA ACCAGCATAA
ATCAGGCCGC GGCTAAAATG
GCACGGGCAG GTCTTCTGGT TATCGAAGGT
AAGGTCTGGC GAACGGTGTA
TTACCGGTTT GCTACCAGGG AAGAACGGGA
AGGAAAGATG AGCACGAACC
TGGTTTTTAA GGAGTGTCGC CAGAGTGCCG
CGATGAAACG GGTATTGGCG
GTATATGGAG TTAAAAGATG ACCATCTACA
TTACTGAGCT AATAACAGGC
CTGCTGGTAA TCGCAGGCCT TTTTATTTGG
GGGAGAGGGA AGTCATGAAA
AAACTAACCT TTGAAATTCG ATCTCCAGCA
CATCAGCAAA ACGCTATTCA
CGCAGTACAG CAAATCCTTC CAGACCCAAC
CAAACCAATC GTAGTAACCA
TTCAGGAACG CAACCGCAGC TTAGACCAAA
```

```
ACAGGAAGCT ATGGGCCTGC

TTAGGTGACG TCTCTCGTCA GGTTGAATGG

CATGGTCGCT GGCTGGATGC

AGAAAGCTGG AAGTGTGTGT TTACCGCAGC

ATTAAAGCAG CAGGATGTTG

TTCCTAACCT TGCCGGGAAT GGCTTTGTGG

TAATAGGCCA GTCAACCAGC

AGGATGCGTG TAGGCGAATT TGCGGAGCTA

TTAGAGCTTA TACAGGCATT

CGGTACAGAG CGTGGCGTTA AGTGGTCAGA

CGAAGCGAGA CTGGCTCTGG

AGTGGAAAGC GAGATGGGGA GACAGGGCTG

CATGATAAAT GTCGTTAGTT

TCTCCGGTGG CAGGACGTCA GCATATTTGC

TCTGGCTAAT GGAGCAAAAG

CGACGGGCAG GTAAAGACGT GCATTACGTT

TTCATGGATA CAGGTTGTGA

ACATCCAATG ACATATCGGT TTGTCAGGGA

AGTTGTGAAG TTCTGGATA

TACCGCTCAC CGTATTGCAG GTTGATATCA

ACCCGGAGCT TGGACAGCCA

AATGGTTATA CGGTATGGGA ACCAAAGGAT

ATTCAGACGC GAATGCCTGT

TCTGAAGCCA TTTATCGATA TGGTAAAGAA

ATATGGCACT CCATACGTCG

GCGGCGCGTT CTGCACTGAC AGATTAAAAC

TCGTTCCCTT CACCAAATAC

TGTGATGACC ATTTCGGGCG AGGGAATTAC

ACCACGTGGA TTGGCATCAG

AGCTGATGAA CCGAAGCGGC TAAAGCCAAA

GCCTGGAATC AGATATCTTG

CTGAACTGTC AGACTTTGAG AAGGAAGATA

TCCTCGCATG GTGGAAGCAA

CAACCATTCG ATTTGCAAAT ACCGGAACAT

CTCGGTAACT GCATATTCTG

CATTAAAAAA TCAACGCAAA AAATCGGACT

TGCCTGCAAA GATGAGGAGG

GATTGCAGCG TGTTTTTAAT GAGGTCATCA CGG

Fragment 7 (positions 41736-48502 of phage lambda)
GATCCCATGT GCGTGACGGA CATCGGGAAA

CGCCAAAGGA GATTATGTAC

CGAGGAAGAA TGTCGCTGGA CGGTATCGCG

AAAATGTATT CAGAAAATGA

TTATCAAGCC CTGTATCAGG ACATGGTACG

AGCTAAAAGA TTCGATACCG

GCTCTTGTTC TGAGTCATGC GAAATATTTG

GAGGGCAGCT TGATTTCGAC

TTCGGGAGGG AAGCTGCATG ATGCGATGTT

ATCGGTGCGG TGAATGCAAA

GAAGATAACC GCTTCCGACC AAATCAACCT

TACTGGAATC GATGGTGTCT

CCGGTGTGAA AGAACACCAA CAGGGGTGTT

ACCACTACCG CAGGAAAAGG

AGGACGTGTG GCGAGACAGC GACGAAGTAT

CACCGACATA ATCTGCGAAA

ACTGCAAATA CCTTCCAACG AAACGCACCA

GAAATAAACC CAAGCCAATC

CCAAAAGAAT CTGACGTAAA AACCTTCAAC

TACACGGCTC ACCTGTGGGA

TATCCGGTGG CTAAGACGTC GTGCGAGGAA

AACAAGGTGA TTGACCAAAA

TCGAAGTTAC GAACAAGAAA GCGTCGAGCG

AGCTTTAACG TGCGCTAACT

GCGGTCAGAA GCTGCATGTG CTGGAAGTTC

ACGTGTGTGA GCACTGCTGC

GCAGAACTGA TGAGCGATCC GAATAGCTCG

ATGCACGAGG AAGAAGATGA

TGGCTAAACC AGCGCGAAGA CGATGTAAAA

ACGATGAATG CCGGGAATGG

TTTCACCCTG CATTCGCTAA TCAGTGGTGG

TGCTCTCCAG AGTGTGGAAC

CAAGATAGCA CTCGAACGAC GAAGTAAAGA

ACGCGAAAAA GCGGAAAAAG

CAGCAGAGAA GAAACGACGA CGAGAGGAGC

AGAAACAGAA AGATAAACTT

AAGATTCGAA AACTCGCCTT AAAGCCCCGC

AGTTACTGGA TTAAACAAGC

CCAACAAGCC GTAAACGCCT TCATCAGAGA

AAGAGACCGC GACTTACCAT
```

-continued
```
GTATCTCGTG CGGAACGCTC ACGTCTGCTC
AGTGGGATGC CGGACATTAC
CGGACAACTG CTGCGGCACC TCAACTCCGA
TTTAATGAAC GCAATATTCA
CAAGCAATGC GTGGTGTGCA ACCAGCACAA
AAGCGGAAAT CTCGTTCCGT
ATCGCGTCGA ACTGATTAGC CGCATCGGGC
AGGAAGCAGT AGACGAAATC
GAATCAAACC ATAACCGCCA TCGCTGGACT
ATCGAAGAGT GCAAGGCGAT
CAAGGCAGAG TACCAACAGA AACTCAAAGA
CCTGCGAAAT AGCAGAAGTG
AGGCCGCATG ACGTTCTCAG TAAAAACCAT
TCCAGACATG CTCGTTGAAA
CATACGGAAA TCAGACAGAA GTAGCACGCA
GACTGAAATG TAGTCGCGGT
ACGGTCAGAA AATACGTTGA TGATAAAGAC
GGGAAAATGC ACGCCATCGT
CAACGACGTT CTCATGGTTC ATCGCGGATG
GAGTGAAAGA GATGCGCTAT
TACGAAAAAA TTGATGGCAG CAAATACCGA
AATATTTGGG TAGTTGGCGA
TCTGCACGGA TGCTACACGA ACCTGATGAA
CAAACTGGAT ACGATTGGAT
TCGACAACAA AAAAGACCTG CTTATCTCGG
TGGGCGATTT GGTTGATCGT
GGTGCAGAGA ACGTTGAATG CCTGGAATTA
ATCACATTCC CCTGGTTCAG
AGCTGTACGT GGAAACCATG AGCAAATGAT
GATTGATGGC TTATCAGAGC
GTGGAAACGT TAATCACTGG CTGCTTAATG
GCGGTGGCTG GTTCTTTAAT
CTCGATTACG ACAAAGAAAT TCTGGCTAAA
GCTCTTGCCC ATAAAGCAGA
TGAACTTCCG TTAATCATCG AACTGGTGAG
CAAAGATAAA AAATATGTTA
TCTGCCACGC CGATTATCCC TTTGACGAAT
ACGAGTTTGG AAAGCCAGTT
GATCATCAGC AGGTAATCTG GAACCGCGAA
CGAATCAGCA ACTCACAAAA
CGGGATCGTG AAAGAAATCA AAGGCGCGGA
```

-continued
```
CACGTTCATC TTTGGTCATA
CGCCAGCAGT GAAACCACTC AAGTTTGCCA
ACCAAATGTA TATCGATACC
GGCGCAGTGT TCTGCGGAAA CCTAACATTG
ATTCAGGTAC AGGGAGAAGG
CGCATGAGAC TCGAAAGCGT AGCTAAATTT
CATTCGCCAA AAAGCCCGAT
GATGAGCGAC TCACCACGGG CCACGGCTTC
TGACTCTCTT TCCGGTACTG
ATGTGATGGC TGCTATGGGA ATGGCGCAAT
CACAAGCCGG ATTCGGTATG
GCTGCATTCT GCGGTAAGCA CGAACTCAGC
CAGAACGACA AACAAAAGGC
TATCAACTAT CTGATGCAAT TTGCACACAA
GGTATCGGGG AAATACCGTG
GTGTGGCAAA GCTTGAAGGA AATACTAAGG
CAAAGGTACT GCAAGTGCTC
GCAACATTCG CTTATGCGGA TTATTGCCGT
AGTGCCGCGA CGCCGGGGGC
AAGATGCAGA GATTGCCATG GTACAGGCCG
TGCGGTTGAT ATTGCCAAAA
CAGAGCTGTG GGGGAGAGTT GTCGAGAAAG
AGTGCGGAAG ATGCAAAGGC
GTCGGCTATT CAAGGATGCC AGCAAGCGCA
GCATATCGCG CTGTGACGAT
GCTAATCCCA AACCTTACCC AACCCACCTG
GTCACGCACT GTTAAGCCGC
TGTATGACGC TCTGGTGGTG CAATGCCACA
AAGAAGAGTC AATCGCAGAC
AACATTTTGA ATGCGGTCAC ACGTTAGCAG
CATGATTGCC ACGGATGGCA
ACATATTAAC GGCATGATAT TGACTTATTG
AATAAAATTG GGTAAATTTG
ACTCAACGAT GGGTTAATTC GCTCGTTGTG
GTAGTGAGAT GAAAAGAGGC
GGCGCTTACT ACCGATTCCG CCTAGTTGGT
CACTTCGACG TATCGTCTGG
AACTCCAACC ATCGCAGGCA GAGAGGTCTG
CAAAATGCAA TCCCGAAACA
GTTCGCAGGT AATAGTTAGA GCCTGCATAA
CGGTTTCGGG ATTTTTTATA
```

```
TCTGCACAAC AGGTAAGAGC ATTGAGTCGA
TAATCGTGAA GAGTCGGCGA
GCCTGGTTAG CCAGTGCTCT TTCCGTTGTG
CTGAATTAAG CGAATACCGG
AAGCAGAACC GGATCACCAA ATGCGTACAG
GCGTCATCGC CGCCCAGCAA
CAGCACAACC CAAACTGAGC CGTAGCCACT
GTCTGTCCTG AATTCATTAG
TAATAGTTAC GCTGCGGCCT TTTACACATG
ACCTTCGTGA AAGCGGGTGG
CAGGAGGTCG CGCTAACAAC CTCCTGCCGT
TTTGCCCGTG CATATCGGTC
ACGAACAAAT CTGATTACTA AACACAGTAG
CCTGGATTTG TTCTATCAGT
AATCGACCTT ATTCCTAATT AAATAGAGCA
AATCCCCTTA TTGGGGGTAA
GACATGAAGA TGCCAGAAAA ACATGACCTG
TTGGCCGCCA TTCTCGCGGC
AAAGGAACAA GGCATCGGGG CAATCCTTGC
GTTTGCAATG GCGTACCTTC
GCGGCAGATA TAATGGCGGT GCGTTTACAA
AAACAGTAAT CGACGCAACG
ATGTGCGCCA TTATCGCCTA GTTCATTCGT
GACCTTCTCG ACTTCGCCGG
ACTAAGTAGC AATCTCGCTT ATATAACGAG
CGTGTTTATC GGCTACATCG
GTACTGACTC GATTGGTTCG CTTATCAAAC
GCTTCGCTGC TAAAAAGCC
GGAGTAGAAG ATGGTAGAAA TCAATAATCA
ACGTAAGGCG TTCCTCGATA
TGCTGGCGTG GTCGGAGGGA ACTGATAACG
GACGTCAGAA AACCAGAAAT
CATGGTTATG ACGTCATTGT AGGCGGAGAG
CTATTTACTG ATTACTCCGA
TCACCCTCGC AAACTTGTCA CGCTAAACCC
AAAACTCAAA TCAACAGGCG
CCGGACGCTA CCAGCTTCTT TCCCGTTGGT
GGGATGCCTA CCGCAAGCAG
CTTGGCCTGA AAGACTTCTC TCCGAAAAGT
CAGGACGCTG TGGCATTGCA
GCAGATTAAG GAGCGTGGCG CTTTACCTAT
GATTGATCGT GGTGATATCC
GTCAGGCAAT CGACCGTTGC AGCAATATCT
GGGCTTCACT GCCGGGCGCT
GGTTATGGTC AGTTCGAGCA TAAGGCTGAC
AGCCTGATTG CAAAATTCAA
AGAAGCGGGC GGAACGGTCA GAGAGATTGA
TGTATGAGCA GAGTCACCGC
GATTATCTCC GCTCTGGTTA TCTGCATCAT
CGTCTGCCTG TCATGGGCTG
TTAATCATTA CCGTGATAAC GCCATTACCT
ACAAAGCCCA GCGCGACAAA
AATGCCAGAG AACTGAAGCT GGCGAACGCG
GCAATTACTG ACATGCAGAT
GCGTCAGCGT GATGTTGCTG CGCTCGATGC
AAAATACACG AAGGAGTTAG
CTGATGCTAA AGCTGAAAAT GATGCTCTGC
GTGATGATGT TGCCGCTGGT
CGTCGTCGGT TGCACATCAA AGCAGTCTGT
CAGTCAGTGC GTGAAGCCAC
CACCGCCTCC GGCGTGGATA ATGCAGCCTC
CCCCCGACTG GCAGACACCG
CTGAACGGGA TTATTTCACC CTCAGAGAGA
GGCTGATCAC TATGCAAAAA
CAACTGGAAG GAACCCAGAA GTATATTAAT
GAGCAGTGCA GATAGAGTTG
CCCATATCGA TGGGCAACTC ATGCAATTAT
TGTGAGCAAT ACACACGCGC
TTCCAGCGGA GTATAAATGC CTAAAGTAAT
AAAACCGAGC AATCCATTTA
CGAATGTTTG CTGGGTTTCT GTTTTAACAA
CATTTTCTGC GCCGCCACAA
ATTTTGGCTG CATCGACAGT TTTCTTCTGC
CCAATTCCAG AAACGAAGAA
ATGATGGGTG ATGGTTTCCT TTGGTGCTAC
TGCTGCCGGT TTGTTTTGAA
CAGTAAACGT CTGTTGAGCA CATCCTGTAA
TAAGCAGGGC CAGCGCAGTA
GCGAGTAGCA TTTTTTTCAT GGTGTTATTC
CCGATGCTTT TTGAAGTTCG
CAGAATCGTA TGTGTAGAAA ATTAAACAAA
CCCTAAACAA TGAGTTGAAA
```

```
TTTCATATTG TTAATATTTA TTAATGTATG
TCAGGTGCGA TGAATCGTCA
TTGTATTCCC GGATTAACTA TGTCCACAGC
CCTGACGGGG AACTTCTCTG
CGGGAGTGTC CGGGAATAAT TAAAACGATG
CACACAGGGT TTAGCGCGTA
CACGTATTGC ATTATGCCAA CGCCCCGGTG
CTGACACGGA AGAAACCGGA
CGTTATGATT TAGCGTGGAA AGATTTGTGT
AGTGTTCTGA ATGCTCTCAG
TAAATAGTAA TGAATTATCA AAGGTATAGT
AATATCTTTT ATGTTCATGG
ATATTTGTAA CCCATCGGAA AACTCCTGCT
TTAGCAAGAT TTTCCCTGTA
TTGCTGAAAT GTGATTCTC TTGATTTCAA
CCTATCATAG GACGTTTCTA
TAAGATGCGT GTTTCTTGAG AATTTAACAT
TTACAACCTT TTTAAGTCCT
TTTATTAACA CGGTGTTATC GTTTTCTAAC
ACGATGTGAA TATTATCTGT
GGCTAGATAG TAAATATAAT GTGAGACGTT
GTGACGTTTT AGTTCAGAAT
AAAACAATTC ACAGTCTAAA TCTTTTCGCA
CTTGATCGAA TATTTCTTTA
AAAATGGCAA CCTGAGCCAT TGGTAAAACC
TTCCATGTGA TACGAGGGCG
CGTAGTTTGC ATTATCGTTT TTATCGTTTC
AATCTGGTCT GACCTCCTTG
TGTTTTGTTG ATGATTATG TCAAATATTA
GGAATGTTTT CACTTAATAG
TATTGGTTGC GTAACAAAGT GCGGTCCTGC
TGGCATTCTG GAGGGAAATA
CAACCGACAG ATGTATGTAA GGCCAACGTG
CTCAAATCTT CATACAGAAA
GATTTGAAGT AATATTTTAA CCGCTAGATG

AAGAGCAAGC GCATGGAGCG
ACAAAATGAA TAAAGAACAA TCTGCTGATG
ATCCCTCCGT GGATCTGATT
CGTGTAAAAA ATATGCTTAA TAGCACCATT
TCTATGAGTT ACCCTGATGT
TGTAATTGCA TGTATAGAAC ATAAGGTGTC
TCTGGAAGCA TTCAGAGCAA
TTGAGGCAGC GTTGGTGAAG CACGATAATA
ATATGAAGGA TTATTCCCTG
GTGGTTGACT GATCACCATA ACTGCTAATC
ATTCAAACTA TTTAGTCTGT
GACAGAGCCA ACACGCAGTC TGTCACTGTC
AGGAAAGTGG TAAAACTGCA
ACTCAATTAC TGCAATGCCC TCGTAATTAA
GTGAATTTAC AATATCGTCC
TGTTCGGAGG GAAGAACGCG GGATGTTCAT
TCTTCATCAC TTTTAATTGA
TGTATATGCT CTCTTTTCTG ACGTTAGTCT
CCGACGGCAG GCTTCAATGA
CCCAGGCTGA GAAATTCCCG GACCCTTTTT
GCTCAAGAGC GATGTTAATT
TGTTCAATCA TTTGGTTAGG AAAGCGGATG
TTGCGGGTTG TTGTTCTGCG
GGTTCTGTTC TTCGTTGACA TGAGGTTGCC
CCGTATTCAG TGTCGCTGAT
TTGTATTGTC TGAAGTTGTT TTTACGTTAA
GTTGATGCAG ATCAATTAAT
ACGATACCTG CGTCATAATT GATTATTTGA
CGTGGTTTGA TGGCCTCCAC
GCACGTTGTG ATATGTAGAT GATAATCATT
ATCACTTTAC GGGTCCTTTC
CGGTGATCCG ACAGGTTACG
```

Sequences of Enzyme Components Used

The tag may be left on to permit purification of a Cas-polynucleotide target complex, or removed by TEV cleavage.

>Spy_Cas9_wild-type: wild-type Cas9 from *Streptococcus pyogenes* bearing C-terminal Strep (II) tag
MDKKYSIGLDIGTNSVGWAVITDEYKVPSKKFKVLGNTDRHSIKKNLIGALLFDSGET

AEATRLKRTARRRYTRRKNRICYLQEIFSNEMAKVDDSFFHRLEESFLVEEDKKHERH

PIFGNIVDEVAYHEKYPTIYHLRKKLVDSTDKADLRLIYLALAHMIKFRGHFLIEGDL

-continued

NPDNSDVDKLFIQLVQTYNQLFEENPINASGVDAKAILSARLSKSRRLENLIAQLPGE

KKNGLFGNLIALSLGLTPNFKSNFDLAEDAKLQLSKDTYDDDLDNLLAQIGDQYADLF

LAAKNLSDAILLSDILRVNTEITKAPLSASMIKRYDEHHQDLTLLKALVRQQLPEKYK

EIFFDQSKNGYAGYIDGGASQEEFYKFIKPILEKMDGTEELLVKLNREDLLRKQRTFD

NGSIPHQIHLGELHAILRRQEDFYPFLKDNREKIEKILTFRIPYYVGPLARGNSRFAW

MTRKSEETITPWNFEEVVDKGASAQSFIERMTNFDKNLPNEKVLPKHSLLYEYFTVYN

ELTKVKYVTEGMRKPAFLSGEQKKAIVDLLFKTNRKVTVKQLKEDYFKKIECFDSVEI

SGVEDRFNASLGTYHDLLKIIKDKDFLDNEENEDILEDIVLTLTLFEDREMIEERLKT

YAHLFDDKVMKQLKRRRYTGWGRLSRKLINGIRDKQSGKTILDFLKSDGFANRNFMQL

IHDDSLTFKEDIQKAQVSGQGDSLHEHIANLAGSPAIKKGILQTVKVVDELVKVMGRH

KPENIVIEMARENQTTQKGQKNSRERMKRIEEGIKELGSQILKEHPVENTQLQNEKLY

LYYLQNGRDMYVDQELDINRLSDYDVDHIVPQSFLKDDSIDNKVLTRSDKNRGKSDNV

PSEEVVKKMKNYWRQLLNAKLITQRKFDNLTKAERGGLSELDKAGFIKRQLVETRQIT

KHVAQILDSRMNTKYDENDKLIREVKVITLKSKLVSDFRKDFQFYKVREINNYHHAHD

AYLNAVVGTALIKKYPKLESEFVYGDYKVYDVRKMIAKSEQEIGKATAKYFFYSNIMN

FFKTEITLANGEIRKRPLIETNGETGEIVWDKGRDFATVRKVLSMPQVNIVKKTEVQT

GGFSKESILPKRNSDKLIARKKDWDPKKYGGFDSPTVAYSVLVVAKVEKGKSKKLKSV

KELLGITIMERSSFEKNPIDFLEAKGYKEVKKDLIIKLPKYSLFELENGRKRMLASAG

ELQKGNELALPSKYVNFLYLASHYEKLKGSPEDNEQKQLFVEQHKHYLDEIIEQISEF

SKRVILADANLDKVLSAYNKHRDKPIREQAENIIHLFTLTNLGAPAAFKYFDTTIDRK

RYTSTKEVLDATLIHQSITGLYETRIDLSQLGGDGGS*ENLYFQGGSWSHPQFEKGGGSWSHPQFEK*

>Spy_Cas9_D10A: Cas9 nickase from Streptococcus pyogenes bearing C-
terminal Strep (II) tag
MDKKYSIGLAIGTNSVGWAVITDEYKVPSKKFKVLGNTDRHSIKKNLIGALLFDSGET

AEATRLKRTARRRYTRRKNRICYLQEIFSNEMAKVDDSFFHRLEESFLVEEDKKHERH

PIFGNIVDEVAYHEKYPTIYHLRKKLVDSTDKADLRLIYLALAHMIKFRGHFLIEGDL

NPDNSDVDKLFIQLVQTYNQLFEENPINASGVDAKAILSARLSKSRRLENLIAQLPGE

KKNGLFGNLIALSLGLTPNFKSNFDLAEDAKLQLSKDTYDDDLDNLLAQIGDQYADLF

LAAKNLSDAILLSDILRVNTEITKAPLSASMIKRYDEHHQDLTLLKALVRQQLPEKYK

EIFFDQSKNGYAGYIDGGASQEEFYKFIKPILEKMDGTEELLVKLNREDLLRKQRTFD

NGSIPHQIHLGELHAILRRQEDFYPFLKDNREKIEKILTFRIPYYVGPLARGNSRFAW

MTRKSEETITPWNFEEVVDKGASAQSFIERMTNFDKNLPNEKVLPKHSLLYEYFTVYN

ELTKVKYVTEGMRKPAFLSGEQKKAIVDLLFKTNRKVTVKQLKEDYFKKIECFDSVEI

SGVEDRFNASLGTYHDLLKIIKDKDFLDNEENEDILEDIVLTLTLFEDREMIEERLKT

YAHLFDDKVMKQLKRRRYTGWGRLSRKLINGIRDKQSGKTILDFLKSDGFANRNFMQL

IHDDSLTFKEDIQKAQVSGQGDSLHEHIANLAGSPAIKKGILQTVKVVDELVKVMGRH

KPENIVIEMARENQTTQKGQKNSRERMKRIEEGIKELGSQILKEHPVENTQLQNEKLY

LYYLQNGRDMYVDQELDINRLSDYDVDHIVPQSFLKDDSIDNKVLTRSDKNRGKSDNV

PSEEVVKKMKNYWRQLLNAKLITQRKFDNLTKAERGGLSELDKAGFIKRQLVETRQIT

KHVAQILDSRMNTKYDENDKLIREVKVITLKSKLVSDFRKDFQFYKVREINNYHHAHD

-continued

AYLNAVVGTALIKKYPKLESEFVYGDYKVYDVRKMIAKSEQEIGKATAKYFFYSNIMN

FFKTEITLANGEIRKRPLIETNGETGEIVWDKGRDFATVRKVLSMPQVNIVKKTEVQT

GGFSKESILPKRNSDKLIARKKDWDPKKYGGFDSPTVAYSVLVVAKVEKGKSKKLKSV

KELLGITIMERSSFEKNPIDFLEAKGYKEVKKDLIIKLPKYSLFELENGRKRMLASAG

ELQKGNELALPSKYVNFLYLASHYEKLKGSPEDNEQKQLFVEQHKHYLDEIIEQISEF

SKRVILADANLDKVLSAYNKHRDKPIREQAENIIHLFTLTNLGAPAAFKYFDTTIDRK

RYTSTKEVLDATLIHQSITGLYETRIDLSQLGGDGGS*ENLYFQGGSWSHPQFEKGGGSWSHPQFEK*

>Spy_Cas9_H840A: Cas9 nickase from *Streptococcus pyogenes* bearing C-terminal Strep (II) tag
MDKKYSIGLDIGTNSVGWAVITDEYKVPSKKFKVLGNTDRHSIKKNLIGALLFDSGET

AEATRLKRTARRRYTRRKNRICYLQEIFSNEMAKVDDSFFHRLEESFLVEEDKKHERH

PIFGNIVDEVAYHEKYPTIYHLRKKLVDSTDKADLRLIYLALAHMIKFRGHFLIEGDL

NPDNSDVDKLFIQLVQTYNQLFEENPINASGVDAKAILSARLSKSRRLENLIAQLPGE

KKNGLFGNLIALSLGLTPNFKSNFDLAEDAKLQLSKDTYDDDLDNLLAQIGDQYADLF

LAAKNLSDAILLSDILRVNTEITKAPLSASMIKRYDEHHQDLTLLKALVRQQLPEKYK

EIFFDQSKNGYAGYIDGGASQEEFYKFIKPILEKMDGTEELLVKLNREDLLRKQRTFD

NGSIPHQIHLGELHAILRRQEDFYPFLKDNREKIEKILTFRIPYYVGPLARGNSRFAW

MTRKSEETITPWNFEEVVDKGASAQSFIERMTNFDKNLPNEKVLPKHSLLYEYFTVYN

ELTKVKYVTEGMRKPAFLSGEQKKAIVDLLFKTNRKVTVKQLKEDYFKKIECFDSVEI

SGVEDRFNASLGTYHDLLKIIKDKDFLDNEENEDILEDIVLTLTLFEDREMIEERLKT

YAHLFDDKVMKQLKRRRYTGWGRLSRKLINGIRDKQSGKTILDFLKSDGFANRNFMQL

IHDDSLTFKEDIQKAQVSGQGDSLHEHIANLAGSPAIKKGILQTVKVVDELVKVMGRH

KPENIVIEMARENQTTQKGQKNSRERMKRIEEGIKELGSQILKEHPVENTQLQNEKLY

LYYLQNGRDMYVDQELDINRLSDYDVDAIVPQSFLKDDSIDNKVLTRSDKNRGKSDNV

PSEEVVKKMKNYWRQLLNAKLITQRKFDNLTKAERGGLSELDKAGFIKRQLVETRQIT

KHVAQILDSRMNTKYDENDKLIREVKVITLKSKLVSDFRKDFQFYKVREINNYHHAHD

AYLNAVVGTALIKKYPKLESEFVYGDYKVYDVRKMIAKSEQEIGKATAKYFFYSNIMN

FFKTEITLANGEIRKRPLIETNGETGEIVWDKGRDFATVRKVLSMPQVNIVKKTEVQT

GGFSKESILPKRNSDKLIARKKDWDPKKYGGFDSPTVAYSVLVVAKVEKGKSKKLKSV

KELLGITIMERSSFEKNPIDFLEAKGYKEVKKDLIIKLPKYSLFELENGRKRMLASAG

ELQKGNELALPSKYVNFLYLASHYEKLKGSPEDNEQKQLFVEQHKHYLDEIIEQISEF

SKRVILADANLDKVLSAYNKHRDKPIREQAENIIHLFTLTNLGAPAAFKYFDTTIDRK

RYTSTKEVLDATLIHQSITGLYETRIDLSQLGGDGGSENLYFQGGSWSHPQFEKGGGSWSHPQFEK

>Spy_Cas9_D10A_H840A: dead Cas9 ('dCas9') from *Streptococcus pyogenes* bearing C-terminal Strep (II) tag
Purified as ONLP11836.
MDKKYSIGLAIGTNSVGWAVITDEYKVPSKKFKVLGNTDRHSIKKNLIGALLFDSGET

AEATRLKRTARRRYTRRKNRICYLQEIFSNEMAKVDDSFFHRLEESFLVEEDKKHERH

PIFGNIVDEVAYHEKYPTIYHLRKKLVDSTDKADLRLIYLALAHMIKFRGHFLIEGDL

NPDNSDVDKLFIQLVQTYNQLFEENPINASGVDAKAILSARLSKSRRLENLIAQLPGE

KKNGLFGNLIALSLGLTPNFKSNFDLAEDAKLQLSKDTYDDDLDNLLAQIGDQYADLF

-continued

```
LAAKNLSDAILLSDILRVNTEITKAPLSASMIKRYDEHHQDLTLLKALVRQQLPEKYK

EIFFDQSKNGYAGYIDGGASQEEFYKFIKPILEKMDGTEELLVKLNREDLLRKQRTFD

NGSIPHQIHLGELHAILRRQEDFYPFLKDNREKIEKILTFRIPYYVGPLARGNSRFAW

MTRKSEETITPWNFEEVVDKGASAQSFIERMTNFDKNLPNEKVLPKHSLLYEYFTVYN

ELTKVKYVTEGMRKPAFLSGEQKKAIVDLLFKTNRKVTVKQLKEDYFKKIECFDSVEI

SGVEDRFNASLGTYHDLLKIIKDKDFLDNEENEDILEDIVLTLTLFEDREMIEERLKT

YAHLFDDKVMKQLKRRRYTGWGRLSRKLINGIRDKQSGKTILDFLKSDGFANRNFMQL

IHDDSLTFKEDIQKAQVSGQGDSLHEHIANLAGSPAIKKGILQTVKVVDELVKVMGRH

KPENIVIEMARENQTTQKGQKNSRERMKRIEEGIKELGSQILKEHPVENTQLQNEKLY

LYYLQNGRDMYVDQELDINRLSDYDVDAIVPQSFLKDDSIDNKVLTRSDKNRGKSDNV

PSEEVVKKMKNYWRQLLNAKLITQRKFDNLTKAERGGLSELDKAGFIKRQLVETRQIT

KHVAQILDSRMNTKYDENDKLIREVKVITLKSKLVSDFRKDFQFYKVREINNYHHAHD

AYLNAVVGTALIKKYPKLESEFVYGDYKVYDVRKMIAKSEQEIGKATAKYFFYSNIMN

FFKTEITLANGEIRKRPLIETNGETGEIVWDKGRDFATVRKVLSMPQVNIVKKTEVQT

GGFSKESILPKRNSDKLIARKKDWDPKKYGGFDSPTVAYSVLVVAKVEKGKSKKLKSV

KELLGITIMERSSFEKNPIDFLEAKGYKEVKKDLIIKLPKYSLFELENGRKRMLASAG

ELQKGNELALPSKYVNFLYLASHYEKLKGSPEDNEQKQLFVEQHKHYLDEIIEQISEF

SKRVILADANLDKVLSAYNKHRDKPIREQAENIIHLFTLTNLGAPAAFKYFDTTIDRK

RYTSTKEVLDATLIHOSITGLYETRIDLSQLGGDGGSENLYFQGGSWSHPQFEKGGGSWSHPQFEK

SK007 adapter comprises the below three sequences hybridised together
/5SpC3//iSpC3//iSpC3//iSpC3//iSpC3//iSpC3//iSpC3//iSpC3//iSpC3/

/iSpC3//iSpC3//iSpC3//iSpC3//iSpC3//iSpC3//iSpC3//iSpC3//iSpC3/

/iSpC3//iSpC3//iSpC3//iSpC3//iSpC3//iSpC3//iSpC3//iSpC3//iSpC3/

/iSpC3//iSpC3//iSpC3/GGCGTCTGCTTGGGTGTTTAACCTTTT

TTTTTT/iSp18//iSp18//iSp18//iSp18/AATGTACTTCGTTCAGT

TACGTATTGCT

/5Phos/GCAATAGGTAACTGAACGAAGT/iBNA-A//iBNA-meC/
/iBNA-A//iBNA-T//iBNA-T/TTTGAGGCGAGCGGTCAA /5BNA-G//iBNA-G//iBNA-T//iBNA-T//iBNA-A/AACACCCAAGCAGACG
CCTT
```

Sequence SK43
/5//CholTEG/TTGACCGCTCGCCTC

Example 4

Figure 14:
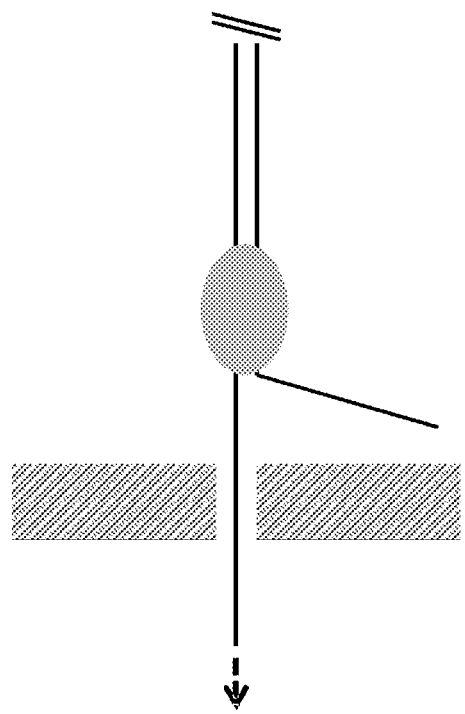
FIG. 14 shows a method for the detection of dCas9 bound to a target polynucleotide analyte in which the target analyte is derivatised with an polynucleotide binding protein free adaptor, as per FIG. 6, and in which one of the two strands of the polynucleotide analyte is translocated through the nanopore, and in which the dCas9 bound to the target analyte produces a characteristic deflection or dwell-time in the ionic current measured through the nanopore.

This Example describes a method for detection of a fragment containing a specific 20 nt target DNA polynucleotide sequence ("target") from a mixture by direct detection of a target/probe complex, wherein the target DNA contacts CRISPR-Cas probe. In this Example, the "target" is positively identified by the unique signal given by the target/probe complex interacting with the Nanopore. In this case the pore is only big enough to admit a single strand of DNA (FIG. 14).

Materials and Methods

A 3.6 kb length of lambda DNA which was end repaired and dA tailed at both ends was ligated to SK007 adapter without helicase (ONLA16389, top+ONLA19936, bottom+ ONLA19750, blocker). This was then purified using SPRI beads as follows: 0.4 volume equivalents of AMPure XP SPRI magnetic beads (Beckman Coulter) were added to the mixture and the resultant mixture agitated for 5 min at 21° C. The magnetic beads were pelleted using a magnetic separator, the supernatant aspirated, and 100 µl of 50 mM Tris-Cl, 2.5 M NaCl, 20% PEG 8,000 (pH 7.5 at 25° C.) added to the beads while still on the rack, turning the pellet through 360° to wash the pellet on the rack. The beads were immediately pelleted once more and the supernatant aspirated, after which the tube was removed from the rack and 45 µl of a buffer containing of 25 mM Tris-Cl, 20 mM NaCl (pH 7.5 at 25° C.) was added to the beads to elute the DNA by incubation for 5 min at 21° C. The beads were pelleted using the magnetic separator, and the eluate retained. This is the "double-Y 3.6 kb".

CRISPR RNA ("crRNA") AR148 which has a sequence targeting a region the 3.6 kb lambda used previously, was hybridised with tracrRNA by annealing to 40 μM "Alt-R™" tracrRNA (purchased from IDT) in 10 mM Tris-Cl (pH 8.0), 1 mM EDTA, 100 mM NaCl from 65° C. to 25° C. at 1.0° C. per minute, resulting in a complex known as a "guide RNA". CRISPR-dCas9 complexes were formed by incubating 100 nM "guide RNA" with 100 nM dCas9 (ONLP11836) in Cas9 binding buffer (20 mM HEPES-NaOH, 100 mM NaCl, 5 mM $MgCl_2$, 0.1 mM EDTA, pH 6.5 at 25° C.) for 10 minutes at 21° C., yielding 100 nM of "CRISPR-dCas9 complex".

0.5 μg of double-Y 3.6 kb was incubated with 50 μL of CRISPR-dCas9 complex for at least 10 minutes at 20° C. To this was then added 65 μL of 2×c17 buffer (1M KCl, 50 mM HEPES, pH8), 12.5 μL of ELB and di water to make the final volume up to 150 μL. This is the "chip sample".

Electrical measurements were acquired from single CsgG nanopores inserted in block co-polymer in buffer at 37° C. (25 mM HEPES-KOH, 150 mM potassium ferrocyanide (II), 150 mM potassium ferricyanide (III), pH 8.0). After achieving a single pore inserted in the block co-polymer, buffer (2 mL, 25 mM HEPES-KOH, 150 mM potassium ferrocyanide (II), 150 mM potassium ferricyanide (III), pH 8.0) was flowed through the system to remove any excess CsgG nanopores. All subsequent steps were performed at 34° C. The cis compartment was equilibrated with 500 μl of 25 mM HEPES (pH 8.0), 500 mM KCl (known as "c17"), with 10 mins between each wash. 150 μl of chip sample was then added to the chip and data recorded at 100 mV at 34° C.

Results

Figure 33:
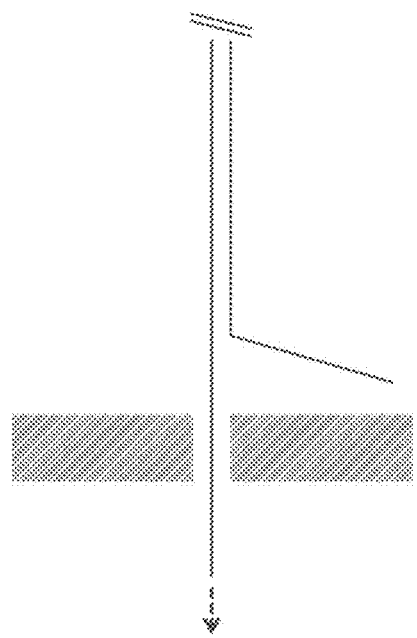
Figure 34:
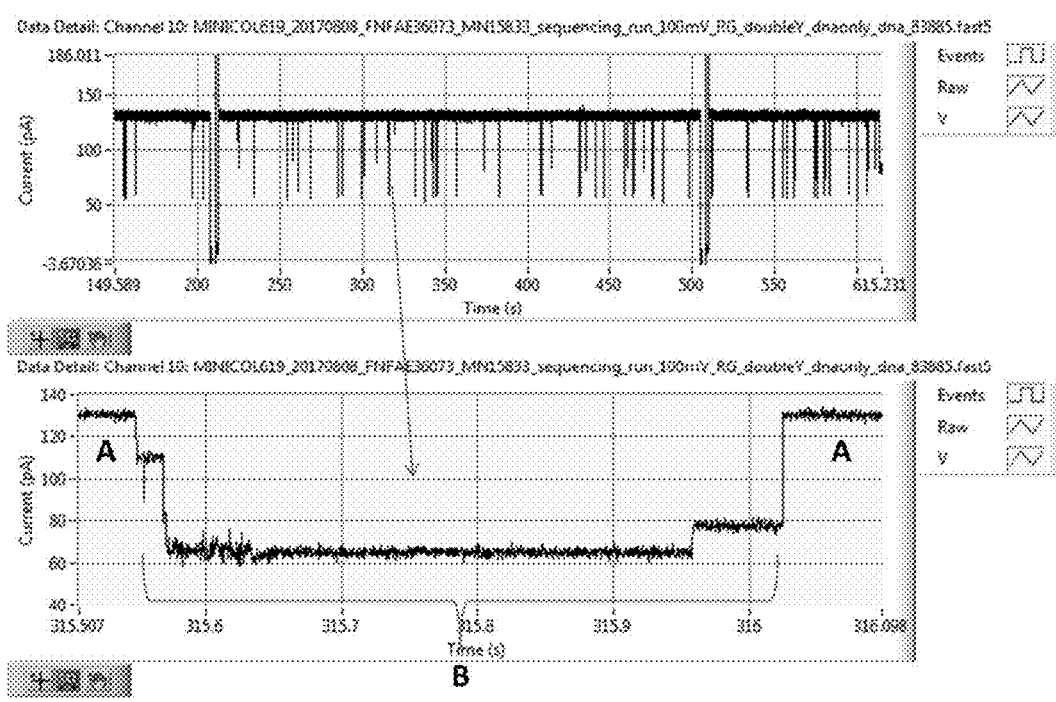
FIG. 34 shows a current vs time plot of a DNA strand translocating through a Nanopore. The trace begins at the open pore level, A, when there is no DNA in the pore. A double stranded DNA strand with an adapter at each end then encounters the pore and begins to translocate. The pore is too small for double stranded DNA to pass through so only a single strand translocates as per FIG. 33. The translocation of the DNA produces a characteristic signal (region B) and then returns to the open pore level, A. The events typically last less than 0.5 s. The lower panel is a zoomed in view of the upper panel.

When a CRISPR-dCas9 complex is not present, or when the CRISPR-dCas9 complex does not have a crRNA sequence that is present in the double-Y 3.6 kb, the signal obtained is characteristic of events at 60-80 pA that typically last <0.5 s. FIGS. 33 and 34 show double-Y 3.6 kb without a CRISPR-dCas9 complex bound to it translocating through the pore.

When CRISPR-dCas9 complex is present but double-Y 3.6 kb is not, there are no events observed.

Figure 35:
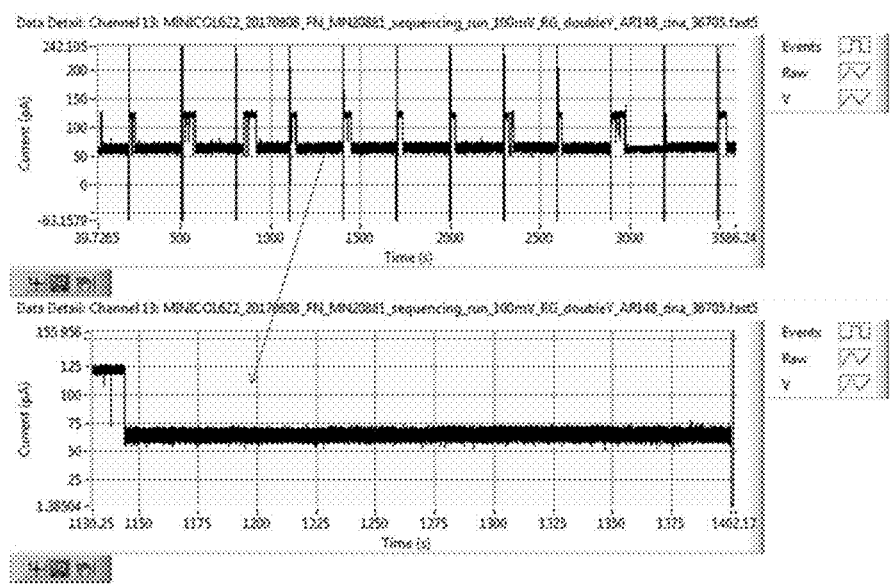
FIG. 35 shows the same experiment as FIG. 34 except that the DNA strand has a dCas9 enzyme bound to it, as illustrated in FIG. 14. Long pauses lasting 10 s of seconds are observed at a current level associated with DNA in the pore. Some of these events only return to the open pore level when the potential is reversed.
Figure 36:
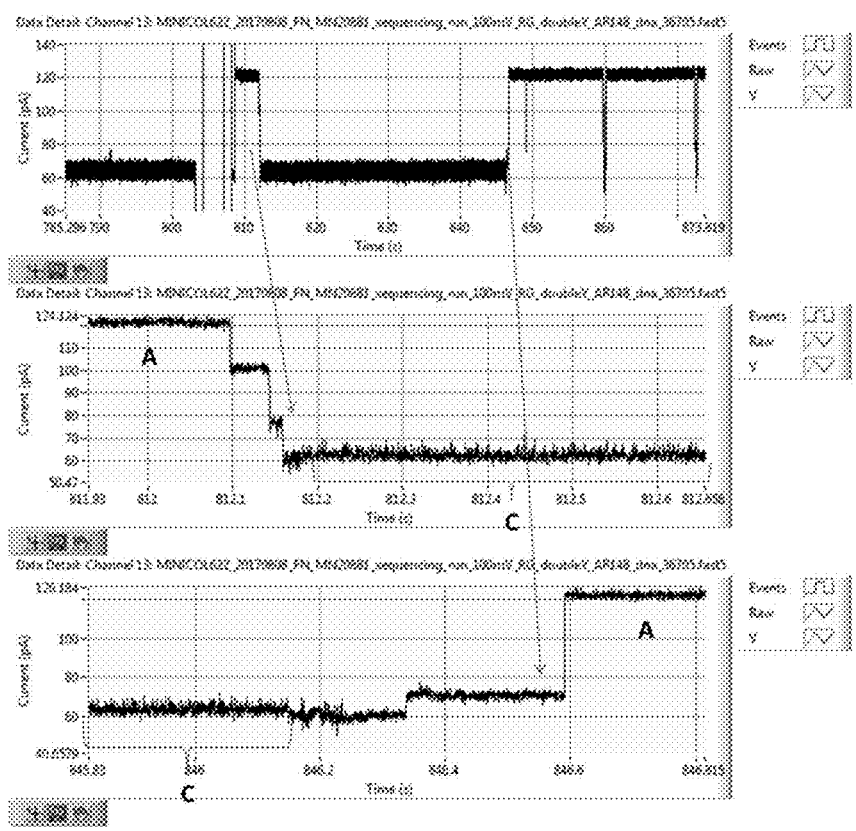
FIG. 36 shows the experiment as FIG. 34 except that the DNA strand has a dCas9 enzyme bound to it, as illustrated in FIG. 14. It shows an event in which the strand translocates and the signal returns to the open pore level, A. The second and third panels are zoomed in views of the first panel, with the second showing the beginning of the event and the third showing the end. It can be seen from this trace that the signal has the same characteristic pattern as in FIG. 34, but with a new long pause level in it, C. This demonstrates that the dCas9 bound to the DNA strand is causing a modification of the signal observed with DNA alone.

When a double-Y 3.6 kb is bound to a CRISPR-dCas9 complex which has a crRNA sequence that is found in the double-Y 3.6 kb as described above, the signal is dominated by long blocks at ~60 pA. These blocks typically last for >>10 s. Sometimes these events spontaneously return to the open pore current. These events have the same characteristic profile as those described above but have a new long static level in between the two Y-adapters. FIG. 14, FIG. 35 and FIG. 36 show the DNA translocating through the pore until the CRISPR-dCas9 complex reaches the pore, at which point the double-Y 3.6 kb pauses until the CRISPR-dCas9 complex is displaced by the force of the pore acting on it, at which point the double-Y 3.6 kb continues to translocate.

Example 5

Figure 12:
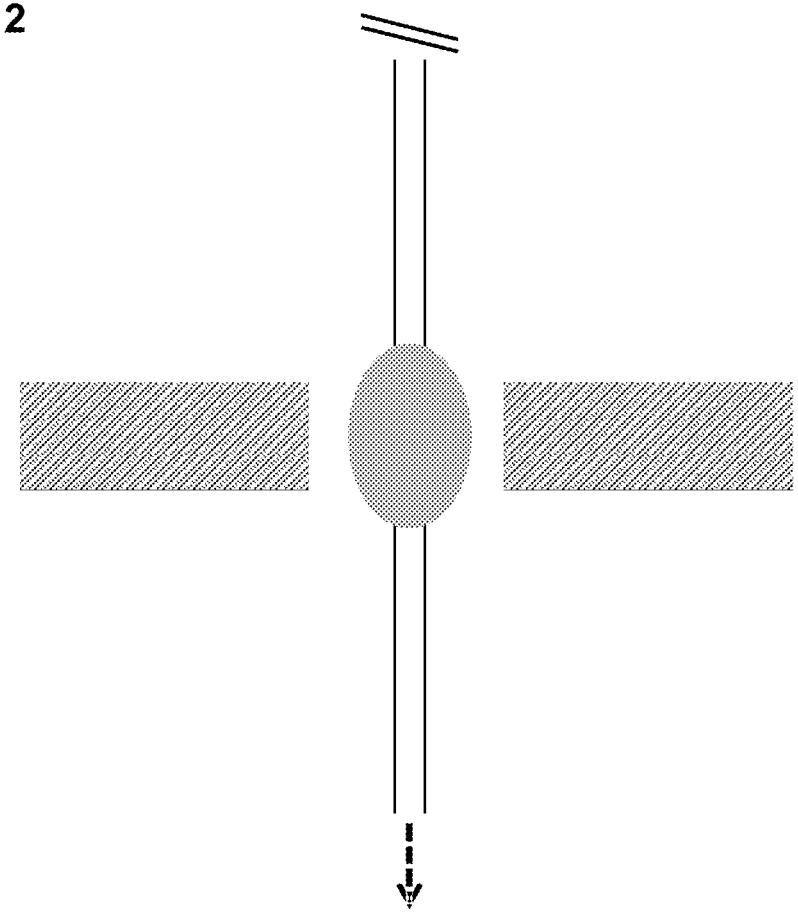
FIG. 12 shows a method for detection of dCas9 bound to a target polynucleotide analyte in which both strands of the target analyte and the bound dCas9 are translocated through a nanopore, where the nanopore bears a constriction that permits passage of the target analyte and bound dCas9, and in which the dCas9 produces a characteristic deflection in the ionic current measured through the nanopore.
Figure 13:
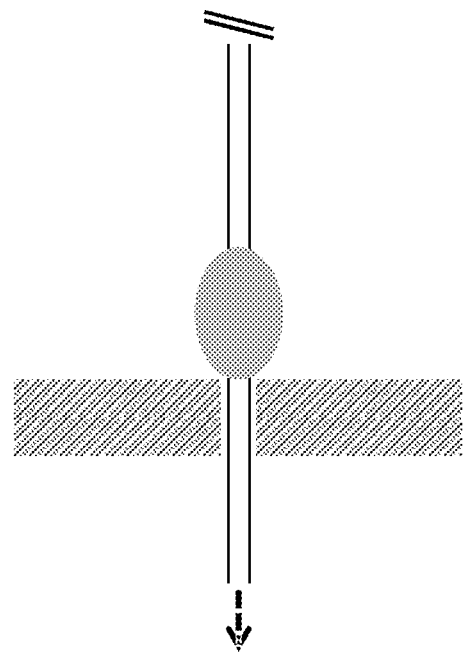
FIG. 13 shows a method for detection of dCas9 bound to a target polynucleotide analyte in which both strands of the target analyte are translocated through a nanopore, but the constriction of the nanopore prevents translocation of the bound dCas9 and produces a characteristic deflection or dwell-time in the ionic current measured through the nanopore.

This Example describes a method for detection of a fragment containing a specific 20 nucleotide target DNA polynucleotide sequence ("target") from a mixture by direct detection of a target/probe complex, wherein the target DNA contacts CRISPR-Cas probe. In this example, the "target" is positively identified by the unique signal given by the target/probe complex interacting with the nanopore. In this case the pore is big enough to admit double stranded DNA with the probe attached (see FIG. 12).

Materials and Methods

A 3.6 kb length of lambda DNA was prepared and purified. This is the 3.6 kb.

CRISPR RNA ("crRNA") AR148 which has a sequence targeting a region the 3.6 kb, was hybridised with tracrRNA by annealing to 40 μM "Alt-R™" tracrRNA (purchased from IDT) in 10 mM Tris-Cl (pH 8.0), 1 mM EDTA, 100 mM NaCl from 65° C. to 25° C. at 1.0° C. per minute, resulting in a complex known as a "guide RNA". CRISPR-dCas9 complexes were formed by incubating 200 nM "guide RNA" with 200 nM dCas9 (ONLP11836) in Cas9 binding buffer (20 mM HEPES-NaOH, 100 mM NaCl, 5 mM $MgCl_2$, 0.1 mM EDTA, pH 6.5 at 25° C.), for 10 minutes at 21° C., yielding 200 nM of CRISPR-dCas9 complex.

0.5 μg of 3.6 kb was incubated with 25 μL of CRISPR-dCas9 complex for at least 10 minutes at 20° C. To this was then added 25 μL of 2×1M buffer (2M KCl, 50 mM HEPES, pH8). This is the chip sample.

Electrical measurements were acquired from a single 15 nm diameter SiN ALD pore formed by dielectric breakdown (but any pore with a diameter of >10 nM could have been used, for example solid state, protein, DNA origami or any other material). The cis and trans were at 1M KCl while the voltage was varied. After a period of pore characterisation with no sample, the volume of the cis compartment was replaced with the chip sample and measurements carried out at different voltages at 20° C.

Results

Figure 37:
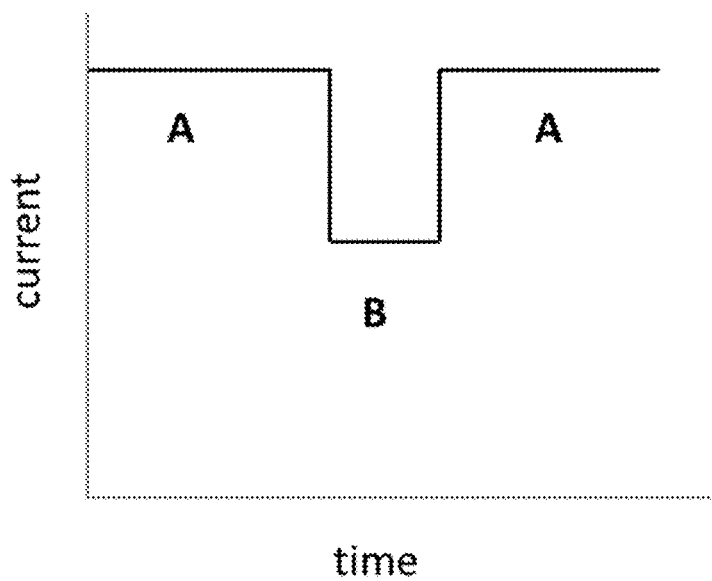
FIG. 37 shows an example current trace of a double stranded DNA strand passing intact through a pore large enough to accommodate it. From the open pore current, A, the current drops to a lower level as the DNA passes through it, B, and then returns to the open pore level.
Figure 38:
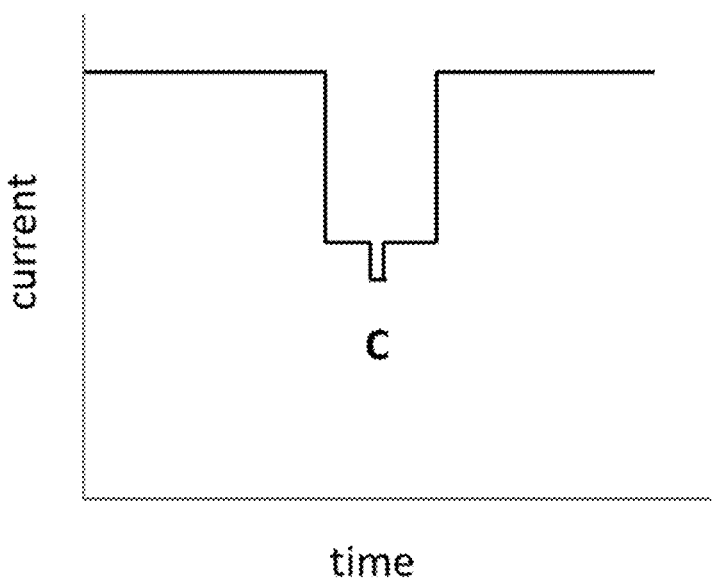
FIG. 38 shows an example current trace of a double stranded DNA strand passing intact through a pore large enough to accommodate it. In this case, the DNA has a protein bound to it as shown in FIG. 12. Here there is an extra deflection in the current coming from the DNA level which represents the protein translocating (C).
Figure 39:
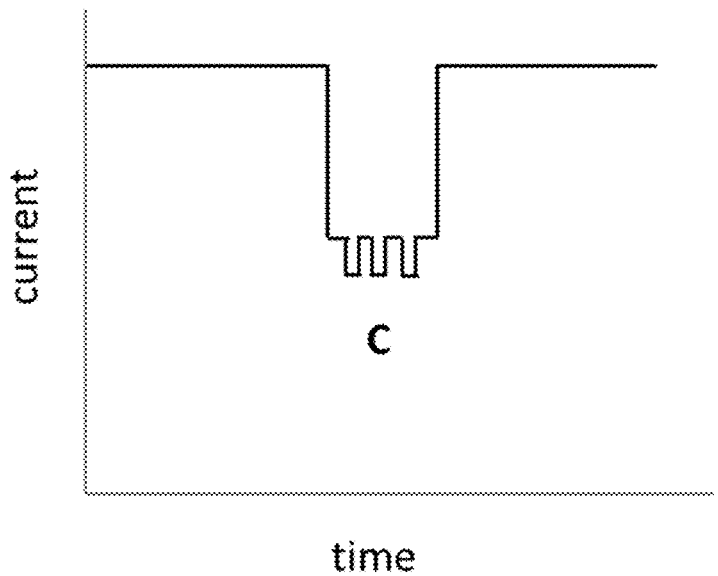
FIG. 39 shows an example current trace of a double stranded DNA strand passing intact through a pore large enough to accommodate it, wherein multiple proteins are bound to the DNA. Each protein causes a separate deflection to the current.
Figure 40:
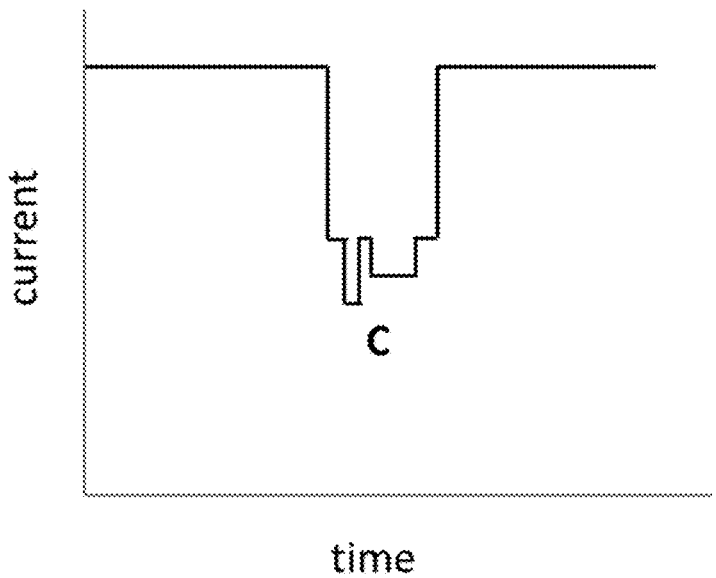
FIG. 40 shows an example current trace of a double stranded DNA strand passing intact through a pore large enough to accommodate it, wherein multiple proteins are bound to the DNA (at different positions to those in FIG. 39) and the proteins have been modified or decorated so that they produce different signals when they pass through the pore.

When a CRISPR-dCas9 complex is not present, or when the CRISPR-dCas9 complex does not have a crRNA sequence that is complementary to a DNA sequence in the 3.6 kb, the signal obtained is of a short lived current deflection as the 3.6 kb passes through the pore (FIG. 37). When a 3.6 kb is bound to a CRISPR-dCas9 complex which has a crRNA sequence that is complementary to a DNA sequence found in the 3.6 kb, as described above, the signal now has an additional sublevel that represents the CRISPR-dCas9 complex passing through the pore (FIG. 38). Where multiple CRISPR-dCas9 complexes are bound to the DNA, each complex causes a separate deflection to the current (FIG. 39). When the dCas is modified or decorated the signal changes as each complex passes through the pore (FIG. 40). The changes in signal positions of the current deflections caused by the complexes can be used to provide information about the polynucleotide (e.g. DNA).

Sequence information

| | |
|---|---|
| AR148 | AltR-CCGACCACGCCAGCAUAUCG-AltR |
| ONLA16389 | /5SpC3//iSpC3//iSpC3//iSpC3//iSpC3//iSpC3//iSpC3//iSpC3//iSpC3/ /iSpC3/ /iSpC3//iSpC3//iSpC3//iSpC3//iSpC3//iSpC3//iSpC3//iSpC3/ /iSpC3/ /iSpC3//iSpC3//iSpC3//iSpC3//iSpC3//iSpC3//iSpC3//iSpC3/ /iSpC3/ GGCGTCTGCTTGGGTGTTTAACCTTTTTTTTT/iSp18//iSp18//iSp18//iSp18/AA TGTACTTCGTTCAGTTACGTATTGCT |

-continued

| Sequence information | |
|---|---|
| AR148 | AltR-CCGACCACGCCAGCAUAUCG-AltR |
| ONLA19936 | /5Phos/GCAATACGTAACTGAACGAAGT/iBNA-A//iBNA-MeC//iBNA-A//iBNA-T//iBNA-T/TTTGAGGCGAGCGGTCAA |
| ONLA19750 | /5BNA-G//iBNA-G//iBNA-T//iBNA-T//iBNA-A/AACACCCAAGCAGACGCCTT |
| AltR tracr | Purchased from IDT |
| Tether | /5Chol-TEG/TT/iSp18//iSp18//iSp18//iSp18/TTGACCGCTCGCCTC |
| 3.6 kb | GCCATCAGATTGTGTTTGTTAGTCGCTGCCATCAGATTGTGTTTGTTAGTCGCTTTTTTTTT<br>TGGAATTTTTTTTTTGGAATTTTTTTTTTGCGCTAACAACCTCCTGCCGTTTTGCCCGTGCATATCGGTC<br>ACGAACAAATCTGATTACTAAACACAGTAGCCTGGATTTGTTCTATCAGTAATCGACCTTATTCCTAATT<br>AAATAGAGCAAATCCCCTTATTGGGGGTAAGACATGAAGATGCCAGAAAAACATGACCTGTTGGCCGCCA<br>TTCTCGCGGCAAAGGAACAAGGCATCGGGGCAATCCTTGCGTTTGCAATGGCGTACCTTCGCGGCAGATA<br>TAATGGCGGTGCGTTTACAAAAACAGTAATCGACGCAACGATGTGCGCCATTATCGCCTAGTTCATTCGT<br>GACCTTCTCGACTTCGCCGGACTAAGTAGCAATCTCGCTTATATAACGAGCGTGTTTATCGGCTACATCG<br>GTACTGACTCGATTGGTTCGCTTATCAAACGCTTCGCTGCTAAAAAAGCCGGAGTAGAAGATGGTAGAAA<br>TCAATAATCAACGTAAGGCGTTCCTCGATATGCTGGCGTGGTCGGAGGGAACTGATAACGGACGTCAGAA<br>AACCAGAAATCATGGTTATGACGTCATTGTAGGCGGAGAGCTATTTACTGATTACTCCGATCACCCTCGC<br>AAACTTGTCACGCTAAACCCAAAACTCAAATCAACAGGCGCCGGACGCTACCAGCTTCTTTCCCGTTGGT<br>GGGATGCCTACCGCAAGCAGCTTGGCCTGAAAGACTTCTCTCCGAAAAGTCAGGACGCTGTGGCATTGCA<br>GCAGATTAAGGAGCGTGGCGCTTTACCTATGATTGATCGTGGTGATATCCGTCAGGCAATCGACCGTTGC<br>AGCAATATCTGGGCTTCACTGCCGGGCGCTGGTTATGGTCAGTTCGAGCATAAGGCTGACAGCCTGATTG<br>CAAAATTCAAAGAAGCGGGCGGAACGGTCAGAGAGATTGATGTATGAGCAGAGTCACCGCGATTATCTCC<br>GCTCTGGTTATCTGCATCATCGTCTGCCTGTCATGGGCTGTTAATCATTACCGTGATAACGCCATTACCT<br>ACAAAGCCCAGCGCGACAAAAATGCCAGAGAACTGAAGCTGGCGAACGCGGCAATTACTGACATGCAGAT<br>GCGTCAGCGTGATGTTGCTGCGCTCGATGCAAAATACACGAAGGAGTTAGCTGATGCTAAAGCTGAAAAT<br>GATGCTCTGCGTGATGATGTTGCCGCTGGTCGTCGTCGGTTGCACATCAAAGCAGTCTGTCAGTCAGTGC<br>GTGAAGCCACCACCGCCTCCGGCGTGGATAATGCAGCCTCCCCCCGACTGGCAGACACCGCTGAACGGGA<br>TTATTTCACCCTCAGAGAGAGGCTGATCACTATGCAAAAACAACTGGAAGGAACCCAGAAGTATATTAAT<br>GAGCAGTGCAGATAGAGTTGCCCATATCGATGGGCAACTCATGCAATTATTGTGAGCAATACACACGCGC<br>TTCCAGCGGAGTATAAATGCCTAAAGTAATAAAACCGAGCAATCCATTTACGAATGTTTGCTGGGTTTCT<br>GTTTTAACAACATTTTCTGCGCCGCCACAAATTTTGGCTGCATCGACAGTTTTCTTCTGCCCAATTCCAG<br>AAACGAAGAAATGATGGGTGATGGTTTCCTTTGGTGCTACTGCTGCCGGTTTGTTTTGAACAGTAAACGT<br>CTGTTGAGCACATCCTGTAATAAGCAGGGCCAGCGCAGTAGCGAGTAGCATTTTTTTCATGGTGTTATTC<br>CCGATGCTTTTTGAAGTTCGCAGAATCGTATGTGTAGAAAATTAAACAAACCCTAAACAATGAGTTGAAA<br>TTTCATATTGTTAATATTTATTAATGTATGTCAGGTGCGATGAATCGTCATTGTATTCCCGGATTAACTA<br>TGTCCACAGCCCTGACGGGGAACTTCTCTGCGGGAGTGTCCGGGAATAATTAAAACGATGCACACAGGGT<br>TTAGCGCGTACACGTATTGCATTATGCCAACGCCCCGGTGCTGACACGGAAGAAACCGGACGTTATGATT<br>TAGCGTGGAAAGATTTGTGTAGTGTTCTGAATGCTCTCAGTAAATAGTAATGAATTATCAAAGGTATAGT<br>AATATCTTTTATGTTCATGGATATTTGTAACCCATCGGAAAACTCCTGCTTTAGCAAGATTTTCCCTGTA<br>TTGCTGAAATGTGATTTCTCTTGATTTCAACCTATCATAGGACGTTTCTATAAGATGCGTGTTTCTTGAG<br>AATTTAACATTTACAACCTTTTTAAGTCCTTTTATTAACACGGTGTTATCGTTTTCTAACACGATGTGAA<br>TATTATCTGTGGCTAGATAGTAAATATAATGTGAGACGTTGTGACGTTTTAGTTCAGAATAAAACAATTC<br>ACAGTCTAAATCTTTTCGCACTTGATCGAATATTTCTTTAAAAATGGCAACCTGAGCCATTGGTAAAACC<br>TTCCATGTGATACGAGGGCGCGTAGTTTGCATTATCGTTTTTATCGTTTCAATCTGGTCTGACCTCCTTG<br>TGTTTTGTTGATGATTTATGTCAAATATTAGGAATGTTTTCACTTAATAGTATTGGTTGCGTAACAAAGT<br>GCGGTCCTGCTGGCATTCTGGAGGGAAATACAACCGACAGATGTATGTAAGGCCAACGTGCTCAAATCTT<br>CATACAGAAAGATTTGAAGTAATATTTTAACCGCTAGATGAAGAGCAAGCGCATGGAGCGACAAAATGAA<br>TAAAGAACAATCTGCTGATGATCCCTCCGTGGATCTGATTCGTGTAAAAAATATGCTTAATAGCACCATT<br>TCTATGAGTTACCCTGATGTTGTAATTGCATGTATAGAACATAAGGTGTCTCTGGAAGCATTCAGAGCAA<br>TTGAGGCAGCGTTGGTGAAGCACGATAATAATATGAAGGATTATTTCCCTGGTGGTTGACTGATCACCATA<br>ACTGCTAATCATTCAAACTATTTAGTCTGTGACAGAGCCAACACGCAGTCTGTCACTGTCAGGAAAGTGG<br>TAAAACTGCAACTCAATTACTGCAATGCCCTCGTAATTAAGTGAATTTACAATATCGTCCTGTTCGGAGG<br>GAAGAACGCGGGATGTTCATTCTTCATCACTTTTAATTGATGTATATGCTCTCTTTTCTGACGTTAGTCT<br>CCGACGGCAGGCTTCAATGACCCAGGCTGAGAAATTCCCGGACCCTTTTTGCTCAAGAGCGATGTTAATT<br>TGTTCAATCATTTGGTTAGGAAAGCGGATGTTGCGGGTTGTTGTTCTGCGGGTTCTGTTCTTCGTTGACA<br>TGAGGTTGCCCCGTATTCAGTGTCGCTGATTTGTATTGTCTGAAGTTGTTTTTACGTTAAGTTGATGCAG<br>ATCAATTAATACGATACCTGCGTCATAATTGATTATTTGACGTGGTTTGATGGCCTCCACGCACGTTGTG<br>ATATGTAGATGATAATCATTATCACTTTACGGGTCCTTTCCGGTGAAAAAAAAGGTACCAAAAAAAACAT<br>CGTCGTGAGTAGTGAACCGTAAGC |

Example 6

This Example describes a method for the detection of a specific polynucleotide in a complex background by nanopore sequencing following the enrichment of the target molecule. In this Example, the target DNA molecule is identified primarily by its sequence. The target molecule is separated from the background by means of a 'pulldown' via a capture moiety on the dCas9 molecule. The dCas9 binds preferably to the target molecule by means of a crRNA directed against the ribosomal 16S (rrs) genes of *Escherichia coli*. 'Off-target' effects are reduced by applying a thermal and salt stress to the bound dCas9 protein, coupled with a SPRI purification step to remove excess, unbound dCas9 before subsequent purification on a capture bead surface. The target DNA molecule is adapted for nanopore sequencing, and the dCas9 remains bound to its target until displaced by the enzyme loaded on the adapter.

Figure 41:
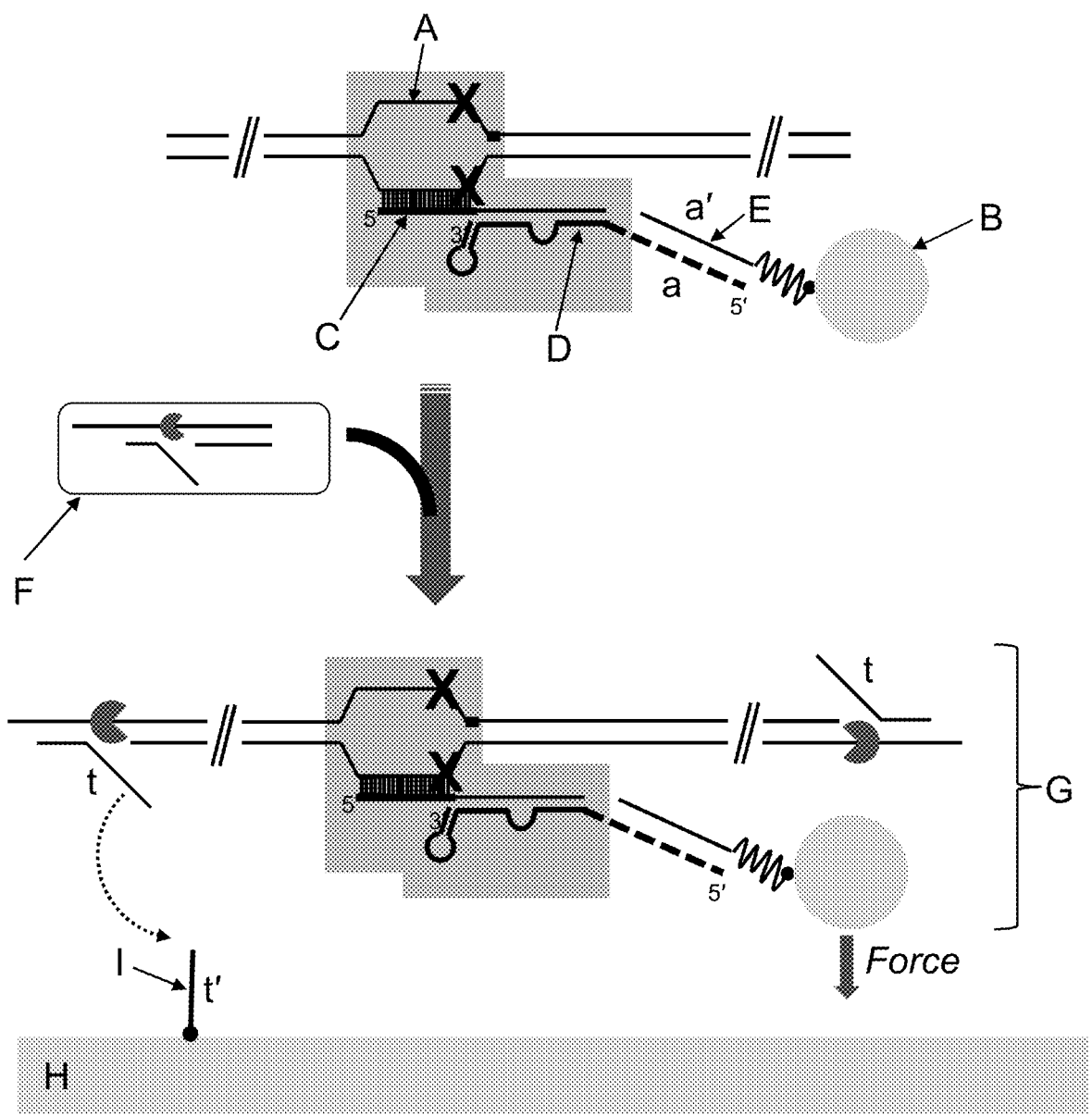
FIG. 41 shows an example method for the enrichment and detection or sequencing of a dCas9-contacted target A to a bead surface B, with crRNA C and tracrRNA bearing a 5' DNA extension D with sequence a. Target A may be any size, ranging from tens of nucleotides to greater than megabases in length. B may for instance be a bead surface (in bulk solution or in column format) or membrane. Attachment to B is mediated by oligonucleotide E, bearing sequence a' complementary to the extension of D, which bears a chemical moiety such as biotin that enables attachment to bead B if B is coated with a protein such as streptavidin. Non-target DNA may subsequently be washed away from B. Enzymatic or click chemistry ligation of adapter F to blunt or complementary ends of target A may be achieved while the target is bound to the bead, with excess adapter washed away, to yield target-dCas9-bead assembly G. Sequencing or detection of the target A is then achieved by delivering assembly G to a flowcell containing membrane H, and cholesterol-modified oligonucleotide tether I, which hybridises to adaptor F via sequence t', complementary to t. Assembly G may be delivered to the membrane by gravity, or by an applied magnetic field if for instance bead B is paramagnetic.

The dCas9 carries a tracrRNA molecule bearing a 5' DNA extension (sequence a of FIG. 41) that enables capture of the target molecule on a bead-capture oligonucleotide conjugate that bears a DNA sequence complementary to this extension (sequence a' of FIG. 41). In this Example, the capture oligonucleotide is linked to the bead via a biotin moiety. In this Example, the non-target DNA is washed away, and target molecules remain bound to the bead. The target molecule is then adapted for nanopore sequencing by ligation to either or both of its free, dA-tailed ends, while the dCas9-target molecule is bound to the bead. The entire bead-target-RNP assembly is then delivered to a flowcell for sequencing. The assembly is brought to the wells of the flowcell by the application of a magnetic field placed underneath the flowcell, or can be allowed to settle by gravity. Sequencing is initiated by flowing an oligonucleotide cholesterol tether, which hybridizes to the adaptor ends, over the beads, which tethers the beads to the membrane. Alternatively, the cholesterol tether can be introduced into the membrane during a 'flush' step, before the bead-target conjugate is added to the flowcell.

Methods

An *E. coli* whole-genome library, ONLA18816 (NCBI Reference Sequence: NC_000913.3), was prepared by random fragmentation of *E. coli* high-molecular weight genomic DNA to a median size of ~5.9 kb using a Covaris gTube following the manufacturer's instructions. This library was then end-repaired and dA-tailed using an NEB Ultra II kit, per the manufacturer's instructions. Following end-repair and dA-tailing, the fragmented genomic DNA was subjected to 0.4×SPRI purification and eluted from the SPRI beads in 0.1×TE.

200 nM DNA-extended tracrRNA (AR363) was added to a buffer containing 25 mM HEPES-NaOH (pH 8.0), 150 mM NaCl and 1 mM $MgCl_2$ (known as dCas9 binding buffer). The tracrRNA was heated to 90° C. for 2 min and snap-cooled on wet ice, after which 100 nM dCas9 (ONLP12326) was added and the reaction incubated for 10 min at room temperature (~21° C.). 250 nM crRNA (AR400) was then added to the reaction and incubated for a further 10 min at room temperature (~21° C.). The final volume was 50 μL. This mixture was known as ribonucleotide-protein complexes (RNPs).

To form dCas9-target complexes, 500 ng (~1.2 μL) of the genomic DNA from above (ONLA18816) was added to the RNPs and incubated for 20 min at room temperature. The mixture was then incubated at 55° C. for 5 min to remove dCas9 not bound to its intended target. The mixture was subjected to 1×SPRI purification as follows: 51 μL AMPure XP beads were added to the mixture, mixed by gentle resuspension, and incubated for 10 min at room temperature. The beads were pelleted using a magnetic separator, and washed twice with ~250 μL of a buffer comprising 50 mM Tris-Cl (pH 8.0 at 4° C.), 2.5 M NaCl, 20% (w/v) PEG-8000, and eluted by incubating the SPRI beads with 12.5 μL of a buffer comprising 40 mM CAPS (pH 10.0), 40 mM KCl for 5 min. The beads were pelleted once more and the supernatant, known as 'SPRI eluate', retained.

50 μg Solulink 'Nanolink' streptavidin magnetic beads (5 μL) were incubated with 2.5 μL of AR364 capture oligo in ~120 μL of a buffer comprising 50 mM Tris-Cl (pH 8.0 at 4° C.), 2 M NaCl, 1 mM EDTA, 0.05% (v/v) Tween-20 for ~1 h with agitation. Unbound oligonucleotide was removed by washing the beads twice with the same buffer, pelleting the beads using a magnetic separator. This conjugate was known as 'capture beads'.

dCas9-bound target molecules were bound to capture beads by incubating 12.5 μL of SPRI eluate with 10 μg capture beads (1 μL) and 65 μL Dynabeads kilobase-BINDER Binding Solution (Thermo Scientific Cat. #60101) for 20 min with agitation. The beads were subsequently washed three times with a buffer containing 50 mM Tris-Cl (pH 8.0 at 4° C.), 150 mM NaCl, 1 mM EDTA, and once with a buffer containing 50 mM Tris-Cl (pH 8.0 at 4° C.), 20 mM NaCl. Following this step, the beads were pelleted and the supernatant removed. This sample was known as 'bead-target complex'.

Enzyme-loaded adaptors (tube 'AMX 1D') from Oxford Nanopore Technologies' 1D Sequencing Kit by Ligation (SQK-LSK108) were ligated to the bead-target complex by resuspending the pelleted beads from above with a ligation mix comprising 12.5 μL 2×LAQA1 buffer (a gift from New England Biolabs, Inc.), 7 μL nuclease-free water, 5 μL AMX 1D (part of SQK-LSK108), and 0.5 μL T4 DNA Ligase (NEB Cat. #M0202). The beads were incubated in the ligation mix with agitation for 10 min, pelleted, and washed once with ~125 μL of a buffer containing 50 mM Tris-Cl (pH 8.0 at 4° C.), 150 mM NaCl, 1 mM EDTA to remove free, unligated adapter. Following the wash, the beads were pelleted once more, and resuspended in 50 μL of RBF (a component of SQK-LSK108), diluted to 1× according to the manufacturer's instructions. This mixture was known as the loading sample.

FIG. 41 shows the expected appearance of the dCas9-crRNA-tracrRNA-target-bead conjugate, also known here as the loading sample.

An Oxford Nanopore MinION flowcell was primed with 800 μL 1×RBF containing 50 nM tether oligo pipetted via its inlet port, followed by a pause of 10 min, then 200 μL of the same mixture pipetted via its inlet port with the SpotON port open. The entire 50 μL of the loading sample was pipetted dropwise into the SpotON port and the fluid allowed to wick into the flowcell. MinION data collection was initiated immediately, and data were collected and analysed according to standard customer protocols.

Results

Figure 42:
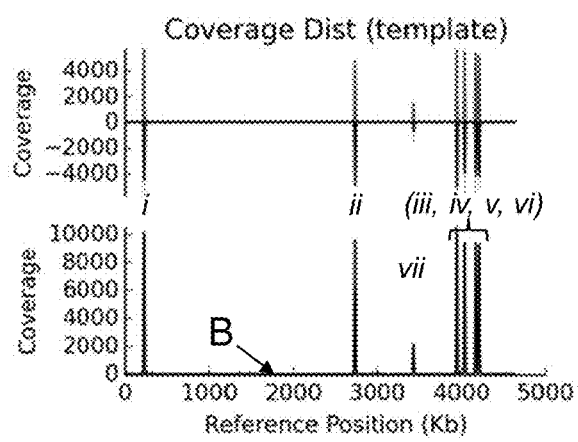
FIG. 42 shows an example coverage plot showing the enrichment of alll 6S (rrs) genes from a total *E. coli* genomic sample, using a crRNA probe directed against the rrsH gene (coordinates 223771-225312 of *E. coli* K-12, strain MG1655, peak i). A, top shows a plot of coverage versus position for forwards (positive numbers) and reverse (negative numbers) direction reads. Seven target peaks, i to vii, are indentified, which are over-represented against background B. A, bottom shows the aggregation of forwards and reverse direction reads. C shows a histogram of the read length of all reads that successfully mapped to the reference, normalised to the number of bases mapped in each bin. D shows the seven expected binding locations of the single probe used in the pulldown. Peak vii is located at a target sequence that is a canonical 'off-target' site, but bears 19 out of 20 matches to the probe sequence.
Figure 42:
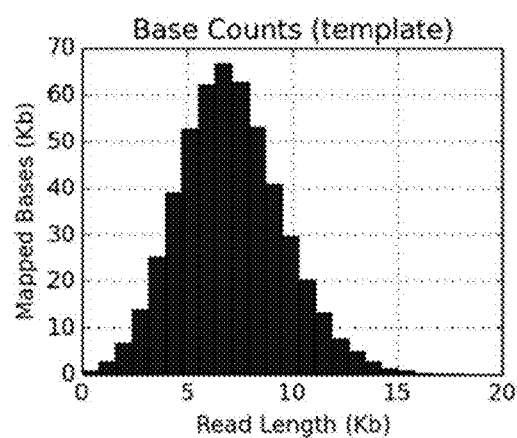
Figure 43:
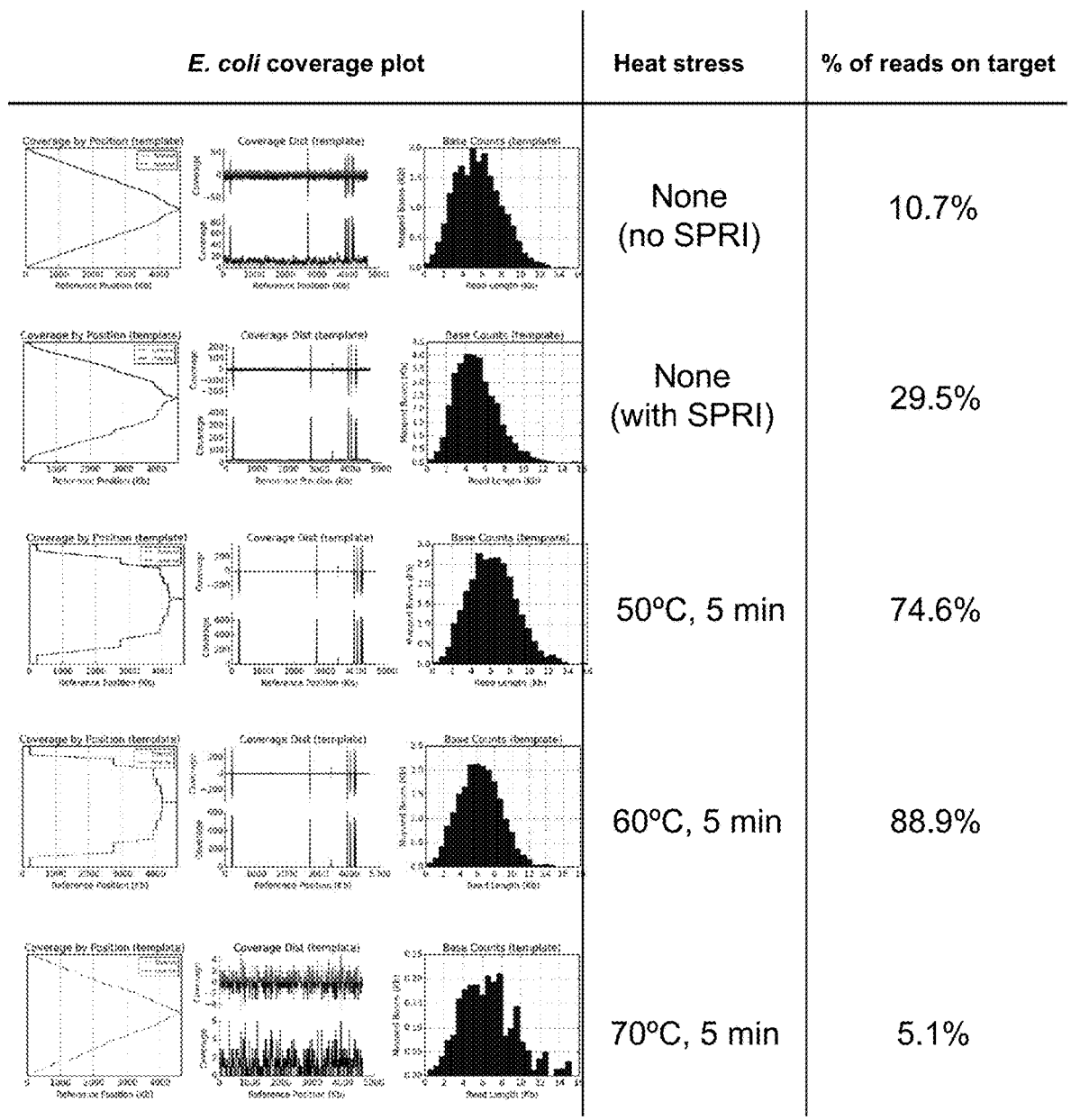
FIG. 43 shows the effect of applying a heat stress, followed by subsequent SPRI-bead cleanup and bead-based dCas9 pulldown to a dCas9-contacted DNA sample on the proportion of target vs. non-target molecules bound, as determined by nanopore sequencing.

FIG. 42 shows data collected over a 6-hour sequencing run using the above protocol using an Oxford Nanopore Technologies MinION flowcell running the standard baseline sequencing script with MinKNOW 1.7.14 software. The single crRNA probe used in this pulldown, AR400, is expected to direct dCas9 to each of the seven 16S ribosomal gene sites listed in FIG. 42D, with one position, identified as position vii, bearing a single mismatch at position −2 relative to the PAM site, and another, identified as peak i, bearing a single mismatch at position −6 relative to the PAM site. Of the ~4.6 Mb genome, ~35 kb (~0.76%) of the input DNA (7× the median read length, 5.9 kb) could be considered target. 92,942 sequencing reads were obtained from this run and placed through a standard basecalling and alignment analysis workflow. 85,126 reads could be mapped to the *E. coli* MG1655 genome (NC_000913.3), of which 62,943 (73.9%) mapped to within 3 median read lengths of each expected probe hybridisation position. Pileup of the sequencing reads yielded a coverage depth of 9,000-10,000× for each of positions i, ii, iii, iv, v and vi.

Materials

| Component name | Sequence (Oligos are IDT codes) |
| --- | --- |
| *E. coli* genomic DNA, str. K-12, substr. MG1655 as ONLA18816 | NCBI Reference Sequence: NC_000913.3 |

| Component name | Sequence (Oligos are IDT codes) |
|---|---|
| AR363 | TACATTTAAGACCCTAATAT/iSp18/mA*mG*mCmAmUmAmGmCmA rArGrUrArArArArUrArArGrGrCrUrArGrUrCrCrGrUrUrA rUrCrArAmCmUmGmAmAmAmAmGmUmGmGmCmAmCmCmGmAmG mUmCmGmGmUmGmCmU*mU*mU |
| AR364 | /5Phos/ATATTAGGGTCTTAAATGTA/iSp18//iSp18//iSp18//3BioTEG/ |
| Tether oligo | /5CholTEG/TT/iSp18//iSp18//iSp18//iSp18/TTGACCGCTCGCCTC |
| AR400 | 'Alt-R' Cas9 crRNA from Integrated DNA Technologies, Inc: /AltR1/agaccaaagagggggaccTT/AltR2/ |

Proteins

ONLP12326: *S. pyogenes* Cas9 D10A/H840A, C-terminal Twin-Strep-tag with TEV-cleavable linker; bold, bracketed shows the portion cleaved by TEV:

MDKKYSIGLAIGTNSVGWAVITDEYKVPSKKFKVLGNTDRHSIKKNLIGALLFDSGET

AEATRLKRTARRRYTRRKNRICYLQEIFSNEMAKVDDSFFHRLEESFLVEEDKKHERH

PIFGNIVDEVAYHEKYPTIYHLRKKLVDSTDKADLRLIYLALAHMIKFRGHFLIEGDL

NPDNSDVDKLFIQLVQTYNQLFEENPINASGVDAKAILSARLSKSRRLENLIAQLPGE

KKNGLFGNLIALSLGLTPNFKSNFDLAEDAKLQLSKDTYDDDLDNLLAQIGDQYADLF

LAAKNLSDAILLSDILRVNTEITKAPLSASMIKRYDEHHQDLTLLKALVRQQLPEKYK

EIFFDQSKNGYAGYIDGGASQEEFYKFIKPILEKMDGTEELLVKLNREDLLRKQRTFD

NGSIPHQIHLGELHAILRRQEDFYPFLKDNREKIEKILTFRIPYYVGPLARGNSRFAW

MTRKSEETITPWNFEEVVDKGASAQSFIERMTNFDKNLPNEKVLPKHSLLYEYFTVYN

ELTKVKYVTEGMRKPAFLSGEQKKAIVDLLFKTNRKVTVKQLKEDYFKKIECFDSVEI

SGVEDRFNASLGTYHDLLKIIKDKDFLDNEENEDILEDIVLTLTLFEDREMIEERLKT

YAHLFDDKVMKQLKRRRYTGWGRLSRKLINGIRDKQSGKTILDFLKSDGFANRNFMQL

IHDDSLTFKEDIQKAQVSGQGDSLHEHIANLAGSPAIKKGILQTVKVVDELVKVMGRH

KPENIVIEMARENQTTQKGQKNSRERMKRIEEGIKELGSQILKEHPVENTQLQNEKLY

LYYLQNGRDMYVDQELDINRLSDYDVDAIVPQSFLKDDSIDNKVLTRSDKNRGKSDNV

PSEEVVKKMKNYWRQLLNAKLITQRKFDNLTKAERGGLSELDKAGFIKRQLVETRQIT

KHVAQILDSRMNTKYDENDKLIREVKVITLKSKLVSDFRKDFQFYKVREINNYHHAHD

AYLNAVVGTALIKKYPKLESEFVYGDYKVYDVRKMIAKSEQEIGKATAKYFFYSNIMN

FFKTEITLANGEIRKRPLIETNGETGEIVWDKGRDFATVRKVLSMPQVNIVKKTEVQT

GGFSKESILPKRNSDKLIARKKDWDPKKYGGFDSPTVAYSVLVVAKVEKGKSKKLKSV

KELLGITIMERSSFEKNPIDFLEAKGYKEVKKDLIIKLPKYSLFELENGRKRMLASAG

ELQKGNELALPSKYVNFLYLASHYEKLKGSPEDNEQKQLFVEQHKHYLDEIIEQISEF

SKRVILADANLDKVLSAYNKHRDKPIREQAENIIHLFTLTNLGAPAAFKYFDTTIDRK

RYTSTKEVLDATLIHQSITGLYETRIDLSQLGGDGGSENLYFQ[GSGGSAWSHPQFEKGGGSGGGSGGGSAWSHPQF EK]

Example 7

This Example describes a method for the detection of a specific polynucleotide in a complex background by nanopore sequencing, following the enrichment of the target molecule. In this Example, the target DNA molecule is identified primarily by its sequence. The target molecule is separated from the background by means of a 'pulldown' via a capture moiety on the dCas9 molecule. The dCas9 binds preferably to the target molecule by means of a crRNA directed against the ribosomal 16S (rrs) genes of *Escherichia coli*. 'Off-target' effects are minimized by applying a thermal and salt stress to the dCas9 protein, followed by the purification and elution of dCas9-target complexes on a capture surface specific to the tracrRNA, and the transfer of the dCas9-target complexes to a second specific capture surface specific to the crRNA. The release of the target from the first 'purification' bead is effected by the phenomenon known as toehold displacement. The target DNA molecule is adapted for nanopore sequencing, and the dCas9 remains bound to its target until displaced by the enzyme loaded on the adapter.

The crRNA also bears a 3' DNA extension used for capture of the target molecule on a bead, column or surface (sequence d of FIG. 44). The dCas9 also carries a tracrRNA molecule bearing a 5' DNA extension (sequence a–c of FIG. 44) that enables capture of the target molecule on a 'purification' bead, column or surface. The target is first separated from non-target DNA by capture on beads bearing an oligonucleotide complementary to the DNA extension of the tracrRNA. Non-target DNA is washed away during this step. The target molecule is eluted from the bead by toehold displacement, via the addition of an oligonucleotide that competes for the binding to the bead with the DNA-extended tracrRNA molecule. Following elution of the target molecule, the target is bound to a second 'delivery' bead via the DNA extension on the crRNA. The target molecule is then adapted for nanopore sequencing by ligation to either or both of its free, dA-tailed ends, while the dCas9-target molecule is still bound to the bead. The entire bead-target-RNP assembly is then delivered to a flowcell for sequencing. The assembly is brought to the wells of the flowcell by the application of a magnetic field placed underneath the flowcell, or can be allowed to settle by gravity. Sequencing is initiated by flowing an oligonucleotide cholesterol tether, which hybridizes to the adaptor ends, over the beads, which tethers the beads to the membrane. Alternatively, the cholesterol tether can be introduced into the membrane during a 'flush' step, before the bead-target conjugate is added to the flowcell.

Methods

An *E. coli* whole-genome library, ONLA18816, was prepared by random fragmentation of *E. coli* high-molecular weight genomic DNA to a median size of ~7 kb using a Covaris gTube, following the manufacturer's instructions. This library was then end-repaired and dA-tailed using an NEB Ultra II kit, per the manufacturer's instructions. The end-repaired, dA-tailed, fragmented genomic DNA was subjected to 0.4×SPRI purification and eluted from the SPRI beads in 0.1×TE.

200 nM DNA-extended tracrRNA (AR363) was added to a buffer containing 25 mM HEPES-NaOH (pH 8.0), 150 mM NaCl and 1 mM $MgCl_2$ (known as dCas9 binding buffer, BB). The tracrRNA was heated to 90° C. for 2 min and snap-cooled on wet ice, after which 100 nM dCas9 (ONLP12326) was added and the reaction incubated for 10 min at room temperature (~21° C.). 250 nM crRNA bearing a 3' DNA extension (AR191) was then added to the reaction and incubated for a further 10 min at room temperature (~21° C.). The final volume was 50 µL. This mixture was known as ribonucleotide-protein complexes (RNPs).

To form dCas9-target complexes, 500 ng (~1.2 µL) of the genomic DNA from above (ONLA18816) was added to the RNPs and incubated for 20 min at room temperature. The mixture was then incubated at 55° C. for 5 min to remove dCas9 not bound to its intended target. The mixture was subjected to 1×SPRI purification as follows: 51 µL AMPure XP beads were added to the mixture, mixed by gentle resuspension, and incubated for 10 min at room temperature. The beads were pelleted using a magnetic separator, and washed twice with ~250 µL of a buffer comprising 50 mM Tris-Cl (pH 8.0 at 4° C.), 2.5 M NaCl, 20% (w/v) PEG-8000, and eluted by incubating the SPRI beads with 12.5 µL of a buffer comprising 40 mM CAPS (pH 10.0), 40 mM KCl for 5 min. The beads were pelleted once more and the supernatant, known as 'SPRI eluate', retained.

50 µg Solulink 'Nanolink' streptavidin magnetic beads (5 µL) were incubated with 2.5 µL of AR667 capture oligo (comprising sequences a'-b', and a 3' biotin moiety) in a buffer comprising 50 mM Tris-Cl (pH 8.0 at 4° C.), 2 M NaCl, 1 mM EDTA, 0.05% (v/v) Tween-20 for ~1 h with agitation. Unbound oligonucleotide was removed by washing the beads twice with the same buffer, pelleting the beads using a magnetic separator. This conjugate was known as 'purification beads'.

Oligonucleotides AR132 and AR196 were hybridised using a PCR thermocycler by incubating 40 µM of each oligonucleotide in standard TE Buffer (10 mM Tris-Cl, 1 mM EDTA, pH 8.0)+200 mM NaCl, heating at 95° C. for 2 min, and cooling slowly to 25° C. over ~2 h. 12.5 µL of this duplex DNA, bearing an overhang complementary to the DNA extension of the crRNA sequence, were incubated with 50 µg Solulink 'Nanolink' streptavidin magnetic beads (5 µL) in ~120 µL of a buffer comprising 50 mM Tris-Cl (pH 8.0 at 4° C.), 2 M NaCl, 1 mM EDTA, 0.05% (v/v) Tween-20 for ~1 h with agitation. Unbound oligonucleotide was removed by washing the beads twice with the same buffer, pelleting the beads using a magnetic separator at each wash step. This conjugate was known as 'delivery beads'.

dCas9-bound target molecules were bound to purification beads by incubating 12.5 µL of SPRI eluate with 50 µg purification beads and 67.5 µL Dynabeads kilobaseBINDER Binding Solution (Thermo Scientific Cat. #60101) for 20 min at room temperature with agitation. The beads were washed three times with a buffer containing 50 mM Tris-Cl (pH 8.0 at 4° C.), 150 mM NaCl, 1 mM EDTA, and once with a buffer containing 50 mM Tris-Cl (pH 8.0 at 4° C.), 20 mM NaCl. Following this step, the beads were pelleted and the supernatant removed. This sample was known as 'purification bead-target complex'.

Following immobilisation of the target DNA-RNP complex, target DNA was eluted from the purification bead by the addition of 20 µL of a buffer containing 25 µM oligonucleotide AR668, bearing sequences a•b from FIG. 44, 20 mM Tris-Cl (pH 8.0), and 100 mM NaCl, for 10 min at room temperature, with gentle agitation. The eluate was retained as 'purification bead eluate'.

The purification bead eluate was then immobilised on delivery beads by incubating the 20 µL of purification bead eluate with 1 µL of delivery beads, and 105 µL Dynabeads kilobaseBINDER Binding Solution (Thermo Scientific Cat. #60101) for 20 min with agitation. The beads were subsequently washed three times with a buffer containing 50 mM Tris-Cl (pH 8.0 at 4° C.), 150 mM NaCl, 1 mM EDTA, and once with a buffer containing 50 mM Tris-Cl (pH 8.0 at 4° C.), 20 mM NaCl. Following this step, the beads were pelleted and the supernatant removed. This sample was known as 'delivery bead-target complex'.

Enzyme-loaded adaptors (tube 'AMX 1D') from Oxford Nanopore Technologies' 1D Sequencing Kit by Ligation (SQK-LSK108) were ligated to the bead-target complex by resuspending the pelleted beads from above with a ligation mix comprising 12.5 µL 2×LAQA1 buffer (a gift from New England Biolabs, Inc.), 7 µL nuclease-free water, 5 µL AMX 1D (part of SQK-LSK108), and 0.5 µL T4 DNA Ligase (NEB Cat. #M0202). The beads were incubated in the ligation mix with agitation for 10 min, pelleted, and washed once with ~125 µL of a buffer containing 50 mM Tris-Cl (pH 8.0 at 4° C.), 150 mM NaCl, 1 mM EDTA. Following the wash, the beads were pelleted once more, and resuspended in 50 µL of RBF (a component of SQK-LSK108), diluted to 1× according to the manufacturer's instructions. This mixture was known as the loading sample.

FIG. 44 shows the sequential series of steps described in this example required to elute a target-bound dCas9 molecule from the purification bead using a toehold displacement oligonucleotide, and transfer to a second delivery bead for loading on an Oxford Nanopore MinION flow-cell.

An Oxford Nanopore MinION flowcell was primed with 800 µL 1×RBF containing 50 nM tether oligo pipetted via its inlet port, followed by a pause of 10 min, then 200 µL of the same mixture pipetted via its inlet port with the SpotON port open. The entire 50 µL of the loading sample was pipetted dropwise into the SpotON port and the fluid allowed to wick into the flowcell. MinION data collection was initiated immediately, and data were collected and analysed according to standard customer protocols.

Results

Figure 45:
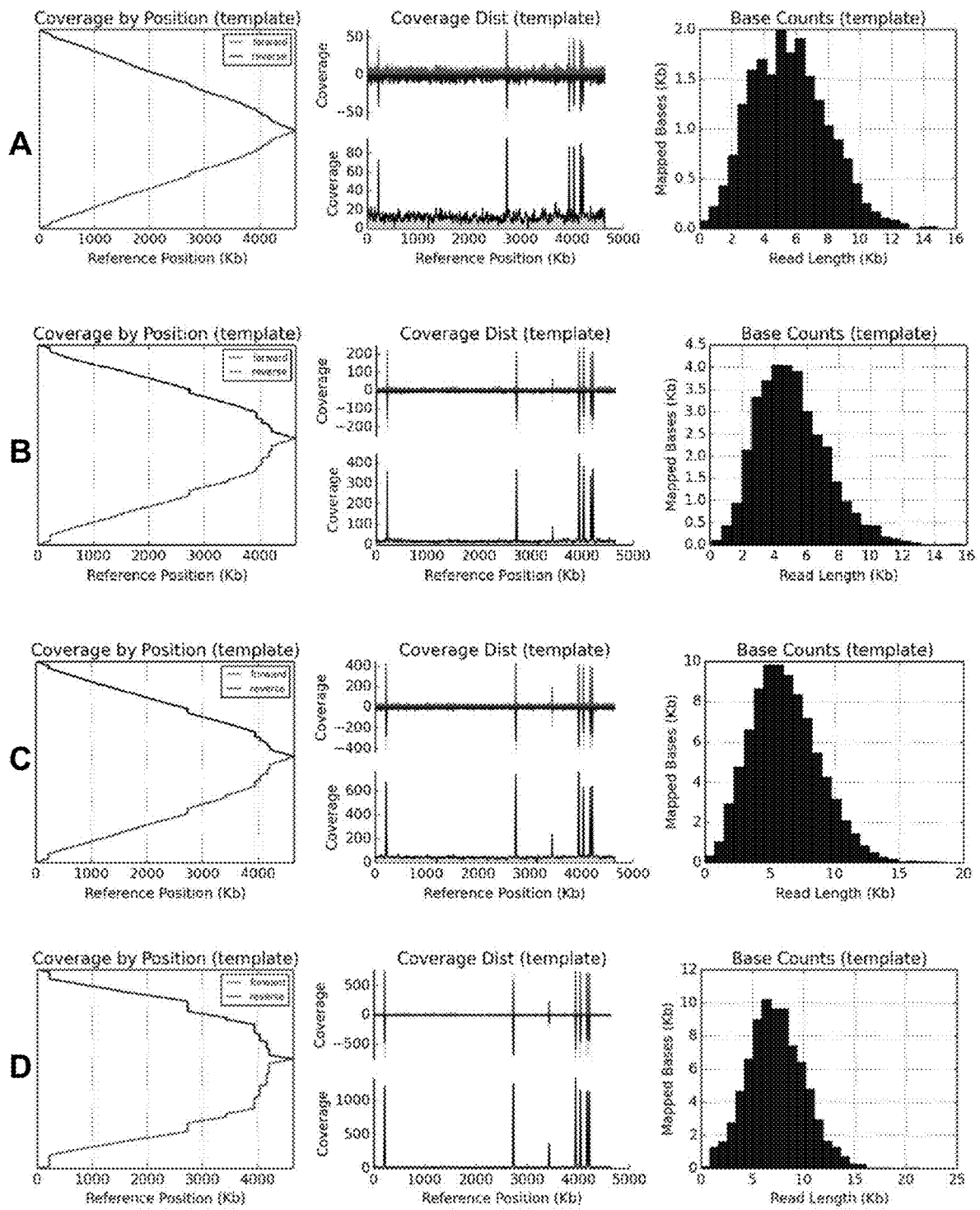
FIG. 45 shows the combinatorial effect of heat stress (55° C., 5 min), SPRI purification (performed after heat stress, where applicable; 1×), and the toehold displacement method (performed after bead capture), from a pulldown of the 16S rrs genes using a single crRNA probe, as described in Example 7. A, control with no heat stress, SRRI or toehold. B, SRRI only. C, heat stress only. D, heat stress and SPRI. E, toehold only. F, SPRI and toehold. G, heat stress and toehold. H, heat stress, SPRI and toehold. Each panel (A through H) shows an example E. coli coverage plot, similar to that shown in FIG. 42.
Figure 45:
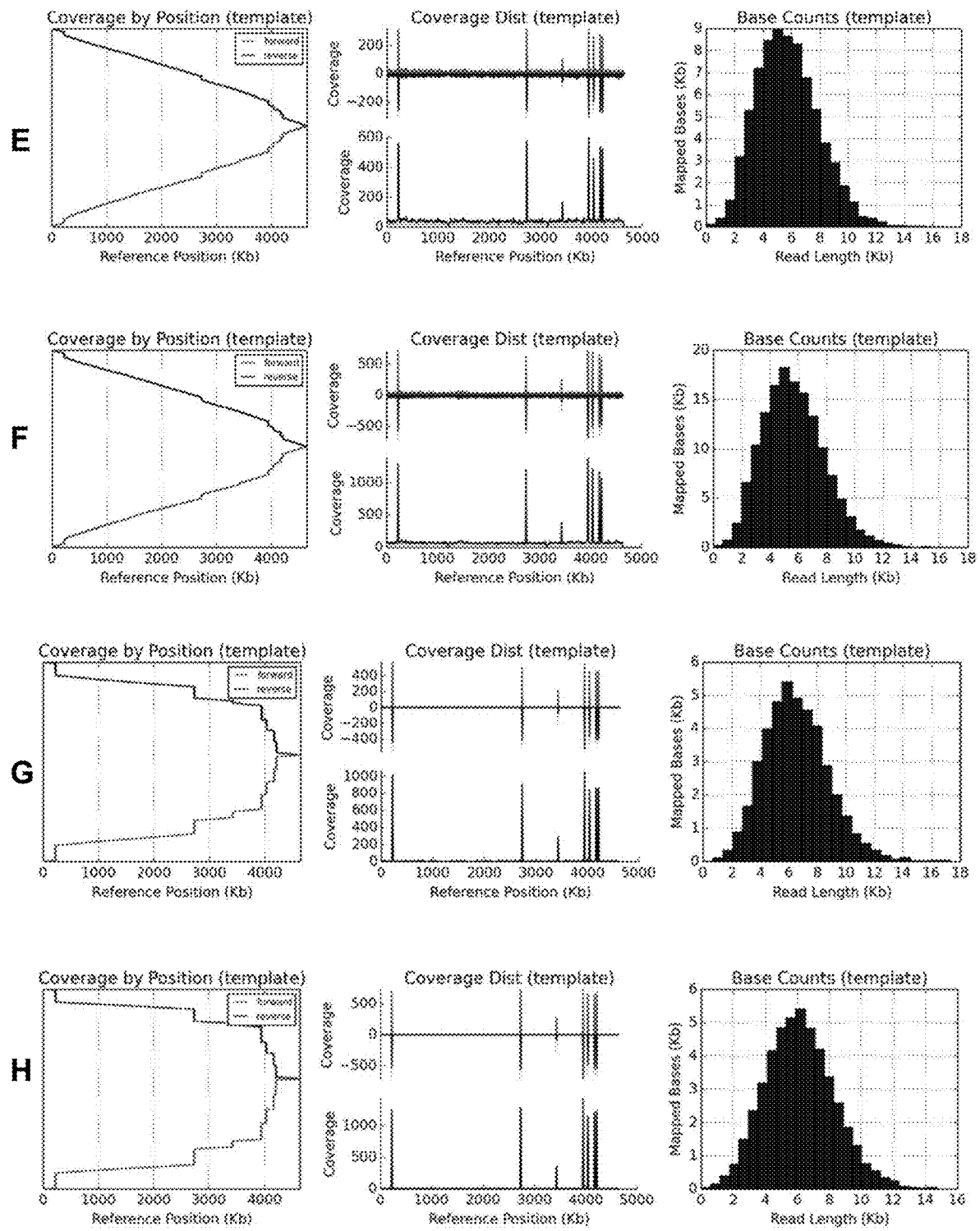

FIG. 45 shows the combinatorial effect of the heat stress, SPRI purification, purification bead binding, toehold displacement, and capture bead binding on the enrichment of *E. coli* 16S gene target from non-target *E. coli* DNA. The results are summarized in the Table below, which shows the % of reads on target.

|   | Heat | SPRI | Toehold | % on target |
|---|------|------|---------|-------------|
| A | No   | No   | No      | 10.7%       |
| B | No   | Yes  | No      | 29.5%       |
| C | Yes  | No   | No      | 26.4%       |
| D | Yes  | Yes  | No      | 48.4%       |
| E | No   | No   | Yes     | 21.4%       |
| F | No   | Yes  | Yes     | 30.0%       |
| G | Yes  | No   | Yes     | 50.2%       |
| H | Yes  | Yes  | Yes     | 76.1%       |

Specifically, FIG. 45, H demonstrates the additive effect of all three enrichment methods. The data of FIG. 45, H were collected over a 6-hour sequencing run using the above protocol using an Oxford Nanopore Technologies MinION flowcell running the standard baseline sequencing script with MinKNOW 1.7.14 software. The single crRNA probe used in this pulldown, AR191, is expected to direct dCas9 to each of the seven 16S ribosomal gene sites listed in FIG. 42D, with one position, identified as position vii, bearing a single mismatch at position −2 relative to the PAM site, and another, identified as peak i, bearing a single mismatch at position −6 relative to the PAM site. Of the ~4.6 Mb genome, ~36 kb (~0.78%) of the input DNA (7× the median read length, 5.1 kb) could be considered target.

10,482 sequencing reads were obtained from this run and placed through a standard basecalling and alignment analysis workflow. 9,245 reads could be mapped to the *E. coli* MG1655 genome (NC_000913.3), of which 7,975 (76.1%) mapped to within 3 median read lengths of each expected probe hybridisation position. Pileup of the sequencing reads yielded a coverage depth of >1,000× for each of positions i, ii, iii, iv, v and vi.

Materials
DNA and Oligonucleotides

| Component name | Sequence (Oligos are IDT codes) |
|---|---|
| *E. coli* genomic DNA, str. K-12, substr. MG1655 as ONLA18816 | NCBI Reference Sequence: NC_000913.3 |
| AR363 | TACATTTAAGACCCTAATAT/iSp18/mA*mG*mCmAmUmAmGmCmA rArGrUrUrArArArArUrArArGrGrCrUrArGrUrCrCrGrUrUrA rUrCrArAmCmUmUmGmAmAmAmAmAmGmUmGmCmAmCmCmGmAmG mUmCmGmGmUmGmCmU*mU*mU |
| AR667 | ATATTAGGGTCTTAAATAGCTCAGAAAAGAGTCATTGCA/iSp18//iSp18//iSp18//3BioTEG/ |
| AR668 | TGCAATGACTCTTTTCTGA/iBNA-meC//iBNA-G//iBNA-T//iBNA-A//iBNA-T//iBNA-T//iBNA-T/AAGACCCTAA/iBNA-T//iBNA-A/T |
| AR132 | /5Phos/CGATCGTTCCGATCAGAACACAAAGATGTATTGCT |
| AR196 | /5Phos/TGTTCTGATCGGAACGATCG/iSp18//iSp18//iSp18//3BioTEG/ |
| Tether oligo | /5CholTEG/TT/iSp18//iSp18//iSp18//iSp18/TTGACCGCTCGCCTC |
| AR191 | /5Phos/rArGrArCrCrArArArArGrArGrGrGrGrArCrCrU rUrGrUrUrUrUrArGrArGrCrUrArUrGrCrUAGCAATACATCTTTG |

Proteins

ONLP12326: *S. pyogenes* Cas9 D10A/H840A, C-terminal Twin-Strep-tag with TEV-cleavable linker; bold, bracketed shows the portion cleaved by TEV (sequence above).

Example 8

This Example describes a method for the detection of a specific polynucleotide in a complex background by nanopore sequencing, following the enrichment of the target molecule. In this Example, the target DNA molecule is identified primarily by its sequence. The target molecule is separated from the background by means of a 'pulldown' via a capture moiety on the dCas9 molecule. The dCas9 binds preferably to the target molecule by means of a crRNA directed against the ribosomal 16S (rrs) genes of *Escherichia coli*. The binding of off-target, i.e., mismatched, regions, is reduced by substituting dCas9 with an otherwise wild-type background for a mutant derivative of the dCas9 enzyme, known as 'enhanced specificity dCas9', and by applying a thermal and salt stress to the bound dCas9 protein, coupled with a SPRI purification step to remove excess, unbound dCas9 before subsequent purification on a capture bead surface. The target DNA molecule is adapted for nanopore sequencing, and the dCas9 remains bound to its target until displaced by the enzyme loaded on the adapter.

The dCas9 carries a tracrRNA molecule bearing a 5' DNA extension (sequence a of FIG. 41) that enables capture of the target molecule on a bead-capture oligonucleotide conjugate that bears a DNA sequence complementary to this extension (sequence a' of FIG. 41). In this Example, the capture oligonucleotide is linked to the bead via a biotin moiety. In this Example, the non-target DNA is washed away, and target molecules remain bound to the bead. The target molecule is then adapted for nanopore sequencing by ligation to either or both of its free, dA-tailed ends, while the dCas9-target molecule is bound to the bead. The entire bead-target-RNP assembly is then delivered to a flowcell for sequencing. The assembly is brought to the wells of the flowcell by the application of a magnetic field placed underneath the flowcell, or can be allowed to settle by gravity. Sequencing is initiated by flowing an oligonucleotide cholesterol tether, which hybridizes to the adaptor ends, over the beads, which tethers the beads to the membrane. Alternatively, the cholesterol tether can be introduced into the membrane during a 'flush' step, before the bead-target conjugate is added to the flowcell.

Methods

An *E. coli* whole-genome library, ONLA18816, was prepared by random fragmentation of *E. coli* high-molecular weight genomic DNA to a median size of ~5.9 kb using a Covaris gTube, following the manufacturer's instructions. This library was then end-repaired and dA-tailed using an NEB Ultra II kit, per the manufacturer's instructions. Following end-repair and dA-tailing, the fragmented genomic DNA was subjected to 0.4×SPRI purification and eluted from the SPRI beads in 0.1×TE.

200 nM DNA-extended tracrRNA (AR363) was added to a buffer containing 25 mM HEPES-NaOH (pH 8.0), 150 mM NaCl and 1 mM $MgCl_2$ (known as dCas9 binding buffer). The tracrRNA was heated to 90° C. for 2 min and snap-cooled on wet ice, after which 100 nM dCas9 with a wild-type (ONLP12326) or the 'enhanced specificity' dCas9 (ONLP12296) was added and the reaction incubated for 10 min at room temperature (~21° C.). 250 nM crRNA bearing a 3' extension (extension not used here; AR191) was then added to the reaction and incubated for a further 10 min at room temperature (~21° C.). The final volume was 50 µL. This mixture was known as ribonucleotide-protein complexes (RNPs).

To form dCas9-target complexes, 500 ng (~1.2 µL) of the genomic DNA from above (ONLA18816) was added to the RNPs and incubated for 20 min at room temperature. The mixture was then incubated at 55° C. for 5 min to remove dCas9 not bound to its intended target. The mixture was subjected to 1×SPRI purification as follows: 51 µL AMPure XP beads were added to the mixture, mixed by gentle resuspension, and incubated for 10 min at room temperature. The beads were pelleted using a magnetic separator, and washed twice with ~250 µL of a buffer comprising 50 mM Tris-Cl (pH 8.0 at 4° C.), 2.5 M NaCl, 20% (w/v) PEG-8000, and eluted by incubating the SPRI beads with 12.5 µL of a buffer comprising 40 mM CAPS (pH 10.0), 40 mM KCl for 5 min. The beads were pelleted once more and the supernatant, known as 'SPRI eluate', retained.

50 µg Solulink 'Nanolink' streptavidin magnetic beads (5 µL) were incubated with 2.5 µL of AR364 capture oligo in ~120 µL of a buffer comprising 50 mM Tris-Cl (pH 8.0 at 4° C.), 2 M NaCl, 1 mM EDTA, 0.05% (v/v) Tween-20 for ~1 h with agitation. Unbound oligonucleotide was removed by washing the beads twice with the same buffer, pelleting the beads using a magnetic separator. This conjugate was known as 'capture beads'.

dCas9-bound target molecules were bound to capture beads by incubating 12.5 µL of SPRI eluate with 10 µg capture beads (1 µL) and 65 µL Dynabeads kilobase-BINDER Binding Solution (Thermo Scientific Cat. #60101) for 20 min with agitation. The beads were subsequently washed three times with a buffer containing 50 mM Tris-Cl (pH 8.0 at 4° C.), 150 mM NaCl, 1 mM EDTA, and once with a buffer containing 50 mM Tris-Cl (pH 8.0 at 4° C.), 20 mM NaCl. Following this step, the beads were pelleted and the supernatant removed. This sample was known as 'bead-target complex'.

Enzyme-loaded adaptors (tube 'AMX 1D') from Oxford Nanopore Technologies' 1D Sequencing Kit by Ligation (SQK-LSK108) were ligated to the bead-target complex by resuspending the pelleted beads from above with a ligation mix comprising 12.5 µL 2×LAQA1 buffer (a gift from New England Biolabs, Inc.), 7 µL nuclease-free water, 5 µL AMX 1D (part of SQK-LSK108), and 0.5 µL T4 DNA Ligase (NEB Cat. #M0202). The beads were incubated in the ligation mix with agitation for 10 min, pelleted, and washed once with ~125 µL of a buffer containing 50 mM Tris-Cl (pH 8.0 at 4° C.), 150 mM NaCl, 1 mM EDTA to remove free, unligated adapter. Following the wash, the beads were pelleted once more, and resuspended in 50 µL of RBF (a component of SQK-LSK108), diluted to 1× according to the manufacturer's instructions. This mixture was known as the loading sample.

FIG. 41 shows the expected appearance of the dCas9-crRNA-tracrRNA-target-bead conjugate, also known here as the loading sample.

An Oxford Nanopore MinION flowcell was primed with 800 µL 1×RBF containing 50 nM tether oligo pipetted via its inlet port, followed by a pause of 10 min, then 200 µL of the same mixture pipetted via its inlet port with the SpotON port open. The entire 50 µL of the loading sample was pipetted dropwise into the SpotON port and the fluid allowed to wick into the flowcell. MinION data collection was initiated immediately, and data were collected and analysed according to standard customer protocols.

Results

Figure 46:
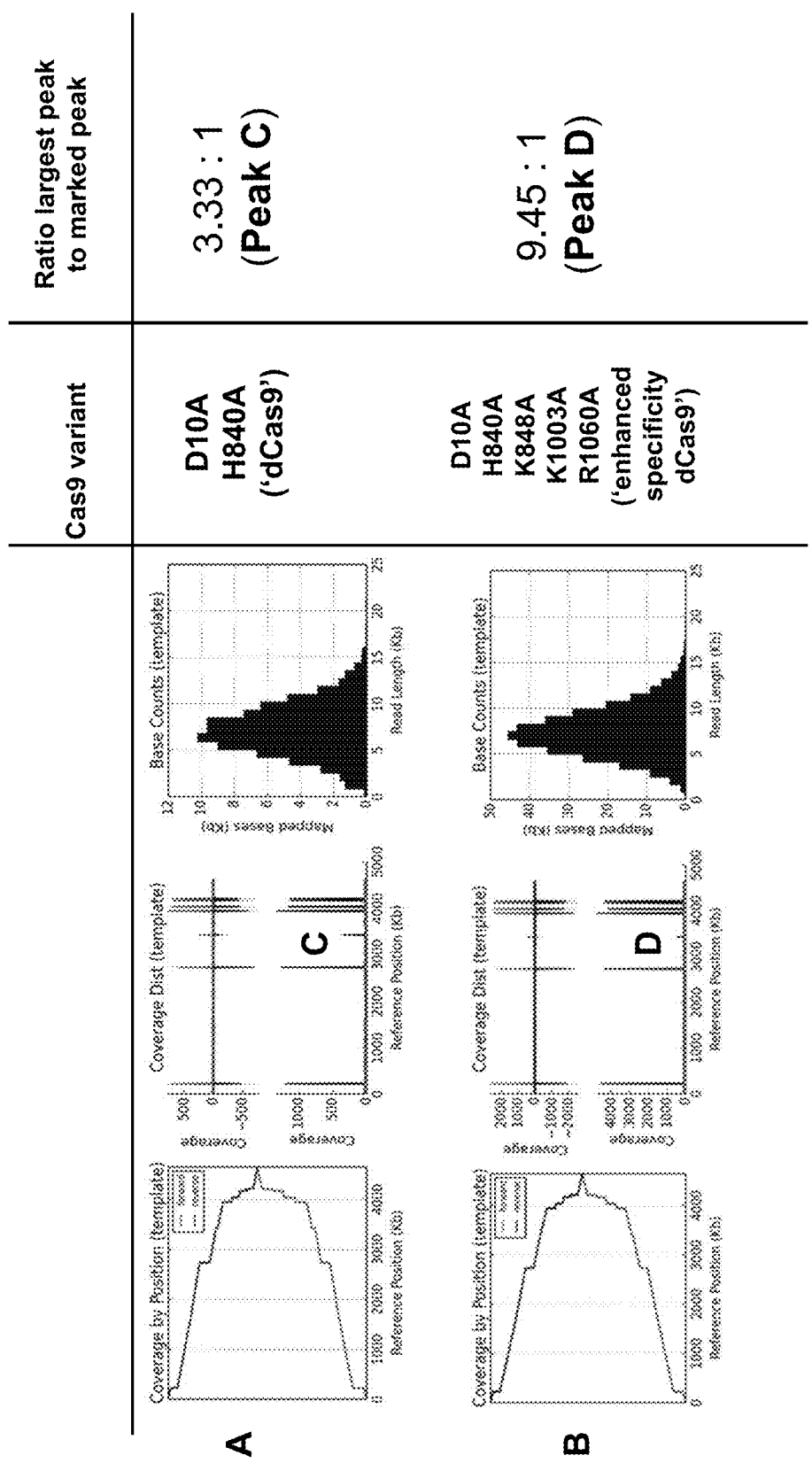
FIG. 46 compares pulldowns performed with wild-type or 'enhanced specificity' mutant of dCas9, as described in Example 8. Panel A shows a control experiment in which the dCas9 mutant variant, in an otherwise wild-type background, was used to pull out the E. coli rrs 16S genes, as described in FIG. 42 and Example 6. Peaks are as identified in FIG. 42. Panel B shows an equivalent experiment in which the wild-type dCas9 mutant variant was replaced with the 'enhanced specificity' dCas9 mutant, D10A/H840A/K848A/K1003A/R1060A. Peaks C and D also corresponds to peak vii of FIG. 42, and correspond to the rrsD gene, which carries a mismatch at position −2 relative to the PAM.

FIG. 46 shows data collected over a 6-hour sequencing run using the above protocol using an Oxford Nanopore Technologies MinION flowcell running the standard baseline sequencing script with MinKNOW 1.7.14 software. The single crRNA probe used in this pulldown, AR191, is expected to direct dCas9 to each of the seven 16S ribosomal gene sites listed in FIG. 42, D, with one position, identified with letters C and D, bearing a single mismatch at position −2 relative to the PAM site. This position corresponds to peak vii as identified in FIG. 42, D. The ratio of the height of the largest peak to the mismatch peak identified as C or D was 3.33:1 and 9.45:1 for the wild-type dCas9 and 'enhanced specificity' dCas9 variants, respectively.

Materials
DNA and Oligonucletides

| Component name | Sequence (Oligos are IDT codes) |
|---|---|
| E. coli genomic DNA, str. K-12, substr. MG1655 as ONLA18816 | NCBI Reference Sequence: NC_000913.3 |
| AR363 | TACATTTAAGACCCTAATAT/iSp18/mA*mG*mCmAmUmAmGmCmA rArGrUrUrArArArArUrArArGrGrCrUrArGrUrCrCrGrUrUrA rUrCrArAmCmUmUmGmAmAmAmAmGmUmGmGmCmAmCmCmGmAmG mUmCmGmGmUmGmCmU*mU*mU |
| AR364 | /5Phos/ATATTAGGGTCTTAAATGTA/iSp18//iSp18//iSp18//3BioTEG/ |
| Tether oligo | /5CholTEG/TT/iSp18//iSp18//iSp18//iSp18/TTGACCGCTCGCCTC |
| AR191 | /5Phos/TArGrArCrCrArArArGrArGrGrGrGrGrArC rCrUrUrGrUrUrUrUrArGrArGrCrUrArUrGrCrU AGCAATACATCTTTG |

Proteins
ONLP12296: S. pyogenes Cas9 D10A/H840A/K848A/K1003A/R1060A, known as 'enhanced specificity dCas9': C-terminal Twin-Strep-tag with TEV-cleavable linker; bold, bracketed shows the portion cleaved by TEV (sequence above).
ONLP12326: S. pyogenes Cas9 D10A/H840A, C-terminal Twin-Strep-tag with TEV-cleavable linker; bold, bracketed shows the portion cleaved by TEV (sequence above).

Example 9

This Example describes a method for the detection of a specific polynucleotide in a complex background by nanopore sequencing, following the enrichment of the target molecule. In this Example, the target DNA molecule is identified primarily by its sequence, and the effects of catalytically active ('live', wild-type) and dead (D10A/H840A) Cas9 on read directionality bias were investigated. The directionality bias may be used to enrich for a specific read direction. The target molecule is separated from the background by means of a 'pulldown' via a capture moiety on the Cas9 molecule. Cas9 binds preferably to the target molecule by means of a crRNA directed against the ribosomal 16S (rrs) genes of Escherichia coli. 'Off-target' effects are reduced by applying a thermal and salt stress to the bound Cas9 protein, coupled with a SPRI purification step to remove excess, unbound Cas9 before subsequent purification on a capture bead surface. The target DNA molecule is adapted for nanopore sequencing, and the Cas9 remains bound to its target until displaced by the enzyme loaded on the adapter.

The Cas9 carries a tracrRNA molecule bearing a 5' DNA extension (sequence a of FIG. 41) that enables capture of the target molecule on a bead-capture oligonucleotide conjugate that bears a DNA sequence complementary to this extension (sequence a' of FIG. 41). In this Example, the capture oligonucleotide is linked to the bead via a biotin moiety. In this Example, the non-target DNA is washed away, and target molecules remain bound to the bead. The target molecule is then adapted for nanopore sequencing by ligation to either or both of its free, dA-tailed ends, while the Cas9-target molecule is bound to the bead. The entire bead-target-RNP assembly is then delivered to a flowcell for sequencing. The assembly is brought to the wells of the flowcell by the application of a magnetic field placed underneath the flowcell, or can be allowed to settle by gravity. Sequencing is initiated by flowing an oligonucleotide cholesterol tether, which hybridizes to the adaptor ends, over the beads, which tethers the beads to the membrane. Alternatively, the cholesterol tether can be introduced into the membrane during a 'flush' step, before the bead-target conjugate is added to the flowcell.

Catalytically active Cas9 would be expected to make a double-strand break at each of the target sites. If live Cas9 were to remain bound to only one side of the cut, as demonstrated by Sternberg et al., Nature 507, 62-67 (2014), then a significant directionality bias would be expected.

Methods
An E. coli whole-genome library, ONLA18816, was prepared by random fragmentation of E. coli high-molecular weight genomic DNA to a median size of ~5.9 kb using a Covaris gTube, following the manufacturer's instructions. This library was then end-repaired and dA-tailed using an NEB Ultra II kit, per the manufacturer's instructions. Following end-repair and dA-tailing, the fragmented genomic DNA was subjected to 0.4×SPRI purification and eluted from the SPRI beads in 0.1×TE.

To form ribonucleotide-protein complexes with dead Cas9, 200 nM DNA-extended tracrRNA (AR363) was added to a buffer containing 25 mM HEPES-NaOH (pH 8.0), 150 mM NaCl and 1 mM MgCl$_2$ (known as dCas9 binding buffer). The tracrRNA was heated to 90° C. for 2 min and snap-cooled on wet ice, after which 100 nM dCas9 (ONLP12326) was added and the reaction incubated for 10 min at room temperature (~21° C.). 250 nM crRNA (AR400) was then added to the reaction and incubated for a further 10 min at room temperature (~21° C.). The final volume was 50 µL. This mixture was known as dead RNPs.

To form ribonucleotide-protein complexes with live Cas9, 200 nM DNA-extended tracrRNA (AR363) was added to a buffer containing 20 mM HEPES, 100 mM NaCl, 5 mM $MgCl_2$, 0.1 mM EDTA, pH 6.5 @ 25° C., known as Cas9 cleavage buffer. The tracrRNA was heated to 90° C. for 2 min and snap-cooled on wet ice, after which 100 nM wild-type S. pyogenes Cas9 (New England Biolabs, Inc., Cat #M0386T) was added and the reaction incubated for 10 min at room temperature (~21° C.). 250 nM crRNA (AR400) was then added to the reaction and incubated for a further 10 min at room temperature (~21° C.). The final volume was 50 µL. This mixture was known as live RNPs.

To form Cas9-target complexes, 500 ng (~1.2 µL) of the genomic DNA from above (ONLA18816) was added to the RNPs and incubated for 30 min at 30° C. (for dead RNPs) or for 30 min at 37° C. (for live RNPs). The mixture was then incubated at 55° C. for 5 min to remove Cas9 not bound to its intended target. The mixture was subjected to 1×SPRI purification as follows: 51 µL AMPure XP beads were added to the mixture, mixed by gentle resuspension, and incubated for 10 min at room temperature. The beads were pelleted using a magnetic separator, and washed twice with ~250 µL of a buffer comprising 50 mM Tris-Cl (pH 8.0 at 4° C.), 2.5 M NaCl, 20% (w/v) PEG-8000, and eluted by incubating the SPRI beads with 12.5 µL of a buffer comprising 40 mM CAPS (pH 10.0), 40 mM KCl for 5 min. The beads were pelleted once more and the supernatant, known as 'SPRI eluate', retained.

50 µg Solulink 'Nanolink' streptavidin magnetic beads (5 µL) were incubated with 2.5 µL of AR364 capture oligo in ~120 µL of a buffer comprising 50 mM Tris-Cl (pH 8.0 at 4° C.), 2 M NaCl, 1 mM EDTA, 0.05% (v/v) Tween-20 for ~1 h with agitation. Unbound oligonucleotide was removed by washing the beads twice with the same buffer, pelleting the beads using a magnetic separator. This conjugate was known as 'capture beads'.

Cas9-bound target molecules were bound to capture beads by incubating 12.5 µL of SPRI eluate with 10 µg capture beads (1 µL) and 65 µL Dynabeads kilobaseBINDER Binding Solution (Thermo Scientific Cat. #60101) for 20 min with agitation. The beads were subsequently washed three times with a buffer containing 50 mM Tris-Cl (pH 8.0 at 4° C.), 150 mM NaCl, 1 mM EDTA, and once with a buffer containing 50 mM Tris-Cl (pH 8.0 at 4° C.), 20 mM NaCl. Following this step, the beads were pelleted and the supernatant removed. This sample was known as 'bead-target complex'.

Enzyme-loaded adaptors (tube 'AMX 1D') from Oxford Nanopore Technologies' 1D Sequencing Kit by Ligation (SQK-LSK108) were ligated to the bead-target complex by resuspending the pelleted beads from above with a ligation mix comprising 12.5 µL 2×LAQA1 buffer (a gift from New England Biolabs, Inc.), 7 µL nuclease-free water, 5 µL AMX 1D (part of SQK-LSK108), and 0.5 µL T4 DNA Ligase (NEB Cat. #M0202). The beads were incubated in the ligation mix with agitation for 10 min, pelleted, and washed once with ~125 µL of a buffer containing 50 mM Tris-Cl (pH 8.0 at 4° C.), 150 mM NaCl, 1 mM EDTA to remove free, unligated adapter. Following the wash, the beads were pelleted once more, and resuspended in 50 µL of RBF (a component of SQK-LSK108), diluted to 1× according to the manufacturer's instructions. This mixture was known as the loading sample.

FIG. 41 shows the expected appearance of the Cas9-crRNA-tracrRNA-target-bead conjugate, also known here as the loading sample.

An Oxford Nanopore MinION flowcell was primed with 800 µL 1×RBF containing 50 nM tether oligo pipetted via its inlet port, followed by a pause of 10 min, then 200 µL of the same mixture pipetted via its inlet port with the SpotON port open. The entire 50 µL of the loading sample was pipetted dropwise into the SpotON port and the fluid allowed to wick into the flowcell. MinION data collection was initiated immediately, and data were collected and analysed according to standard customer protocols.

Results

Figure 47:
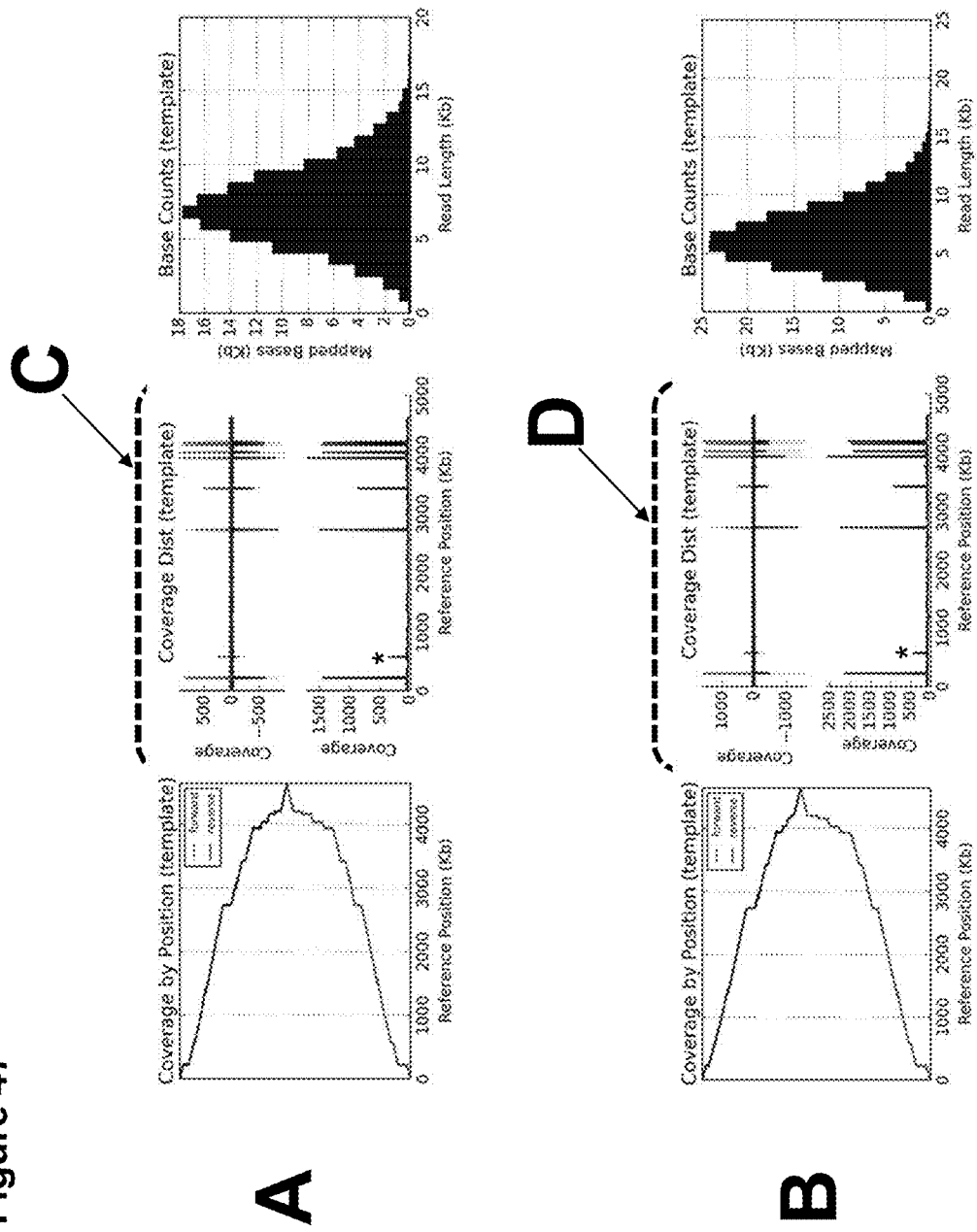
FIG. 47 shows coverage plots from nanopore DNA sequencing runs of pulldowns performed with catalytically dead (dCas9, A) or live (B) Cas9, as described in Example 9. Panel A shows a control experiment in which the dCas9 mutant variant, in an otherwise wild-type background, was used to pull out the E. coli rrs 16S genes, as described in FIG. 42 and Example 6. The incubation temperature in this experiment was 30° C. Panel B shows a similar pulldown experiment in which the dCas9 mutant was replaced with catalytically active Cas9. The incubation temperature in this experiment was 37° C. * denotes an additional peak attributable to the higher incubation temperatures used in this experiment compared with Example 6. Panels C and D show coverage plots for the dCas9 and live Cas9 pulldowns in which the coverage is grouped by the directionality of the read; positive numbers denote forwards reads, while negative numbers denote reverse reads.

FIG. 47 shows data collected over a 6-hour sequencing run using the above protocol using an Oxford Nanopore Technologies MinION flowcell running the standard baseline sequencing script with MinKNOW 1.7.14 software, with either catalytically-dead Cas9 ('dead', A) or live Cas9 ('live', B) used in the pulldown. The single crRNA probe used in this pulldown, AR400, is expected to direct Cas9 to each of the seven 16S ribosomal gene sites listed in FIG. 42, D. An additional peak, *, is also seen, attributable to the elevated incubation temperature in this example. Coverage directionality plots for the 'dead' and 'live' Cas9, identified as C and D respectively, demonstrate the slight additional directionality bias imposed by live Cas9.

Materials

DNA and Oligonucletides

| Component name | Sequence (Oligos are IDT codes) |
|---|---|
| E. coli genomic K-12, substr. MG1655 as ONLA18816 | NCBI Reference Sequence: NC_000913.3 |
| AR363 | TACATTTAAGACCCTAATAT/iSp18/mA*mG*mCmAmUmAmGmCmArUrCrArAmCmUmUmGmAmAmAmAmGmUmGmGmCmAmCmCmGmAmGmUmCmGmGmUmGmCmU*mU*mU |
| AR364 | /5Phos/ATATTAGGGTCTTAAATGTA/iSp18//iSp18//iSp18//3BioTEG/ |
| Tether oligo | /5CholTEG/TT/iSp18//iSp18//iSp18//iSp18/TTGACCGCTCGCCTC |
| AR400 | 'Alt-R' Cas9 crRNA from Integrated DNA Technologies, Inc: /AltR1/agaccaaagagggggacctt/AltR2/ |

Proteins

ONLP12326: *S. pyogenes* Cas9 D10A/H840A, C-terminal Twin-Strep-tag with TEV-cleavable linker; bold, bracketed shows the portion cleaved by TEV (sequence above).

Example 10

This Example describes a method for multiplexing the detection of a mixture of specific polynucleotides in a complex background by nanopore sequencing, following the enrichment of the target molecules. In this example, the same *E. coli* total genomic sample was subjected to multiple, separate enrichment dCas9 'pulldowns' involving different combinations of crRNA probes. Each sample was ligated with a specific DNA barcode adapter sequence, enabling all samples to be sequenced simultaneously using the same flowcell, and identified using their barcode adapter.

Methods

An *E. coli* whole-genome library, ONLA18816, was prepared by random fragmentation of *E. coli* high-molecular weight genomic DNA to a median size of ~5.9 kb using a Covaris gTube, following the manufacturer's instructions. This library was then end-repaired and dA-tailed using an NEB Ultra II kit, per the manufacturer's instructions. Following end-repair and dA-tailing, the fragmented genomic DNA was subjected to 0.4×SPRI purification and eluted from the SPRI beads in 0.1×TE. 500 ng of this library was then ligated to each of seven native barcode (NB) adapters, NB01, NB02, NB03, NB04, NB05, NB06 and NB07, from Oxford Nanopore Technologies' Native Barcoding Kit 1D (Cat #EXP-NBD103), according to the manufacturer's instructions.

Seven samples were prepared individually, each with a different combination of crRNA probes, as follows: 220 nM DNA-extended tracrRNA (AR363) was added to a buffer containing 50 mM Tris-Cl (pH 8.0), 150 mM NaCl and 1 mM EDTA (known as dCas9-EDTA buffer). 100 nM dCas9 (ONLP12326) was added and the reaction incubated for 10 min at room temperature (~21° C.). 200 nM crRNA (total) was then added to the reaction and incubated for a further 10 min at room temperature (~21° C.). The final volume was 50 µL. The combinations of crRNAs were as follows: (NB01) AR398, (NB02) AR399, (NB03) AR400, (NB04) AR398 and AR399, (NB05) AR398 and AR400, (NB06) AR399 and AR400, (NB07) AR398, AR399 and AR400. These seven mixtures were known as ribonucleotide-protein complexes (RNPs).

Each of the three crRNA probes used in this example target unique regions of the *E. coli* chromosome, according to the table below:

| crRNA probe | Target gene name | Target gene locations in *E. coli* chromosome (bp) |
| --- | --- | --- |
| AR398 | ftsK | 937,211 |
| AR399 | csgG | 1,099,778 |
| AR400 | Seven 16S ribosomal genes (rrs) | 224,037; 2,700,448; 3,380,179; 3,893,622; 3,987,345; 4,118,473; 4,159,961. |

To form RNP-target complexes, 500 ng of the genomic DNA carrying each barcode from above (ONLA18816) was added, separately, to each mixture of RNPs (NB01 to NB07; seven in total) and incubated for 20 min at room temperature. Each mixture was then incubated at 55° C. for 5 min to remove dCas9 not bound to its intended target. The mixtures were subjected to 1×SPRI purification as follows: ~50 µL AMPure XP beads were added to the mixture, mixed by gentle resuspension, and incubated for 10 min at room temperature. At this point, all seven samples were combined into a single tube. The beads were pelleted using a magnetic separator, and washed twice with ~1 mL of a buffer comprising 50 mM Tris-Cl (pH 8.0 at 4° C.), 2.5 M NaCl, 20% (w/v) PEG-8000, and eluted by incubating the SPRI beads with 12.5 µL of a buffer comprising 40 mM CAPS (pH 10.0), 40 mM KCl for 5 min. The beads were pelleted once more and the supernatant, known as 'SPRI eluate', retained.

50 µg Solulink 'Nanolink' streptavidin magnetic beads (5 µL) were incubated with 2.5 µL of AR364 capture oligo in ~120 µL of a buffer comprising 50 mM Tris-Cl (pH 8.0 at 4° C.), 2 M NaCl, 1 mM EDTA, 0.05% (v/v) Tween-20 for ~1 h with agitation. Unbound oligonucleotide was removed by washing the beads twice with the same buffer, pelleting the beads using a magnetic separator. This conjugate was known as 'capture beads'.

dCas9-bound target molecules were bound to capture beads by incubating 12.5 µL of SPRI eluate with 30 µg capture beads (1 µL) and 65 µL of a buffer comprising 50 mM Tris-Cl (pH 8.0 at 4° C.), 2 M NaCl, 1 mM EDTA, 0.05% (v/v) Tween-20 for 20 min with agitation. The beads were subsequently washed three times with a buffer containing 50 mM Tris-Cl (pH 8.0 at 4° C.), 150 mM NaCl, 1 mM EDTA. Following this step, the beads were pelleted and the supernatant removed. This sample was known as 'barcoded bead-target complexes'.

Enzyme-loaded adapter mix (tube TAM') from Oxford Nanopore Technologies' Native Barcoding Kit 1D (EXP-NBD103) was ligated to the barcoded bead-target complexes by resuspending the pelleted beads from above with a ligation mix comprising 12.5 µL 2× Blunt/TA Ligase Master Mix (New England Biolabs, Inc., Cat #M0367), 5 µL BAM (Oxford Nanopore Technologies, Ltd., kit EXP-NBD103), and 7.5 µL nuclease-free water for 10 min at room temperature, pelleted, and washed once with ~125 µL of a buffer containing 50 mM Tris-Cl (pH 8.0 at 4° C.), 150 mM NaCl, 1 mM EDTA to remove free, unligated adapter. Following the wash, the beads were pelleted once more, and resuspended in 50 µL of RBF (a component of SQK-LSK108), diluted to 1× according to the manufacturer's instructions. This mixture was known as the barcoded loading sample.

Figure 48:
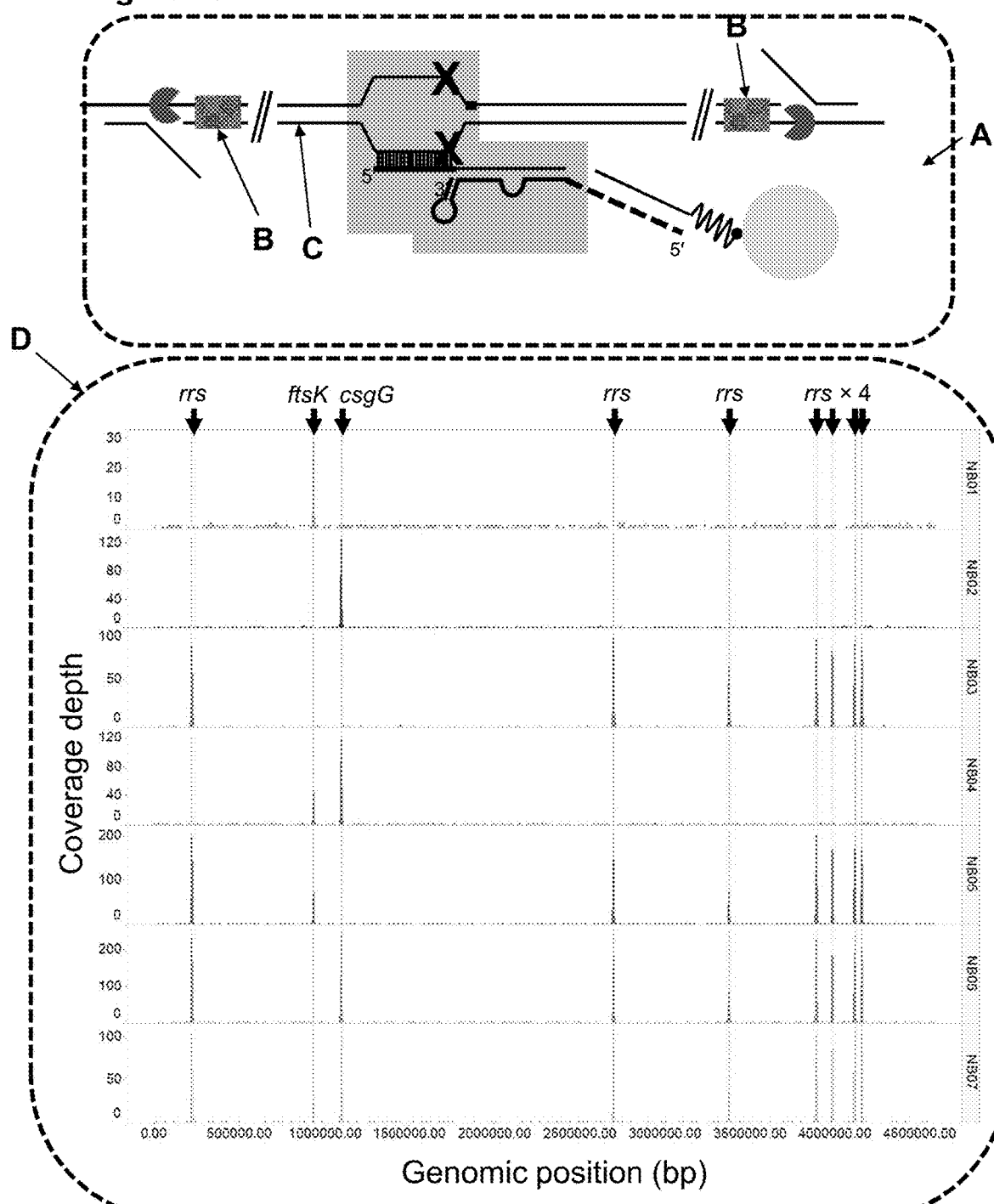
FIG. 48, A shows a bead-target conjugate, similar to that shown in FIG. 41, but additionally containing a barcode adapter B between the enzyme-loaded adapter and the target molecule A. Other components are as described in FIG. 41. Panel D shows coverage plots from a single 6-hour sequencing run that contained seven individually-barcoded samples, NB01 through NB07. Each barcode is associated with a different set of crRNA probes, and therefore a different target region of the E. coli genome, as described in the text of Example 10. Probe combinations are listed in the text of Example 10.

FIG. 48, A shows the expected appearance of the dCas9-crRNA-tracrRNA-target-bead conjugate, with ligated barcode adapter, also known here as the barcoded loading sample. The sample is similar to that shown in FIG. 41, except for the presence of a barcode adapter sequence between target and enzyme-loaded adapter, which (besides the target sequence) identifies the sample.

An Oxford Nanopore MinION flowcell was primed with 800 µL 1×RBF containing 50 nM tether oligo pipetted via its inlet port, followed by a pause of 10 min, then 200 µL of the same mixture pipetted via its inlet port with the SpotON port open. The entire 50 µL of the barcoded loading sample was pipetted dropwise into the SpotON port and the fluid allowed to wick into the flowcell. MinION data collection was initiated immediately, and data were collected and analysed according to standard customer workflows for Oxford Nanopore Technologies' Native Barcoding Kits.

Results

FIG. 48, D shows coverage plots from reads aligned to the *E. coli* genome, collected over a 6-hour sequencing run using the above multiplexing protocol. The sample was run on a single Oxford Nanopore Technologies MinION flowcell running the standard baseline sequencing script with MinKNOW 1.7.14 software and analysed using Oxford Nanopore Technologies workflows appropriate for the Native Barcoding Kit used.

Each barcode, NB01-NB07, is associated with the pull-down of a specific region of the *E. coli* sequence according to the table below. The coverage plots of FIG. 48, D show the successful deconvolution of the barcode sequence for each specific target region.

| Barcode | Probe(s) | Intended targets |
|---|---|---|
| NB01 | AR398 | ftsK |
| NB02 | AR399 | csgG |
| NB03 | AR400 | rrs genes |
| NB04 | AR398 AR399 | ftsK, csgG |
| NB05 | AR398 AR400 | ftsK, rrs genes |
| NB06 | AR399 AR400 | csgG, rrsB |
| NB07 | AR398 AR399 AR400 | ftsK, csgG, rrs genes |

Materials
DNA and Oligonucletides

| Component name | Sequence (Oligos are IDT codes) |
|---|---|
| *E. coli* genomic DNA, str. K-12, substr. MG1655 as ONLA18816 | NCBI Reference Sequence: NC_000913.3 |
| AR363 | TACATTTAAGACCCTAATAT/iSp18/mA*mG*mCmAmUmAmGmCmA rArGrUrUrArArArArUrArArGrGrCrUrArGrUrCrCrGrUrUrA rUrCrArAmCmUmUmGmAmAmAmAmAmGmUmGmCmCmAmCmCmGmAmG mUmCmGmGmUmGmCmU*mU*mU |
| AR364 | /5Phos/ATATTAGGGTCTTAAATGTA/iSp18//iSp18//iSp18//3BioTEG/ |
| Tether oligo | /5CholTEG/TT/iSp18//iSp18//iSp18//iSp18/TTGACCGCTCGCCTC |
| AR398 | 'Alt-R' Cas9 crRNA from Integrated DNA Technologies, Inc: /AltR1/tagatgatcaacgtaagtag/AltR2/ |
| AR399 | 'Alt-R' Cas9 crRNA from Integrated DNA Technologies, Inc: /AltR1/ggatgggtggctgtttccct/AltR2/ |
| AR400 | 'Alt-R' Cas9 crRNA from Integrated DNA Technologies, Inc: /AltR1/agaccaaagagggggacctt/AltR2/ |

Proteins
ONLP12326: *S. pyogenes* Cas9 D10A/H840A, C-terminal Twin-Strep-tag with TEV-cleavable linker; bold, bracketed shows the portion cleaved by TEV (sequence above).

Example 11

This Example describes a method for the detection of a specific polynucleotide in a complex background by nanopore sequencing, following the enrichment of the target molecule. In this Example, the target DNA molecule is identified primarily by its sequence. The target molecule is separated from the background by means of a 'pulldown' via a capture moiety on the dCas9 molecule. The dCas9 binds preferably to the target molecule by means of a crRNA directed against the ribosomal 16S (rrs) genes of *Escherichia coli*. 'Off-target' effects are reduced by applying a thermal and salt stress to the bound dCas9 protein, coupled with a SPRI purification step to remove excess, unbound dCas9 before subsequent capture on a bead surface.

In this Example, the DNA analyte may be adapted in different ways while bound to the capture beads: either (1) high-molecular weight genomic DNA may be sheared, end-repaired, dA-tailed, and ligated to an adapter using appropriate ends; or (2) high-molecular weight DNA may be concomitantly sheared and adapted using a transposase system such as that employed by the Oxford Nanopore Technologies Rapid 1D Sequencing Kit (SQK-RAD003). The adapter may permit other chemistries to be performed on the captured analyte while on the bead, while excess components such as free adapters are washed away. As examples, the analyte may be adapted for Oxford Nanopore Technologies' 1D$^2$ technology by ligating an appropriate adapter chemistry before ligating the enzyme adapter. Alternatively, adapters may be ligated that permit the amplification of the captured target by PCR, and release of the captured analyte from the bead.

Except for the example in which the captured target is released by PCR, the entire bead-target-RNP assembly is delivered to a flowcell for sequencing. The assembly is brought to the wells of the flowcell by the application of a magnetic field placed underneath the flowcell, or can be allowed to settle by gravity. Sequencing is initiated by flowing an oligonucleotide cholesterol tether, which hybridizes to the adaptor ends, over the beads, which tethers the beads to the membrane. Alternatively, the cholesterol tether can be introduced into the membrane during a 'flush' step, before the bead-target conjugate is added to the flowcell.

Methods
An *E. coli* whole-genome library, ONLA18816, is prepared by random fragmentation of *E. coli* high-molecular weight genomic DNA to a median size of ~5.9 kb using a Covaris gTube, following the manufacturer's instructions. This library is end-repaired and dA-tailed using an NEB Ultra II kit, per the manufacturer's instructions. Following end-repair and dA-tailing, the fragmented genomic DNA is subjected to 0.4×SPRI purification and eluted from the SPRI beads in 0.1×TE. This sample is known as 'dA-tailed genomic DNA'.

500 ng of the dA-tailed genomic DNA is ligated to enzyme-loaded adaptors ('AMX 1D') from Oxford Nanopore Technologies' 1D Sequencing Kit by Ligation (SQK-LSK108) in a comprising 12.5 µL 2× Blunt/TA Master Mix (New England Biolabs, Inc., Cat #M0367), 7.5 µL nuclease-free water and 5 µL AMX 1D (part of SQK-LSK108) for 10 min at room temperature. Following the ligation, unligated adapter is purified away by 0.4×SPRI purification and adapted library eluted from the SPRI beads in 10 mM Tris-Cl, 20 mM NaCl, pH 8.0. This sample is known as 'pre-ligated genomic DNA'.

1 µg of an *E. coli* high-molecular weight genomic DNA sample is sheared and sticky-ends introduced in a single step by incubation of ~1 µg DNA with 2.5 µL FRA (from the SQK-RAD003 of Oxford Nanopore Technologies, Ltd.) in a total volume of 10 µL at 30° C. for 20 min, followed by 80° C. for 1 min. 500 µL AMPure XP SPRI beads are washed five times in nuclease-free water, followed by resuspension in the original volume of a buffer comprising 50 mM Tris-Cl (pH 8.0 at 4° C.), 2.5 M NaCl, 20% (w/v) PEG-8000, yielding 'washed SPRI beads'. The genomic DNA sample is subjected to purification using 0.4× 'washed SPRI beads', and eluted by incubating the SPRI beads with 12.5 µL of a buffer comprising 0.1×TE at room temperature for 5 min. The beads are pelleted once more and the supernatant, known as 'transposase-fragmented genomic DNA', retained.

200 nM DNA-extended tracrRNA (AR363) is added to a buffer containing 25 mM HEPES-NaOH (pH 8.0), 150 mM NaCl and 1 mM $MgCl_2$ (known as dCas9 binding buffer). The tracrRNA is heated to 90° C. for 2 min and snap-cooled on wet ice, after which 100 nM dCas9 (ONLP12326) was added and the reaction incubated for 10 min at room temperature (~21° C.). 250 nM crRNA (AR400) is then added to the reaction and incubated for a further 10 min at room temperature (~21° C.). The final volume was 50 µL per reaction. This mixture is known as ribonucleotide-protein complexes (RNPs).

To form dCas9-target complexes, 500 ng (~1.2 µL) of either the transposase-fragmented genomic DNA, dA-tailed genomic DNA or pre-ligated genomic DNA is added to the RNPs per reaction and incubated for 20 min at room temperature. The mixture is then incubated at 55° C. for 5 min to remove dCas9 not bound to its intended target. Each mixture is subjected to 1×SPRI purification as follows: 51 µL AMPure XP beads are added to the mixture, mixed by gentle resuspension, and incubated for 10 min at room temperature. The beads are pelleted using a magnetic separator, washed twice with ~250 µL of a buffer comprising 50 mM Tris-Cl (pH 8.0 at 4° C.), 2.5 M NaCl, 20% (w/v) PEG-8000, and eluted by incubating the SPRI beads with 12.5 µL of a buffer comprising 40 mM CAPS (pH 10.0), 40 mM KCl for 5 min. The beads were pelleted once more and the supernatant, known as 'SPRI eluate', retained.

50 µg Solulink 'Nanolink' streptavidin magnetic beads (5 µL) are incubated with 2.5 µL of AR364 capture oligo in ~120 µL of a buffer comprising 50 mM Tris-Cl (pH 8.0 at 4° C.), 2 M NaCl, 1 mM EDTA, 0.05% (v/v) Tween-20 for ~1 h with agitation. Unbound oligonucleotide was removed by washing the beads twice with the same buffer, pelleting the beads using a magnetic separator. This conjugate was known as 'capture beads'.

dCas9-bound target molecules (bound to transposase-fragmented genomic DNA, dA-tailed genomic DNA or pre-adapted genomic DNA) are bound to capture beads by incubating 12.5 µL of SPRI eluate with 10 µg capture beads (1 µL) and 65 µL Dynabeads kilobaseBINDER Binding Solution (Thermo Scientific Cat. #60101) for 20 min with agitation. The beads are washed three times with a buffer containing 50 mM Tris-Cl (pH 8.0 at 4° C.), 150 mM NaCl, 1 mM EDTA, and once with a buffer containing 50 mM Tris-Cl (pH 8.0 at 4° C.), 20 mM NaCl. Following this step, the beads are pelleted and the supernatant removed. This sample is known as 'bead-target complex'.

In one reaction, enzyme-loaded adaptors (tube 'AMX 1D') from Oxford Nanopore Technologies' 1D Sequencing Kit by Ligation (SQK-LSK108) are ligated to dA-tailed genomic DNA captured on beads by resuspending the pelleted beads from above with a ligation mix comprising 12.5 µL 2× Blunt/TA Master Mix (New England Biolabs, Inc., Cat #M0367), 7.5 µL nuclease-free water and 5 µL AMX 1D (part of SQK-LSK108) for 10 min at room temperature. This sample is known as the 'bead-ligated 1D' sample.

In a second reaction, the analyte is prepared for '1D²' sequencing by performing two sequential ligations while the target is bound to the beads. In the first ligation reaction, the beads are resuspended in 2.5 µl $1D^2$ Adapter, 25 µl Blunt/TA Ligase Master Mix, and 22.5 µL nuclease-free water and incubated for 10 min at room temperature. After 10 min incubation, a further 10 µL BAM and 10 µL Blunt/TA Ligase Master Mix are added to the beads and incubated for a further 10 min at room temperature. This sample is known as the '1D²' sample.

In a third reaction, the transposase-fragmented genomic DNA bound to beads is adapted for sequencing by resuspending the beads in a buffer containing 1×RBF, and 1 µL RPD (from SQK-RAD003) for 10 min. This sample is known as the 'Rapid 1D' sample.

Following each of the above ligations, the beads are pelleted after the ligation, washed once in 125 µL of a buffer containing 50 mM Tris-Cl (pH 8.0 at 4° C.), 150 mM NaCl, 1 mM EDTA, and resuspended in 50 µL of RBF (from SQK-LSK108), diluted to 1× according to the manufacturer's instructions. This mixture is known as the loading sample.

For the sample containing pre-adapted genomic DNA bound to beads, the beads are washed once more in 125 µL of a buffer containing 50 mM Tris-Cl (pH 8.0 at 4° C.), 150 mM NaCl, 1 mM EDTA, and resuspended in 50 µL of RBF (a component of SQK-LSK108), diluted to 1× according to the manufacturer's instructions. This mixture is known as the 'pre-ligated sample'.

In a further reaction, PCR-adaptors (tube 'PCA') from Oxford Nanopore Technologies' Low-Input By PCR kit (SQK-LWP001) are ligated to dA-tailed genomic DNA captured on beads by resuspending the pelleted beads from above with a ligation mix comprising 50 µL 2× Blunt/TA Master Mix (New England Biolabs, Inc., Cat #M0367), 30 µL nuclease-free water and 20 µL PCA for 10 min at room temperature. Following the ligation, the beads are washed in a further 125 µL of 10 mM Tris-Cl (pH 8.0), 20 mM NaCl, and resuspended in a mixture containing 50 µL LongAmp Taq 2× Master Mix (NEB Cat #M0287), 2 µL WGP primers, and 48 µL nuclease-free water. The mixture is subjected to PCR amplification, including 30 sec denaturation at 94° C., and 10 cycles of 30 sec denaturation at 94° C., 30 sec annealing at 62° C., and 500 sec extension at 65° C. This sample is subjected to 0.4×SPRI purification using AMPure XP beads pre-washed as described above. The sample is eluted from SPRI beads in 10 µL of 10 mM Tris-Cl (pH 8.0), 20 mM NaCl, for 5 min at room temperature. Following elution from the SPRI beads, 1 μL of RPD (SQK-LWP001) are added and the mixture incubated for 10 min at room temperature to ligate sequencing adapters by click chemistry. A further 35 μL of RBF, 25 μL of LLB and 5 μL nuclease-free water are also added. This sample is known as the 'PCR' sample.

Five Oxford Nanopore MinION flowcells are primed with 800 μL 1×RBF containing 50 nM tether oligo pipetted via its inlet port, followed by a pause of 10 min, then 200 μL of the same mixture pipetted via its inlet port with the SpotON port open. Each sample: $1D^2$, PCR, Rapid 1D, bead-ligated, and pre-ligated, is pipetted dropwise into the SpotON port of each of the five flowcells and the fluid allowed to wick into the flowcell. MinION data collection is initiated immediately, and data are collected and analysed according to standard customer protocols.

of a barcode followed by an enzyme-loaded sequencing adapter, increases the single-molecule accuracy of nanopore sequencing. The ability to attach adapters via a transposase, followed by enzyme-free ligation via click chemistry, may afford the end-user greater convenience, enabling a faster sample preparation time. The ability to attach PCR adapters may afford the end-user considerably improved sensitivity, enabling the detection of the enriched target from much lower input amounts of starting material.

The ligation of sequencing adapters while the target analyte is bound to beads enables excess adapters, which may poison the nanopore sequencing reaction by fouling the pore, or depleting nucleotide concentration, to be conveniently washed away after the ligation step Materials DNA and Oligonucletides

| Component name | Sequence (Oligos are IDT codes) |
|---|---|
| E. coli genomic DNA, str. K-12, substr. MG1655 as ONLA18816 | NCBI Reference Sequence: NC_000913.3 |
| AR363 | TACATTTAAGACCCTAATAT/iSp18/mA*mG*mCmAmUmAmGmCmA rArGrUrUrArArArArArUrArArGrGrCrUrArGrUrCrGrUrUrA rUrCrArAmCmUmUmGmAmAmAmAmGmUmGmGmCmAmCmCmGmAmG mUmCmGmGmUmGmCmU*mU*mU |
| AR364 | /5Phos/ATATTAGGGTCTTAAATGTA/iSp18//iSp18//iSp18//3BioTEG/ |
| Tether oligo | /5CholTEG/TT/iSp18//iSp18//iSp18//iSp18/TTGACCGCTCGCCTC |
| AR400 | 'Alt-R' Cas9 crRNA from Integrated DNA Technologies, Inc: /AltR1/agaccaaagagggggaccctt/AltR2/ |

Figure 49:
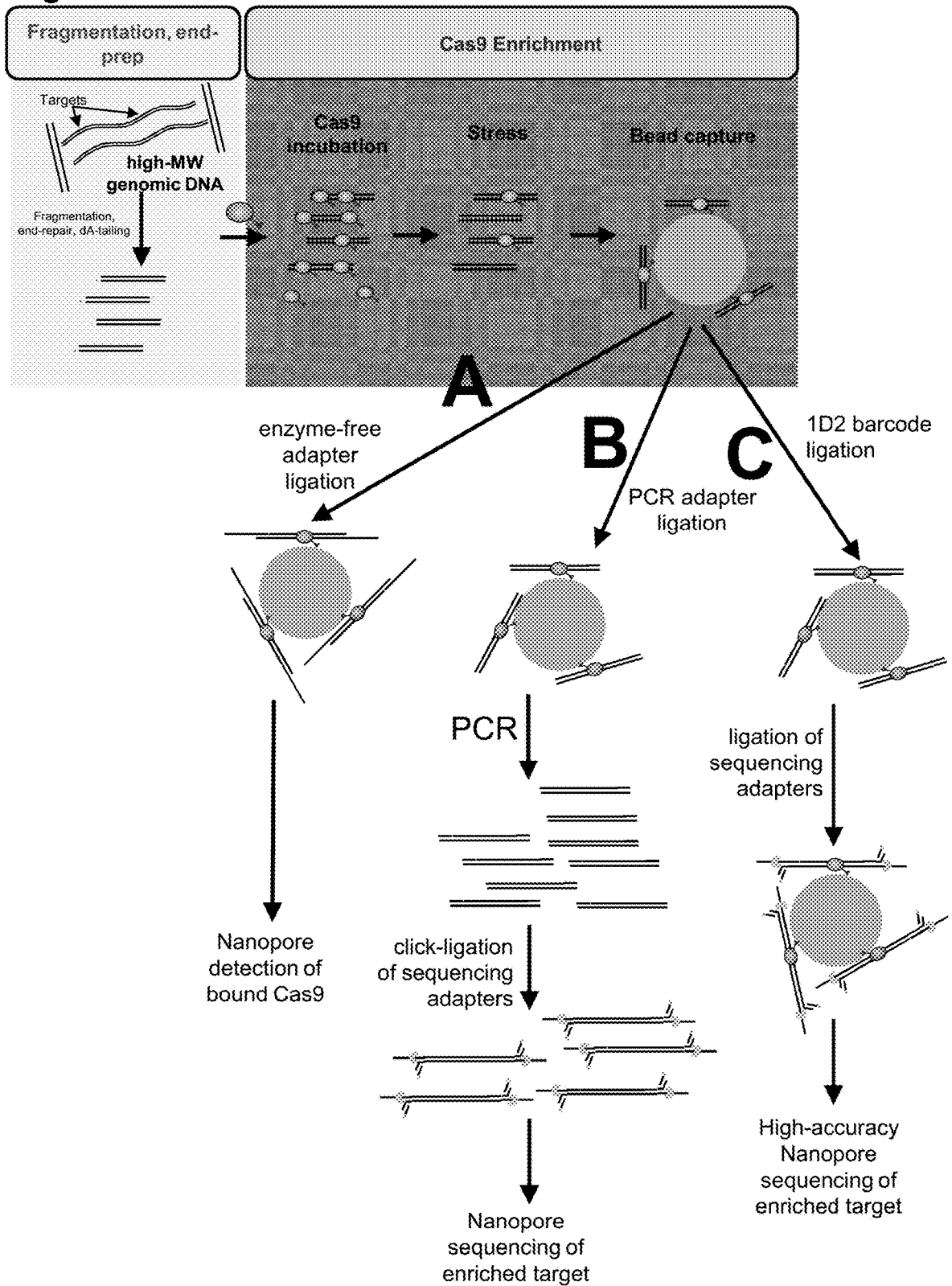
FIG. 49 shows three example workflows involving the attachment of adapters to a captured target analyte, while the analyte is bound via dCas9 to beads. A, the enzyme-free detection of dCas9, via the ligation of an enzyme-free adapter to the ends of a captured target analyte bound to beads; B, the enrichment of target by the ligation of PCR adapters, followed by PCR amplification of the target, as described above, to release, amplify and sequence target from beads; and C, the sequential ligation of $1D^2$ barcode adapters, followed by sequencing adapters, for high-accuracy nanopore sequencing, while dCas9 is bound to the target, and the target bound to beads.

FIG. 49 shows three example workflows for (1) the enzyme-free detection of dCas9, via the ligation of an enzyme-free adapter to the ends of a captured target analyte bound to beads; (2) the enrichment of target by the ligation of PCR adapters, followed by PCR amplification of the target, as described above, to release target from beads; and (3) the sequential ligation of $1D^2$ barcode adapters, followed by sequencing adapters, for high-accuracy nanopore sequencing.

Figure 50:
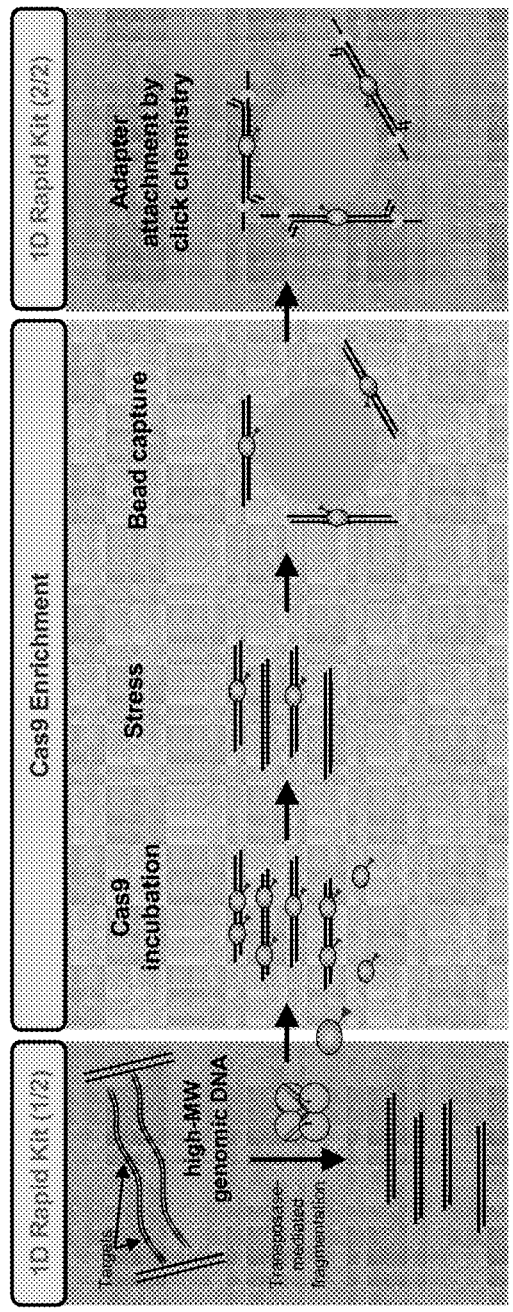
FIG. 50 shows an example workflow, described in Example 11, for the rapid enrichment of target from high-molecular weight DNA, by transposase-mediated shearing of the DNA, while concomitantly adding a sticky end for adapter ligation by click chemistry. dCas9 is then bound to the sheared DNA, as described in Example 11; off-target effects are minimised by a stress step, as previously described in Example 6, and sequencing adapters ligated via click chemistry. This workflow makes use of the Oxford Nanopore Technologies SQK-RAD003 kit, with the insertion of a Cas9 binding and bead capture step between the transposase fragmentation and adapter attachment steps, as described in Example 11.
Figure 51:
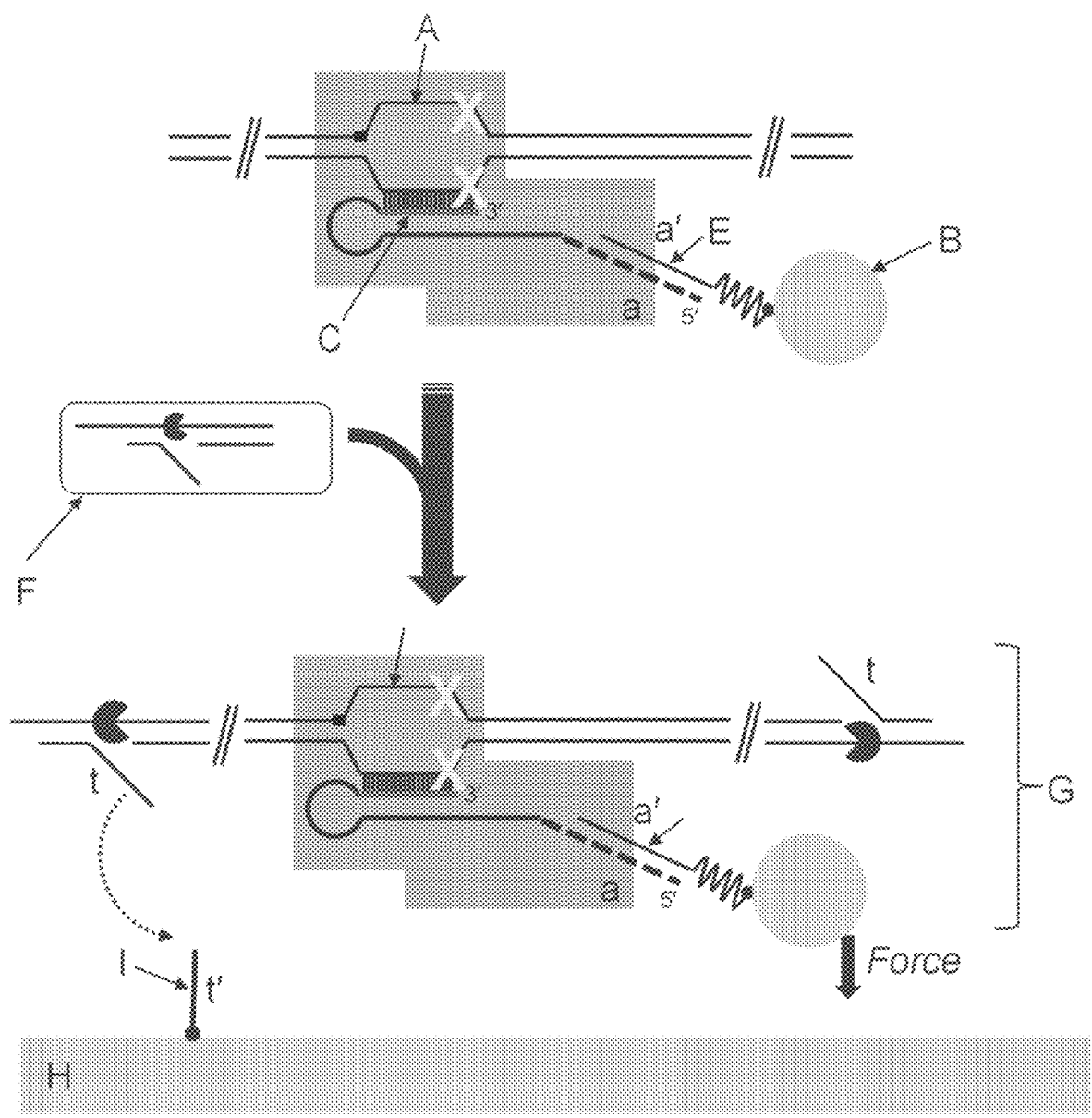
FIG. 51 shows a hypothetical example method for the enrichment and detection or sequencing of a Cpf1 or dCpf1-contacted target A to a bead surface B, with crRNA bearing a 5' DNA extension C with sequence a. Target A may be any size, ranging from tens of nucleotides to greater than megabases in length. B may for instance be a bead surface (in bulk solution or in column format) or membrane. Attachment to B is mediated by oligonucleotide E, bearing sequence a' complementary to the extension of C, which bears a chemical moiety such as biotin that enables attachment to bead B if B is coated with a protein such as streptavidin. Non-target DNA may subsequently be washed away from B. Enzymatic or click chemistry ligation of adapter F to blunt or complementary ends of target A may be achieved while the target is bound to the bead, with excess adapter washed away, to yield target-Cpf1-bead assembly G. Sequencing or detection of the target A is then achieved by delivering assembly G to a flowcell containing membrane H, and cholesterol-modified oligonucleotide tether I, which hybridises to adaptor F via sequence t', complementary to t. Assembly G may be delivered to the membrane by gravity, or by an applied magnetic field if for instance bead B is paramagnetic.

FIG. 50 shows an example workflow, described in Example 11, for the rapid enrichment of target from high-molecular weight DNA, by transposase-mediated shearing of the DNA, while concomitantly adding a sticky end for adapter ligation. dCas9 is then bound to the sheared DNA, as described in Example 11; off-target effects are minimised by a stress step, and sequencing adapters ligated via click chemistry. This workflow makes use of the Oxford Nanopore Technologies SQK-RAD003 kit, with the insertion of a Cas9 binding and bead capture step between the transposase fragmentation and adapter attachment steps, as described in Example 10.

Results

The results from each of the workflows described above yield results very similar to those depicted in FIG. 42, i.e., targeted enrichment of the *E. coli* rrs genes from a whole-genome sample. The only differences in this example are the methods of end-preparation for attaching sequencing adapters. The ability to attach $1D^2$ adapters, via sequential ligation Proteins ONLP12326: *S. pyogenes* Cas9 D10A/H840A, C-terminal Twin-Strep-tag with TEV-cleavable linker; bold, bracketed shows the portion cleaved by TEV (sequence above).

Example 12

This Example describes a method for the detection of a specific polynucleotide in a complex background by nanopore sequencing, following the enrichment of the target molecule. In this example, the target DNA molecule is identified primarily by its sequence. The target molecule is separated from the background by means of a 'pulldown' via a capture moiety on the catalytically active ('live', wild-type) Cpf1 (ONLP12350) or dead (E993A or D908A) dCpf1 (ONLZ11882 or ONLZ11883). The Cpf1 or dCpf1 binds preferably to the target molecule by means of a crRNA directed against the ribosomal 16S (rrs) genes of *Escherichia coli*. 'Off-target' effects are reduced by applying a thermal and salt stress to the bound Cpf1 or dCpf1 protein, coupled with a SPRI purification step to remove excess, unbound Cpf1 or dCpf1 before subsequent capture on a bead surface.

The Cpf1 or dCpf1 carries a crRNA molecule bearing a 5' DNA extension (AR766) that enables capture of the target molecule on a bead-capture oligonucleotide conjugate that bears a DNA sequence complementary to this extension (AR364), as depicted in figure RB12. In this Example, the capture oligonucleotide is linked to the bead via a biotin moiety. In this Example, the non-target DNA is washed away, and target molecules remain bound to the bead. The target molecule is then adapted for nanopore sequencing by ligation to either or both of its free, dA-tailed ends, while the Cpf1 target molecule is bound to the bead. The entire bead-target-RNP assembly is then delivered to a flowcell for sequencing. The assembly is brought to the wells of the flowcell by the application of a magnetic field placed underneath the flowcell, or can be allowed to settle by gravity. Sequencing is initiated by flowing an oligonucleotide cholesterol tether, which hybridizes to the adaptor ends, over the beads, which tethers the beads to the membrane. Alternatively, the cholesterol tether can be introduced into the membrane during a 'flush' step, before the bead-target conjugate is added to the flowcell.

Methods

An *E. coli* whole-genome library, ONLA18816, is prepared by random fragmentation of *E. coli* high-molecular weight genomic DNA to a median size of ~5.9 kb using a Covaris gTube, following the manufacturer's instructions. This library is end-repaired and dA-tailed using an NEB Ultra II kit, per the manufacturer's instructions. Following end-repair and dA-tailing, the fragmented genomic DNA is subjected to 0.4×SPRI purification and eluted from the SPRI beads in 0.1×TE. This sample is known as 'dA-tailed genomic DNA'.

250 nM DNA-extended crRNA (AR766) is added to a buffer containing 50 mM Tris-HCl (pH 8.0), 100 mM NaCl, 10 mM MgCl$_2$ and 1 mM DTT (known as Cpf1 binding buffer). The crRNA is heated to 95° C. for 2 min and allowed to cool to room temperature, after which 500 nM Cpf1 (ONLP12326) is added and the reaction incubated for 20 min at room temperature (~21° C.). This mixture is known as ribonucleotide-protein complexes (RNPs).

To form Cpf1-target complexes, 500 ng (~1.2 μL) of the genomic DNA from above (ONLA18816) is added to the RNPs and incubated for 60 min at room temperature. The mixture is incubated at 55° C. for 5 min to remove Cpf1 not bound to its intended target. The mixture is subjected to 1×SPRI purification as follows: 51 μL AMPure XP beads are added to the mixture, mixed by gentle resuspension, and incubated for 10 min at room temperature. The beads are pelleted using a magnetic separator, and washed twice with ~250 μL of a buffer comprising 50 mM Tris-Cl (pH 8.0 at 4° C.), 2.5 M NaCl, 20% (w/v) PEG-8000, and eluted by incubating the SPRI beads with 12.5 μL of a buffer comprising 40 mM CAPS (pH 10.0), 40 mM KCl for 5 min. The beads are pelleted once more and the supernatant, known as 'SPRI eluate', retained.

50 μg Solulink 'Nanolink' streptavidin magnetic beads (5 μL) are incubated with 2.5 μL of AR364 capture oligo in ~120 μL of a buffer comprising 50 mM Tris-Cl (pH 8.0 at 4° C.), 2 M NaCl, 1 mM EDTA, 0.05% (v/v) Tween-20 for ~1 h with agitation. Unbound oligonucleotide is removed by washing the beads twice with the same buffer, pelleting the beads using a magnetic separator. This conjugate was known as 'capture beads'.

Cpf1 or dCpf1-bound target molecules are bound to capture beads by incubating 12.5 μL of SPRI eluate with 10 μg capture beads (1 μL) and 65 μL Dynabeads kilobase-BINDER Binding Solution (Thermo Scientific Cat. #60101) for 20 min with agitation. The beads are washed three times with a buffer containing 50 mM Tris-Cl (pH 8.0 at 4° C.), 150 mM NaCl, 1 mM EDTA, and once with a buffer containing 50 mM Tris-Cl (pH 8.0 at 4° C.), 20 mM NaCl. Following this step, the beads are pelleted and the supernatant removed. This sample is known as 'bead-target complex'.

Enzyme-loaded adaptors (tube 'AMX 1D') from Oxford Nanopore Technologies' 1D Sequencing Kit by Ligation (SQK-LSK108) are ligated to dA-tailed genomic DNA captured on beads by resuspending the pelleted beads from above with a ligation mix comprising 12.5 μL 2× Blunt/TA Master Mix (New England Biolabs, Inc., Cat #M0367), 7.5 μL nuclease-free water and 5 μL AMX 1D (part of SQK-LSK108) for 10 min at room temperature. This sample is known as the 'bead-ligated 1D' sample.

The beads are pelleted after the ligation, washed once in 125 μL of a buffer containing 50 mM Tris-Cl (pH 8.0 at 4° C.), 150 mM NaCl, 1 mM EDTA, and resuspended in 50 μL of RBF (from SQK-LSK108), diluted to 1× according to the manufacturer's instructions. This mixture is known as the loading sample.

An Oxford Nanopore MinION flowcell is primed with 800 μL 1×RBF containing 50 nM tether oligo pipetted via its inlet port, followed by a pause of 10 min, then 200 μL of the same mixture pipetted via its inlet port with the SpotON port open. The loading sample is pipetted dropwise into the SpotON port of the flowcell and the fluid allowed to wick into the flowcell. MinION data collection is initiated immediately, and data are collected and analysed according to standard customer protocols.

Results

The results from the workflow described above yields results very similar to those depicted in FIG. 42 and to those depicted in FIG. 47, i.e., targeted enrichment of the *E. coli* rrs genes from a whole-genome sample. The live Cpf1 could impose a directionality bias. The differences in this Example are the CRISPR protein used to form the RNPs (i.e. Cpf1 or dCpf1, not Cas9 or dCas9), and the use of a single DNA-extended crRNA to form the RNPs.

The ligation of sequencing adapters while the target analyte is bound to beads enables excess adapters, which may poison the nanopore sequencing reaction by fouling the pore, or depleting nucleotide concentration, to be conveniently washed away after the ligation step.

Materials

DNA and Oligonucletides

| Component name | Sequence (Oligos are IDT codes) |
|---|---|
| *E. coli* genomic DNA, str. K-12, substr. MG1655 as ONLA18816 | NCBI Reference Sequence: NC_000913.3 |

-continued

| Component name | Sequence (Oligos are IDT codes) |
|---|---|
| AR766 | TACATTTAAGACCCTAATATttttttrUrArArUrUrUrCrUrArCrUrCrUrUrGrUrArG rArUrArUrCrArUrGrGrCrUrCrArGrArUrUrGrArArCrGrC |
| AR364 | /5Phos/ATATTAGGGTCTTAAATGTA/iSp18//iSp18//iSp18//3BioTEG/ |
| Tether oligo | /5CholTEG/TT/iSp18//iSp18//iSp18//iSp18/TTGACCGCTCGCCTC |

Proteins

ONLP12350: *Acidaminococcus* sp. Cpf1, N-terminal Twin-Strep-tag with TEV-cleavable linker; bold, bracketed shows the portion cleaved by TEV:
[MSAWSHPQFEKGGGSGGGSGGSAWSHPQFEKSGGGGGENLYFQ]GMTQFEGFTNLYQVSKTLRFELIPQGKTLKHI

QEQGFIEEDKARNDHYKELKPIIDRIYKTYADQCLQLVQLDWENLSAAIDSYRKEKTEETRNALIEEQATYRNAIHD

YFIGRTDNLTDAINKRHAEIYKGLFKAELFNGKVLKQLGTVTTTEHENALLRSFDKFTTYFSGFYENRKNVFSAEDI

STAIPHRIVQDNFPKFKENCHIFTRLITAVPSLREHFENVKKAIGIFVSTSIEEVFSFPFYNQLLTQTQIDLYNQLL

GGISREAGTEKIKGLNEVLNLAIQKNDETAHIIASLPHRFIPLFKQILSDRNTLSFILEEFKSDEEVIQSFCKYKTL

LRNENVLETAEALFNELNSIDLTHIFISHKKLETISSALCDHWDTLRNALYERRISELTGKITKSAKEKVQRSLKHE

DINLQEIISAAGKELSEAFKQKTSEILSHAHAALDQPLPTTLKKQEEKEILKSQLDSLLGLYHLLDWFAVDESNEVD

PEFSARLTGIKLEMEPSLSFYNKARNYATKKPYSVEKFKLNFQMPTLASGWDVNKEKNNGAILFVKNGLYYLGIMPK

QKGRYKALSFEPTEKTSEGFDKMYYDYFPDAAKMIPKCSTQLKAVTAHFQTHTTPILLSNNFIEPLEITKEIYDLNN

PEKEPKKFQTAYAKKTGDQKGYREALCKWIDFTRDFLSKYTKTTSIDLSSLRPSSQYKDLGEYYAELNPLLYHISFQ

RIAEKEIMDAVETGKLYLFQIYNKDFAKGHHGKPNLHTLYWTGLFSPENLAKTSIKLNGQAELFYRPKSRMKRMAHR

LGEKMLNKKLKDQKTPIPDTLYQELYDYVNHRLSHDLSDEARALLPNVITKEVSHEIIKDRRFTSDKFFFHVPITLN

YQAANSPSKFNQRVNAYLKEHPETPIIGIDRGERNLIYITVIDSTGKILEQRSLNTIQQFDYQKKLDNREKERVAAR

QAWSVVGTIKDLKQGYLSQVIHEIVDLMIHYQAVVVLENLNFGFKSKRTGIAEKAVYQQFEKMLIDKLNCLVLKDYP

AEKVGGVLNPYQLTDQFTSFAKMGTQSGFLFYVPAPYTSKIDPLTGFVDPFVWKTIKNHESRKHFLEGFDFLHYDVK

TGDFILHFKMNRNLSFQRGLPGFMPAWDIVFEKNETQFDAKGTPFIAGKRIVPVIENHRFTGRYRDLYPANELIALL

EEKGIVFRDGSNILPKLLENDDSHAIDTMVALIRSVLQMRNSNAATGEDYINSPVRDLNGVCFDSRFQNPEWPMDAD

ANGAYHIALKGQLLLNHLKESKDLKLQNGISNQDWLAYIQELRNGSGLNDIFEAQKIEWHE

ONLZ11882: *Acidaminococcus* sp. Cpf1 D908A, N-terminal Twin-Strep-tag with TEV-cleavable linker; bold, bracketed shows the portion cleaved by TEV:
[MSAWSHPQFEKGGGSGGGSGGSAWSHPQFEKSGGGGGENLYFQ]GMTQFEGFTNLYQVSKTLRFELIPQGKTLKHI

QEQGFIEEDKARNDHYKELKPIIDRIYKTYADQCLQLVQLDWENLSAAIDSYRKEKTEETRNALIEEQATYRNAIHD

YFIGRTDNLTDAINKRHAEIYKGLFKAELFNGKVLKQLGTVTTTEHENALLRSFDKFTTYFSGFYENRKNVFSAEDI

STAIPHRIVQDNFPKFKENCHIFTRLITAVPSLREHFENVKKAIGIFVSTSIEEVFSFPFYNQLLTQTQIDLYNQLL

GGISREAGTEKIKGLNEVLNLAIQKNDETAHIIASLPHRFIPLFKQILSDRNTLSFILEEFKSDEEVIQSFCKYKTL

LRNENVLETAEALFNELNSIDLTHIFISHKKLETISSALCDHWDTLRNALYERRISELTGKITKSAKEKVQRSLKHE

DINLQEIISAAGKELSEAFKQKTSEILSHAHAALDQPLPTTLKKQEEKEILKSQLDSLLGLYHLLDWFAVDESNEVD

PEFSARLTGIKLEMEPSLSFYNKARNYATKKPYSVEKFKLNFQMPTLASGWDVNKEKNNGAILFVKNGLYYLGIMPK

QKGRYKALSFEPTEKTSEGFDKMYYDYFPDAAKMIPKCSTQLKAVTAHFQTHTTPILLSNNFIEPLEITKEIYDLNN

PEKEPKKFQTAYAKKTGDQKGYREALCKWIDFTRDFLSKYTKTTSIDLSSLRPSSQYKDLGEYYAELNPLLYHISFQ

RIAEKEIMDAVETGKLYLFQIYNKDFAKGHHGKPNLHTLYWTGLFSPENLAKTSIKLNGQAELFYRPKSRMKRMAHR

-continued

```
LGEKMLNKKLKDQKTPIPDTLYQELYDYVNHRLSHDLSDEARALLPNVITKEVSHEIIKDRRFTSDKFFFHVPITLN

YQAANSPSKFNQRVNAYLKEHPETPIIGIARGERNLIYITVIDSTGKILEQRSLNTIQQFDYQKKLDNREKERVAAR

QAWSVVGTIKDLKQGYLSQVIHEIVDLMIHYQAVVVLENLNFGFKSKRTGIAEKAVYQQFEKMLIDKLNCLVLKDYP

AEKVGGVLNPYQLTDQFTSFAKMGTQSGFLFYVPAPYTSKIDPLTGFVDPFVWKTIKNHESRKHFLEGFDFLHYDVK

TGDFILHFKMNRNLSFQRGLPGFMPAWDIVFEKNETQFDAKGTPFIAGKRIVPVIENHRFTGRYRDLYPANELIALL

EEKGIVFRDGSNILPKLLENDDSHAIDTMVALIRSVLQMRNSNAATGEDYINSPVRDLNGVCFDSRFQNPEWPMDAD

ANGAYHIALKGQLLLNHLKESKDLKLQNGISNQDWLAYIQELRNGSGLNDIFEAQKIEWHE

ONLZ11883: Acidaminococcus sp. Cpf1 E993A, N-terminal Twin-Strep-tag with TEV-
cleavable linker; bold, bracketed shows the portion cleaved by TEV:
[MSAWSHPQFEKGGGSGGGSGGSAWSHPQFEKSGGGGGENLYFQ]GMTQFEGFTNLYQVSKTLRFELIPQGKTLKHI

QEQGFIEEDKARNDHYKELKPIIDRIYKTYADQCLQLVQLDWENLSAAIDSYRKEKTEETRNALIEEQATYRNAIHD

YFIGRTDNLTDAINKRHAEIYKGLFKAELFNGKVLKQLGTVTTTEHENALLRSFDKFTTYFSGFYENRKNVFSAEDI

STAIPHRIVQDNFPKFKENCHIFTRLITAVPSLREHFENVKKAIGIFVSTSIEEVFSFPFYNQLLTQTQIDLYNQLL

GGISREAGTEKIKGLNEVLNLAIQKNDETAHIIASLPHRFIPLFKQILSDRNTLSFILEEFKSDEEVIQSFCKYKTL

LRNENVLETAEALFNELNSIDLTHIFISHKKLETISSALCDHWDTLRNALYERRISELTGKITKSAKEKVQRSLKHE

DINLQEIISAAGKELSEAFKQKTSEILSHAHAALDQPLPTTLKKQEEKEILKSQLDSLLGLYHLLDWFAVDESNEVD

PEFSARLTGIKLEMEPSLSFYNKARNYATKKPYSVEKFKLNFQMPTLASGWDVNKEKNNGAILFVKNGLYYLGIMPK

QKGRYKALSFEPTEKTSEGFDKMYYDYFPDAAKMIPKCSTQLKAVTAHFQTHTTPILLSNNFIEPLEITKEIYDLNN

PEKEPKKFQTAYAKKTGDQKGYREALCKWIDFTRDFLSKYTKTTSIDLSSLRPSSQYKDLGEYYAELNPLLYHISFQ

RIAEKEIMDAVETGKLYLFQIYNKDFAKGHHGKPNLHTLYWTGLFSPENLAKTSIKLNGQAELFYRPKSRMKRMAHR

LGEKMLNKKLKDQKTPIPDTLYQELYDYVNHRLSHDLSDEARALLPNVITKEVSHEIIKDRRFTSDKFFFHVPITLN

YQAANSPSKFNQRVNAYLKEHPETPIIGIDRGERNLIYITVIDSTGKILEQRSLNTIQQFDYQKKLDNREKERVAAR

QAWSVVGTIKDLKQGYLSQVIHEIVDLMIHYQAVVVLANLNFGFKSKRTGIAEKAVYQQFEKMLIDKLNCLVLKDYP

AEKVGGVLNPYQLTDQFTSFAKMGTQSGFLFYVPAPYTSKIDPLTGFVDPFVWKTIKNHESRKHFLEGFDFLHYDVK

TGDFILHFKMNRNLSFQRGLPGFMPAWDIVFEKNETQFDAKGTPFIAGKRIVPVIENHRFTGRYRDLYPANELIALL

EEKGIVFRDGSNILPKLLENDDSHAIDTMVALIRSVLQMRNSNAATGEDYINSPVRDLNGVCFDSRFQNPEWPMDAD

ANGAYHIALKGQLLLNHLKESKDLKLQNGISNQDWLAYIQELRNGSGLNDIFEAQKIEWHE
```

Example 13

This Example describes a method for the rapid detection and quantitation of a specific bacteriophage lambda polynucleotide in a human background by nanopore detection. In this Example, the target DNA is contacted by one or more dCas9-RNP complex(es) carrying an affinity tag that may be used for the immobilization of the target molecule on a surface ('immobilisation dCas9 complex(es)'), while one or more additional dCas9-RNP complexes ('barcode Cas9 complex(es)') contact the target DNA molecule in a second region. The 'barcode dCas9 complexes' carry an enzyme-loaded adapter molecule whose current signature is used to confirm that the dCas9 bound to its target. The presence of the target region is identified by the barcode, while the sensitivity of detection of the target over non-target DNA is enhanced by immobilisation on the membrane surface. Thus, both types of dCas9 complex are required to be bound to the same target molecule for the successful detection of the barcode sequence. In this example, the non-target DNA need not be washed away.

Methods

A bacteriophage lambda whole-genome library (NEB Cat #N3013) is prepared by random fragmentation of E. coli high-molecular weight genomic DNA to a median size of ~5 kb using a Covaris gTube, following the manufacturer's instructions. A human whole-genome library is also prepared by random fragmentation of high-molecular weight genomic DNA (Sigma Aldrich, Cat #000000011691112001) to a median size of ~5 kb using a Covaris gTube, following the manufacturer's instructions.

'Enzyme-loaded crRNAs' are prepared by hybridising oligonucleotides OLIGO_1, a crRNA oligonucleotide bearing a 3' DNA extension, and OLIGO_2, a DNA adapter oligonucleotide, in a PCR machine in 10 mM Tris-Cl (pH 8.0), 1 mM EDTA, 200 mM NaCl at 40 µM of each oligonucleotide by heating to 95° C. for 2 min and slow cooling to 20° C. over ~2 h. This annealing reaction yields a hybrid molecule with a crRNA portion, and a DNA-extended portion that is duplex and bears a 3' dA-overhang, known as 'crRNA adapter'. The AMX 1D enzyme adaptor from Oxford Nanopore Technologies' 1D Sequencing Kit By Ligation (SQK-LSK108) is ligated to 'crRNA adapter' by incubating 5 µL AMX 1D (which carries a dT-overhang) with 1 µM of 'crRNA adapter' (1.25 µL), 50 µL 2×NEB Blunt/TA Master Mix and 43.8 µL nuclease-free water in a total volume of ~100 µL for 10 min at room temperature.

The excess unligated material is purified away by the addition 3.8× volumes of AMPure XP SPRI beads that have been equilibrated in 50 mM Tris-Cl (pH 8.0 at 4° C.), 2.5 M NaCl, 28% (w/v) PEG-8000, eluting the 'enzyme-loaded crRNAs' in a buffer comprising 10 mM Tris-Cl (pH 8.0), 20 mM NaCl.

'Cholesterol tethers' were prepared by hybridising oligonucleotides AR131 and AR132 in a PCR machine in 10 mM Tris-Cl (pH 8.0), 1 mM EDTA, 200 mM NaCl at 40 μM of each oligonucleotide by heating to 95° C. for 2 min and slow cooling to 20° C. over ~2 h. This annealing reaction yields a hybrid molecule with a 3' overhang bearing complementarity to the crRNA AR140 below.

200 nM 'Alt-R' tracrRNA (Integrated DNA Technologies, Inc., Cat #1072532), is added to a buffer containing 25 mM HEPES-NaOH (pH 8.0), 150 mM NaCl and 1 mM $MgCl_2$ (known as dCas9 binding buffer). The tracrRNA is heated to 90° C. for 2 min and snap-cooled on wet ice, after which 100 nM dCas9 (ONLP12326) is added and the reaction incubated for 10 min at room temperature (~21° C.). An equimolar mix of two crRNAs is added: 125 nM AR140, bearing one 3' DNA extension sequence, and 125 nM 'enzyme-loaded crRNA' from above, bearing the sequencing adapter. The incubation is continued at room temperature (~21° C.) for 10 min. The final volume is ~50 μL. This mixture is known as ribonucleotide-protein complexes (RNPs).

To form dCas9-target complexes, a varying amount of the bacteriophage lambda genomic DNA from above from 0 to 100 ng is mixed with a constant 1 μg (in 5 μL total) of human DNA from above, added to the RNPs and incubated for 20 min at room temperature. The mixture is subjected to 1×SPRI purification to remove excess unbound dCas9, crRNA and tracrRNA as follows: 51 μL AMPure XP beads are added to the mixture, mixed by gentle resuspension, and incubated for 10 min at room temperature. The beads are pelleted using a magnetic separator, and washed twice with ~250 μL of a buffer comprising 50 mM Tris-Cl (pH 8.0 at 4° C.), 2.5 M NaCl, 20% (w/v) PEG-8000, and eluted by incubating the SPRI beads with 12.5 μL of 10 mM Tris-Cl (pH 8.0), 20 mM NaCl. To 12.5 μL of the eluate is added 35 μL RBF, 25 μL LLB (both components of SQK-LSK108, Oxford Nanopore Technologies) and 2.5 μL nuclease-free water. This sample is known as the 'loading sample'.

An Oxford Nanopore MinION flowcell is primed with 800 μL 1×RBF containing 50 nM 'cholesterol tethers', bearing complementarity to AR134A and a cholesterol moiety, pipetted via its inlet port, followed by a pause of 10 min, then 200 μL of the same mixture pipetted via its inlet port with the SpotON port open. The entire 75 μL of the loading sample was pipetted dropwise into the SpotON port and the fluid allowed to wick into the flowcell. The flowcell is not flushed, and the quantification of target analyte over background is possible because membrane tethered analyte is captured preferentially by the nanopore. MinION data collection is initiated immediately, and data are collected and analysed by counting the number of adapter events.

Results

Figure 52:
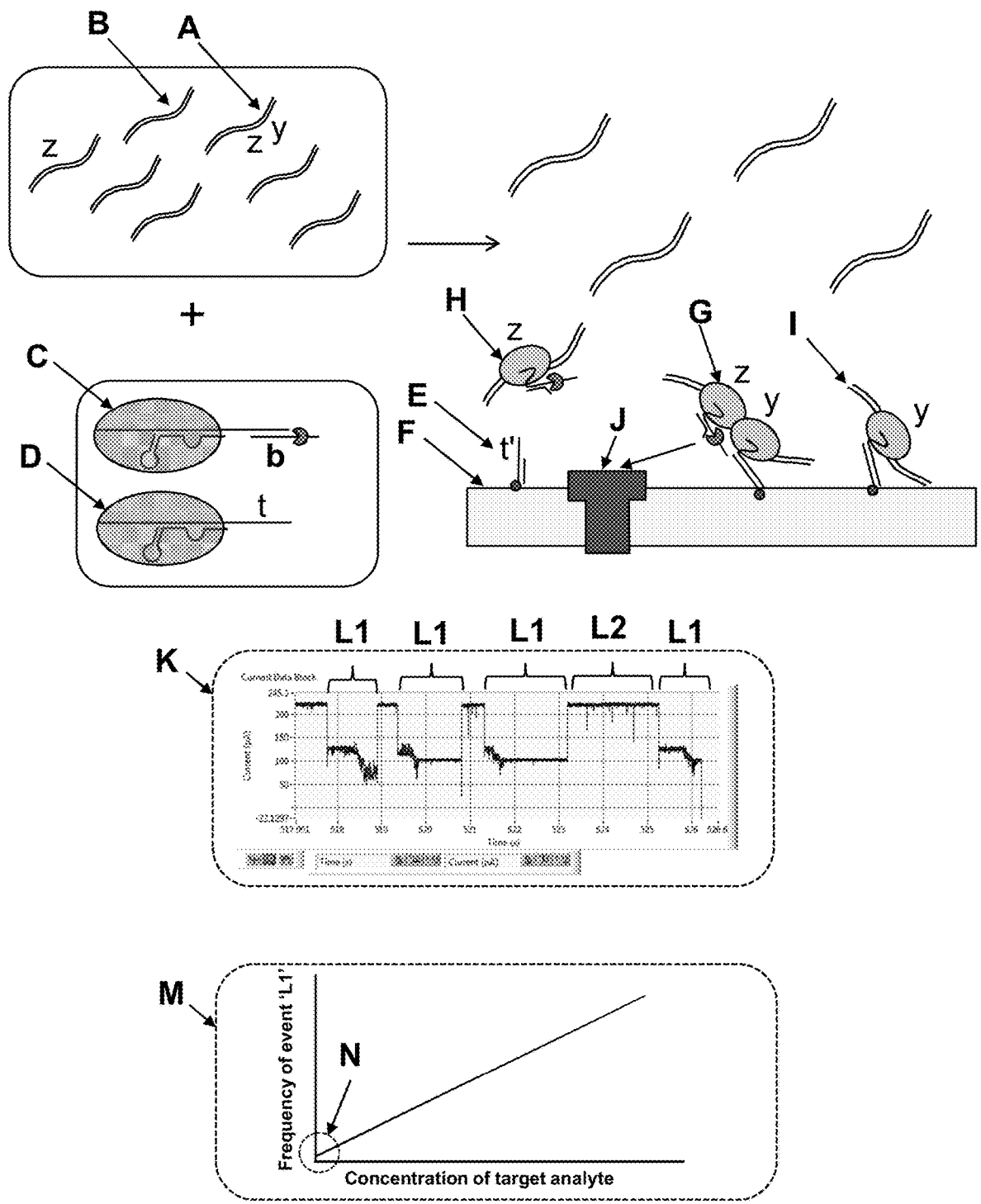
FIG. 52 shows a hypothetical example in which a 'paired-adaptor' pulldown is performed, such as that described in Example 13. A target DNA analyte A (bearing target sequences y and z) is mixed with a non-target DNA analyte B at varying concentrations of A ranging from zero to hundreds of nanograms. C as described in Example 8 is a dCas9-tracrRNA-crRNA complex bearing a DNA extension on the crRNA that carries a nanopore sequencing adapter and optional barcode sequence b. D is a dCas9-tracrRNA-crRNA complex bearing a DNA extension on the crRNA that carries a sequence t that enables the crRNA to be tethered to a surface. Addition of species C and D to the mixture of A and B allows detection of A in the background of B. Only target molecules bearing sequences y and z are both tethered via cholesterol modified oligonucleotide E (with sequence t' complementary to the extension t of D) to membrane surface F and carry an enzyme adapter that permits detection of the target analyte. Nanopore capture of G is therefore enhanced over capture of H. Capture of G and H by nanopore J is measured electronically. K shows an example nanopore current trace punctuated by capture event L1 and open-pore current L2. The frequency of L1 is dependent on the concentration of species G on the membrane and the background level of H in solution. M shows a hypothetical plot of the frequency of event L1 against the concentration of target analyte A. N shows the level of background capture of species 'G' from solution and thus is the 'false-positive' rate.

FIG. 52 shows, in cartoon form, the example described above. The nanopore sequencing readout is punctuated by a characteristic event L1 (which may be basecalled to yield barcode sequence b) that is dependent on the enzyme-loaded adapter C, the frequency of which is dependent on the concentration of target analyte (membrane-tethered species G, and solution species H); membrane-tethered species G is captured preferentially by nanopore J because of its proximity to the nanopore. Titration of the target analyte (bacteriophage lambda) against the constant amount of human non-target DNA yields a plot M of the frequency of event L1 against target analyte concentration. The frequency of event L1 at zero target analyte concentration (N) demonstrates the 'false-positive' or background rate of detection of species H captured from solution (i.e., not tethered to the surface).

Materials

DNA and Oligonucletides

| Component name | Sequence (Oligos are IDT codes) |
| --- | --- |
| Bacteriophage lambda DNA | NCBI Reference Sequence: NC_001416.1 |
| AR134A | /5Phos/rCrCrGrArCrCrArCrGrCrCrArGrCrArUrArUrCrGrGrUrUrUrUrArGrArG rCrUrArUrGrCrUAGGTTAAACACCCAAGA |
| OLIGO_2 | /5Phos/CTTGGGTGTTTAACCT |
| AR140 | /5Phos/rUrGrCrArArCrGrGrUrCrGrArUrUrGrCrCrUrGrArGrUrUrUrArGrArG rCrUrArUrGrCrUAGCAATACATCTTTG |
| AR131 | /5Phos/TGTTCTGATCGGAACGATCG/iSp18//iSp18//iSp18//3CholTEG/ |
| AR132 | /5Phos/CGATCGTTCCGATCAGAACACAAAGATGTATTGCT |

Proteins
ONLP12326: *S. pyogenes* Cas9 D10A/H840A, C-terminal Twin-Strep-tag with TEV-cleavable linker; bold, bracketed shows the portion cleaved by TEV (sequence above).

The invention claimed is:

1. A method of detecting a target polynucleotide in a sample comprising:
   (a) contacting the sample with:
      (i) a first guide polynucleotide that binds to a first sequence in the target polynucleotide and a first polynucleotide-guided effector protein, wherein the first guide polynucleotide has an adaptor attached thereto,
      (ii) a second guide polynucleotide that binds to a second sequence in the target polynucleotide and a second polynucleotide-guided effector protein, wherein the second guide polynucleotide or the second polynucleotide-guided effector protein has a membrane anchor capable of coupling to a membrane attached thereto, wherein the guide polynucleotides and polynucleotide-guided effector proteins form a complex with any target polynucleotide present in the sample;
   (b) contacting the sample with a membrane comprising a transmembrane pore, wherein the second polynucleotide-guided effector protein tethers to the membrane via its membrane anchor;
   (c) applying a potential difference across the membrane; and
   (d) monitoring for the presence or absence of an effect resulting from the interaction of the complex with the transmembrane pore to determine the presence or absence of the complex, thereby detecting the target polynucleotide in the sample.

2. A panel of two or more guide RNAs (gRNAs), each gRNA comprising:
   (i) a nucleotide sequence that binds to a sequence in the target polynucleotide,
   (ii) a nucleotide sequence that binds to a polynucleotide guided effector protein, and
   (iii) an adaptor and/or an anchor capable of coupling to a surface,
   wherein each guide RNA comprises a crRNA and a tracrRNA, wherein the anchor or the adaptor is present at the 5' end of the tracrRNA, the 3' end of the tracrRNA, the 3' end of the crRNA, or internally wherein the tracrRNA and crRNA are comprised in a sgRNA, wherein the two or more guide RNAs bind to different sequences in the same target polynucleotide.

3. A method according to claim 1, wherein the guide polynucleotide is a guide RNA and the polynucleotide-guided effector protein is a RNA-guided effector protein.

4. A method according to claim 3, wherein the RNA-guided effector protein is a RNA-guided endonuclease or a RNA-guided endonuclease wherein the nuclease activity of the RNA-guided endonuclease is disabled.

5. A method according to claim 1, wherein:
   (i) one or more catalytic nuclease sites of the RNA-guided endonuclease are inactivated; and/or
   (ii) the RNA-guided endonuclease is Cas, Cpf1 or C2c2, optionally Cas 9.

6. A method according to claim 1, further comprising selectively denaturing any polynucleotide-guided effector protein that is not specifically bound to the target polynucleotide prior to step (b) and/or removing any polynucleotide-guided effector protein that is not specifically bound to the target polynucleotide.

7. A method according to claim 1, wherein the guide polynucleotide is a guide RNA comprising a crRNA that binds to a sequence in the target polynucleotide and a tracrRNA, optionally wherein the guide RNA is a sgRNA.

8. A method according to claim 1, wherein the anchor is attached to the guide polynucleotide via a polynucleotide hybridized to an extension on the guide polynucleotide and optionally comprises cholesterol.

9. A method according to claim 1, wherein the adaptor comprises a barcode and/or a leader sequence.

10. A method according to claim 1, wherein the adaptor comprises a barcode and/or a leader sequence and a polynucleotide binding protein is attached to the leader sequence.

11. A method according to claim 1, wherein the adaptor comprises a barcode and/or a leader sequence and a polynucleotide binding protein is attached to the leader sequence, the method comprising before step (c) a step of allowing the polynucleotide binding protein to move along the polynucleotides, wherein the movement of the polynucleotide binding protein is stalled when it reaches a guide polynucleotide/polynucleotide-guided effector protein complex bound to the target polynucleotide.

12. A method according to claim 1, wherein the adaptor comprises a barcode and/or a leader sequence and a polynucleotide binding protein is attached to the leader sequence, the method comprising before step (c) a step of allowing the polynucleotide binding protein to move along the polynucleotides, wherein the movement of the polynucleotide binding protein is stalled when it reaches a guide polynucleotide/polynucleotide-guided effector protein complex bound to the target polynucleotide and wherein in step (d) the transmembrane pore is dimensioned such that the guide polynucleotide/polynucleotide-guided effector protein complex bound to the target polynucleotide is displaced from the complex during translocation of the target polynucleotide through the pore.

13. A method according to claim 1, wherein the guide polynucleotide or polynucleotide-guided effector protein has a binding moiety capable of coupling to a bead attached thereto and in step (a) the guide polynucleotide or polynucleotide-guided effector protein is coupled to a bead, or step (a) further comprises contacting the sample with beads.

14. A method according to claim 1, further comprising determining the amount of the target polypeptide or one or more characteristics of the target polynucleotide.

15. A method according to claim 1, wherein the pore is dimensioned such that the whole complex passes through the pore.

16. A method according to claim 1, wherein before step (c) any guide polynucleotides and polynucleotide-guided effector proteins that have not formed a complex with any target polynucleotide present in the sample are washed away.

17. A panel of two or more guide RNAs, each guide RNA comprising:
  (i) a nucleotide sequence that binds to a sequence in a target polynucleotide;
  (ii) a nucleotide sequence that binds to a polynucleotide guided effector protein; and
  (iii) an anchor capable of coupling to a surface or an adaptor, wherein each guide RNA comprises a crRNA and a tracrRNA,
  wherein the anchor or the adaptor is present at the 5' end of the tracrRNA, the 3' end of the tracrRNA, the 3' end of the crRNA, or internally wherein the tracrRNA and crRNA are comprised in a sgRNA, wherein the two or more guide RNAs bind to different sequences in the same target polynucleotide, wherein the adaptor further comprises a polynucleotide binding protein capable of moving along a polynucleotide attached thereto and the anchor comprises cholesterol.

* * * * *

SEQUENCE LISTING

<160> NUMBER OF SEQ ID NOS: 60

<210> SEQ ID NO 1
<211> LENGTH: 38
<212> TYPE: DNA
<213> ORGANISM: Artificial Sequence -continued

```
<220> FEATURE:
<223> OTHER INFORMATION: Polynucleotide used in Example 1
<220> FEATURE:
<221> NAME/KEY: misc_feature
<222> LOCATION: (31)..(35)
<223> OTHER INFORMATION: branched nucleic acid
<220> FEATURE:
<221> NAME/KEY: modified_base
<222> LOCATION: (31)..(31)
<223> OTHER INFORMATION: methylcytosine
<220> FEATURE:
<221> NAME/KEY: modified_base
<222> LOCATION: (34)..(35)
<223> OTHER INFORMATION: methylcytosine

<400> SEQUENCE: 1
cagacgccgc aatatcagca ccaacagaaa caacctttt                              38

<210> SEQ ID NO 2
<211> LENGTH: 12
<212> TYPE: DNA
<213> ORGANISM: Artificial Sequence
<220> FEATURE:
<223> OTHER INFORMATION: Polynucleotide used in Example 1

<400> SEQUENCE: 2
tttttttttt tt                                                           12

<210> SEQ ID NO 3
<211> LENGTH: 51
<212> TYPE: DNA
<213> ORGANISM: Artificial Sequence
<220> FEATURE:
<223> OTHER INFORMATION: Polynucleotide used in Example 1

<400> SEQUENCE: 3
ggttgtttct gttggtgctg atattgcggc gtctgcttgg gtgtttaacc t                51

<210> SEQ ID NO 4
<211> LENGTH: 20
<212> TYPE: DNA
<213> ORGANISM: Artificial Sequence
<220> FEATURE:
<223> OTHER INFORMATION: Polynucleotide used in Examples 1, 2, 3 and 13

<400> SEQUENCE: 4
tgttctgatc ggaacgatcg                                                   20

<210> SEQ ID NO 5
<211> LENGTH: 35
<212> TYPE: DNA
<213> ORGANISM: Artificial Sequence
<220> FEATURE:
<223> OTHER INFORMATION: Polynucleotide used in Examples 1, 2, 3, 7 and
      13

<400> SEQUENCE: 5
cgatcgttcc gatcagaaca caaagatgta ttgct                                  35

<210> SEQ ID NO 6
<211> LENGTH: 52
<212> TYPE: DNA
<213> ORGANISM: Artificial Sequence
<220> FEATURE:
<223> OTHER INFORMATION: Polynucleotide used in Example 1
<220> FEATURE:
<221> NAME/KEY: misc_feature
<222> LOCATION: (1)..(36)
<223> OTHER INFORMATION: Is a ribonucleotide
```

```
<400> SEQUENCE: 6
cuucgcggca gauauaaugg guuuuagagc uaugcuaggt taaacaccca ag            52

<210> SEQ ID NO 7
<211> LENGTH: 52
<212> TYPE: DNA
<213> ORGANISM: Artificial Sequence
<220> FEATURE:
<223> OTHER INFORMATION: Polynucleotide used in Examples 1 and 13
<220> FEATURE:
<221> NAME/KEY: misc_feature
<222> LOCATION: (1)..(36)
<223> OTHER INFORMATION: is a ribonucleotide

<400> SEQUENCE: 7
ccgaccacgc cagcauaucg guuuuagagc uaugcuaggt taaacaccca ag            52

<210> SEQ ID NO 8
<211> LENGTH: 52
<212> TYPE: DNA
<213> ORGANISM: Artificial Sequence
<220> FEATURE:
<223> OTHER INFORMATION: Polynucleotide used in Example 1
<220> FEATURE:
<221> NAME/KEY: misc_feature
<222> LOCATION: (1)..(36)
<223> OTHER INFORMATION: is a ribonucleotide

<400> SEQUENCE: 8
ugcaacgguc gauugccuga guuuuagagc uaugcuaggt taaacaccca ag            52

<210> SEQ ID NO 9
<211> LENGTH: 52
<212> TYPE: DNA
<213> ORGANISM: Artificial Sequence
<220> FEATURE:
<223> OTHER INFORMATION: Polynucleotide used in the Examples
<220> FEATURE:
<221> NAME/KEY: misc_feature
<222> LOCATION: (1)..(36)
<223> OTHER INFORMATION: is a ribonucleotide

<400> SEQUENCE: 9
ggugaaauaa ucccguucag guuuuagagc uaugcuaggt taaacaccca ag            52

<210> SEQ ID NO 10
<211> LENGTH: 52
<212> TYPE: DNA
<213> ORGANISM: Artificial Sequence
<220> FEATURE:
<223> OTHER INFORMATION: Polynucleotide used in the Examples
<220> FEATURE:
<221> NAME/KEY: misc_feature
<222> LOCATION: (1)..(36)
<223> OTHER INFORMATION: is a ribonucleotide

<400> SEQUENCE: 10
ccggacguua ugauuuagcg guuuuagagc uaugcuaggt taaacaccca ag            52

<210> SEQ ID NO 11
<211> LENGTH: 51
<212> TYPE: DNA
<213> ORGANISM: Artificial Sequence
<220> FEATURE:
<223> OTHER INFORMATION: Polynucleotide used in Example 1
<220> FEATURE:
<221> NAME/KEY: misc_feature
<222> LOCATION: (1)..(36)
<223> OTHER INFORMATION: is a ribonucleotide
```

```
<400> SEQUENCE: 11
cuucgcggca gauauaaugg guuuuagagc uaugcuagca atacatcttt g            51

<210> SEQ ID NO 12
<211> LENGTH: 51
<212> TYPE: DNA
<213> ORGANISM: Artificial Sequence
<220> FEATURE:
<223> OTHER INFORMATION: Polynucleotide used in Example 2
<220> FEATURE:
<221> NAME/KEY: misc_feature
<222> LOCATION: (1)..(36)
<223> OTHER INFORMATION: is a ribonucleotide

<400> SEQUENCE: 12
ccgaccacgc cagcauaucg guuuuagagc uaugcuagca atacatcttt g            51

<210> SEQ ID NO 13
<211> LENGTH: 51
<212> TYPE: DNA
<213> ORGANISM: Artificial Sequence
<220> FEATURE:
<223> OTHER INFORMATION: Polynucleotide used in Example 13
<220> FEATURE:
<221> NAME/KEY: misc_feature
<222> LOCATION: (1)..(36)
<223> OTHER INFORMATION: is a ribonucleotide

<400> SEQUENCE: 13
ugcaacgguc gauugccuga guuuuagagc uaugcuagca atacatcttt g            51

<210> SEQ ID NO 14
<211> LENGTH: 51
<212> TYPE: DNA
<213> ORGANISM: Artificial Sequence
<220> FEATURE:
<223> OTHER INFORMATION: Polynucleotide used in Example 1
<220> FEATURE:
<221> NAME/KEY: misc_feature
<222> LOCATION: (1)..(36)
<223> OTHER INFORMATION: is a ribonucleotide

<400> SEQUENCE: 14
ggugaaauaa ucccguucag guuuuagagc uaugcuagca atacatcttt g            51

<210> SEQ ID NO 15
<211> LENGTH: 51
<212> TYPE: DNA
<213> ORGANISM: Artificial Sequence
<220> FEATURE:
<223> OTHER INFORMATION: Polynucleotide used in Example 1
<220> FEATURE:
<221> NAME/KEY: misc_feature
<222> LOCATION: (1)..(36)
<223> OTHER INFORMATION: is a ribonucleotide

<400> SEQUENCE: 15
ccggacguua ugauuuagcg guuuuagagc uaugcuagca atacatcttt g            51

<210> SEQ ID NO 16
<211> LENGTH: 51
<212> TYPE: DNA
<213> ORGANISM: Artificial Sequence
<220> FEATURE:
<223> OTHER INFORMATION: Polynucleotide used in the Examples
<220> FEATURE:
<221> NAME/KEY: misc_feature
<222> LOCATION: (1)..(36)
<223> OTHER INFORMATION: is a ribonucleotide
```

```
<400> SEQUENCE: 16
gguacgccau ugcaaacgca guuuuagagc uaugcuagca atacatcuuu g         51

<210> SEQ ID NO 17
<211> LENGTH: 51
<212> TYPE: DNA
<213> ORGANISM: Artificial Sequence
<220> FEATURE:
<223> OTHER INFORMATION: Polynucleotide used in the Examples
<220> FEATURE:
<221> NAME/KEY: misc_feature
<222> LOCATION: (1)..(36)
<223> OTHER INFORMATION: is a ribonucleotide

<400> SEQUENCE: 17
acgaaugaac uaggcgauaa guuuuagagc uaugcuagca atacatcuuu g         51

<210> SEQ ID NO 18
<211> LENGTH: 51
<212> TYPE: DNA
<213> ORGANISM: Artificial Sequence
<220> FEATURE:
<223> OTHER INFORMATION: Polynucleotide used in Examples 1 and 3
<220> FEATURE:
<221> NAME/KEY: misc_feature
<222> LOCATION: (1)..(36)
<223> OTHER INFORMATION: is a ribonucleotide

<400> SEQUENCE: 18
aaaaaagccg gaguagaaga guuuuagagc uaugcuagca atacatcuuu g         51

<210> SEQ ID NO 19
<211> LENGTH: 52
<212> TYPE: DNA
<213> ORGANISM: Artificial Sequence
<220> FEATURE:
<223> OTHER INFORMATION: Polynucleotide used in the Examples
<220> FEATURE:
<221> NAME/KEY: misc_feature
<222> LOCATION: (1)..(36)
<223> OTHER INFORMATION: is a ribonucleotide

<400> SEQUENCE: 19
gacgucauaa ccaugauuuc guurruagag cuaugcuagc aatacatctt tg        52

<210> SEQ ID NO 20
<211> LENGTH: 15
<212> TYPE: DNA
<213> ORGANISM: Artificial Sequence
<220> FEATURE:
<223> OTHER INFORMATION: Polynucleotide used in Example 2

<400> SEQUENCE: 20
ttgaccgctc gcctc                                                 15

<210> SEQ ID NO 21
<211> LENGTH: 3587
<212> TYPE: DNA
<213> ORGANISM: Bacteriophage lambda

<400> SEQUENCE: 21
gccatcagat tgtgtttgtt agtcgctgcc atcagattgt gtttgttagt cgcttttttt    60
ttttggaatt tttttttttgg aattttttttt ttgcgctaac aacctcctgc cgttttgccc   120
gtgcatatcg gtcacgaaca aatctgatta ctaaacacag tagcctggat tgttctatc    180 agtaatcgac cttattccta attaaataga gcaaatcccc ttattggggg taagacatga   240
```

```
agatgccaga aaaacatgac ctgttggccg ccattctcgc ggcaaaggaa caaggcatcg      300
gggcaatcct tgcgtttgca atggcgtacc ttcgcggcag atataatggc ggtgcgttta      360
caaaaacagt aatcgacgca acgatgtgcg ccattatcgc ctagttcatt cgtgaccttc      420
tcgacttcgc cggactaagt agcaatctcg cttatataac gagcgtgttt atcggctaca      480
tcggtactga ctcgattggt tcgcttatca aacgcttcgc tgctaaaaaa gccggagtag      540
aagatggtag aaatcaataa tcaacgtaag gcgttcctcg atatgctggc gtggtcggag      600
ggaactgata acggacgtca gaaaaccaga aatcatggtt atgacgtcat tgtaggcgga      660
gagctattta ctgattactc cgatcaccct cgcaaacttg tcacgctaaa cccaaaactc      720 aaaatcaacag gcgccggacg ctaccagctt cttttcccgtt ggtgggatgc ctaccgcaag      780
cagcttggcc tgaaagactt ctctccgaaa agtcaggacg ctgtggcatt gcagcagatt      840
aaggagcgtg gcgctttacc tatgattgat cgtggtgata tccgtcaggc aatcgaccgt      900
tgcagcaata tctgggcttc actgccgggc gctggttatg gtcagttcga gcataaggct      960
gacagcctga ttgcaaaatt caaagaagcg ggcggaacgg tcagagagat tgatgtatga     1020
gcagagtcac cgcgattatc tccgctctgg ttatctgcat catcgtctgc ctgtcatggg     1080
ctgttaatca ttaccgtgat aacgccatta cctacaaagc ccagcgcgac aaaaatgcca     1140
gagaactgaa gctggcgaac gcggcaatta ctgacatgca gatgcgtcag cgtgatgttg     1200
ctgcgctcga tgcaaaatac acgaaggagt tagctgatgc taaagctgaa aatgatgctc     1260
tgcgtgatga tgttgccgct ggtcgtcgtc ggttgcacat caaagcagtc tgtcagtcag     1320
tgcgtgaagc caccaccgcc tccggcgtgg ataatgcagc ctccccccga ctggcagaca     1380
ccgctgaacg ggattatttc accctcagag agaggctgat cactatgcaa aaacaactgg     1440
aaggaaccca gaagtatatt aatgagcagt gcagatagag ttgcccatat cgatgggcaa     1500
ctcatgcaat tattgtgagc aatacacacg cgcttccagc ggagtataaa tgcctaaagt     1560
aataaaaccg agcaatccat ttacgaatgt ttgctgggtt tctgttttaa caacattttc     1620
tgcgccgcca caaattttgg ctgcatcgac agttttcttc tgcccaattc cagaaacgaa     1680
gaaatgatgg gtgatggttt cctttggtgc tactgctgcc ggtttgtttt gaacagtaaa     1740
cgtctgttga gcacatcctg taataagcag ggccagcgca gtagcgagta gcattttttt     1800
catggtgtta ttcccgatgc ttttttgaagt tcgcagaatc gtatgtgtag aaaattaaac     1860
aaaccctaaa caatgagttg aaatttcata ttgttaatat ttattaatgt atgtcaggtg     1920
cgatgaatcg tcattgtatt cccggattaa ctatgtccac agccctgacg gggaacttct     1980
ctgcgggagt gtccgggaat aattaaaacg atgcacacag ggtttagcgc gtacacgtat     2040
tgcattatgc caacgccccg gtgctgacac ggaagaaacc ggacgttatg atttagcgtg     2100
gaaagatttg tgtagtgttc tgaatgctct cagtaaatag taatgaatta tcaaaggtat     2160
agtaatatct tttatgttca tggatatttg taacccatcg gaaaactcct gctttagcaa     2220 gatttccct gtattgctga aatgtgattt ctcttgattt caacctatca taggacgttt      2280
ctataagatg cgtgtttctt gagaatttaa catttacaac ctttttaagt ccttttatta     2340
acacggtgtt atcgttttct aacacgatgt gaatattatc tgtggctaga tagtaaatat     2400
aatgtgagac gttgtgacgt tttagttcag aataaaacaa ttcacagtct aaatcttttc     2460
gcacttgatc gaatatttct ttaaaaatgt caacctgagc cattggtaaa accttccatg     2520
tgatacgagg gcgcgtagtt tgcattatcg tttttatcgt ttcaatctgg tctgacctcc     2580
ttgtgttttg ttgatgattt atgtcaaata ttaggaatgt tttcacttaa tagtattggt     2640
```

| | |
|---|---|
| tgcgtaacaa agtgcggtcc tgctggcatt ctggagggaa atacaaccga cagatgtatg | 2700 |
| taaggccaac gtgctcaaat cttcatacag aaagatttga agtaatattt taaccgctag | 2760 |
| atgaagagca agcgcatgga gcgacaaaat gaataaagaa caatctgctg atgatccctc | 2820 |
| cgtggatctg attcgtgtaa aaaatatgct taatagcacc atttctatga gttaccctga | 2880 |
| tgttgtaatt gcatgtatag aacataaggt gtctctggaa gcattcagag caattgaggc | 2940 |
| agcgttggtg aagcacgata ataatatgaa ggattattcc ctggtggttg actgatcacc | 3000 |
| ataactgcta atcattcaaa ctatttagtc tgtgacagag ccaacacgca gtctgtcact | 3060 |
| gtcaggaaag tggtaaaact gcaactcaat tactgcaatg ccctcgtaat taagtgaatt | 3120 |
| tacaatatcg tcctgttcgg agggaagaac gcgggatgtt cattcttcat cacttttaat | 3180 |
| tgatgtatat gctctctttt ctgacgttag tctccgacgg caggcttcaa tgacccaggc | 3240 |
| tgagaaattc ccggacccTt tttgctcaag agcgatgtta atttgttcaa tcatttggtt | 3300 |
| aggaaagcgg atgttgcggg ttgttgttct gcgggttctg ttcttcgttg acatgaggtt | 3360 |
| gccccgtatt cagtgtcgct gatttgtatt gtctgaagtt gttttttacgt taagttgatg | 3420 |
| cagatcaatt aatacgatac ctgcgtcata attgattatt tgacgtggtt tgatggcctc | 3480 |
| cacgcacgtt gtgatatgta gatgataatc attatcactt tacgggtcct ttccggtgaa | 3540 |
| aaaaaaggta ccaaaaaaaa catcgtcgtg agtagtgaac cgtaagc | 3587 |

<210> SEQ ID NO 22
<211> LENGTH: 5505
<212> TYPE: DNA
<213> ORGANISM: Bacteriophage lambda

<400> SEQUENCE: 22

| | |
|---|---|
| gggcggcgac ctcgcgggtt ttcgctattt atgaaaattt tccggtttaa ggcgtttccg | 60 |
| ttcttcttcg tcataactta atgtttttat ttaaaatacc ctctgaaaag aaaggaaacg | 120 |
| acaggtgctg aaagcgaggc tttttggcct ctgtcgtttc cttctctgtt ttttgtccgt | 180 |
| ggaatgaaca atggaagtca acaaaaagca gctggctgac attttcggtg cgagtatccg | 240 |
| taccattcag aactggcagg aacagggaat gcccgttctg cgaggcggtg caagggtaa | 300 |
| tgaggtgctt tatgactctg ccgccgtcat aaaatggtat gccgaaaggg atgctgaaat | 360 |
| tgagaacgaa aagctgcgcc gggaggttga agaactgcgg caggccagcg aggcagatct | 420 |
| ccagccagga actattgagt acgaacgcca tcgacttacg cgtgcgcagg ccgacgcaca | 480 |
| ggaactgaag aatgccagag actccgctga agtggtggaa accgcattct gtactttcgt | 540 |
| gctgtcgcgg atcgcaggtg aaattgccag tattctcgac gggctccccc tgtcggtgca | 600 |
| gcggcgtttt ccggaactgg aaaaccgaca tgttgatttc ctgaaacggg atatcatcaa | 660 |
| agccatgaac aaagcagccg cgctggatga actgataccg ggttgctga gtgaatatat | 720 |
| cgaacagtca ggttaacagg ctgcggcatt ttgtccgcgc cgggcttcgc tcactgttca | 780 |
| ggccggagcc acagaccgcc gttgaatggg cggatgctaa ttactatctc ccgaaagaat | 840 |
| ccgcatacca ggaagggcgc tgggaaacac tgcccttTca gcgggccatc atgaatgcga | 900 |
| tgggcagcga ctacatccgt gaggtgaatg tggtgaagtc tgcccgtgtc ggttattcca | 960 |
| aaatgctgct gggtgtttat gcctacttta tagagcataa gcagcgcaac acccttatct | 1020 |
| ggttgccgac ggatggtgat gccgagaact ttatgaaaac ccacgttgag ccgactattc | 1080 |
| gtgatattcc gtcgctgctg gcgctggccc cgtggtatgg caaaaagcac cgggataaca | 1140 |
| cgctcaccat gaagcgtttc actaatgggc gtggcttctg gtgcctgggc ggtaaagcgg | 1200 |

```
caaaaaacta ccgtgaaaag tcggtggatg tggcgggtta tgatgaactt gctgcttttg    1260
atgatgatat tgaacaggaa ggctctccga cgttcctggg tgacaagcgt attgaaggct    1320
cggtctggcc aaagtccatc cgtggctcca cgccaaaagt gagaggcacc tgtcagattg    1380
agcgtgcagc cagtgaatcc ccgcatttta tgcgttttca tgttgcctgc ccgcattgcg    1440
gggaggagca gtatcttaaa tttggcgaca aagagacgcc gtttggcctc aaatggacgc    1500
cggatgaccc ctccagcgtg ttttatctct gcgagcataa tgcctgcgtc atccgccagc    1560
aggagctgga ctttactgat gcccgttata tctgcgaaaa gaccgggatc tggacccgtg    1620
atggcattct ctggttttcg tcatccggtg aagagattga gccacctgac agtgtgacct    1680
ttcacatctg gacagcgtac agcccgttca ccacctgggt gcagattgtc aaagactgga    1740
tgaaaacgaa aggggatacg ggaaaacgta aaaccttcgt aaacaccacg ctcggtgaga    1800
cgtgggaggc gaaaattggc gaacgtccgg atgctgaagt gatggcagag cggaaagagc    1860
attattcagc gcccgttcct gaccgtgtgg cttacctgac cgccggtatc gactcccagc    1920
tggaccgcta cgaaatgcgc gtatggggat ggggccggg tgaggaaagc tggctgattg    1980
accggcagat tattatgggc cgccacgacg atgaacagac gctgctgcgt gtggatgagg    2040
ccatcaataa aacctatacc cgccggaatg gtgcagaaat gtcgatatcc cgtatctgct    2100
gggatactgg cgggattgac ccgaccattg tgtatgaacg ctcgaaaaaa catgggctgt    2160
tccgggtgat ccccattaaa ggggcatccg tctacgaaaa gccggtggcc agcatgccac    2220
gtaagcgaaa caaaaacggg gtttaccttaa ccgaaatcgg tacggatacc gcgaaagagc    2280
agatttataa ccgcttcaca ctgacgccgg aaggggatga accgcttccc ggtgccgttc    2340
acttcccgaa taacccggat attttttgatc tgaccgaagc gcagcagctg actgctgaag    2400
agcaggtcga aaaatgggtg gatggcagga aaaaaatact gtgggacagc aaaaagcgac    2460
gcaatgaggc actcgactgc ttcgtttatg cgctggcggc gctgcgcatc agtatttccc    2520
gctggcagct ggatctcagt gcgctgctgg cgagcctgca ggaagaggat ggtgcagcaa    2580
ccaacaagaa aacactggca gattacgccc gtgccttatc cggagaggat gaatgacgcg    2640
acaggaagaa cttgccgctg cccgtgcggc actgcatgac ctgatgacag gtaaacgggt    2700
ggcaacagta cagaaagacg gacgaagggt ggagtttacg gccacttccg tgtctgacct    2760
gaaaaaatat attgcagagc tggaagtgca gaccggcatg acacagcgac gcaggggacc    2820
tgcaggattt tatgtatgaa aacgcccacc attcccaccc ttctggggcc ggacggcatg    2880
acatcgctgc gcgaatatgc cggttatcac ggcggtggca gcggatttgg agggcagttg    2940
cggtcgtgga acccaccgag tgaaagtgtg gatgcagccc tgttgcccaa ctttacccgt    3000
ggcaatgccc gcgcagacga tctggtacgc aataacggct atgccgccaa cgccatccag    3060
ctgcatcagg atcatatcgt cgggtctttt ttccggctca gtcatcgccc aagctggcgc    3120
tatctgggca tcggggagga agaagcccgt gccttttccc gcgaggttga agcggcatgg    3180
aaagagtttg ccgaggatga ctgctgctgc attgacgttg agcgaaaacg cacgtttacc    3240
atgatgattc gggaaggtgt ggccatgcac gcctttaacg tgaactgtt cgttcaggcc    3300 acctgggata ccagttcgtc gcggcttttc cggacacagt tccggatggt cagcccgaag    3360
cgcatcagca acccgaacaa taccggcgac agccggaact gccgtgccgg tgtgcagatt    3420
aatgacagcg gtgcggcgct gggatattac gtcagcgagg acgggtatcc tggctggatg    3480
ccgcagaaat ggacatggat accccgtgag ttacccggcg gcgcgcctc gttcattcac    3540 gttttttgaac ccgtggagga cgggcagact cgcggtgcaa atgtgttta cagcgtgatg    3600
```

```
gagcagatga agatgctcga cacgctgcag aacacgcagc tgcagagcgc cattgtgaag      3660
gcgatgtatg ccgccaccat tgagagtgag ctggatacgc agtcagcgat ggatttat       3720 ctgggcgcga acagtcagga gcagcgggaa aggctgaccg gctggattgg tgaaattgcc     3780
gcgtattacg ccgcagcgcc ggtccggctg ggaggcgcaa aagtaccgca cctgatgccg     3840
ggtgactcac tgaacctgca gacggctcag gatacggata acggctactc cgtgtttgag    3900
cagtcactgc tgcggtatat cgctgccggg ctgggtgtct cgtatgagca gctttcccgg    3960
aattacgccc agatgagcta ctccacggca cgggccagtg cgaacgagtc gtgggcgtac    4020
tttatggggc ggcgaaaatt cgtcgcatcc cgtcaggcga gccagatgtt tctgtgctgg    4080
ctggaagagg ccatcgttcg ccgcgtggtg acgttaccct caaaagcgcg cttcagtttt    4140
caggaagccc gcagtgcctg ggggaactgc gactggatag gctccggtcg tatggccatc    4200
gatggtctga agaagttca ggaagcggtg atgctgatag aagccggact gagtacctac    4260
gagaaagagt gcgcaaaacg cggtgacgac tatcaggaaa ttttttgccca gcaggtccgt   4320 gaaacgatgg agcgccgtgc agccggtctt aaaccgcccg cctgggcggc tgcagcattt    4380
gaatccgggc tgcgacaatc aacagaggag gagaagagtg acagcagagc tgcgtaatct    4440
cccgcatatt gccagcatgg cctttaatga gccgctgatg cttgaacccg cctatgcgcg    4500
ggttttcttt tgtgcgcttg caggccagct tgggatcagc agcctgacgg atgcggtgtc    4560
cggcgacagc ctgactgccc aggaggcact cgcgacgctg gcattatccg gtgatgatga    4620
cggaccacga caggcccgca gttatcaggt catgaacggc atcgccgtgc tgccggtgtc    4680
cggcacgctg gtcagccgga cgcgggcgct gcagccgtac tcggggatga ccggttacaa    4740
cggcattatc gcccgtctgc aacaggctgc cagcgatccg atggtggacg cattctgct    4800 cgatatggac acgcccggcg ggatggtggc ggggcattt gactgcgctg acatcatcgc    4860
ccgtgtgcgt gacataaaac cggtatgggc gcttgccaac gacatgaact gcagtgcagg   4920
tcagttgctt gccagtgccg cctcccggcg tctggtcacg cagaccgccc ggacaggctc    4980
catcggcgtc atgatggctc acagtaatta cggtgctgcg ctggagaaac agggtgtgga    5040
aatcacgctg atttacagcg gcagccataa ggtggatggc aaccctaca gccatcttcc    5100 ggatgacgtc cgggagacac tgcagtcccg gatggacgca acccgccaga tgtttgcgca    5160
gaaggtgtcg gcatataccg gcctgtccgt gcaggttgtg ctggataccg aggctgcagt    5220
gtacagcggt caggaggcca ttgatgccgg actggctgat gaacttgtta acagcaccga    5280
tgcgatcacc gtcatgcgtg atgcactgga tgcacgtaaa tcccgtctct caggagggcg    5340
aatgaccaaa gagactcaat caacaactgt ttcagccact gcttcgcagg ctgacgttac    5400
tgacgtggtg ccagcgacgg agggcgagaa cgccagcgcg gcgcagccgg acgtgaacgc    5460
gcagatcacc gcagcggttg cggcagaaaa cagccgcatt atggg                   5505
```

<210> SEQ ID NO 23
<211> LENGTH: 6685
<212> TYPE: DNA
<213> ORGANISM: Bacteriophage lambda

<400> SEQUENCE: 23

```
gatcctcaac tgtgaggagg ctcacggacg cgaagaacag gcacgcgtgc tggcagaaac       60
ccccggtatg accgtgaaaa cggcccgccg cattctggcc gcagcaccac agagtgcaca      120
ggcgcgcagt gacactgcgc tggatcgtct gatgcagggg gcaccggcac cgctggctgc     180
aggtaacccg gcatctgatg ccgttaacga tttgctgaac acaccagtgt aagggatgtt    240
```

```
tatgacgagc aaagaaacct ttacccatta ccagccgcag ggcaacagtg acccggctca    300
taccgcaacc gcgcccggcg gattgagtgc gaaagcgcct gcaatgaccc cgctgatgct    360
ggacacctcc agccgtaagc tggttgcgtg ggatggcacc accgacggtg ctgccgttgg    420
cattcttgcg gttgctgctg accagaccag caccacgctg acgttctaca agtccggcac    480
gttccgttat gaggatgtgc tctggccgga ggctgccagc gacgagacga aaaacggac    540 cgcgttttgcc ggaacggcaa tcagcatcgt ttaactttac ccttcatcac taaaggccgc    600
ctgtgcggct tttttttacgg gattttttta tgtcgatgta cacaaccgcc caactgctgg    660
cggcaaatga gcagaaattt aagtttgatc cgctgtttct gcgtctcttt ttccgtgaga    720
gctatccctt caccacggag aaagtctatc tctcacaaat tccgggactg gtaaacatgg    780
cgctgtacgt ttcgccgatt gtttccggtg aggttatccg ttcccgtggc ggctccacct    840
ctgaatttac gccgggatat gtcaagccga agcatgaagt gaatccgcag atgaccctgc    900
gtcgcctgcc ggatgaagat ccgcagaatc tggcggaccc ggcttaccgc cgccgtcgca    960
tcatcatgca gaacatgcgt gacgaagagc tggccattgc tcaggtcgaa gagatgcagg   1020
cagtttctgc cgtgcttaag gcaaataca ccatgaccgg tgaagccttc gatccggttg   1080
aggtggatat gggccgcagt gaggagaata acatcacgca gtccggcggc acggagtgga   1140
gcaagcgtga caagtccacg tatgacccga ccgacgatat cgaagcctac gcgctgaacg   1200
ccagcggtgt ggtgaatatc atcgtgttcg atccgaaagg ctgggcgctg ttccgttcct   1260
tcaaagccgt caaggagaag ctggatacccc gtcgtggctc taattccgag ctggagacag   1320
cggtgaaaga cctgggcaaa gcggtgtcct ataaggggat gtatggcgat gtggccatcg   1380
tcgtgtattc cggacagtac gtggaaaacg gcgtcaaaaa gaacttcctg ccggacaaca   1440
cgatggtgct ggggaacact caggcacgcg gtctgcgcac ctatggctgc attcaggatg   1500
cggacgcaca gcgcgaaggc attaacgcct ctgcccgtta cccgaaaaac tgggtgacca   1560
ccggcgatcc ggcgcgtgag ttcaccatga ttcagtcagc accgctgatg ctgctggctg   1620
accctgatga gttcgtgtcc gtacaactgg cgtaatcatg gcccttcggg gccattgttt   1680
ctctgtggag gagtccatga cgaaagatga actgattgcc cgtctccgct cgctgggtga   1740
acaactgaac cgtgatgtca gcctgacggg gacgaaagaa gaactggcgc tccgtgtggc   1800
agagctgaaa gaggagcttg atgacacgga tgaaactgcc ggtcaggaca ccctctcag   1860 ccgggaaaat gtgctgaccg gacatgaaaa tgaggtggga tcagcgcagc cggataccgt   1920
gattctggat acgtctgaac tggtcacggt cgtggcactg gtgaagctgc atactgatgc   1980
acttcacgcc acgcgggatg aacctgtggc atttgtgctg ccgggaacgg cgtttcgtgt   2040
ctctgccggt gtggcagccg aaatgacaga gcgcggcctg gccagaatgc aataacggga   2100
ggcgctgtgg ctgatttcga taacctgttc gatgctgcca ttgcccgcgc cgatgaaacg   2160
atacgcgggt acatgggaac gtcagccacc attacatccg gtgagcagtc aggtgcggtg   2220
atacgtggtg ttttttgatga ccctgaaaat atcagctatg ccggacaggg cgtgcgcgtt   2280
gaaggctcca gcccgtccct gtttgtccgg actgatgagg tgcggcagct gcggcgtgga   2340
gacacgctga ccatcggtga ggaaaatttc tgggtagatc gggtttcgcc ggatgatggc   2400
ggaagttgtc atctctggct tggacggggc gtaccgcctg ccgttaaccg tcgccgctga   2460 aaggggggatg tatggccata aaaggtcttg agcaggccgt tgaaaacctc agccgtatca   2520
gcaaaacggc ggtgcctggt gccgccgcaa tggccattaa ccgcgttgct tcatccgcga   2580
tatcgcagtc ggcgtcacag gttgcccgtg agacaaaggt acgccggaaa ctggtaaagg   2640
```

```
aaagggccag gctgaaaagg gccacggtca aaaatccgca ggccagaatc aaagttaacc   2700 gggggattt gcccgtaatc aagctgggta atgcgcgggt tgtcctttcg cgccgcaggc   2760
gtcgtaaaaa ggggcagcgt tcatccctga aaggtggcgg cagcgtgctt gtggtgggta   2820
accgtcgtat tcccggcgcg tttattcagc aactgaaaaa tggccggtgg catgtcatgc   2880
agcgtgtggc tgggaaaaac cgttacccca ttgatgtggt gaaaatcccg atggcggtgc   2940
cgctgaccac ggcgtttaaa caaaatattg agcggatacg gcgtgaacgt cttccgaaag   3000
agctgggcta tgcgctgcag catcaactga ggatggtaat aaagcgatga acatactga   3060 actccgtgca gccgtactgg atgcactgga gaagcatgac accggggcga cgttttttga   3120
tggtcgcccc gctgtttttg atgaggcgga ttttccggca gttgccgttt atctcaccgg   3180
cgctgaatac acgggcgaag agctggacag cgatacctgg caggcggagc tgcatatcga   3240
agttttcctg cctgctcagg tgccggattc agagctggat gcgtggatgg agtcccggat   3300
ttatccggtg atgagcgata tcccggcact gtcagatttg atcaccagta tggtggccag   3360
cggctatgac taccggcgcg acgatgatgc gggcttgtgg agttcagccg atctgactta   3420
tgtcattacc tatgaaatgt gaggacgcta tgcctgtacc aaatcctaca atgccggtga   3480
aaggtgccgg gaccaccctg tgggtttata aggggagcgg tgacccttac gcgaatccgc   3540
tttcagacgt tgactggtcg cgtctggcaa aagttaaaga cctgacgccc ggcgaactga   3600
ccgctgagtc ctatgacgac agctatctcg atgatgaaga tgcagactgg actgcgaccg   3660
ggcaggggca gaaatctgcc ggagatacca gcttcacgct ggcgtggatg cccggagagc   3720
aggggcagca ggcgctgctg gcgtggttta tgaaggcga tacccgtgcc tataaaatcc   3780
gcttcccgaa cggcacggtc gatgtgttcc gtggctgggt cagcagtatc ggtaaggcgg   3840
tgacggcgaa ggaagtgatc acccgcacgg tgaaagtcac caatgtggga cgtccgtcga   3900
tggcagaaga tcgcagcacg gtaacagcgg caaccggcat gaccgtgacg cctgccagca   3960
cctcggtggt gaaagggcag agcaccacgc tgaccgtggc cttccagccg gagggcgtaa   4020
ccgacaagag ctttcgtgcg gtgtctgcgg ataaaacaaa agccaccgtg tcggtcagtg   4080
gtatgaccat caccgtgaac ggcgttgctg caggcaaggt caacattccg gttgtatccg   4140
gtaatggtga gtttgctgcg gttgcagaaa ttaccgtcac cgccagttaa tccggagagt   4200
cagcgatgtt cctgaaaacc gaatcatttg aacataacgg tgtgaccgtc acgctttctg   4260
aactgtcagc cctgcagcgc attgagcatc tcgccctgat gaaacggcag gcagaacagg   4320
cggagtcaga cagcaaccgg aagtttactg tggaagacgc catcagaacc ggcgcgtttc   4380
tggtggcgat gtccctgtgg cataaccatc cgcagaagac gcagatgccg tccatgaatg   4440
aagccgttaa acagattgag caggaagtgc ttaccacctg gcccacggag gcaatttctc   4500
atgctgaaaa cgtggtgtac cggctgtctg gtatgtatga gtttgtggtg aataatgccc   4560
ctgaacagac agaggacgcc gggcccgcag agcctgtttc tgcggaaaag tgttcgacgg   4620
tgagctgagt tttgccctga aactggcgcg tgagatgggg cgaccccgact ggcgtgccat   4680 gcttgccggg atgtcatcca cggagtatgc cgactggcac cgcttttaca gtacccatta   4740
ttttcatgat gttctgctgg atatgcactt ttccgggctg acgtacaccg tgctcagcct   4800 gttttcagc gatccggata tgcatccgct ggatttcagt ctgctgaacc ggcgcgaggc   4860
tgacgaagag cctgaagatg atgtgctgat gcagaaagcg gcagggcttg ccggaggtgt   4920
ccgctttggc ccggacggga atgaagttat ccccgcttcc ccggatgtgg cggacatgac   4980
ggaggatgac gtaatgctga tgacagtatc agaagggatc gcaggaggag tccggtatgg   5040
```

| | |
|---|---|
| ctgaaccggt aggcgatctg gtcgttgatt tgagtctgga tgcggccaga tttgacgagc | 5100 |
| agatggccag agtcaggcgt cattttttctg gtacggaaag tgatgcgaaa aaaacagcgg | 5160 |
| cagtcgttga acagtcgctg agccgacagg cgctggctgc acagaaagcg gggatttccg | 5220 |
| tcgggcagta taaagccgcc atgcgtatgc tgcctgcaca gttcaccgac gtggccacgc | 5280 |
| agcttgcagg cgggcaaagt ccgtggctga tcctgctgca cagggggggg caggtgaagg | 5340 |
| actccttcgg cgggatgatc cccatgttca gggggcttgc cggtgcgatc accctgccga | 5400 |
| tggtggggggc cacctcgctg gcggtggcga ccggtgcgct ggcgtatgcc tggtatcagg | 5460 |
| gcaactcaac cctgtccgat ttcaacaaaa cgctggtcct ttccggcaat caggcgggac | 5520 |
| tgacggcaga tcgtatgctg gtcctgtcca gagccgggca ggcggcaggg ctgacgttta | 5580 |
| accagaccag cgagtcactc agcgcactgg ttaaggcggg ggtaagcggt gaggctcaga | 5640 |
| ttgcgtccat cagccagagt gtggcgcgtt tctcctctgc atccggcgtg gaggtggaca | 5700 |
| aggtcgctga agccttcggg aagctgacca cagacccgac gtcggggctg acggcgatgg | 5760 |
| ctcgccagtt ccataacgtg tcggcggagc agattgcgta tgttgctcag ttgcagcgtt | 5820 |
| ccggcgatga agccggggca ttgcaggcgg cgaacgaggc cgcaacgaaa gggtttgatg | 5880 |
| accagacccg ccgcctgaaa gagaacatgg gcacgctgga cctgggca gacaggactg | 5940 |
| cgcgggcatt caaatccatg tgggatgcgg tgctggatat tggtcgtcct gataccgcgc | 6000 |
| aggagatgct gattaaggca gaggctgcgt ataagaaagc agacgacatc tggaatctgc | 6060 |
| gcaaggatga ttattttgtt aacgatgaag cgcgggcgcg ttactgggat gatcgtgaaa | 6120 |
| aggcccgtct tgcgcttgaa gccgcccgaa agaaggctga gcagcagact caacaggaca | 6180 |
| aaaatgcgca gcagcagagc gataccgaag cgtcacggct gaaatatacc gaagaggcgc | 6240 |
| agaaggctta cgaacggctg cagacgccgc tggagaaata taccgcccgt caggaagaac | 6300 |
| tgaacaaggc actgaaagac gggaaaatcc tgcaggcgga ttacaacacg ctgatggcgg | 6360 |
| cggcgaaaaa ggattatgaa gcgacgctga aaaagccgaa acagtccagc gtgaaggtgt | 6420 |
| ctgcgggcga tcgtcaggaa gacagtgctc atgctgccct gctgacgctt caggcagaac | 6480 |
| tccggacgct ggagaagcat gccggagcaa atgagaaaat cagccagcag cgccgggatt | 6540 |
| tgtggaaggc ggagagtcag ttcgcggtac tggaggaggc ggcgcaacgt cgccagctgt | 6600 |
| ctgcacagga gaaatccctg ctggcgcata aagatgagac gctggagtac aaacgccagc | 6660 |
| tggctgcact tggcgacaag gttac | 6685 |

<210> SEQ ID NO 24
<211> LENGTH: 10156
<212> TYPE: DNA
<213> ORGANISM: Bacteriophage lambda

<400> SEQUENCE: 24

| | |
|---|---|
| gtatcaggag cgcctgaacg cgctggcgca gcaggcggat aaaattcgcac agcagcaacg | 60 |
| ggcaaaacgg gccgccattg atgcgaaaag ccggggggctg actgaccggc aggcagaacg | 120 |
| ggaagccacg gaacagcgcc tgaaggaaca gtatggcgat aatccgctgg cgctgaataa | 180 |
| cgtcatgtca gagcagaaaa agacctgggc ggctgaagac cagcttcgcg ggaactggat | 240 |
| ggcaggcctg aagtccggct ggagtgagtg gaagagagc gccacggaca gtatgtcgca | 300 |
| ggtaaaaagt gcagccacgc agaccttga tggtattgca cagaatatgg cggcgatgct | 360 |
| gaccggcagt gagcagaact ggcgcagctt caccgttcc gtgctgtcca tgatgacaga | 420 |
| aattctgctt aagcaggcaa tggtggggat tgtcgggagt atcggcagcg ccattggcgg | 480 |

```
ggctgttggt ggcggcgcat ccgcgtcagg cggtacagcc attcaggccg ctgcggcgaa    540
attccatttt gcaaccggag gatttacggg aaccggcggc aaatatgagc cagcggggat    600
tgttcaccgt ggtgagtttg tcttcacgaa ggaggcaacc agccggattg gcgtggggaa    660
tctttaccgg ctgatgcgcg gctatgccac cggcggttat gtcggtacac cgggcagcat    720
ggcagacagc cggtcgcagg cgtccgggac gtttgagcag aataaccatg tggtgattaa    780
caacgacgga acgaacgggc agataggtcc ggctgctctg aaggcggtgt atgacatggc    840
ccgcaagggt gcccgtgatg aaattcagac acagatgcgt gatggtggcc tgttctccgg    900
aggtggacga tgaagacctt ccgctggaaa gtgaaacccg gtatgatgt ggcttcggtc    960 ccttctgtaa gaaaggtgcg ctttggtgat ggctattctc agcgagcgcc tgccgggctg   1020
aatgccaacc tgaaaacgta cagcgtgacg ctttctgtcc cccgtgagga ggccacggta   1080
ctggagtcgt ttctggaaga gcacgggggc tggaaatcct ttctgtggac gccgccttat   1140
gagtggcggc agataaaggt gacctgcgca aatggtcgt cgcgggtcag tatgctgcgt   1200
gttgagttca gcgcagagtt tgaacaggtg gtgaactgat gcaggatatc cggcaggaaa   1260
cactgaatga atgcacccgt gcggagcagt cggccagcgt ggtgctctgg gaaatcgacc   1320
tgacagaggt cggtggagaa cgttattttt tctgtaatga gcagaacgaa aaaggtgagc   1380
cggtcacctg gcaggggcga cagtatcagc cgtatcccat tcaggggagc ggttttgaac   1440
tgaatggcaa aggcaccagt acgcgccccca cgctgacggt ttctaacctg tacggtatgg   1500
tcaccgggat ggcggaagat atgcagagtc tggtcggcgg aacggtggtc cggcgtaagg   1560
tttacgcccg ttttctggat gcggtgaact tcgtcaacgg aaacagttac gccgatccgg   1620
agcaggaggt gatcagccgc tggcgcattg agcagtgcag cgaactgagc gcggtgagtg   1680
cctcctttgt actgtccacg ccgacggaaa cggatgcgc tgttttccg ggacgtatca   1740 tgctggccaa cacctgcacc tggacctatc gcggtgacga gtgcggttat agcggtccgg   1800
ctgtcgcgga tgaatatgac cagccaacgt ccgatatcac gaaggataaa tgcagcaaat   1860
gcctgagcgg ttgtaagttc cgcaataacg tcggcaactt tggcggcttc ctttccatta   1920
acaaactttc gcagtaaatc ccatgacaca gacagaatca gcgattctgg cgcacgcccg   1980
gcgatgtgcg ccagcggagt cgtgcggctt cgtggtaagc acgccggagg gggaaagata   2040
tttcccctgc gtgaatatct ccggtgagcc ggaggctatt tccgtatgtc gccggaagac   2100
tggctgcagg cagaaatgca gggtgagatt gtggcgctgg tccacagcca ccccggtggt   2160
ctgccctggc tgagtgaggc cgaccggcgg ctgcaggtgc agagtgattt gccgtggtgg   2220
ctggtctgcc gggggacgat tcataagttc cgctgtgtgc cgcatctcac cgggcggcgc   2280
tttgagcacg gtgtgacgga ctgttacaca ctgttccggg atgcttatca tctggcgggg   2340
attgagatgc cggactttca tcgtgaggat gactggtggc gtaacggcca gaatctctat   2400
ctggataatc tggaggcgac ggggctgtat caggtgccgt tgtcagcggc acagccgggc   2460
gatgtgctgc tgtgctgttt tggttcatca gtgccgaatc acgccgcaat ttactgcggc   2520
gacggcgagc tgctgcacca tattcctgaa caactgagca acgagagag gtacaccgac   2580 aaatggcagc gacgcacaca ctccctctgg cgtcaccggg catggcgcgc atctgccttt   2640
acggggattt acaacgattt ggtcgccgca tcgaccttcg tgtgaaaacg ggggctgaag   2700
ccatccgggc actggccaca cagctccccg cgtttcgtca gaaactgagc gacggctggt   2760
atcaggtacg gattgccggg cgggacgtca gcacgtccgg gttaacgcg cagttacatg   2820 agactctgcc tgatggcgct gtaattcata ttgttcccag agtcgccggg gccaagtcag   2880
```

```
gtggcgtatt ccagattgtc ctgggggctg ccgccattgc cggatcattc tttaccgccg   2940
gagccaccct tgcagcatgg ggggcagcca ttggggccgg tggtatgacc ggcatcctgt   3000
tttctctcgg tgccagtatg gtgctcggtg gtgtggcgca gatgctggca ccgaaagcca   3060
gaactccccg tatacagaca acggataacg gtaagcagaa cacctatttc tcctcactgg   3120
ataacatggt tgcccagggc aatgttctgc ctgttctgta cggggaaatg cgcgtggggt   3180
cacgcgtggt ttctcaggag atcagcacgg cagacgaagg ggacggtggt caggttgtgg   3240
tgattggtcg ctgatgcaaa atgttttatg tgaaaccgcc tgcgggcggt tttgtcattt   3300
atggagcgtg aggaatgggt aaaggaagca gtaaggggca tacccgcgc gaagcgaagg    3360 acaacctgaa gtccacgcag ttgctgagtg tgatcgatgc catcagcgaa gggccgattg   3420
aaggtccggt ggatggctta aaaagcgtgc tgctgaacag tacgccggtg ctggacactg   3480
aggggaatac caacatatcc ggtgtcacgg tggtgttccg ggctggtgag caggagcaga   3540
ctccgccgga gggatttgaa tcctccggct ccgagacggt gctgggtacg gaagtgaaat   3600
atgacacgcc gatcacccgc accattacgt ctgcaaacat cgaccgtctg cgctttacct   3660
tcggtgtaca ggcactggtg gaaaccacct caaagggtga caggaatccg tcggaagtcc   3720
gcctgctggt tcagatacaa cgtaacggtg gctgggtgac ggaaaaagac atcaccatta   3780
agggcaaaac cacctcgcag tatctggcct cggtggtgat gggtaacctg ccgccgcgcc   3840
cgtttaatat ccggatgcgc aggatgacgc cggacagcac cacagaccag ctgcagaaca   3900
aaacgctctg gtcgtcatac actgaaatca tcgatgtgaa acagtgctac ccgaacacgg   3960
cactggtcgg cgtgcaggtg gactcggagc agttcggcag ccagcaggtg agccgtaatt   4020
atcatctgcg cgggcgtatt ctgcaggtgc cgtcgaacta taacccgcag acgcggcaat   4080
acagcggtat ctgggacgga acgtttaaac cggcatacag caacaacatg gcctggtgtc   4140
tgtgggatat gctgacccat ccgcgctacg gcatggggaa acgtcttggt gcggcggatg   4200
tggataaatg ggcgctgtat gtcatcggcc agtactgcga ccagtcagtg ccggacggct   4260
ttggcggcac ggagccgcgc atcacctgta atgcgtacct gaccacacag cgtaaggcgt   4320
gggatgtgct cagcgatttc tgctcggcga tgcgctgtat gccggtatgg aacgggcaga   4380
cgctgacgtt cgtgcaggac cgaccgtcgg ataagacgtg gacctataac cgcagtaatg   4440
tggtgatgcc ggatgatggc gcgccgttcc gctacagctt cagcgccctg aaggaccgcc   4500
ataatgccgt tgaggtgaac tggattgacc cgaacaacgg ctgggagacg gcgacagagc   4560
ttgttgaaga tacgcaggcc attgcccgtt acggtcgtaa tgttacgaag atggatgcct   4620
ttggctgtac cagccggggg caggcacacc gcgccgggct gtggctgatt aaaacagaac   4680
tgctggaaac gcagaccgtg gatttcagcg tcggcgcaga agggcttcgc catgtaccgg   4740
gcgatgttat tgaaatctgc gatgatgact atgccggtat cagcaccggt ggtcgtgtgc   4800
tggcggtgaa cagccagacc cggacgctga cgctcgaccg tgaaatcacg ctgccatcct   4860
ccggtaccgc gctgataagc ctggttgacg gaagtggcaa tccggtcagc gtggaggttc   4920
agtccgtcac cgacggcgtg aaggtaaaag tgagccgtgt tcctgacggt gttgctgaat   4980
acagcgtatg ggagctgaag ctgccgacgc tgcgccagcg actgttccgc tgcgtgagta   5040
tccgtgagaa cgacgacggc acgtatgcca tcaccgccgt gcagcatgtg ccggaaaaag   5100
aggccatcgt ggataacggg gcgcacttttg acggcgaaca gagtggcacg gtgaatggtg   5160
tcacgccgcc agcggtgcag cacctgaccg cagaagtcac tgcagacagc ggggaatatc   5220
aggtgctggc gcgatgggac acaccgaagg tggtgaaggg cgtgagtttc ctgctccgtc   5280
```

-continued

```
tgaccgtaac agcggacgac ggcagtgagc ggctggtcag cacggcccgg acgacggaaa    5340
ccacataccg cttcacgcaa ctggcgctgg ggaactacag gctgacagtc cgggcggtaa    5400
atgcgtgggg gcagcagggc gatccggcgt cggtatcgtt ccggattgcc gcaccggcag    5460
caccgtcgag gattgagctg acgccgggct attttcagat aaccgccacg ccgcatcttg    5520
ccgtttatga cccgacggta cagtttgagt tctggttctc ggaaaagcag attgcggata    5580
tcagacaggt tgaaaccagc acgcgttatc ttggtacggc gctgtactgg atagccgcca    5640
gtatcaatat caaaccgggc catgattatt acttttatat ccgcagtgtg aacaccgttg    5700
gcaaatcggc attcgtggag gccgtcggtc gggcgagcga tgatgcggaa ggttacctgg    5760 atttttcaa aggcaagata accgaatccc atctcggcaa ggagctgctg gaaaaagtcg    5820
agctgacgga ggataacgcc agcagactgg aggagttttc gaaagagtgg aaggatgcca    5880
gtgataagtg gaatgccatg tgggctgtca aaattgagca gaccaaagac ggcaaacatt    5940
atgtcgcggg tattggcctc agcatggagg acacggagga aggcaaactg agccagtttc    6000
tggttgccgc caatcgtatc gcattttattg acccggcaaa cggaatgaa acgccgatgt    6060 ttgtggcgca gggcaaccag atattcatga acgacgtgtt cctgaagcgc ctgacggccc    6120
ccaccattac cagcggcggc aatcctccgg ccttttccct gacaccggac ggaaagctga    6180
ccgctaaaaa tgcggatatc agtggcagtg tgaatgcgaa ctccgggacg ctcagtaatg    6240
tgacgatagc tgaaaactgt acgataaacg gtacgctgag ggcggaaaaa atcgtcgggg    6300
acattgtaaa ggcggcgagc gcggcttttc cgcgccagcg tgaaagcagt gtggactggc    6360
cgtcaggtac ccgtactgtc accgtgaccg atgaccatcc ttttgatcgc cagatagtgg    6420
tgcttccgct gacgtttcgc ggaagtaagc gtactgtcag cggcaggaca acgtattcga    6480
tgtgttatct gaaagtactg atgaacggtc cggtgattta tgatggcgcg gcgaacgagg    6540
cggtacaggt gttctcccgt attgttgaca tgccagcggg tcggggaaac gtgatcctga    6600
cgttcacgct tacgtccaca cggcattcgg cagatattcc gccgtatacg tttgccagcg    6660
atgtgcaggt tatggtgatt aagaaacagg cgctgggcat cagcgtggtc tgagtgtgtt    6720
acagaggttc gtccgggaac gggcgtttta ttataaaaca gtgagaggtg aacgatgcgt    6780
aatgtgtgta ttgccgttgc tgtctttgcc gcacttgcgg tgacagtcac tccggcccgt    6840
gcggaaggtg gacatggtac gtttacggtg ggctattttc aagtgaaacc gggtacattg    6900
ccgtcgttgt cggcggggga taccggtgtg agtcatctga aagggattaa cgtgaagtac    6960
cgttatgagc tgacgacag tgtggggtg atggcttccc tggggttcgc cgcgtcgaaa    7020
aagagcagca cagtgatgac cggggaggat acgtttcact atgagagcct gcgtggacgt    7080
tatgtgagcg tgatggccgg accggtttta caaatcagta agcaggtcag tgcgtacgcc    7140
atggccggag tggctcacag tcggtggtcc ggcagtacaa tggattaccg taagacggaa    7200
atcactcccg ggtatatgaa agagacgacc actgccaggg acgaaagtgc aatgcggcat    7260
acctcagtgg cgtggagtgc aggtatacag attaatccgg cagcgtccgt cgttgttgat    7320
attgcttatg aaggctccgg cagtggcgac tggcgtactg acggattcat cgttggggtc    7380
ggttataaat tctgattagc caggtaacac agtgttatga cagcccgccg gaaccggtgg    7440 gctttttgt ggggtgaata tggcagtaaa gatttcagga gtcctgaaag acggcacagg    7500
aaaaccggta cagaactgca ccattcagct gaaagccaga cgtaacagca ccacggtggt    7560
ggtgaacacg gtgggctcag agaatccgga tgaagccggg cgttacagca tggatgtgga    7620
gtacggtcag tacagtgtca tcctgcaggt tgacggtttt ccaccatcgc acgccgggac    7680
```

```
catcaccgtg tatgaagatt cacaaccggg gacgctgaat gattttctct gtgccatgac    7740
ggaggatgat gcccggccgg aggtgctgcg tcgtcttgaa ctgatggtgg aagaggtggc    7800
gcgtaacgcg tccgtggtgg cacagagtac ggcagacgcg aagaaatcag ccggcgatgc    7860
cagtgcatca gctgctcagg tcgcggccct tgtgactgat gcaactgact cagcacgcgc    7920
cgccagcacg tccgccggac aggctgcatc gtcagctcag gaagcgtcct ccggcgcaga    7980
agcggcatca gcaaaggcca ctgaagcgga aaaagtgcc gcagccgcag agtcctcaaa     8040
aaacgcggcg gccaccagtg ccggtgcggc gaaaacgtca gaaacgaatg ctgcagcgtc    8100
acaacaatca gccgccacgt ctgcctccac cgcggccacg aaagcgtcag aggccgccac    8160
ttcagcacga gatgcggtgg cctcaaaaga ggcagcaaaa tcatcagaaa cgaacgcatc    8220
atcaagtgcc ggtcgtgcag cttcctcggc aacggcggca gaaaattctg ccagggcggc    8280
aaaaacgtcc gagacgaatg ccaggtcatc tgaaacagca gcggaacgga gcgcctctgc    8340
cgcggcagac gcaaaaacag cggcggcggg gagtgcgtca acggcatcca cgaaggcgac    8400
agaggctgcg ggaagtgcgg tatcagcatc gcagagcaaa agtgcggcag aagcggcggc    8460
aatacgtgca aaaaattcgg caaaacgtgc agaagatata gcttcagctg tcgcgcttga    8520
ggatgcggac acaacgagaa aggggatagt gcagctcagc agtgcaacca acagcacgtc    8580
tgaaacgctt gctgcaacgc caaaggcggt taaggtggta atggatgaaa cgaacagaaa    8640
agcccactgg acagtccggc actgaccgga acgccaacag caccaaccgc gctcagggga    8700
acaaacaata cccagattgc gaacaccgct tttgtactgg ccgcgattgc agatgttatc    8760
gacgcgtcac ctgacgcact gaatacgctg aatgaactgg ccgcagcgct cgggaatgat    8820
ccagattttg ctaccaccat gactaacgcg cttgcgggta acaaccgaa gaatgcgaca     8880 ctgacgcgc tggcagggct ttccacggcg aaaaataaat taccgtattt tgcggaaaat     8940
gatgccgcca gcctgactga actgactcag gttggcaggg atattctggc aaaaaattcc    9000
gttgcagatg ttcttgaata ccttgggggcc ggtgagaatt cggcctttcc ggcaggtgcg   9060
ccgatcccgt ggccatcaga tatcgttccg tctggctacg tcctgatgca ggggcaggcg    9120
tttgacaaat cagcctaccc aaaacttgct gtcgcgtatc catcgggtgt gcttcctgat    9180
atgcgaggct ggacaatcaa ggggaaaccc gccagcggtc gtgctgtatt gtctcaggaa    9240
caggatggaa ttaagtcgca cacccacagt gccagtgcat ccggtacgga tttggggacg    9300
aaaaccacat cgtcgtttga ttacgggacg aaaacaacag gcagtttcga ttacggcacc    9360
aaatcgacga ataacacggg ggctcatgct cacagtctga gcggttcaac aggggccgcg    9420
ggtgctcatg cccacacaag tggtttaagg atgaacagtt ctggctggag tcagtatgga    9480
acagcaacca ttacaggaag tttatccaca gttaaaggaa ccagcacaca gggtattgct    9540
tatttatcga aaacggacag tcagggcagc cacagtcact cattgtccgg tacagccgtg    9600
agtgccggtg cacatgcgca tacagttggt attggtgcgc accagcatcc ggttgttatc    9660
ggtgctcatg cccattcttt cagtattggt tcacacggac acaccatcac cgttaacgct    9720
gcgggtaacg cggaaaacac cgtcaaaaac attgcattta actatattgt gaggcttgca    9780
taatggcatt cagaatgagt gaacaaccac ggaccataaa aatttataat ctgctggccg    9840
gaactaatga atttattggt gaaggtgacg catatattcc gcctcatacc ggtctgcctg    9900
caaacagtac cgatattgca ccgccagata ttccggctgg ctttgtggct gttttcaaca    9960
gtgatgaggc atcgtggcat ctcgttgaag accatcgggg taaaaccgtc tatgacgtgg    10020
cttccggcga cgcgttattt atttctgaac tcggtccgtt accggaaaat tttacctggt    10080
```

```
tatcgccggg agggggaatat cagaagtgga acggcacagc ctgggtgaag gatacggaag    10140
cagaaaaact gttccg                                                     10156

<210> SEQ ID NO 25
<211> LENGTH: 5626
<212> TYPE: DNA
<213> ORGANISM: Bacteriophage lambda

<400> SEQUENCE: 25
gatccgggag gcggaagaaa caaaaaaaag cctgatgcag gtagccagtg agcatattgc      60
gccgcttcag gatgctgcag atctggaaat tgcaacgaag gaagaaacct cgttgctgga    120
agcctggaag aagtatcggg tgttgctgaa ccgtgttgat acatcaactg cacctgatat    180
tgagtggcct gctgtccctg ttatggagta atcgttttgt gatatgccgc agaaacgttg    240
tatgaaataa cgttctgcgg ttagttagta tattgtaaag ctgagtattg gtttatttgg    300
cgattattat cttcaggaga ataatggaag ttctatgact caattgttca tagtgtttac    360
atcaccgcca attgctttta agactgaacg catgaaaatat ggttttttcgt catgttttga    420 gtctgctgtt gatatttcta aagtcggttt ttttttcttcg ttttctctaa ctattttcca    480
tgaaatacat ttttgattat tatttgaatc aattccaatt acctgaagtc tttcatctat    540
aattggcatt gtatgtattg gtttattgga gtagatgctt gcttttctga gccatagctc    600
tgatatccaa atgaagccat aggcatttgt tattttggct ctgtcagctg cataacgcca    660
aaaaatatat ttatctgctt gatcttcaaa tgttgtattg attaaatcaa ttggatggaa    720
ttgtttatca taaaaaatta atgtttgaat gtgataaccg tcctttaaaa aagtcgtttc    780
tgcaagcttg gctgtatagt caactaactc ttctgtcgaa gtgatatttt taggcttatc    840
taccagtttt agacgctctt taatatcttc aggaattatt ttattgtcat attgtatcat    900
gctaaatgac aatttgctta tggagtaatc ttttaatttt aaataagtta ttctcctggc    960
ttcatcaaat aaagagtcga atgatgttgg cgaaatcaca tcgtcaccca ttggattgtt   1020
tatttgtatg ccaagagagt tacagcagtt atacattctg ccatagatta tagctaaggc   1080
atgtaataat tcgtaatctt ttagcgtatt agcgacccat cgtctttctg atttaataat   1140
agatgattca gttaaatatg aaggtaattt cttttgtgca agtctgacta actttttttat   1200 accaatgttt aacatacttt catttgtaat aaactcaatg tcattttctt caatgtaaga   1260
tgaaataaga gtagcctttg cctcgctata catttctaaa tcgccttgtt tttctatcgt   1320
attgcgagaa ttttttagccc aagccattaa tggatcattt ttccatttttt caataacatt   1380 attgttatac caaatgtcat atcctataat ctggtttttg ttttttttgaa aataaaatgt   1440 tactgttctt gcggtttgga ggaattgatt caaattcaag cgaaataatt cagggtcaaa   1500
atatgtatca atgcagcatt tgagcaagtg cgataaatct ttaagtcttc tttcccatgg   1560
ttttttagtc ataaaactct ccattttgat aggttgcatg ctagatgctg atatatttta   1620
gaggtgataa aattaactgc ttaactgtca atgtaataca agttgtttga tctttgcaat   1680
gattcttatc agaaaccata tagtaaatta gttacacagg aaattttttaa tattattatt   1740 atcattcatt atgtattaaa attagagttg tggcttggct ctgctaacac gttgctcata   1800
ggagatatgg tagagccgca gacacgtcgt atgcaggaac gtgctgcggc tggctggtga   1860
acttccgata gtgcgggtgt tgaatgattt ccagttgcta ccgatttttac atatttttg    1920 catgagagaa tttgtaccac ctcccaccga ccatctgatga ctgtacgcca ctgtccctag   1980
gactgctatg tgccggagcg gacattacaa acgtccttct cggtgcatgc cactgttgcc   2040
```

```
aatgacctgc ctaggaattg gttagcaagt tactaccgga ttttgtaaaa acagccctcc    2100
tcatataaaa agtattcgtt cacttccgat aagcgtcgta attttctatc tttcatcata    2160
ttctagatcc ctctgaaaaa atcttccgag tttgctaggc actgatacat aactctttc    2220 caataattgg ggaagtcatt caaatctata ataggtttca gatttgcttc aataaattct    2280
gactgtagct gctgaaacgt tgcggttgaa ctatatttcc ttataacttt tacgaaagag    2340
tttctttgag taatcacttc actcaagtgc ttccctgcct ccaaacgata cctgttagca    2400
atatttaata gcttgaaatg atgaagagct ctgtgtttgt cttcctgcct ccagttcgcc    2460
gggcattcaa cataaaaact gatagcaccc ggagttccgg aaacgaaatt tgcatatacc    2520
cattgctcac gaaaaaaaat gtccttgtcg atataggat gaatcgcttg gtgtacctca    2580
tctactgcga aaacttgacc tttctctccc atattgcagt cgcggcacga tggaactaaa    2640
ttaataggca tcaccgaaaa ttcaggataa tgtgcaatag aagaaaatg atctatattt    2700 tttgtctgtc ctatatcacc acaaaatgga catttttcac ctgatgaaac aagcatgtca    2760
tcgtaatatg ttctagcggg tttgttttta tctcggagat tatttcata aagcttttct    2820 aatttaacct ttgtcaggtt accaactact aaggttgtag gctcaagagg gtgtgtcctg    2880
tcgtaggtaa ataactgacc tgtcgagctt aatattctat attgttgttc tttctgcaaa    2940
aaagtgggga agtgagtaat gaaattattt ctaacattta tctgcatcat accttccgag    3000
catttattaa gcatttcgct ataagttctc gctggaagag gtagttttt cattgtactt    3060 taccttcatc tctgttcatt atcatcgctt ttaaaacggt tcgaccttct aatcctatct    3120
gaccattata atttttaga atggtttcat aagaaagctc tgaatcaacg gactgcgata    3180
ataagtggtg gtatccagaa tttgtcactt caagtaaaaa cacctcacga gttaaaacac    3240
ctaagttctc accgaatgtc tcaatatccg gacggataat atttattgct tctcttgacc    3300
gtaggacttt ccacatgcag gattttggaa cctcttgcag tactactggg gaatgagttg    3360
caattattgc tacaccattg cgtgcatcga gtaagtcgct taatgttcgt aaaaaagcag    3420
agagcaaagg tggatgcaga tgaacctctg gttcatcgaa taaaactaat gactttttcgc    3480 caacgacatc tactaatctt gtgatagtaa ataaaacaat tgcatgtcca gagctcattc    3540
gaagcagata tttctggata ttgtcataaa acaatttagt gaatttatca tcgtccactt    3600
gaatctgtgg ttcattacgt cttaactctt catatttaga aatgaggctg atgagttcca    3660
tatttgaaaa gttttcatca ctacttagtt ttttgatagc ttcaagccag agttgtcttt    3720
ttctatctac tctcatacaa ccaataaatg ctgaaatgaa ttctaagcgg agatcgccta    3780
gtgattttaa actattgctg gcagcattct tgagtccaat ataaaagtat tgtgtacctt    3840
ttgctgggtc aggttgttct ttaggaggag taaaaggatc aaatgcacta aacgaaactg    3900
aaacaagcga tcgaaaatat ccctttggga ttcttgactc gataagtcta ttattttcag    3960
agaaaaaata ttcattgttt tctgggttgg tgattgcacc aatcattcca ttcaaaattg    4020
ttgttttacc acacccattc cgcccgataa aagcatgaat gttcgtgctg ggcatagaat    4080
taaccgtcac ctcaaaaggt atagttaaat cactgaatcc gggagcactt tttctattaa    4140
atgaaaagtg gaaatctgac aattctggca aaccatttaa cacacgtgcg aactgtccat    4200
gaatttctga aagagttacc cctctaagta atgaggtgtt aaggacgctt tcattttcaa    4260
tgtcggctaa tcgatttggc catactacta aatcctgaat agctttaaga aggttatgtt    4320
taaaaccatc gcttaattg ctgagattaa catagtagtc aatgctttca cctaaggaaa    4380
aaaacatttc agggagttga ctgaattttt tatctattaa tgaataagtg cttacttctt    4440
```

-continued

```
cttttttgacc tacaaaacca attttaacat ttccgatatc gcattttca  ccatgctcat    4500
caaagacagt  aagataaaac attgtaacaa aggaatagtc attccaacca  tctgctcgta    4560
ggaatgcctt  attttttttct actgcaggaa tatacccgcc tctttcaata  acactaaact    4620
ccaacatata  gtaacccttat attttattaa aataaccgca atttatttgg  cggcaacaca    4680
ggatctctct  tttaagttac tctctattac atacgttttc catctaaaaa  ttagtagtat    4740
tgaacttaac  ggggcatcgt attgtagttt tccatattta gctttctgct  tccttttgga    4800
taacccactg  ttattcatgt tgcatggtgc actgtttata ccaacgatat  agtctattaa    4860
tgcatatata  gtatcgccga acgattagct cttcaggctt ctgaagaagc  gtttcaagta    4920
ctaataagcc  gatagatagc cacggacttc gtagccattt ttcataagtg  ttaacttccg    4980
ctcctcgctc  ataacagaca ttcactacag ttatggcgga aaggtatgca  tgctgggtgt    5040
ggggaagtcg  tgaaagaaaa gaagtcagct gcgtcgtttg acatcactgc  tatcttctta    5100
ctggttatgc  aggtcgtagt gggtggcaca caaagctttg cactggattg  cgaggctttg    5160
tgcttctctg  gagtgcgaca ggtttgatga caaaaaatta gcgcaagaag  acaaaaatca    5220
ccttgcgcta  atgctctgtt acaggtcact aataccatct aagtagttga  ttcatagtga    5280
ctgcatatgt  tgtgttttac agtattatgt agtctgtttt ttatgcaaaa  tctaatttaa    5340
tatattgata  tttatatcat tttacgtttc tcgttcagct tttttatact  aagttggcat    5400
tataaaaaag  cattgcttat caatttgttg caacgaacag gtcactatca  gtcaaaataa    5460
aatcattatt  tgatttcaat tttgtcccac tccctgcctc tgtcatcacg  atactgtgat    5520
gccatggtgt  ccgacttatg cccgagaaga tgttgagcaa acttatcgct  tatctgcttc    5580
tcatagagtc  ttgcagacaa actgcgcaac tcgtgaaagg taggcg                    5626
```

<210> SEQ ID NO 26
<211> LENGTH: 6527
<212> TYPE: DNA
<213> ORGANISM: Bacteriophage lambda

<400> SEQUENCE: 26

```
gatccccttc gaaggaaaga cctgatgctt ttcgtgcgcg cataaaatac cttgatactg      60
tgccggatga aagcggttcg cgacgagtag atgcaattat ggtttctccg ccaagaatct     120
ctttgcattt atcaagtgtt tccttcattg atattccgag agcatcaata tgcaatgctg     180
ttgggatggc aattttttacg cctgttttgc tttgctcgac ataaagatat ccatctacga     240
tatcagacca cttcatttcg cataaatcac caactcgttg cccggtaaca acagccagtt     300
ccattgcaag tctgagccaa catggtgatg attctgctgc ttgataaatt ttcaggtatt     360
cgtcagccgt aagtcttgat ctccttacct ctgattttgc tgcgcgagtg gcagcgacat     420
ggtttgttgt tatatggcct tcagctattg cctctcggaa tgcatcgctc agtgttgatc     480
tgattaactt ggctgacgcc gccttgccct cgtctatgta tccattgagc attgccgcaa     540
tttctttttgt ggtgatgtct tcaagtggag catcaggcag accctccctt attgctttaa     600
ttttgctcat gtaatttatg agtgtcttct gcttgattcc tctgctggcc aggattttttt     660
cgtagcgatc aagccatgaa tgtaacgtaa cggaattatc actgttgatt ctcgctgtca     720
gaggcttgtg tttgtgtcct gaaaataact caatgttggc ctgtatagct tcagtgattg     780
cgattcgcct gtctctgcct aatccaaact ctttacccgt ccttgggtcc ctgtagcagt     840
aatatccatt gtttcttata taaaggttag ggggtaaatc ccggcgctca tgacttcgcc     900
ttcttcccat ttctgatcct cttcaaaagg ccacctgtta ctggtcgatt taagtcaacc     960
```

```
tttaccgctg attcgtggaa cagatactct cttccatcct taaccggagg tgggaatatc      1020
ctgcattccc gaacccatcg acgaactgtt tcaaggcttc ttggacgtcg ctggcgtgcg      1080
ttccactcct gaagtgtcaa gtacatcgca aagtctccgc aattacacgc aagaaaaaac      1140
cgccatcagg cggcttggtg ttctttcagt tcttcaattc gaatattggt tacgtctgca      1200
tgtgctatct gcgcccatat catccagtgg tcgtagcagt cgttgatgtt ctccgcttcg      1260
ataactctgt tgaatggctc tccattccat tctcctgtga ctcggaagtg catttatcat      1320
ctccataaaa caaacccgc cgtagcgagt tcagataaaa taaatccccg cgagtgcgag      1380
gattgttatg taatattggg tttaatcatc tatatgtttt gtacagagag ggcaagtatc      1440
gtttccaccg tactcgtgat aataattttg cacggtatca gtcatttctc gcacattgca      1500
gaatggggat ttgtcttcat tagacttata aaccttcatg gaatatttgt atgccgactc      1560
tatatctata ccttcatcta cataaacacc ttcgtgatgt ctgcatggag acaagacacc      1620
ggatctgcac aacattgata acgcccaatc tttttgctca gactctaact cattgatact      1680
catttataaa ctccttgcaa tgtatgtcgt ttcagctaaa cggtatcagc aatgtttatg      1740
taaagaaaca gtaagataat actcaacccg atgtttgagt acggtcatca tctgacacta      1800
cagactctgg catcgctgtg aagacgacgc gaaattcagc atttcacaa gcgttatctt       1860 ttacaaaacc gatctcactc tcctttgatg cgaatgccag cgtcagacat catatgcaga      1920
tactcacctg catcctgaac ccattgacct ccaaccccgt aatagcgatg cgtaatgatg      1980
tcgatagtta ctaacgggtc ttgttcgatt aactgccgca gaaactcttc caggtcacca      2040
gtgcagtgct tgataacagg agtcttccca ggatggcgaa caacaagaaa ctggtttccg      2100
tcttcacgga cttcgttgct ttccagttta gcaatacgct tactcccatc cgagataaca      2160
ccttcgtaat actcacgctg ctcgttgagt tttgattttg ctgtttcaag ctcaacacgc      2220
agtttcccta ctgttagcgc aatatcctcg ttctcctggt cgcggcgttt gatgtattgc      2280
tggtttcttt cccgttcatc cagcagttcc agcacaatcg atggtgttac caattcatgg      2340
aaaaggtctg cgtcaaatcc ccagtcgtca tgcattgcct gctctgccgc ttcacgcagt      2400
gcctgagagt taatttcgct cacttcgaac ctctctgttt actgataagt tccagatcct      2460
cctggcaact tgcacaagtc cgacaaccct gaacgaccag gcgtcttcgt tcatctatcg      2520
gatcgccaca ctcacaacaa tgagtggcag atatagcctg gtggttcagg cggcgcattt      2580
ttattgctgt gttgcgctgt aattcttcta tttctgatgc tgaatcaatg atgtctgcca      2640
tctttcatta atccctgaac tgttggttaa tacgcttgag ggtgaatgcg aataataaaa      2700
aaggagcctg tagctccctg atgattttgc ttttcatgtt catcgttcct taaagacgcc      2760
gtttaacatg ccgattgcca ggcttaaatg agtcggtgtg aatcccatca gcgttaccgt      2820
ttcgcggtgc ttcttcagta cgctacggca aatgtcatcg acgtttttat ccggaaactg      2880
ctgtctggct ttttttgatt tcagaattag cctgacgggc aatgctgcga agggcgtttt      2940
cctgctgagg tgtcattgaa caagtcccat gtcggcaagc ataagcacac agaatatgaa      3000
gcccgctgcc agaaaaatgc attccgtggt tgtcatacct ggtttctctc atctgcttct      3060
gctttcgcca ccatcatttc cagcttttgt gaaagggatg cggctaacgt atgaaattct      3120
tcgtctgttt ctactggtat tggcacaaac ctgattccaa tttgagcaag ctatgtgcc       3180 atctcgatac tcgttcttaa ctcaacagaa gatgctttgt gcatacagcc cctcgtttat      3240
tatttatctc ctcagccagc cgctgtgctt tcagtggatt tcggataaca gaaaggccgg      3300 gaaatacccca gcctcgcttt gtaacggagt agacgaaagt gattgcgcct acccggatat     3360
```

```
tatcgtgagg atgcgtcatc gccattgctc cccaaataca aaaccaattt cagccagtgc    3420
ctcgtccatt ttttcgatga actccggcac gatctcgtca aaactcgcca tgtacttttc    3480
atcccgctca atcacgacat aatgcaggcc ttcacgcttc atacgcgggt catagttggc    3540
aaagtaccag gcattttttc gcgtcaccca catgctgtac tgcacctggg ccatgtaagc    3600
tgactttatg gcctcgaaac caccgagccg gaacttcatg aaatcccggg aggtaaacgg    3660
gcatttcagt tcaaggccgt tgccgtcact gcataaacca tcgggagagc aggcggtacg    3720
catactttcg tcgcgataga tgatcgggga ttcagtaaca ttcacgccgg aagtgaattc    3780
aaacagggtt ctggcgtcgt tctcgtactg ttttccccag gccagtgctt tagcgttaac    3840
ttccggagcc acaccggtgc aaacctcagc aagcagggtg tggaagtagg acattttcat    3900
gtcaggccac ttctttccgg agcggggttt tgctatcacg ttgtgaactt ctgaagcggt    3960
gatgacgccg agccgtaatt tgtgccacgc atcatccccc tgttcgacag ctctcacatc    4020
gatcccggta cgctgcagga taatgtccgg tgtcatgctg ccaccttctg ctctgcggct    4080
ttctgtttca ggaatccaag agcttttact gcttcggcct gtgtcagttc tgacgatgca    4140
cgaatgtcgc ggcgaaatat ctgggaacag agcggcaata agtcgtcatc ccatgtttta    4200
tccagggcga tcagcagagt gttaatctcc tgcatggttt catcgttaac cggagtgatg    4260
tcgcgttccg gctgacgttc tgcagtgtat gcagtatttt cgacaatgcg ctcggcttca    4320
tccttgtcat agataccagc aaatccgaag gccagacggg cacactgaat catggcttta    4380
tgacgtaaca tccgtttggg atgcgactgc cacggccccg tgatttctct gccttcgcga    4440
gttttgaatg gttcgcggcg gcattcatcc atccattcgg taacgcagat cggatgatta    4500
cggtccttgc ggtaaatccg gcatgtacag gattcattgt cctgctcaaa gtccatgcca    4560
tcaaactgct ggttttcatt gatgatgcgg gaccagccat caacgcccac caccggaacg    4620
atgccattct gcttatcagg aaaggcgtaa atttctttcg tccacggatt aaggccgtac    4680
tggttggcaa cgatcagtaa tgcgatgaac tgcgcatcgc tggcatcacc tttaaatgcc    4740
gtctggcgaa gagtggtgat cagttcctgt gggtcgacag aatccatgcc gacacgttca    4800
gccagcttcc cagccagcgt tgcgagtgca gtactcattc gttttatacc tctgaatcaa    4860
tatcaacctg gtggtgagca atggtttcaa ccatgtaccg gatgtgttct gccatgcgct    4920
cctgaaactc aacatcgtca tcaaacgcac gggtaatgga ttttttgctg gccccgtggc    4980
gttgcaaatg atcgatgcat agcgattcaa acaggtgctg gggcaggcct ttttccatgt    5040
cgtctgccag ttctgcctct ttctcttcac gggcgagctg ctggtagtga cgcgcccagc    5100
tctgagcctc aagacgatcc tgaatgtaat aagcgttcat ggctgaactc ctgaaatagc    5160
tgtgaaaata tcgcccgcga aatgccgggc tgattaggaa aacaggaaag ggggttagtg    5220
aatgcttttg cttgatctca gtttcagtat taatatccat tttttataag cgtcgacggc    5280
ttcacgaaac atcttttcat cgccaataaa agtggcgata gtgaatttag tctggatagc    5340
cataagtgtt tgatccattc tttgggactc ctggctgatt aagtatgtcg ataaggcgtt    5400
tccatccgtc acgtaattta cgggtgattc gttcaagtaa agattcggaa gggcagccag    5460
caacaggcca ccctgcaatg gcatattgca tggtgtgctc cttatttata cataacgaaa    5520
aacgcctcga gtgaagcgtt attggtatgc ggtaaaaccg cactcaggcg gccttgatag    5580
tcatatcatc tgaatcaaat attcctgatg tatcgatatc ggtaattctt attccttcgc    5640
taccatccat tggaggccat ccttcctgac catttccatc attccagtcg aactcacaca    5700
caacaccata tgcatttaag tcgcttgaaa ttgctataag cagagcatgt tgcgccagca    5760
```

-continued

| | |
|---|---|
| tgattaatac agcatttaat acagagccgt gtttattgag tcggtattca gagtctgacc | 5820 |
| agaaattatt aatctggtga agttttcct ctgtcattac gtcatggtcg atttcaattt | 5880 |
| ctattgatgc tttccagtcg taatcaatga tgtatttttt gatgtttgac atctgttcat | 5940 |
| atcctcacag ataaaaaatc gccctcacac tggagggcaa agaagatttc caataatcag | 6000 |
| aacaagtcgg ctcctgttta gttacgagcg acattgctcc gtgtattcac tcgttggaat | 6060 |
| gaatacacag tgcagtgttt attctgttat ttatgccaaa aataaaggcc actatcaggc | 6120 |
| agctttgttg ttctgtttac caagttctct ggcaatcatt gccgtcgttc gtattgccca | 6180 |
| tttatcgaca tatttcccat cttccattac aggaaacatt tcttcaggct taaccatgca | 6240 |
| ttccgattgc agcttgcatc cattgcatcg cttgaattgt ccacaccatt gattttatc | 6300 |
| aatagtcgta gtcatacgga tagtcctggt attgttccat cacatcctga ggatgctctt | 6360 |
| cgaactcttc aaattcttct tccatatatc accttaaata gtggattgcg gtagtaaaga | 6420 |
| ttgtgcctgt cttttaacca catcaggctc ggtggttctc gtgtacccct acagcgagaa | 6480 |
| atcggataaa ctattacaac ccctacagtt tgatgagtat agaaatg | 6527 |

<210> SEQ ID NO 27
<211> LENGTH: 7233
<212> TYPE: DNA
<213> ORGANISM: Bacteriophage lambda

<400> SEQUENCE: 27

| | |
|---|---|
| gatccactcg ttattctcgg acgagtgttc agtaatgaac ctctggagag aaccatgtat | 60 |
| atgatcgtta tctgggttgg acttctgctt ttaagcccag ataactggcc tgaatatgtt | 120 |
| aatgagagaa tcggtattcc tcatgtgtgg catgtttcg tctttgctct tgcattttcg | 180 |
| ctagcaatta atgtgcatcg attatcagct attgccagcg ccagatataa gcgatttaag | 240 |
| ctaagaaaac gcattaagat gcaaaacgat aaagtgcgat cagtaattca aaaccttaca | 300 |
| gaagagcaat ctatggtttt gtgcgcagcc cttaatgaag gcaggaagta tgtggttaca | 360 |
| tcaaaacaat tcccatacat tagtgagttg attgagcttg gtgtgttgaa caaaacttt | 420 |
| tcccgatgga atggaaagca tatattattc cctattgagg atatttactg gactgaatta | 480 |
| gttgccagct atgatccata taatattgag ataaagccaa ggccaatatc taagtaacta | 540 |
| gataagagga atcgatttc ccttaatttt ctggcgtcca ctgcatgtta tgccgcgttc | 600 |
| gccaggcttg ctgtaccatg tgcgctgatt cttgcgctca atacgttgca ggttgctttc | 660 |
| aatctgtttg tggtattcag ccagcactgt aaggtctatc ggatttagtg cgctttctac | 720 |
| tcgtgatttc ggtttgcgat tcagcgagag aatagggcgg ttaactggtt ttgcgcttac | 780 |
| cccaaccaac aggggatttg ctgctttcca ttgagcctgt ttctctgcgc gacgttcgcg | 840 |
| gcggcgtgtt tgtgcatcca tctggattct cctgtcagtt agctttggtg gtgtgtggca | 900 |
| gttgtagtcc tgaacgaaaa ccccccgcga ttggcacatt ggcagctaat ccggaatcgc | 960 |
| acttacggcc aatgcttcgt ttcgtatcac acaccccaaa gccttctgct ttgaatgctg | 1020 |
| cccttcttca gggcttaatt tttaagagcg tcaccttcat ggtggtcagt gcgtcctgct | 1080 |
| gatgtgctca gtatcaccgc cagtggtatt tatgtcaaca ccgccagaga taatttatca | 1140 |
| ccgcagatgg ttatctgtat gttttttata tgaatttatt ttttgcaggg gggcattgtt | 1200 |
| tggtaggtga gagatctgaa ttgctatgtt tagtgagttg tatctatttta tttttcaata | 1260 |
| aatacaattg gttatgtgtt ttgggggcga tcgtgaggca agaaaaccc ggcgctgagg | 1320 |
| ccgggttatt cttgttctct ggtcaaatta tatagttgga aaacaaggat gcatatatga | 1380 |

-continued

```
atgaacgatg cagaggcaat gccgatggcg atagtgggta tcatgtagcc gcttatgctg    1440
gaaagaagca ataacccgca gaaaaacaaa gctccaagct caacaaaact aagggcatag    1500
acaataacta ccgatgtcat atacccatac tctctaatct tggccagtcg gcgcgttctg    1560
cttccgatta gaaacgtcaa ggcagcaatc aggattgcaa tcatggttcc tgcatatgat    1620
gacaatgtcg ccccaagacc atctctatga gctgaaaaag aaacaccagg aatgtagtgg    1680
cggaaaagga gatagcaaat gcttacgata acgtaaggaa ttattactat gtaaacacca    1740
ggcatgattc tgttccgcat aattactcct gataattaat ccttaacttt gcccacctgc    1800
cttttaaaac attccagtat atcactttc attcttgcgt agcaatatgc catctcttca     1860
gctatctcag cattggtgac cttgttcaga ggcgctgaga gatggccttt ttctgataga    1920
taatgttctg ttaaaatatc tccggcctca tcttttgccc gcaggctaat gtctgaaaat    1980
tgaggtgacg ggttaaaaat aatatccttg caaccttttt ttatatccct tttaaatttt    2040
ggcttaatga ctatatccaa tgagtcaaaa agctcccctt caatatctgt tgcccctaag    2100
acctttaata tatcgccaaa tacaggtagc ttggcttcta ccttcaccgt tgttcggccg    2160
atgaaatgca tatgcataac atcgtctttg gtggttcccc tcatcagtgg ctctatctga    2220
acgcgctctc cactgcttaa tgacattcct ttcccgatta aaaaatctgt cagatcggat    2280
gtggtcggcc cgaaaacagt tctggcaaaa ccaatggtgt cgccttcaac aaacaaaaaa    2340
gatgggaatc ccaatgattc gtcatctgcg aggctgttct taatatcttc aactgaagct    2400
ttagagcgat ttatcttctg aaccagactc ttgtcatttg ttttggtaaa gagaaaagtt    2460
tttccatcga ttttatgaat atacaaataa ttggagccaa cctgcaggtg atgattatca    2520
gccagcagag aattaaggaa aacagacagg tttattgagc gcttatcttt cccttttattt   2580 ttgctgcggt aagtcgcata aaaaccattc ttcataattc aatccattta ctatgttatg    2640
ttctgagggg agtgaaaatt cccctaattc gatgaagatt cttgctcaat tgttatcagc    2700
tatgcgccga ccagaacacc ttgccgatca gccaaacgtc tcttcaggcc actgactagc    2760
gataactttc cccacaacgg aacaactctc attgcatggg atcattgggt actgtgggtt    2820
tagtggttgt aaaaacacct gaccgctatc cctgatcagt ttcttgaagg taaactcatc    2880 accccccaagt ctggctatgc agaaatcacc tggctcaaca gcctgctcag ggtcaacgag   2940
aattaacatt ccgtcaggaa agcttggctt ggagcctgtt ggtgcggtca tggaattacc    3000
ttcaacctca agccagaatg cagaatcact ggctttttg gttgtgctta cccatctctc     3060
cgcatcacct ttggtaaagg ttctaagctt aggtgagaac atccctgcct gaacatgaga    3120
aaaaacaggg tactcatact cacttctaag tgacggctgc atactaaccg cttcatacat    3180
ctcgtagatt tctctggcga ttgaagggct aaattcttca acgctaactt tgagaatttt    3240
tgtaagcaat gcggcgttat aagcatttaa tgcattgatg ccattaaata aagcaccaac    3300
gcctgactgc cccatcccca tcttgtctgc gacagattcc tgggataagc caagttcatt    3360
tttctttttt tcataaattg ctttaaggcg acgtgcgtcc tcaagctgct cttgtgttaa    3420 tggtttctttt tttgtgctca tacgttaaat ctatcaccgc aagggataaa tatctaacac   3480
cgtgcgtgtt gactatttta cctctggcgg tgataatggt tgcatgtact aaggaggttg    3540
tatggaacaa cgcataaccc tgaaagatta tgcaatgcgc tttgggcaaa ccaagacagc    3600
taaagatctc ggcgtatatc aaagcgcgat caacaaggcc attcatgcag gccgaaagat    3660
ttttttaact ataaacgctg atggaagcgt ttatgcggaa gaggtaaagc ccttcccgag    3720
taacaaaaaa acaacagcat aaataacccc gctcttacac attccagccc tgaaaagggg    3780
```

```
catcaaatta aaccacacct atggtgtatg catttatttg catacattca atcaattgtt   3840
atctaaggaa atacttacat atggttcgtg caaacaaacg caacgaggct ctacgaatcg   3900
agagtgcgtt gcttaacaaa atcgcaatgc ttggaactga aagacagcg gaagctgtgg    3960 gcgttgataa gtcgcagatc agcaggtgga agagggactg gattccaaag ttctcaatgc   4020
tgcttgctgt tcttgaatgg ggggtcgttg acgacgacat ggctcgattg gcgcgacaag   4080
ttgctgcgat tctcaccaat aaaaaacgcc cggcggcaac cgagcgttct gaacaaatcc   4140
agatggagtt ctgaggtcat tactggatct atcaacagga gtcattatga caaatacagc   4200
aaaaatactc aacttcggca gaggtaactt tgccggacag gagcgtaatg tggcagatct   4260
cgatgatggt tacgccagac tatcaaatat gctgcttgag gcttattcgg gcgcagatct   4320
gaccaagcga cagtttaaag tgctgcttgc cattctgcgt aaaacctatg ggtggaataa   4380
accaatggac agaatcaccg attctcaact tagcgagatt acaaagttac ctgtcaaacg   4440
gtgcaatgaa gccaagttag aactcgtcag aatgaatatt atcaagcagc aaggcggcat   4500
gtttggacca aataaaaaca tctcagaatg gtgcatccct caaaacgagg gaaaatcccc   4560
taaaacgagg gataaaacat ccctcaaatt ggggattgc tatccctcaa acaggggga    4620 cacaaaagac actattacaa aagaaaaaag aaaagattat tcgtcagaga attctggcga   4680
atcctctgac cagccagaaa acgacctttc tgtggtgaaa ccggatgctg caattcagag   4740
cggcagcaag tggggacag cagaagacct gaccgccgca gagtggatgt ttgacatggt    4800
gaagactatc gcaccatcag ccagaaaacc gaattttgct gggtgggcta acgatatccg   4860
cctgatgcgt gaacgtgacg gacgtaacca ccgcgacatg tgtgtgctgt tccgctgggc   4920
atgccaggac aacttctggt ccggtaacgt gctgagcccg gccaaactcc gcgataagtg   4980
gacccaactc gaaatcaacc gtaacaagca acaggcaggc gtgacagcca gcaaaccaaa   5040
actcgacctg acaaacacag actggattta cggggtggat ctatgaaaaa catcgccgca   5100
cagatggtta actttgaccg tgagcagatg cgtcggatcg ccaacaacat gccggaacag   5160
tacgacgaaa agccgcaggt acagcaggta gcgcagatca tcaacggtgt gttcagccag   5220
ttactggcaa ctttccccggc gagcctggct aaccgtgacc agaacgaagt gaacgaaatc   5280
cgtcgccagt gggttctggc ttttcgggaa acgggatca ccacgatgga acaggttaac    5340
gcaggaatgc gcgtagcccg tcggcagaat cgaccatttc tgccatcacc cgggcagttt   5400
gttgcatggt gccgggaaga agcatccgtt accgccggac tgccaaacgt cagcgagctg   5460
gttgatatgg tttacgagta ttgccggaag cgaggcctgt atccggatgc ggagtcttat   5520
ccgtggaaat caaacgcgca ctactggctg gttaccaacc tgtatcagaa catgcgggcc   5580
aatgcgctta ctgatgcgga attacgccgt aaggccgcag atgagcttgt ccatatgact   5640
gcgagaatta accgtggtga ggcgatccct gaaccagtaa acaacttcc tgtcatgggc    5700 ggtagacctc taaatcgtgc acaggctctg gcgaagatcg cagaaatcaa agctaagttc   5760
ggactgaaag gagcaagtgt atgacgggca aagaggcaat tattcattac ctggggacgc   5820
ataatagctt ctgtgcgccg gacgttgccg cgctaacagg cgcaacagta accagcataa   5880
atcaggccgc ggctaaaatg gcacgggcag gtcttctggt tatcgaaggt aaggtctggc   5940
gaacggtgta ttaccggttt gctaccaggg aagaacggga aggaaagatg agcacgaacc   6000 tggttttaa ggagtgtcgc cagagtgccg cgatgaaacg ggtattggcg gtatatggag    6060
ttaaaagatg accatctaca ttactgagct aataacaggc ctgctggtaa tcgcaggcct   6120
ttttatttgg gggagaggga agtcatgaaa aaactaacct ttgaaattcg atctccagca   6180
```

| | |
|---|---:|
| catcagcaaa acgctattca cgcagtacag caaatccttc cagacccaac caaaccaatc | 6240 |
| gtagtaacca ttcaggaacg caaccgcagc ttagaccaaa acaggaagct atgggcctgc | 6300 |
| ttaggtgacg tctctcgtca ggttgaatgg catggtcgct ggctggatgc agaaagctgg | 6360 |
| aagtgtgtgt ttaccgcagc attaaagcag caggatgttg ttcctaacct tgccgggaat | 6420 |
| ggctttgtgg taataggcca gtcaaccagc aggatgcgtg taggcgaatt tgcggagcta | 6480 |
| ttagagctta tacaggcatt cggtacagag cgtggcgtta agtggtcaga cgaagcgaga | 6540 |
| ctggctctgg agtggaaagc gagatgggga gacagggctg catgataaat gtcgttagtt | 6600 |
| tctccggtgg caggacgtca gcatatttgc tctggctaat ggagcaaaag cgacgggcag | 6660 |
| gtaaagacgt gcattacgtt ttcatggata caggttgtga acatccaatg acatatcggt | 6720 |
| ttgtcaggga agttgtgaag ttctgggata taccgctcac cgtattgcag gttgatatca | 6780 |
| acccggagct tggacagcca atggttata cggtatggga accaaggat attcagacgc | 6840 |
| gaatgcctgt tctgaagcca tttatcgata tggtaaagaa atatggcact ccatacgtcg | 6900 |
| gcggcgcgtt ctgcactgac agattaaaac tcgttcccct caccaaatac tgtgatgacc | 6960 |
| atttcgggcg agggaattac accacgtgga ttggcatcag agctgatgaa ccgaagcggc | 7020 |
| taaagccaaa gcctggaatc agatatcttg ctgaactgtc agactttgag aaggaagata | 7080 |
| tcctcgcatg gtggaagcaa caaccattcg atttgcaaat accggaacat ctcggtaact | 7140 |
| gcatattctg cattaaaaaa tcaacgcaaa aaatcggact tgcctgcaaa gatgaggagg | 7200 |
| gattgcagcg tgttttaat gaggtcatca cgg | 7233 |

<210> SEQ ID NO 28
<211> LENGTH: 6770
<212> TYPE: DNA
<213> ORGANISM: Bacteriophage lambda

<400> SEQUENCE: 28

| | |
|---|---:|
| gatcccatgt gcgtgacgga catcgggaaa cgccaaagga gattatgtac cgaggaagaa | 60 |
| tgtcgctgga cggtatcgcg aaaatgtatt cagaaaatga ttatcaagcc ctgtatcagg | 120 |
| acatggtacg agctaaaaga ttcgataccg gctcttgttc tgagtcatgc gaaatatttg | 180 |
| gagggcagct tgatttcgac ttcgggaggg aagctgcatg atgcgatgtt atcggtgcgg | 240 |
| tgaatgcaaa gaagataacc gcttccgacc aaatcaacct tactggaatc gatggtgtct | 300 |
| ccggtgtgaa agaacaccaa cagggtgtt accactaccg caggaaaagg aggacgtgtg | 360 |
| gcgagacagc gacgaagtat caccgacata atctgcgaaa actgcaaata ccttccaacg | 420 |
| aaacgcacca gaaataaacc caagccaatc ccaaaagaat ctgacgtaaa accttcaac | 480 |
| tacacggctc acctgtggga tatccggtgg ctaagacgtc gtgcgaggaa acaaggtga | 540 |
| ttgaccaaaa tcgaagttac gaacaagaaa gcgtcgagcg agctttaacg tgcgctaact | 600 |
| gcggtcagaa gctgcatgtg ctggaagttc acgtgtgtga gcactgctgc gcagaactga | 660 |
| tgagcgatcc gaatagctcg atgcacgagg aagaagatga tggctaaacc agcgcgaaga | 720 |
| cgatgtaaaa acgatgaatg ccgggaatgg tttcaccctg cattcgctaa tcagtggtgg | 780 |
| tgctctccag agtgtggaac caagatagca ctcgaacgac gaagtaaaga acgcgaaaaa | 840 |
| gcggaaaaag cagcagagaa gaaacgacga cgagaggagc agaaacagaa agataaactt | 900 |
| aagattcgaa aactcgcctt aaagccccgc agttactgga ttaaacaagc caacaagcc | 960 |
| gtaaacgcct tcatcagaga aagagaccgc gacttaccat gtatctcgtg cggaacgctc | 1020 |
| acgtctgctc agtgggatgc cggacattac cggacaactg ctgcggcacc tcaactccga | 1080 |

```
tttaatgaac gcaatattca caagcaatgc gtggtgtgca accagcacaa aagcggaaat    1140
ctcgttccgt atcgcgtcga actgattagc cgcatcgggc aggaagcagt agacgaaatc    1200
gaatcaaacc ataaccgcca tcgctggact atcgaagagt gcaaggcgat caaggcagag    1260
taccaacaga aactcaaaga cctgcgaaat agcagaagtg aggccgcatg acgttctcag    1320
taaaaaccat tccagacatg ctcgttgaaa catacgaaaa tcagacagaa gtagcacgca    1380
gactgaaatg tagtcgcggt acggtcagaa aatacgttga tgataaagac gggaaaatgc    1440
acgccatcgt caacgacgtt ctcatggttc atcgcggatg gagtgaaaga gatgcgctat    1500
tacgaaaaaa ttgatggcag caaataccga aatatttggg tagttggcga tctgcacgga    1560
tgctacacga acctgatgaa caaactggat acgattggat tcgacaacaa aaaagacctg    1620
cttatctcgg tgggcgattt ggttgatcgt ggtgcagaga acgttgaatg cctggaatta    1680
atcacattcc cctggttcag agctgtacgt ggaaaccatg agcaaatgat gattgatggc    1740
ttatcagagc gtggaaacgt taatcactgg ctgcttaatg gcggtggctg gttctttaat    1800
ctcgattacg acaaagaaat tctggctaaa gctcttgccc ataaagcaga tgaacttccg    1860
ttaatcatcg aactggtgag caaagataaa aaatatgtta tctgccacgc cgattatccc    1920
tttgacgaat acgagtttgg aaagccagtt gatcatcagc aggtaatctg gaaccgcgaa    1980
cgaatcagca actcacaaaa cgggatcgtg aaagaaatca aaggcgcgga cacgttcatc    2040
tttggtcata cgccagcagt gaaaccactc aagtttgcca accaaatgta tatcgatacc    2100
ggcgcagtgt tctgcggaaa cctaacattg attcaggtac agggagaagg cgcatgagac    2160
tcgaaagcgt agctaaattt cattcgccaa aaagcccgat gatgagcgac tcaccacggg    2220
ccacggcttc tgactctctt tccggtactg atgtgatggc tgctatgggg atggcgcaat    2280
cacaagccgg attcggtatg gctgcattct gcggtaagca cgaactcagc cagaacgaca    2340
aacaaaaggc tatcaactat ctgatgcaat ttgcacacaa ggtatcgggg aaataccgtg    2400
gtgtggcaaa gcttgaagga atactaagg caaaggtact gcaagtgctc gcaacattcg    2460
cttatgcgga ttattgccgt agtgccgcga cgccggggc aagatgcaga gattgccatg    2520
gtacaggccg tgcggttgat attgccaaaa cagagctgtg ggggagagtt gtcgagaaag    2580
agtgcggaag atgcaaaggc gtcggctatt caaggatgcc agcaagcgca gcatatcgcg    2640
ctgtgacgat gctaatccca aaccttaccc aacccacctg gtcacgcact gttaagccgc    2700
tgtatgacgc tctggtggtg caatgccaca agaagagtc aatcgcagac aacattttga    2760
atgcggtcac acgttagcag catgattgcc acggatggca acatattaac ggcatgatat    2820
tgacttattg aataaaattg ggtaaatttg actcaacgat gggttaattc gctcgttgtg    2880
gtagtgagat gaaaagaggc ggcgcttact accgattccg cctagttggt cacttcgacg    2940
tatcgtctgg aactccaacc atcgcaggca gagaggtctg caaaatgcaa tcccgaaaca    3000
gttcgcaggt aatagttaga gcctgcataa cggtttcggg attttttata tctgcacaac    3060
aggtaagagc attgagtcga taatcgtgaa gagtcggcga gcctggttag ccagtgctct    3120
ttccgttgtg ctgaattaag cgaataccgg aagcagaacc ggatcaccaa atgcgtacag    3180
gcgtcatcgc cgcccagcaa cagcacaacc caaactgagc cgtagccact gtctgtcctg    3240
aattcattag taatagttac gctgcggcct tttacacatg accttcgtga aagcgggtgg    3300
caggaggtcg cgctaacaac ctcctgccgt tttgcccgtg catatcggtc acgaacaaat    3360
ctgattacta aacacagtag cctggatttg ttctatcagt aatcgacctt attcctaatt    3420
aaatagagca aatcccctta ttgggggtaa gacatgaaga tgccagaaaa acatgacctg    3480
```

```
ttggccgcca ttctcgcggc aaaggaacaa ggcatcgggg caatccttgc gtttgcaatg    3540
gcgtaccttc gcggcagata taatggcggt gcgtttacaa aaacagtaat cgacgcaacg    3600
atgtgcgcca ttatcgccta gttcattcgt gaccttctcg acttcgccgg actaagtagc    3660
aatctcgctt atataacgag cgtgtttatc ggctacatcg gtactgactc gattggttcg    3720
cttatcaaac gcttcgctgc taaaaagcc ggagtagaag atggtagaaa tcaataatca    3780
acgtaaggcg ttcctcgata tgctggcgtg gtcggaggga actgataacg gacgtcagaa    3840
aaccagaaat catggttatg acgtcattgt aggcggagag ctatttactg attactccga    3900
tcaccctcgc aaacttgtca cgctaaaccc aaaactcaaa tcaacaggcg ccggacgcta    3960
ccagcttctt tcccgttggt gggatgccta ccgcaagcag cttggcctga aagacttctc    4020
tccgaaaagt caggacgctg tggcattgca gcagattaag gagcgtggcg ctttacctat    4080
gattgatcgt ggtgatatcc gtcaggcaat cgaccgttgc agcaatatct gggcttcact    4140
gccgggcgct ggttatggtc agttcgagca taaggctgac agcctgattg caaaattcaa    4200
agaagcgggc ggaacggtca gagagattga tgtatgagca gagtcaccgc gattatctcc    4260
gctctggtta tctgcatcat cgtctgcctg tcatgggctg ttaatcatta ccgtgataac    4320
gccattacct acaaagccca gcgcgacaaa atgccagaa aactgaagct ggcgaacgcg    4380
gcaattactg acatgcagat gcgtcagcgt gatgttgctg cgctcgatgc aaaatacacg    4440
aaggagttag ctgatgctaa agctgaaaat gatgctctgc gtgatgatgt tgccgctggt    4500
cgtcgtcggt tgcacatcaa agcagtctgt cagtcagtgc gtgaagccac caccgcctcc    4560
ggcgtggata atgcagcctc cccccgactg gcagacaccg ctgaacggga ttatttcacc    4620
ctcagagaga ggctgatcac tatgcaaaaa caactggaag gaacccagaa gtatattaat    4680
gagcagtgca gatagagttg cccatatcga tgggcaactc atgcaattat tgtgagcaat    4740
acacacgcgc ttccagcgga gtataaatgc ctaaagtaat aaaaccgagc aatccattta    4800
cgaatgtttg ctgggtttct gttttaacaa catttctgc gccgccacaa attttggctg    4860
catcgacagt tttcttctgc ccaattccag aaacgaagaa atgatgggtg atggtttcct    4920
ttggtgctac tgctgccggt ttgttttgaa cagtaaacgt ctgttgagca catcctgtaa    4980
taagcagggc cagcgcagta gcgagtagca ttttttttcat ggtgttattc ccgatgcttt    5040
ttgaagttcg cagaatcgta tgtgtagaaa attaaacaaa ccctaaacaa tgagttgaaa    5100
tttcatattg ttaatattta ttaatgtatg tcaggtgcga tgaatcgtca ttgtattccc    5160
ggattaacta tgtccacagc cctgacgggg aacttctctg cgggagtgtc cgggaataat    5220
taaaacgatg cacacagggt ttagcgcgta cacgtattgc attatgccaa cgccccggtg    5280
ctgacacgga agaaaccgga cgttatgatt tagcgtggaa agatttgtgt agtgttctga    5340
atgctctcag taaatagtaa tgaattatca aaggtatagt aatatctttt atgttcatgg    5400
atatttgtaa cccatcggaa aactcctgct ttagcaagat tttccctgta ttgctgaaat    5460
gtgatttctc ttgatttcaa cctatcatag gacgtttcta aagatgcgt gtttcttgag    5520 aatttaacat ttacaacctt tttaagtcct tttattaaca cggtgttatc gttttctaac    5580
acgatgtgaa tattatctgt ggctagatag taaatataat gtgagacgtt gtgacgtttt    5640
agttcagaat aaaacaattc acagtctaaa tcttttcgca cttgatcgaa tatttcttta    5700
aaaatggcaa cctgagccat tggtaaaacc ttccatgtga tacgagggcg cgtagtttgc    5760
attatcgttt ttatcgtttc aatctggtct gacctccttg tgttttgttg atgatttatg    5820
tcaaatatta ggaatgtttt cacttaatag tattggttgc gtaacaaagt gcggtcctgc    5880
```

| | | |
|---|---|---|
| tggcattctg gagggaaata caaccgacag atgtatgtaa ggccaacgtg ctcaaatctt | 5940 | |
| catacagaaa gatttgaagt aatattttaa ccgctagatg aagagcaagc gcatggagcg | 6000 | |
| acaaaatgaa taaagaacaa tctgctgatg atccctccgt ggatctgatt cgtgtaaaaa | 6060 | |
| atatgcttaa tagcaccatt tctatgagtt accctgatgt tgtaattgca tgtatagaac | 6120 | |
| ataaggtgtc tctggaagca ttcagagcaa ttgaggcagc gttggtgaag cacgataata | 6180 | |
| atatgaagga ttattccctg gtggttgact gatcaccata actgctaatc attcaaacta | 6240 | |
| tttagtctgt gacagagcca acacgcagtc tgtcactgtc aggaaagtgg taaaactgca | 6300 | |
| actcaattac tgcaatgccc tcgtaattaa gtgaatttac aatatcgtcc tgttcggagg | 6360 | |
| gaagaacgcg ggatgttcat tcttcatcac ttttaattga tgtatatgct ctcttttctg | 6420 | |
| acgttagtct ccgacggcag gcttcaatga cccaggctga gaaattcccg gaccctttt | 6480 | |
| gctcaagagc gatgttaatt tgttcaatca tttggttagg aaagcggatg ttgcgggttg | 6540 | |
| ttgttctgcg ggttctgttc ttcgttgaca tgaggttgcc ccgtattcag tgtcgctgat | 6600 | |
| ttgtattgtc tgaagttgtt tttacgttaa gttgatgcag atcaattaat acgatacctg | 6660 | |
| cgtcataatt gattatttga cgtggtttga tggcctccac gcacgttgtg atatgtagat | 6720 | |
| gataatcatt atcactttac gggtcctttc cggtgatccg acaggttacg | 6770 | |

```
<210> SEQ ID NO 29
<211> LENGTH: 1400
<212> TYPE: PRT
<213> ORGANISM: Artificial Sequence
<220> FEATURE:
<223> OTHER INFORMATION: Polypeptide used in the Examples

<400> SEQUENCE: 29
```

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

```
Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
610                 615                 620
```

-continued

Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Tyr
            645                 650                 655

Thr Gly Trp Gly Arg Leu Ser Arg Lys Leu Ile Asn Gly Ile Arg Asp
        660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
        820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
        900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

```
Tyr Ser Asn Ile Met Asn Phe Phe Lys Thr Glu Ile Thr Leu Ala
    1040            1045                1050

Asn Gly Glu Ile Arg Lys Arg Pro Leu Ile Glu Thr Asn Gly Glu
    1055            1060                1065

Thr Gly Glu Ile Val Trp Asp Lys Gly Arg Asp Phe Ala Thr Val
    1070            1075                1080

Arg Lys Val Leu Ser Met Pro Gln Val Asn Ile Val Lys Lys Thr
    1085            1090                1095

Glu Val Gln Thr Gly Gly Phe Ser Lys Glu Ser Ile Leu Pro Lys
    1100            1105                1110

Arg Asn Ser Asp Lys Leu Ile Ala Arg Lys Lys Asp Trp Asp Pro
    1115            1120                1125

Lys Lys Tyr Gly Gly Phe Asp Ser Pro Thr Val Ala Tyr Ser Val
    1130            1135                1140

Leu Val Val Ala Lys Val Glu Lys Gly Lys Ser Lys Lys Leu Lys
    1145            1150                1155

Ser Val Lys Glu Leu Leu Gly Ile Thr Ile Met Glu Arg Ser Ser
    1160            1165                1170

Phe Glu Lys Asn Pro Ile Asp Phe Leu Glu Ala Lys Gly Tyr Lys
    1175            1180                1185

Glu Val Lys Lys Asp Leu Ile Ile Lys Leu Pro Lys Tyr Ser Leu
    1190            1195                1200

Phe Glu Leu Glu Asn Gly Arg Lys Arg Met Leu Ala Ser Ala Gly
    1205            1210                1215

Glu Leu Gln Lys Gly Asn Glu Leu Ala Leu Pro Ser Lys Tyr Val
    1220            1225                1230

Asn Phe Leu Tyr Leu Ala Ser His Tyr Glu Lys Leu Lys Gly Ser
    1235            1240                1245

Pro Glu Asp Asn Glu Gln Lys Gln Leu Phe Val Glu Gln His Lys
    1250            1255                1260

His Tyr Leu Asp Glu Ile Ile Glu Gln Ile Ser Glu Phe Ser Lys
    1265            1270                1275

Arg Val Ile Leu Ala Asp Ala Asn Leu Asp Lys Val Leu Ser Ala
    1280            1285                1290

Tyr Asn Lys His Arg Asp Lys Pro Ile Arg Glu Gln Ala Glu Asn
    1295            1300                1305

Ile Ile His Leu Phe Thr Leu Thr Asn Leu Gly Ala Pro Ala Ala
    1310            1315                1320

Phe Lys Tyr Phe Asp Thr Thr Ile Asp Arg Lys Arg Tyr Thr Ser
    1325            1330                1335

Thr Lys Glu Val Leu Asp Ala Thr Leu Ile His Gln Ser Ile Thr
    1340            1345                1350

Gly Leu Tyr Glu Thr Arg Ile Asp Leu Ser Gln Leu Gly Gly Asp
    1355            1360                1365

Gly Gly Ser Glu Asn Leu Tyr Phe Gln Gly Gly Ser Trp Ser His
    1370            1375                1380

Pro Gln Phe Glu Lys Gly Gly Gly Ser Trp Ser His Pro Gln Phe
    1385            1390                1395

Glu Lys
    1400
```

-continued

```
<210> SEQ ID NO 30
<211> LENGTH: 1400
<212> TYPE: PRT
<213> ORGANISM: Artificial Sequence
<220> FEATURE:
<223> OTHER INFORMATION: Polypeptide used in the Examples

<400> SEQUENCE: 30
```

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

```
Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
770                 775                 780
```

```
Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Val Val Lys Lys Met Lys Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185
```

```
Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

Gly Gly Ser Glu Asn Leu Tyr Phe Gln Gly Gly Ser Trp Ser His
    1370                1375                1380

Pro Gln Phe Glu Lys Gly Gly Gly Ser Trp Ser His Pro Gln Phe
    1385                1390                1395

Glu Lys
    1400

<210> SEQ ID NO 31
<211> LENGTH: 1400
<212> TYPE: PRT
<213> ORGANISM: Artificial Sequence
<220> FEATURE:
<223> OTHER INFORMATION: Polypeptide used in the Examples

<400> SEQUENCE: 31

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125
```

```
His Glu Lys Tyr Pro Thr Ile Tyr His Leu Arg Lys Lys Leu Val Asp
    130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                165                 170                 175
Asp Asn Ser Asp Val Asp Lys Leu Phe Ile Gln Leu Val Gln Thr Tyr
            180                 185                 190
Asn Gln Leu Phe Glu Glu Asn Pro Ile Asn Ala Ser Gly Val Asp Ala
        195                 200                 205
Lys Ala Ile Leu Ser Ala Arg Leu Ser Lys Ser Arg Arg Leu Glu Asn
210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
            260                 265                 270
Asp Asp Leu Asp Asn Leu Leu Ala Gln Ile Gly Asp Gln Tyr Ala Asp
        275                 280                 285
Leu Phe Leu Ala Ala Lys Asn Leu Ser Asp Ala Ile Leu Leu Ser Asp
290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
        355                 360                 365
Gln Glu Glu Phe Tyr Lys Phe Ile Lys Pro Ile Leu Glu Lys Met Asp
370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
        435                 440                 445
Pro Tyr Tyr Val Gly Pro Leu Ala Arg Gly Asn Ser Arg Phe Ala Trp
450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
        515                 520                 525
Tyr Val Thr Glu Gly Met Arg Lys Pro Ala Phe Leu Ser Gly Glu Gln
530                 535                 540
```

```
Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp Ala Ile Val Pro Gln Ser Phe Leu Lys
                835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
                930                 935                 940

Glu Asn Asp Lys Leu Ile Arg Glu Val Lys Val Ile Thr Leu Lys Ser
945                 950                 955                 960
```

```
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
            980                 985                 990
Val Gly Thr Ala Leu Ile Lys Lys Tyr Pro Lys Leu Glu Ser Glu Phe
        995                 1000                1005
Val Tyr Gly Asp Tyr Lys Val Tyr Asp Val Arg Lys Met Ile Ala
    1010                1015                1020
Lys Ser Glu Gln Glu Ile Gly Lys Ala Thr Ala Lys Tyr Phe Phe
    1025                1030                1035
Tyr Ser Asn Ile Met Asn Phe Phe Lys Thr Glu Ile Thr Leu Ala
    1040                1045                1050
Asn Gly Glu Ile Arg Lys Arg Pro Leu Ile Glu Thr Asn Gly Glu
    1055                1060                1065
Thr Gly Glu Ile Val Trp Asp Lys Gly Arg Asp Phe Ala Thr Val
    1070                1075                1080
Arg Lys Val Leu Ser Met Pro Gln Val Asn Ile Val Lys Lys Thr
    1085                1090                1095
Glu Val Gln Thr Gly Gly Phe Ser Lys Glu Ser Ile Leu Pro Lys
    1100                1105                1110
Arg Asn Ser Asp Lys Leu Ile Ala Arg Lys Lys Asp Trp Asp Pro
    1115                1120                1125
Lys Lys Tyr Gly Gly Phe Asp Ser Pro Thr Val Ala Tyr Ser Val
    1130                1135                1140
Leu Val Val Ala Lys Val Glu Lys Gly Lys Ser Lys Lys Leu Lys
    1145                1150                1155
Ser Val Lys Glu Leu Leu Gly Ile Thr Ile Met Glu Arg Ser Ser
    1160                1165                1170
Phe Glu Lys Asn Pro Ile Asp Phe Leu Glu Ala Lys Gly Tyr Lys
    1175                1180                1185
Glu Val Lys Lys Asp Leu Ile Ile Lys Leu Pro Lys Tyr Ser Leu
    1190                1195                1200
Phe Glu Leu Glu Asn Gly Arg Lys Arg Met Leu Ala Ser Ala Gly
    1205                1210                1215
Glu Leu Gln Lys Gly Asn Glu Leu Ala Leu Pro Ser Lys Tyr Val
    1220                1225                1230
Asn Phe Leu Tyr Leu Ala Ser His Tyr Glu Lys Leu Lys Gly Ser
    1235                1240                1245
Pro Glu Asp Asn Glu Gln Lys Gln Leu Phe Val Glu Gln His Lys
    1250                1255                1260
His Tyr Leu Asp Glu Ile Ile Glu Gln Ile Ser Glu Phe Ser Lys
    1265                1270                1275
Arg Val Ile Leu Ala Asp Ala Asn Leu Asp Lys Val Leu Ser Ala
    1280                1285                1290
Tyr Asn Lys His Arg Asp Lys Pro Ile Arg Glu Gln Ala Glu Asn
    1295                1300                1305
Ile Ile His Leu Phe Thr Leu Thr Asn Leu Gly Ala Pro Ala Ala
    1310                1315                1320
Phe Lys Tyr Phe Asp Thr Thr Ile Asp Arg Lys Arg Tyr Thr Ser
    1325                1330                1335
Thr Lys Glu Val Leu Asp Ala Thr Leu Ile His Gln Ser Ile Thr
    1340                1345                1350
```

-continued

```
Gly Leu Tyr Glu Thr Arg Ile Asp Leu Ser Gln Leu Gly Gly Asp
    1355                1360                1365

Gly Gly Ser Glu Asn Leu Tyr Phe Gln Gly Gly Ser Trp Ser His
    1370                1375                1380

Pro Gln Phe Glu Lys Gly Gly Ser Trp Ser His Pro Gln Phe
    1385                1390                1395

Glu Lys
    1400

<210> SEQ ID NO 32
<211> LENGTH: 1400
<212> TYPE: PRT
<213> ORGANISM: Artificial Sequence
<220> FEATURE:
<223> OTHER INFORMATION: Polypeptide used in the Examples

<400> SEQUENCE: 32

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300
```

```
Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
            325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
        370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
            405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
            645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720
```

His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
            740                 745                 750
Arg His Lys Pro Glu Asn Ile Val Ile Glu Met Ala Arg Glu Asn Gln
        755                 760                 765
Thr Thr Gln Lys Gly Gln Lys Asn Ser Arg Glu Arg Met Lys Arg Ile
    770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
                805                 810                 815
Gln Asn Gly Arg Asp Met Tyr Val Asp Gln Glu Leu Asp Ile Asn Arg
            820                 825                 830
Leu Ser Asp Tyr Asp Val Asp Ala Ile Val Pro Gln Ser Phe Leu Lys
        835                 840                 845
Asp Asp Ser Ile Asp Asn Lys Val Leu Thr Arg Ser Asp Lys Asn Arg
    850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
            900                 905                 910
Lys Ala Gly Phe Ile Lys Arg Gln Leu Val Glu Thr Arg Gln Ile Thr
        915                 920                 925
Lys His Val Ala Gln Ile Leu Asp Ser Arg Met Asn Thr Lys Tyr Asp
    930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
            980                 985                 990
Val Gly Thr Ala Leu Ile Lys Lys Tyr Pro Lys Leu Glu Ser Glu Phe
        995                 1000                1005
Val Tyr Gly Asp Tyr Lys Val Tyr Asp Val Arg Lys Met Ile Ala
    1010                1015                1020
Lys Ser Glu Gln Glu Ile Gly Lys Ala Thr Ala Lys Tyr Phe Phe
    1025                1030                1035
Tyr Ser Asn Ile Met Asn Phe Phe Lys Thr Glu Ile Thr Leu Ala
    1040                1045                1050
Asn Gly Glu Ile Arg Lys Arg Pro Leu Ile Glu Thr Asn Gly Glu
    1055                1060                1065
Thr Gly Glu Ile Val Trp Asp Lys Gly Arg Asp Phe Ala Thr Val
    1070                1075                1080
Arg Lys Val Leu Ser Met Pro Gln Val Asn Ile Val Lys Lys Thr
    1085                1090                1095
Glu Val Gln Thr Gly Gly Phe Ser Lys Glu Ser Ile Leu Pro Lys
    1100                1105                1110
Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
1130                    1135                1140

Leu Val Val Ala Lys Val Glu Lys Gly Lys Ser Lys Lys Leu Lys
1145                    1150                1155

Ser Val Lys Glu Leu Leu Gly Ile Thr Ile Met Glu Arg Ser Ser
1160                    1165                1170

Phe Glu Lys Asn Pro Ile Asp Phe Leu Glu Ala Lys Gly Tyr Lys
1175                    1180                1185

Glu Val Lys Lys Asp Leu Ile Ile Lys Leu Pro Lys Tyr Ser Leu
1190                    1195                1200

Phe Glu Leu Glu Asn Gly Arg Lys Arg Met Leu Ala Ser Ala Gly
1205                    1210                1215

Glu Leu Gln Lys Gly Asn Glu Leu Ala Leu Pro Ser Lys Tyr Val
1220                    1225                1230

Asn Phe Leu Tyr Leu Ala Ser His Tyr Glu Lys Leu Lys Gly Ser
1235                    1240                1245

Pro Glu Asp Asn Glu Gln Lys Gln Leu Phe Val Glu Gln His Lys
1250                    1255                1260

His Tyr Leu Asp Glu Ile Ile Glu Gln Ile Ser Glu Phe Ser Lys
1265                    1270                1275

Arg Val Ile Leu Ala Asp Ala Asn Leu Asp Lys Val Leu Ser Ala
1280                    1285                1290

Tyr Asn Lys His Arg Asp Lys Pro Ile Arg Glu Gln Ala Glu Asn
1295                    1300                1305

Ile Ile His Leu Phe Thr Leu Thr Asn Leu Gly Ala Pro Ala Ala
1310                    1315                1320

Phe Lys Tyr Phe Asp Thr Thr Ile Asp Arg Lys Arg Tyr Thr Ser
1325                    1330                1335

Thr Lys Glu Val Leu Asp Ala Thr Leu Ile His Gln Ser Ile Thr
1340                    1345                1350

Gly Leu Tyr Glu Thr Arg Ile Asp Leu Ser Gln Leu Gly Gly Asp
1355                    1360                1365

Gly Gly Ser Glu Asn Leu Tyr Phe Gln Gly Gly Ser Trp Ser His
1370                    1375                1380

Pro Gln Phe Glu Lys Gly Gly Gly Ser Trp Ser His Pro Gln Phe
1385                    1390                1395

Glu Lys
1400

<210> SEQ ID NO 33
<211> LENGTH: 33
<212> TYPE: DNA
<213> ORGANISM: Artificial Sequence
<220> FEATURE:
<223> OTHER INFORMATION: Polynucleotide used in Examples 2 and 4

<400> SEQUENCE: 33
ggcgtctgct tgggtgttta acctttttttt ttt        33

<210> SEQ ID NO 34
<211> LENGTH: 28
<212> TYPE: DNA
<213> ORGANISM: Artificial Sequence
<220> FEATURE:
<223> OTHER INFORMATION: Polynucleotide used in Examples 2 and 4

<400> SEQUENCE: 34
aatgtacttc gttcagttac gtattgct					28

<210> SEQ ID NO 35
<211> LENGTH: 45
<212> TYPE: DNA
<213> ORGANISM: Artificial Sequence
<220> FEATURE:
<223> OTHER INFORMATION: Polynucleotide used in Examples 2 and 4
<220> FEATURE:
<221> NAME/KEY: misc_feature
<222> LOCATION: (1)..(1)
<223> OTHER INFORMATION: 5' phosphate moiety
<220> FEATURE:
<221> NAME/KEY: misc_feature
<222> LOCATION: (23)..(27)
<223> OTHER INFORMATION: branched nucleic acid
<220> FEATURE:
<221> NAME/KEY: modified_base
<222> LOCATION: (24)..(24)
<223> OTHER INFORMATION: methylcytosine

<400> SEQUENCE: 35
gcaatacgta actgaacgaa gtacattttt gaggcgagcg gtcaa					45

<210> SEQ ID NO 36
<211> LENGTH: 25
<212> TYPE: DNA
<213> ORGANISM: Artificial Sequence
<220> FEATURE:
<223> OTHER INFORMATION: Polynucleotide used in Examples 2 and 4
<220> FEATURE:
<221> NAME/KEY: misc_feature
<222> LOCATION: (1)..(5)
<223> OTHER INFORMATION: branched nucleic acid

<400> SEQUENCE: 36
ggttaaacac ccaagcagac gcctt					25

<210> SEQ ID NO 37
<211> LENGTH: 15
<212> TYPE: DNA
<213> ORGANISM: Artificial Sequence
<220> FEATURE:
<223> OTHER INFORMATION: Polynucleotide used in Example 3
<220> FEATURE:
<221> NAME/KEY: misc_feature
<222> LOCATION: (1)..(1)
<223> OTHER INFORMATION: 3' cholesterol moiety

<400> SEQUENCE: 37
ttgaccgctc gcctc					15

<210> SEQ ID NO 38
<211> LENGTH: 20
<212> TYPE: RNA
<213> ORGANISM: Artificial Sequence
<220> FEATURE:
<223> OTHER INFORMATION: Polynucleotide used in Examples 4 and 5

<400> SEQUENCE: 38
ccgaccacgc cagcauaucg					20

<210> SEQ ID NO 39
<211> LENGTH: 33
<212> TYPE: DNA
<213> ORGANISM: Artificial Sequence
<220> FEATURE:
<223> OTHER INFORMATION: Polynucleotide used in Example 4

```
<400> SEQUENCE: 39
ggcgtctgct tgggtgttta acctttttt ttt                            33

<210> SEQ ID NO 40
<211> LENGTH: 28
<212> TYPE: DNA
<213> ORGANISM: Artificial Sequence
<220> FEATURE:
<223> OTHER INFORMATION: Polynucleotide used in Example 4

<400> SEQUENCE: 40
aatgtacttc gttcagttac gtattgct                                 28

<210> SEQ ID NO 41
<211> LENGTH: 45
<212> TYPE: DNA
<213> ORGANISM: Artificial Sequence
<220> FEATURE:
<223> OTHER INFORMATION: Polynucleotide used in Example 4
<220> FEATURE:
<221> NAME/KEY: misc_feature
<222> LOCATION: (1)..(1)
<223> OTHER INFORMATION: 5' phosphate moiety
<220> FEATURE:
<221> NAME/KEY: misc_feature
<222> LOCATION: (23)..(27)
<223> OTHER INFORMATION: branched nucleic acid
<220> FEATURE:
<221> NAME/KEY: modified_base
<222> LOCATION: (24)..(24)
<223> OTHER INFORMATION: methylcytosine

<400> SEQUENCE: 41
gcaatacgta actgaacgaa gtacattttt gaggcgagcg gtcaa              45

<210> SEQ ID NO 42
<211> LENGTH: 25
<212> TYPE: DNA
<213> ORGANISM: Artificial Sequence
<220> FEATURE:
<223> OTHER INFORMATION: Polynucleotide used in Example 4
<220> FEATURE:
<221> NAME/KEY: misc_feature
<222> LOCATION: (1)..(5)
<223> OTHER INFORMATION: branched nucleic acid

<400> SEQUENCE: 42
ggttaaacac ccaagcagac gcctt                                    25

<210> SEQ ID NO 43
<211> LENGTH: 15
<212> TYPE: DNA
<213> ORGANISM: Artificial Sequence
<220> FEATURE:
<223> OTHER INFORMATION: Polynucleotide used in the Examples

<400> SEQUENCE: 43
ttgaccgctc gcctc                                               15

<210> SEQ ID NO 44
<211> LENGTH: 20
<212> TYPE: DNA
<213> ORGANISM: Artificial Sequence
<220> FEATURE:
<223> OTHER INFORMATION: Polynucleotide used in Examples 6, 7, 8, 9, 10
      and 11
```

-continued

```
<400> SEQUENCE: 44
tacatttaag accctaatat                                                  20

<210> SEQ ID NO 45
<211> LENGTH: 67
<212> TYPE: RNA
<213> ORGANISM: Artificial Sequence
<220> FEATURE:
<223> OTHER INFORMATION: Polynucleotide used in Examples 1, 6, 7, 8, 9,
      10 and 11
<220> FEATURE:
<221> NAME/KEY: modified_base
<222> LOCATION: (1)..(2)
<223> OTHER INFORMATION: Phosphorothioated 2'O-Methyl RNA
<220> FEATURE:
<221> NAME/KEY: modified_base
<222> LOCATION: (3)..(9)
<223> OTHER INFORMATION: methylated
<220> FEATURE:
<221> NAME/KEY: modified_base
<222> LOCATION: (38)..(64)
<223> OTHER INFORMATION: methylated
<220> FEATURE:
<221> NAME/KEY: modified_base
<222> LOCATION: (65)..(66)
<223> OTHER INFORMATION: Phosphorothioated 2'O-Methyl RNA
<220> FEATURE:
<221> NAME/KEY: modified_base
<222> LOCATION: (67)..(67)
<223> OTHER INFORMATION: methylated

<400> SEQUENCE: 45
agcauagcaa guuaaaauaa ggcuaguccg uuaucaacuu gaaaaagugg caccgagucg      60
gugcuuu                                                                67

<210> SEQ ID NO 46
<211> LENGTH: 20
<212> TYPE: DNA
<213> ORGANISM: Artificial Sequence
<220> FEATURE:
<223> OTHER INFORMATION: Polynucleotide used in Examples 6, 8, 9, 10, 11
      and 12

<400> SEQUENCE: 46
atattagggt cttaaatgta                                                  20

<210> SEQ ID NO 47
<211> LENGTH: 20
<212> TYPE: DNA
<213> ORGANISM: Artificial Sequence
<220> FEATURE:
<223> OTHER INFORMATION: Polynucleotide used in Examples 9, 10 and 11

<400> SEQUENCE: 47
agaccaaaga gggggacctt                                                  20

<210> SEQ ID NO 48
<211> LENGTH: 1412
<212> TYPE: PRT
<213> ORGANISM: Artificial Sequence
<220> FEATURE:
<223> OTHER INFORMATION: Polypeptide used in the Examples

<400> SEQUENCE: 48

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30
```

-continued

```
Lys Val Leu Gly Asn Thr Asp Arg His Ser Ile Lys Lys Asn Leu Ile
            35                  40                  45
Gly Ala Leu Leu Phe Asp Ser Gly Glu Thr Ala Glu Ala Thr Arg Leu
    50                  55                  60
Lys Arg Thr Ala Arg Arg Tyr Thr Arg Arg Lys Asn Arg Ile Cys
65                  70                  75                  80
Tyr Leu Gln Glu Ile Phe Ser Asn Glu Met Ala Lys Val Asp Asp Ser
                85                  90                  95
Phe Phe His Arg Leu Glu Glu Ser Phe Leu Val Glu Glu Asp Lys Lys
            100                 105                 110
His Glu Arg His Pro Ile Phe Gly Asn Ile Val Asp Glu Val Ala Tyr
        115                 120                 125
His Glu Lys Tyr Pro Thr Ile Tyr His Leu Arg Lys Lys Leu Val Asp
    130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                165                 170                 175
Asp Asn Ser Asp Val Asp Lys Leu Phe Ile Gln Leu Val Gln Thr Tyr
            180                 185                 190
Asn Gln Leu Phe Glu Glu Asn Pro Ile Asn Ala Ser Gly Val Asp Ala
        195                 200                 205
Lys Ala Ile Leu Ser Ala Arg Leu Ser Lys Ser Arg Arg Leu Glu Asn
    210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
            260                 265                 270
Asp Asp Leu Asp Asn Leu Leu Ala Gln Ile Gly Asp Gln Tyr Ala Asp
        275                 280                 285
Leu Phe Leu Ala Ala Lys Asn Leu Ser Asp Ala Ile Leu Leu Ser Asp
    290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
        355                 360                 365
Gln Glu Glu Phe Tyr Lys Phe Ile Lys Pro Ile Leu Glu Lys Met Asp
    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
        435                 440                 445
```

```
Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
    755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
    835                 840                 845

Asp Asp Ser Ile Asp Asn Lys Val Leu Thr Arg Ser Asp Lys Asn Arg
850                 855                 860
```

```
Gly Lys Ser Asp Asn Val Pro Ser Glu Glu Val Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val
        1130                1135                1140

Leu Val Val Ala Lys Val Glu Lys Gly Lys Ser Lys Lys Leu Lys
        1145                1150                1155

Ser Val Lys Glu Leu Leu Gly Ile Thr Ile Met Glu Arg Ser Ser
        1160                1165                1170

Phe Glu Lys Asn Pro Ile Asp Phe Leu Glu Ala Lys Gly Tyr Lys
        1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Gly
        1205                1210                1215

Glu Leu Gln Lys Gly Asn Glu Leu Ala Leu Pro Ser Lys Tyr Val
        1220                1225                1230

Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys
        1250                1255                1260
```

| His | Tyr | Leu | Asp | Glu | Ile | Ile | Glu | Gln | Ile | Ser | Glu | Phe | Ser | Lys |
|  | 1265 |  |  |  |  | 1270 |  |  |  |  | 1275 |  |  |  |

| Arg | Val | Ile | Leu | Ala | Asp | Ala | Asn | Leu | Asp | Lys | Val | Leu | Ser | Ala |
| 1280 |  |  |  |  | 1285 |  |  |  |  | 1290 |  |  |  |  |

| Tyr | Asn | Lys | His | Arg | Asp | Lys | Pro | Ile | Arg | Glu | Gln | Ala | Glu | Asn |
| 1295 |  |  |  |  | 1300 |  |  |  |  | 1305 |  |  |  |  |

| Ile | Ile | His | Leu | Phe | Thr | Leu | Thr | Asn | Leu | Gly | Ala | Pro | Ala | Ala |
| 1310 |  |  |  |  | 1315 |  |  |  |  | 1320 |  |  |  |  |

| Phe | Lys | Tyr | Phe | Asp | Thr | Thr | Ile | Asp | Arg | Lys | Arg | Tyr | Thr | Ser |
| 1325 |  |  |  |  | 1330 |  |  |  |  | 1335 |  |  |  |  |

| Thr | Lys | Glu | Val | Leu | Asp | Ala | Thr | Leu | Ile | His | Gln | Ser | Ile | Thr |
| 1340 |  |  |  |  | 1345 |  |  |  |  | 1350 |  |  |  |  |

| Gly | Leu | Tyr | Glu | Thr | Arg | Ile | Asp | Leu | Ser | Gln | Leu | Gly | Gly | Asp |
| 1355 |  |  |  |  | 1360 |  |  |  |  | 1365 |  |  |  |  |

| Gly | Gly | Ser | Glu | Asn | Leu | Tyr | Phe | Gln | Gly | Ser | Gly | Gly | Ser | Ala |
| 1370 |  |  |  |  | 1375 |  |  |  |  | 1380 |  |  |  |  |

| Trp | Ser | His | Pro | Gln | Phe | Glu | Lys | Gly | Gly | Gly | Ser | Gly | Gly | Gly |
| 1385 |  |  |  |  | 1390 |  |  |  |  | 1395 |  |  |  |  |

| Ser | Gly | Gly | Gly | Ser | Ala | Trp | Ser | His | Pro | Gln | Phe | Glu | Lys |  |
| 1400 |  |  |  |  | 1405 |  |  |  |  | 1410 |  |  |  |  |

<210> SEQ ID NO 49
<211> LENGTH: 39
<212> TYPE: DNA
<213> ORGANISM: Artificial Sequence
<220> FEATURE:
<223> OTHER INFORMATION: Polynucleotide used in Example 7

<400> SEQUENCE: 49
atattagggt cttaaatagc tcagaaaaga gtcattgca            39

<210> SEQ ID NO 50
<211> LENGTH: 39
<212> TYPE: DNA
<213> ORGANISM: Artificial Sequence
<220> FEATURE:
<223> OTHER INFORMATION: Polynucleotide used in Example 7
<220> FEATURE:
<221> NAME/KEY: misc_feature
<222> LOCATION: (20)..(26)
<223> OTHER INFORMATION: branched nucleic acid
<220> FEATURE:
<221> NAME/KEY: modified_base
<222> LOCATION: (20)..(20)
<223> OTHER INFORMATION: methylcytosine
<220> FEATURE:
<221> NAME/KEY: misc_feature
<222> LOCATION: (37)..(38)
<223> OTHER INFORMATION: branched nucleic acid

<400> SEQUENCE: 50
tgcaatgact cttttctgac gtatttaaga ccctaatat            39

<210> SEQ ID NO 51
<211> LENGTH: 20
<212> TYPE: DNA
<213> ORGANISM: Artificial Sequence
<220> FEATURE:
<223> OTHER INFORMATION: Polynucleotide used in Example 7

<400> SEQUENCE: 51
tgttctgatc ggaacgatcg            20

-continued

```
<210> SEQ ID NO 52
<211> LENGTH: 51
<212> TYPE: DNA
<213> ORGANISM: Artificial Sequence
<220> FEATURE:
<223> OTHER INFORMATION: Polynucleotide used in Examples 7 and 8
<220> FEATURE:
<221> NAME/KEY: misc_feature
<222> LOCATION: (1)..(36)
<223> OTHER INFORMATION: is a ribonucleotide

<400> SEQUENCE: 52
agaccaaaga gggggaccuu guuuuagagc uaugcuagca atacatcttt g        51

<210> SEQ ID NO 53
<211> LENGTH: 20
<212> TYPE: DNA
<213> ORGANISM: Artificial Sequence
<220> FEATURE:
<223> OTHER INFORMATION: Polynucleotide used in Example 10

<400> SEQUENCE: 53
tagatgatca acgtaagtag                                           20

<210> SEQ ID NO 54
<211> LENGTH: 20
<212> TYPE: DNA
<213> ORGANISM: Artificial Sequence
<220> FEATURE:
<223> OTHER INFORMATION: Polynucleotide used in Example 10

<400> SEQUENCE: 54
ggatgggtgg ctgtttccct                                           20

<210> SEQ ID NO 55
<211> LENGTH: 67
<212> TYPE: DNA
<213> ORGANISM: Artificial Sequence
<220> FEATURE:
<223> OTHER INFORMATION: Polynucleotide used in Example 12
<220> FEATURE:
<221> NAME/KEY: misc_feature
<222> LOCATION: (27)..(67)
<223> OTHER INFORMATION: is a ribonucleotide

<400> SEQUENCE: 55
tacatttaag accctaatat tttttuaau uucuacucuu guagauauca uggcucagau   60
ugaacgc                                                          67

<210> SEQ ID NO 56
<211> LENGTH: 1368
<212> TYPE: PRT
<213> ORGANISM: Artificial Sequence
<220> FEATURE:
<223> OTHER INFORMATION: Polypeptide used in Example 12

<400> SEQUENCE: 56

Met Ser Ala Trp Ser His Pro Gln Phe Glu Lys Gly Gly Gly Ser Gly
1               5                   10                  15

Gly Gly Ser Gly Gly Ser Ala Trp Ser His Pro Gln Phe Glu Lys Ser
            20                  25                  30

Gly Gly Gly Gly Gly Glu Asn Leu Tyr Phe Gln Gly Met Thr Gln Phe
        35                  40                  45

Glu Gly Phe Thr Asn Leu Tyr Gln Val Ser Lys Thr Leu Arg Phe Glu
    50                  55                  60
```

```
Leu Ile Pro Gln Gly Lys Thr Leu Lys His Ile Gln Glu Gln Gly Phe
 65                  70                  75                  80

Ile Glu Glu Asp Lys Ala Arg Asn Asp His Tyr Lys Glu Leu Lys Pro
                 85                  90                  95

Ile Ile Asp Arg Ile Tyr Lys Thr Tyr Ala Asp Gln Cys Leu Gln Leu
                100                 105                 110

Val Gln Leu Asp Trp Glu Asn Leu Ser Ala Ala Ile Asp Ser Tyr Arg
            115                 120                 125

Lys Glu Lys Thr Glu Thr Arg Asn Ala Leu Ile Glu Glu Gln Ala
            130                 135                 140

Thr Tyr Arg Asn Ala Ile His Asp Tyr Phe Ile Gly Arg Thr Asp Asn
145                 150                 155                 160

Leu Thr Asp Ala Ile Asn Lys Arg His Ala Glu Ile Tyr Lys Gly Leu
                165                 170                 175

Phe Lys Ala Glu Leu Phe Asn Gly Lys Val Leu Lys Gln Leu Gly Thr
            180                 185                 190

Val Thr Thr Thr Glu His Glu Asn Ala Leu Leu Arg Ser Phe Asp Lys
            195                 200                 205

Phe Thr Thr Tyr Phe Ser Gly Phe Tyr Glu Asn Arg Lys Asn Val Phe
210                 215                 220

Ser Ala Glu Asp Ile Ser Thr Ala Ile Pro His Arg Ile Val Gln Asp
225                 230                 235                 240

Asn Phe Pro Lys Phe Lys Glu Asn Cys His Ile Phe Thr Arg Leu Ile
                245                 250                 255

Thr Ala Val Pro Ser Leu Arg Glu His Phe Glu Asn Val Lys Lys Ala
            260                 265                 270

Ile Gly Ile Phe Val Ser Thr Ser Ile Glu Glu Val Phe Ser Phe Pro
            275                 280                 285

Phe Tyr Asn Gln Leu Leu Thr Gln Thr Gln Ile Asp Leu Tyr Asn Gln
290                 295                 300

Leu Leu Gly Gly Ile Ser Arg Glu Ala Gly Thr Glu Lys Ile Lys Gly
305                 310                 315                 320

Leu Asn Glu Val Leu Asn Leu Ala Ile Gln Lys Asn Asp Glu Thr Ala
                325                 330                 335

His Ile Ile Ala Ser Leu Pro His Arg Phe Ile Pro Leu Phe Lys Gln
            340                 345                 350

Ile Leu Ser Asp Arg Asn Thr Leu Ser Phe Ile Leu Glu Glu Phe Lys
            355                 360                 365

Ser Asp Glu Glu Val Ile Gln Ser Phe Cys Lys Tyr Lys Thr Leu Leu
370                 375                 380

Arg Asn Glu Asn Val Leu Glu Thr Ala Glu Ala Leu Phe Asn Glu Leu
385                 390                 395                 400

Asn Ser Ile Asp Leu Thr His Ile Phe Ile Ser His Lys Lys Leu Glu
                405                 410                 415

Thr Ile Ser Ser Ala Leu Cys Asp His Trp Asp Thr Leu Arg Asn Ala
            420                 425                 430

Leu Tyr Glu Arg Arg Ile Ser Glu Leu Thr Gly Lys Ile Thr Lys Ser
            435                 440                 445

Ala Lys Glu Lys Val Gln Arg Ser Leu Lys His Glu Asp Ile Asn Leu
450                 455                 460

Gln Glu Ile Ile Ser Ala Ala Gly Lys Glu Leu Ser Glu Ala Phe Lys
465                 470                 475                 480
```

```
Gln Lys Thr Ser Glu Ile Leu Ser His Ala His Ala Leu Asp Gln
                485                 490                 495

Pro Leu Pro Thr Thr Leu Lys Lys Gln Glu Lys Glu Ile Leu Lys
            500                 505                 510

Ser Gln Leu Asp Ser Leu Leu Gly Leu Tyr His Leu Asp Trp Phe
        515                 520                 525

Ala Val Asp Glu Ser Asn Glu Val Asp Pro Glu Phe Ser Ala Arg Leu
    530                 535                 540

Thr Gly Ile Lys Leu Glu Met Glu Pro Ser Leu Ser Phe Tyr Asn Lys
545                 550                 555                 560

Ala Arg Asn Tyr Ala Thr Lys Pro Tyr Ser Val Glu Lys Phe Lys
                565                 570                 575

Leu Asn Phe Gln Met Pro Thr Leu Ala Ser Gly Trp Asp Val Asn Lys
            580                 585                 590

Glu Lys Asn Asn Gly Ala Ile Leu Phe Val Lys Asn Gly Leu Tyr Tyr
        595                 600                 605

Leu Gly Ile Met Pro Lys Gln Lys Gly Arg Tyr Lys Ala Leu Ser Phe
    610                 615                 620

Glu Pro Thr Glu Lys Thr Ser Glu Gly Phe Asp Lys Met Tyr Tyr Asp
625                 630                 635                 640

Tyr Phe Pro Asp Ala Ala Lys Met Ile Pro Lys Cys Ser Thr Gln Leu
                645                 650                 655

Lys Ala Val Thr Ala His Phe Gln Thr His Thr Thr Pro Ile Leu Leu
            660                 665                 670

Ser Asn Asn Phe Ile Glu Pro Leu Glu Ile Thr Lys Glu Ile Tyr Asp
        675                 680                 685

Leu Asn Asn Pro Glu Lys Glu Pro Lys Lys Phe Gln Thr Ala Tyr Ala
    690                 695                 700

Lys Lys Thr Gly Asp Gln Lys Gly Tyr Arg Glu Ala Leu Cys Lys Trp
705                 710                 715                 720

Ile Asp Phe Thr Arg Asp Phe Leu Ser Lys Tyr Thr Lys Thr Thr Ser
                725                 730                 735

Ile Asp Leu Ser Ser Leu Arg Pro Ser Ser Gln Tyr Lys Asp Leu Gly
            740                 745                 750

Glu Tyr Tyr Ala Glu Leu Asn Pro Leu Leu Tyr His Ile Ser Phe Gln
        755                 760                 765

Arg Ile Ala Glu Lys Glu Ile Met Asp Ala Val Glu Thr Gly Lys Leu
    770                 775                 780

Tyr Leu Phe Gln Ile Tyr Asn Lys Asp Phe Ala Lys Gly His His Gly
785                 790                 795                 800

Lys Pro Asn Leu His Thr Leu Tyr Trp Thr Gly Leu Phe Ser Pro Glu
                805                 810                 815

Asn Leu Ala Lys Thr Ser Ile Lys Leu Asn Gly Gln Ala Glu Leu Phe
            820                 825                 830

Tyr Arg Pro Lys Ser Arg Met Lys Arg Met Ala His Arg Leu Gly Glu
    835                 840                 845

Lys Met Leu Asn Lys Lys Leu Lys Asp Gln Lys Thr Pro Ile Pro Asp
850                 855                 860

Thr Leu Tyr Gln Glu Leu Tyr Asp Tyr Val Asn His Arg Leu Ser His
865                 870                 875                 880

Asp Leu Ser Asp Glu Ala Arg Ala Leu Leu Pro Asn Val Ile Thr Lys
                885                 890                 895
```

-continued

Glu Val Ser His Glu Ile Ile Lys Asp Arg Arg Phe Thr Ser Asp Lys
            900                 905                 910

Phe Phe Phe His Val Pro Ile Thr Leu Asn Tyr Gln Ala Ala Asn Ser
        915                 920                 925

Pro Ser Lys Phe Asn Gln Arg Val Asn Ala Tyr Leu Lys Glu His Pro
    930                 935                 940

Glu Thr Pro Ile Ile Gly Ile Asp Arg Gly Glu Arg Asn Leu Ile Tyr
945                 950                 955                 960

Ile Thr Val Ile Asp Ser Thr Gly Lys Ile Leu Glu Gln Arg Ser Leu
                965                 970                 975

Asn Thr Ile Gln Gln Phe Asp Tyr Gln Lys Lys Leu Asp Asn Arg Glu
            980                 985                 990

Lys Glu Arg Val Ala Ala Arg Gln Ala Trp Ser Val Val Gly Thr Ile
        995                 1000                1005

Lys Asp Leu Lys Gln Gly Tyr Leu Ser Gln Val Ile His Glu Ile
    1010                1015                1020

Val Asp Leu Met Ile His Tyr Gln Ala Val Val Leu Glu Asn
    1025                1030                1035

Leu Asn Phe Gly Phe Lys Ser Lys Arg Thr Gly Ile Ala Glu Lys
    1040                1045                1050

Ala Val Tyr Gln Gln Phe Glu Lys Met Leu Ile Asp Lys Leu Asn
    1055                1060                1065

Cys Leu Val Leu Lys Asp Tyr Pro Ala Glu Lys Val Gly Gly Val
    1070                1075                1080

Leu Asn Pro Tyr Gln Leu Thr Asp Gln Phe Thr Ser Phe Ala Lys
    1085                1090                1095

Met Gly Thr Gln Ser Gly Phe Leu Phe Tyr Val Pro Ala Pro Tyr
    1100                1105                1110

Thr Ser Lys Ile Asp Pro Leu Thr Gly Phe Val Asp Pro Phe Val
    1115                1120                1125

Trp Lys Thr Ile Lys Asn His Glu Ser Arg Lys His Phe Leu Glu
    1130                1135                1140

Gly Phe Asp Phe Leu His Tyr Asp Val Lys Thr Gly Asp Phe Ile
    1145                1150                1155

Leu His Phe Lys Met Asn Arg Asn Leu Ser Phe Gln Arg Gly Leu
    1160                1165                1170

Pro Gly Phe Met Pro Ala Trp Asp Ile Val Phe Glu Lys Asn Glu
    1175                1180                1185

Thr Gln Phe Asp Ala Lys Gly Thr Pro Phe Ile Ala Gly Lys Arg
    1190                1195                1200

Ile Val Pro Val Ile Glu Asn His Arg Phe Thr Gly Arg Tyr Arg
    1205                1210                1215

Asp Leu Tyr Pro Ala Asn Glu Leu Ile Ala Leu Leu Glu Glu Lys
    1220                1225                1230

Gly Ile Val Phe Arg Asp Gly Ser Asn Ile Leu Pro Lys Leu Leu
    1235                1240                1245

Glu Asn Asp Asp Ser His Ala Ile Asp Thr Met Val Ala Leu Ile
    1250                1255                1260

Arg Ser Val Leu Gln Met Arg Asn Ser Asn Ala Ala Thr Gly Glu
    1265                1270                1275

Asp Tyr Ile Asn Ser Pro Val Arg Asp Leu Asn Gly Val Cys Phe
    1280                1285                1290

```
Asp Ser Arg Phe Gln Asn Pro Glu Trp Pro Met Asp Ala Asp Ala
    1295                1300                1305

Asn Gly Ala Tyr His Ile Ala Leu Lys Gly Gln Leu Leu Leu Asn
    1310                1315                1320

His Leu Lys Glu Ser Lys Asp Leu Lys Leu Gln Asn Gly Ile Ser
    1325                1330                1335

Asn Gln Asp Trp Leu Ala Tyr Ile Gln Glu Leu Arg Asn Gly Ser
    1340                1345                1350

Gly Leu Asn Asp Ile Phe Glu Ala Gln Lys Ile Glu Trp His Glu
    1355                1360                1365
```

<210> SEQ ID NO 57
<211> LENGTH: 1368
<212> TYPE: PRT
<213> ORGANISM: Artificial Sequence
<220> FEATURE:
<223> OTHER INFORMATION: Polypeptide used in Example 12

<400> SEQUENCE: 57

```
Met Ser Ala Trp Ser His Pro Gln Phe Glu Lys Gly Gly Gly Ser Gly
1               5                   10                  15

Gly Gly Ser Gly Gly Ser Ala Trp Ser His Pro Gln Phe Glu Lys Ser
            20                  25                  30

Gly Gly Gly Gly Gly Glu Asn Leu Tyr Phe Gln Gly Met Thr Gln Phe
        35                  40                  45

Glu Gly Phe Thr Asn Leu Tyr Gln Val Ser Lys Thr Leu Arg Phe Glu
    50                  55                  60

Leu Ile Pro Gln Gly Lys Thr Leu Lys His Ile Gln Glu Gln Gly Phe
65                  70                  75                  80

Ile Glu Glu Asp Lys Ala Arg Asn Asp His Tyr Lys Glu Leu Lys Pro
                85                  90                  95

Ile Ile Asp Arg Ile Tyr Lys Thr Tyr Ala Asp Gln Cys Leu Gln Leu
            100                 105                 110

Val Gln Leu Asp Trp Glu Asn Leu Ser Ala Ala Ile Asp Ser Tyr Arg
        115                 120                 125

Lys Glu Lys Thr Glu Glu Thr Arg Asn Ala Leu Ile Glu Glu Gln Ala
    130                 135                 140

Thr Tyr Arg Asn Ala Ile His Asp Tyr Phe Ile Gly Arg Thr Asp Asn
145                 150                 155                 160

Leu Thr Asp Ala Ile Asn Lys Arg His Ala Glu Ile Tyr Lys Gly Leu
                165                 170                 175

Phe Lys Ala Glu Leu Phe Asn Gly Lys Val Leu Lys Gln Leu Gly Thr
            180                 185                 190

Val Thr Thr Thr Glu His Glu Asn Ala Leu Leu Arg Ser Phe Asp Lys
        195                 200                 205

Phe Thr Thr Tyr Phe Ser Gly Phe Tyr Glu Asn Arg Lys Asn Val Phe
    210                 215                 220

Ser Ala Glu Asp Ile Ser Thr Ala Ile Pro His Arg Ile Val Gln Asp
225                 230                 235                 240

Asn Phe Pro Lys Phe Lys Glu Asn Cys His Ile Phe Thr Arg Leu Ile
                245                 250                 255

Thr Ala Val Pro Ser Leu Arg Glu His Phe Glu Asn Val Lys Lys Ala
            260                 265                 270

Ile Gly Ile Phe Val Ser Thr Ser Ile Glu Glu Val Phe Ser Phe Pro
        275                 280                 285
```

Phe Tyr Asn Gln Leu Leu Thr Gln Thr Gln Ile Asp Leu Tyr Asn Gln
    290                 295                 300

Leu Leu Gly Gly Ile Ser Arg Glu Ala Gly Thr Glu Lys Ile Lys Gly
305                 310                 315                 320

Leu Asn Glu Val Leu Asn Leu Ala Ile Gln Lys Asn Asp Glu Thr Ala
                325                 330                 335

His Ile Ile Ala Ser Leu Pro His Arg Phe Ile Pro Leu Phe Lys Gln
            340                 345                 350

Ile Leu Ser Asp Arg Asn Thr Leu Ser Phe Ile Leu Glu Glu Phe Lys
        355                 360                 365

Ser Asp Glu Glu Val Ile Gln Ser Phe Cys Lys Tyr Lys Thr Leu Leu
370                 375                 380

Arg Asn Glu Asn Val Leu Glu Thr Ala Glu Ala Leu Phe Asn Glu Leu
385                 390                 395                 400

Asn Ser Ile Asp Leu Thr His Ile Phe Ile Ser His Lys Lys Leu Glu
                405                 410                 415

Thr Ile Ser Ser Ala Leu Cys Asp His Trp Asp Thr Leu Arg Asn Ala
            420                 425                 430

Leu Tyr Glu Arg Arg Ile Ser Glu Leu Thr Gly Lys Ile Thr Lys Ser
        435                 440                 445

Ala Lys Glu Lys Val Gln Arg Ser Leu Lys His Glu Asp Ile Asn Leu
450                 455                 460

Gln Glu Ile Ile Ser Ala Ala Gly Lys Glu Leu Ser Glu Ala Phe Lys
465                 470                 475                 480

Gln Lys Thr Ser Glu Ile Leu Ser His Ala His Ala Ala Leu Asp Gln
                485                 490                 495

Pro Leu Pro Thr Thr Leu Lys Lys Gln Glu Lys Glu Ile Leu Lys
            500                 505                 510

Ser Gln Leu Asp Ser Leu Leu Gly Leu Tyr His Leu Leu Asp Trp Phe
        515                 520                 525

Ala Val Asp Glu Ser Asn Glu Val Asp Pro Glu Phe Ser Ala Arg Leu
530                 535                 540

Thr Gly Ile Lys Leu Glu Met Glu Pro Ser Leu Ser Phe Tyr Asn Lys
545                 550                 555                 560

Ala Arg Asn Tyr Ala Thr Lys Lys Pro Tyr Ser Val Glu Lys Phe Lys
                565                 570                 575

Leu Asn Phe Gln Met Pro Thr Leu Ala Ser Gly Trp Asp Val Asn Lys
            580                 585                 590

Glu Lys Asn Asn Gly Ala Ile Leu Phe Val Lys Asn Gly Leu Tyr Tyr
        595                 600                 605

Leu Gly Ile Met Pro Lys Gln Lys Gly Arg Tyr Lys Ala Leu Ser Phe
610                 615                 620

Glu Pro Thr Glu Lys Thr Ser Glu Gly Phe Asp Lys Met Tyr Tyr Asp
625                 630                 635                 640

Tyr Phe Pro Asp Ala Ala Lys Met Ile Pro Lys Cys Ser Thr Gln Leu
                645                 650                 655

Lys Ala Val Thr Ala His Phe Gln Thr His Thr Thr Pro Ile Leu Leu
            660                 665                 670

Ser Asn Asn Phe Ile Glu Pro Leu Glu Ile Thr Lys Glu Ile Tyr Asp
        675                 680                 685

Leu Asn Asn Pro Glu Lys Glu Pro Lys Lys Phe Gln Thr Ala Tyr Ala
690                 695                 700

-continued

Lys Lys Thr Gly Asp Gln Lys Gly Tyr Arg Glu Ala Leu Cys Lys Trp
705                 710                 715                 720

Ile Asp Phe Thr Arg Asp Phe Leu Ser Lys Tyr Thr Lys Thr Thr Ser
            725                 730                 735

Ile Asp Leu Ser Ser Leu Arg Pro Ser Ser Gln Tyr Lys Asp Leu Gly
            740                 745                 750

Glu Tyr Tyr Ala Glu Leu Asn Pro Leu Leu Tyr His Ile Ser Phe Gln
        755                 760                 765

Arg Ile Ala Glu Lys Glu Ile Met Asp Ala Val Glu Thr Gly Lys Leu
770                 775                 780

Tyr Leu Phe Gln Ile Tyr Asn Lys Asp Phe Ala Lys Gly His His Gly
785                 790                 795                 800

Lys Pro Asn Leu His Thr Leu Tyr Trp Thr Gly Leu Phe Ser Pro Glu
                805                 810                 815

Asn Leu Ala Lys Thr Ser Ile Lys Leu Asn Gly Gln Ala Glu Leu Phe
                820                 825                 830

Tyr Arg Pro Lys Ser Arg Met Lys Arg Met Ala His Arg Leu Gly Glu
            835                 840                 845

Lys Met Leu Asn Lys Lys Leu Lys Asp Gln Lys Thr Pro Ile Pro Asp
850                 855                 860

Thr Leu Tyr Gln Glu Leu Tyr Asp Tyr Val Asn His Arg Leu Ser His
865                 870                 875                 880

Asp Leu Ser Asp Glu Ala Arg Ala Leu Leu Pro Asn Val Ile Thr Lys
                885                 890                 895

Glu Val Ser His Glu Ile Ile Lys Asp Arg Arg Phe Thr Ser Asp Lys
                900                 905                 910

Phe Phe Phe His Val Pro Ile Thr Leu Asn Tyr Gln Ala Ala Asn Ser
                915                 920                 925

Pro Ser Lys Phe Asn Gln Arg Val Asn Ala Tyr Leu Lys Glu His Pro
930                 935                 940

Glu Thr Pro Ile Ile Gly Ile Ala Arg Gly Glu Arg Asn Leu Ile Tyr
945                 950                 955                 960

Ile Thr Val Ile Asp Ser Thr Gly Lys Ile Leu Glu Gln Arg Ser Leu
                965                 970                 975

Asn Thr Ile Gln Gln Phe Asp Tyr Gln Lys Lys Leu Asp Asn Arg Glu
            980                 985                 990

Lys Glu Arg Val Ala Ala Arg Gln Ala Trp Ser Val Val Gly Thr Ile
            995                 1000                1005

Lys Asp Leu Lys Gln Gly Tyr Leu Ser Gln Val Ile His Glu Ile
    1010                1015                1020

Val Asp Leu Met Ile His Tyr Gln Ala Val Val Val Leu Glu Asn
    1025                1030                1035

Leu Asn Phe Gly Phe Lys Ser Lys Arg Thr Gly Ile Ala Glu Lys
    1040                1045                1050

Ala Val Tyr Gln Gln Phe Glu Lys Met Leu Ile Asp Lys Leu Asn
    1055                1060                1065

Cys Leu Val Leu Lys Asp Tyr Pro Ala Glu Lys Val Gly Gly Val
    1070                1075                1080

Leu Asn Pro Tyr Gln Leu Thr Asp Gln Phe Thr Ser Phe Ala Lys
    1085                1090                1095

Met Gly Thr Gln Ser Gly Phe Leu Phe Tyr Val Pro Ala Pro Tyr
    1100                1105                1110

```
Thr Ser Lys Ile Asp Pro Leu Thr Gly Phe Val Asp Pro Phe Val
    1115                1120                1125

Trp Lys Thr Ile Lys Asn His Glu Ser Arg Lys His Phe Leu Glu
    1130                1135                1140

Gly Phe Asp Phe Leu His Tyr Asp Val Lys Thr Gly Asp Phe Ile
    1145                1150                1155

Leu His Phe Lys Met Asn Arg Asn Leu Ser Phe Gln Arg Gly Leu
    1160                1165                1170

Pro Gly Phe Met Pro Ala Trp Asp Ile Val Phe Glu Lys Asn Glu
    1175                1180                1185

Thr Gln Phe Asp Ala Lys Gly Thr Pro Phe Ile Ala Gly Lys Arg
    1190                1195                1200

Ile Val Pro Val Ile Glu Asn His Arg Phe Thr Gly Arg Tyr Arg
    1205                1210                1215

Asp Leu Tyr Pro Ala Asn Glu Leu Ile Ala Leu Leu Glu Glu Lys
    1220                1225                1230

Gly Ile Val Phe Arg Asp Gly Ser Asn Ile Leu Pro Lys Leu Leu
    1235                1240                1245

Glu Asn Asp Asp Ser His Ala Ile Asp Thr Met Val Ala Leu Ile
    1250                1255                1260

Arg Ser Val Leu Gln Met Arg Asn Ser Asn Ala Ala Thr Gly Glu
    1265                1270                1275

Asp Tyr Ile Asn Ser Pro Val Arg Asp Leu Asn Gly Val Cys Phe
    1280                1285                1290

Asp Ser Arg Phe Gln Asn Pro Glu Trp Pro Met Asp Ala Asp Ala
    1295                1300                1305

Asn Gly Ala Tyr His Ile Ala Leu Lys Gly Gln Leu Leu Leu Asn
    1310                1315                1320

His Leu Lys Glu Ser Lys Asp Leu Lys Leu Gln Asn Gly Ile Ser
    1325                1330                1335

Asn Gln Asp Trp Leu Ala Tyr Ile Gln Glu Leu Arg Asn Gly Ser
    1340                1345                1350

Gly Leu Asn Asp Ile Phe Glu Ala Gln Lys Ile Glu Trp His Glu
    1355                1360                1365

<210> SEQ ID NO 58
<211> LENGTH: 1368
<212> TYPE: PRT
<213> ORGANISM: Artificial Sequence
<220> FEATURE:
<223> OTHER INFORMATION: Polypeptide used in Example 12

<400> SEQUENCE: 58

Met Ser Ala Trp Ser His Pro Gln Phe Glu Lys Gly Gly Gly Ser Gly
1               5                   10                  15

Gly Gly Ser Gly Gly Ser Ala Trp Ser His Pro Gln Phe Glu Lys Ser
                20                  25                  30

Gly Gly Gly Gly Gly Glu Asn Leu Tyr Phe Gln Gly Met Thr Gln Phe
                35                  40                  45

Glu Gly Phe Thr Asn Leu Tyr Gln Val Ser Lys Thr Leu Arg Phe Glu
        50                  55                  60

Leu Ile Pro Gln Gly Lys Thr Leu Lys His Ile Gln Glu Gln Gly Phe
65                  70                  75                  80

Ile Glu Glu Asp Lys Ala Arg Asn Asp His Tyr Lys Glu Leu Lys Pro
                85                  90                  95
```

```
Ile Ile Asp Arg Ile Tyr Lys Thr Tyr Ala Asp Gln Cys Leu Gln Leu
            100                 105                 110

Val Gln Leu Asp Trp Glu Asn Leu Ser Ala Ala Ile Asp Ser Tyr Arg
            115                 120                 125

Lys Glu Lys Thr Glu Glu Thr Arg Asn Ala Leu Ile Glu Glu Gln Ala
            130                 135                 140

Thr Tyr Arg Asn Ala Ile His Asp Tyr Phe Ile Gly Arg Thr Asp Asn
145                 150                 155                 160

Leu Thr Asp Ala Ile Asn Lys Arg His Ala Glu Ile Tyr Lys Gly Leu
                165                 170                 175

Phe Lys Ala Glu Leu Phe Asn Gly Lys Val Leu Lys Gln Leu Gly Thr
            180                 185                 190

Val Thr Thr Thr Glu His Glu Asn Ala Leu Leu Arg Ser Phe Asp Lys
            195                 200                 205

Phe Thr Thr Tyr Phe Ser Gly Phe Tyr Glu Asn Arg Lys Asn Val Phe
            210                 215                 220

Ser Ala Glu Asp Ile Ser Thr Ala Ile Pro His Arg Ile Val Gln Asp
225                 230                 235                 240

Asn Phe Pro Lys Phe Lys Glu Asn Cys His Ile Phe Thr Arg Leu Ile
                245                 250                 255

Thr Ala Val Pro Ser Leu Arg Glu His Phe Glu Asn Val Lys Lys Ala
            260                 265                 270

Ile Gly Ile Phe Val Ser Thr Ser Ile Glu Glu Val Phe Ser Phe Pro
            275                 280                 285

Phe Tyr Asn Gln Leu Leu Thr Gln Thr Gln Ile Asp Leu Tyr Asn Gln
            290                 295                 300

Leu Leu Gly Gly Ile Ser Arg Glu Ala Gly Thr Glu Lys Ile Lys Gly
305                 310                 315                 320

Leu Asn Glu Val Leu Asn Leu Ala Ile Gln Lys Asn Asp Glu Thr Ala
                325                 330                 335

His Ile Ile Ala Ser Leu Pro His Arg Phe Ile Pro Leu Phe Lys Gln
            340                 345                 350

Ile Leu Ser Asp Arg Asn Thr Leu Ser Phe Ile Leu Glu Glu Phe Lys
            355                 360                 365

Ser Asp Glu Glu Val Ile Gln Ser Phe Cys Lys Tyr Lys Thr Leu Leu
370                 375                 380

Arg Asn Glu Asn Val Leu Glu Thr Ala Glu Ala Leu Phe Asn Glu Leu
385                 390                 395                 400

Asn Ser Ile Asp Leu Thr His Ile Phe Ile Ser His Lys Lys Leu Glu
                405                 410                 415

Thr Ile Ser Ser Ala Leu Cys Asp His Trp Asp Thr Leu Arg Asn Ala
            420                 425                 430

Leu Tyr Glu Arg Arg Ile Ser Glu Leu Thr Gly Lys Ile Thr Lys Ser
            435                 440                 445

Ala Lys Glu Lys Val Gln Arg Ser Leu Lys His Glu Asp Ile Asn Leu
450                 455                 460

Gln Glu Ile Ile Ser Ala Gly Lys Glu Leu Ser Glu Ala Phe Lys
465                 470                 475                 480

Gln Lys Thr Ser Glu Ile Leu Ser His Ala His Ala Ala Leu Asp Gln
            485                 490                 495

Pro Leu Pro Thr Thr Leu Lys Lys Gln Glu Glu Lys Glu Ile Leu Lys
            500                 505                 510
```

```
Ser Gln Leu Asp Ser Leu Leu Gly Leu Tyr His Leu Asp Trp Phe
        515                 520                 525

Ala Val Asp Glu Ser Asn Glu Val Asp Pro Glu Phe Ser Ala Arg Leu
530                 535                 540

Thr Gly Ile Lys Leu Glu Met Glu Pro Ser Leu Ser Phe Tyr Asn Lys
545                 550                 555                 560

Ala Arg Asn Tyr Ala Thr Lys Pro Tyr Ser Val Glu Lys Phe Lys
                565                 570                 575

Leu Asn Phe Gln Met Pro Thr Leu Ala Ser Gly Trp Asp Val Asn Lys
            580                 585                 590

Glu Lys Asn Asn Gly Ala Ile Leu Phe Val Lys Asn Gly Leu Tyr Tyr
        595                 600                 605

Leu Gly Ile Met Pro Lys Gln Lys Gly Arg Tyr Lys Ala Leu Ser Phe
    610                 615                 620

Glu Pro Thr Glu Lys Thr Ser Glu Gly Phe Asp Lys Met Tyr Tyr Asp
625                 630                 635                 640

Tyr Phe Pro Asp Ala Ala Lys Met Ile Pro Lys Cys Ser Thr Gln Leu
                645                 650                 655

Lys Ala Val Thr Ala His Phe Gln Thr His Thr Pro Ile Leu Leu
                660                 665                 670

Ser Asn Asn Phe Ile Glu Pro Leu Glu Ile Thr Lys Glu Ile Tyr Asp
        675                 680                 685

Leu Asn Asn Pro Glu Lys Glu Pro Lys Lys Phe Gln Thr Ala Tyr Ala
    690                 695                 700

Lys Lys Thr Gly Asp Gln Lys Gly Tyr Arg Glu Ala Leu Cys Lys Trp
705                 710                 715                 720

Ile Asp Phe Thr Arg Asp Phe Leu Ser Lys Tyr Thr Lys Thr Thr Ser
                725                 730                 735

Ile Asp Leu Ser Ser Leu Arg Pro Ser Ser Gln Tyr Lys Asp Leu Gly
                740                 745                 750

Glu Tyr Tyr Ala Glu Leu Asn Pro Leu Leu Tyr His Ile Ser Phe Gln
        755                 760                 765

Arg Ile Ala Glu Lys Glu Ile Met Asp Ala Val Glu Thr Gly Lys Leu
    770                 775                 780

Tyr Leu Phe Gln Ile Tyr Asn Lys Asp Phe Ala Lys Gly His His Gly
785                 790                 795                 800

Lys Pro Asn Leu His Thr Leu Tyr Trp Thr Gly Leu Phe Ser Pro Glu
                805                 810                 815

Asn Leu Ala Lys Thr Ser Ile Lys Leu Asn Gly Gln Ala Glu Leu Phe
                820                 825                 830

Tyr Arg Pro Lys Ser Arg Met Lys Arg Met Ala His Arg Leu Gly Glu
        835                 840                 845

Lys Met Leu Asn Lys Lys Leu Lys Asp Gln Lys Thr Pro Ile Pro Asp
850                 855                 860

Thr Leu Tyr Gln Glu Leu Tyr Asp Tyr Val Asn His Arg Leu Ser His
865                 870                 875                 880

Asp Leu Ser Asp Glu Ala Arg Ala Leu Leu Pro Asn Val Ile Thr Lys
                885                 890                 895

Glu Val Ser His Glu Ile Ile Lys Asp Arg Arg Phe Thr Ser Asp Lys
                900                 905                 910

Phe Phe Phe His Val Pro Ile Thr Leu Asn Tyr Gln Ala Ala Asn Ser
            915                 920                 925
```

-continued

```
Pro Ser Lys Phe Asn Gln Arg Val Asn Ala Tyr Leu Lys Glu His Pro
930                 935                 940

Glu Thr Pro Ile Ile Gly Ile Asp Arg Gly Glu Arg Asn Leu Ile Tyr
945                 950                 955                 960

Ile Thr Val Ile Asp Ser Thr Gly Lys Ile Leu Glu Gln Arg Ser Leu
                965                 970                 975

Asn Thr Ile Gln Gln Phe Asp Tyr Gln Lys Lys Leu Asp Asn Arg Glu
                980                 985                 990

Lys Glu Arg Val Ala Ala Arg Gln Ala Trp Ser Val Val Gly Thr Ile
            995                 1000                1005

Lys Asp Leu Lys Gln Gly Tyr Leu Ser Gln Val Ile His Glu Ile
    1010                1015                1020

Val Asp Leu Met Ile His Tyr Gln Ala Val Val Leu Ala Asn
    1025                1030                1035

Leu Asn Phe Gly Phe Lys Ser Lys Arg Thr Gly Ile Ala Glu Lys
    1040                1045                1050

Ala Val Tyr Gln Gln Phe Glu Lys Met Leu Ile Asp Lys Leu Asn
    1055                1060                1065

Cys Leu Val Leu Lys Asp Tyr Pro Ala Glu Lys Val Gly Gly Val
    1070                1075                1080

Leu Asn Pro Tyr Gln Leu Thr Asp Gln Phe Thr Ser Phe Ala Lys
    1085                1090                1095

Met Gly Thr Gln Ser Gly Phe Leu Phe Tyr Val Pro Ala Pro Tyr
    1100                1105                1110

Thr Ser Lys Ile Asp Pro Leu Thr Gly Phe Val Asp Pro Phe Val
    1115                1120                1125

Trp Lys Thr Ile Lys Asn His Glu Ser Arg Lys His Phe Leu Glu
    1130                1135                1140

Gly Phe Asp Phe Leu His Tyr Asp Val Lys Thr Gly Asp Phe Ile
    1145                1150                1155

Leu His Phe Lys Met Asn Arg Asn Leu Ser Phe Gln Arg Gly Leu
    1160                1165                1170

Pro Gly Phe Met Pro Ala Trp Asp Ile Val Phe Glu Lys Asn Glu
    1175                1180                1185

Thr Gln Phe Asp Ala Lys Gly Thr Pro Phe Ile Ala Gly Lys Arg
    1190                1195                1200

Ile Val Pro Val Ile Glu Asn His Arg Phe Thr Gly Arg Tyr Arg
    1205                1210                1215

Asp Leu Tyr Pro Ala Asn Glu Leu Ile Ala Leu Leu Glu Glu Lys
    1220                1225                1230

Gly Ile Val Phe Arg Asp Gly Ser Asn Ile Leu Pro Lys Leu Leu
    1235                1240                1245

Glu Asn Asp Asp Ser His Ala Ile Asp Thr Met Val Ala Leu Ile
    1250                1255                1260

Arg Ser Val Leu Gln Met Arg Asn Ser Asn Ala Ala Thr Gly Glu
    1265                1270                1275

Asp Tyr Ile Asn Ser Pro Val Arg Asp Leu Asn Gly Val Cys Phe
    1280                1285                1290

Asp Ser Arg Phe Gln Asn Pro Glu Trp Pro Met Asp Ala Asp Ala
    1295                1300                1305

Asn Gly Ala Tyr His Ile Ala Leu Lys Gly Gln Leu Leu Leu Asn
    1310                1315                1320
```

```
His Leu Lys Glu Ser Lys Asp  Leu Lys Leu Gln Asn  Gly Ile Ser
    1325                1330                1335

Asn Gln Asp Trp Leu Ala Tyr  Ile Gln Glu Leu Arg  Asn Gly Ser
    1340                1345                1350

Gly Leu Asn Asp Ile Phe Glu  Ala Gln Lys Ile Glu  Trp His Glu
    1355                1360                1365

<210> SEQ ID NO 59
<211> LENGTH: 53
<212> TYPE: DNA
<213> ORGANISM: Artificial Sequence
<220> FEATURE:
<223> OTHER INFORMATION: Polynucleotide used in Example 13
<220> FEATURE:
<221> NAME/KEY: misc_feature
<222> LOCATION: (1)..(36)
<223> OTHER INFORMATION: is a ribonucleotide

<400> SEQUENCE: 59
ccgaccacgc cagcauaucg guuuuagagc uaugcuaggu taaacaccca aga         53

<210> SEQ ID NO 60
<211> LENGTH: 16
<212> TYPE: DNA
<213> ORGANISM: Artificial Sequence
<220> FEATURE:
<223> OTHER INFORMATION: Polynucleotide used in Example 13

<400> SEQUENCE: 60
cttgggtgtt taacct                                                  16
```